US012690986B1

(12) United States Patent
Garvey et al.

(10) Patent No.: US 12,690,986 B1
(45) Date of Patent: Jul. 28, 2026

(54) TOTAL ANKLE REPLACEMENT SYSTEM AND PROCESSES FOR MAKING AND USING THE SAME

(71) Applicant: RESTOR3D, INC., Durham, NC (US)

(72) Inventors: Brian Garvey, Raleigh, NC (US); Deepak Padmanabhan, Cary, NC (US); Michael Balog, Durham, NC (US); Jordyn Sak, Durham, NC (US); Nicholas James Heydinger, Durham, NC (US)

(73) Assignee: RESTOR3D, INC., Durham, NC (US)

( * ) Notice: Subject to any disclaimer, the term of this patent is extended or adjusted under 35 U.S.C. 154(b) by 0 days.

(21) Appl. No.: 18/627,137

(22) Filed: Apr. 4, 2024

Related U.S. Application Data

(60) Provisional application No. 63/518,237, filed on Aug. 8, 2023, provisional application No. 63/518,235, filed on Aug. 8, 2023.

(51) Int. Cl.
*A61F 2/46* (2006.01)
*A61B 17/16* (2006.01)
(Continued)

(52) U.S. Cl.
CPC ........ *A61F 2/4606* (2013.01); *A61B 17/1682* (2013.01); *A61B 17/1775* (2016.11); *A61F 2/4684* (2013.01); *A61F 2002/30387* (2013.01); *A61F 2002/30604* (2013.01); *A61F 2002/30878* (2013.01); *A61F 2002/3093* (2013.01);
(Continued)

(58) Field of Classification Search
CPC ................... A61F 2/3868; A61F 2/389; A61F 2002/4205; A61F 2/42; A61F 2/4202; A61F 2002/4207; A61F 2/4606; A61F 2220/0025; A61F 2220/0033; A61F 2250/006; A61F 2250/0063; A61F 2250/0065; A61F 2/30734; A61B 17/72; A61B 17/7241; A61B 17/862
See application file for complete search history.

(56) References Cited

U.S. PATENT DOCUMENTS

| | | | |
|---|---|---|---|
| 1,428,247 | A | 9/1922 | Morris |
| D220,184 | S | 3/1971 | Boone |
(Continued)

FOREIGN PATENT DOCUMENTS

| | | |
|---|---|---|
| CN | 304140566 S | 5/2017 |
| CN | 109567913 A | 4/2019 |
(Continued)

OTHER PUBLICATIONS

Extended European Search Report dated Feb. 12, 2021 for European Patent Application No. EP20196410.3.
(Continued)

*Primary Examiner* — Anu Ramana
(74) *Attorney, Agent, or Firm* — Husch Blackwell LLP; Bryan D. Stewart; Andrew C. Landsman

(57) ABSTRACT

A system for replacing a tibial side of patient's ankle joint, wherein the tibial side of the ankle joint includes a tibia having a medullary cavity. The system includes a tibial implant having a stem component and a base component; one or more tools for preparing the tibia for installation of the tibial implant; and one or more instruments for installing the tibial implant into a prepared tibial surface.

14 Claims, 119 Drawing Sheets

(51) Int. Cl.

| | |
|---|---|
| *A61B 17/17* | (2006.01) |
| *A61F 2/30* | (2006.01) |
| *A61F 2/42* | (2006.01) |

(52) U.S. Cl.
CPC ................. *A61F 2002/4205* (2013.01); *A61F 2002/4681* (2013.01)

(56) References Cited

U.S. PATENT DOCUMENTS

| 3,872,519 | A | 3/1975 | Giannestras |
|---|---|---|---|
| D242,957 | S | 1/1977 | Treace |
| 4,207,627 | A | 6/1980 | Cloutier |
| 4,232,404 | A | 11/1980 | Samuelson et al. |
| D265,288 | S | 7/1982 | Mclean |
| 4,440,835 | A | 4/1984 | Vignaud |
| 4,586,933 | A | 5/1986 | Shoji et al. |
| 4,588,574 | A | 5/1986 | Felder et al. |
| 4,829,152 | A | 5/1989 | Rostoker |
| D309,185 | S | 7/1990 | Lockawich |
| 4,944,756 | A | 7/1990 | Kenna |
| 5,137,536 | A | 8/1992 | Koshino |
| D336,517 | S | 6/1993 | Mckeown |
| 5,248,456 | A | 9/1993 | Evans, Jr. et al. |
| D358,211 | S | 5/1995 | Cohen |
| D358,647 | S | 5/1995 | Cohen et al. |
| 5,497,783 | A | 3/1996 | Urick et al. |
| 5,497,785 | A | 3/1996 | Viera |
| 5,497,786 | A | 3/1996 | Urick |
| 5,591,191 | A | 1/1997 | Kieturakis |
| 5,766,259 | A * | 6/1998 | Sammarco ............. A61B 17/15 |
| | | | 623/21.18 |
| 5,947,965 | A | 9/1999 | Bryan |
| 6,183,519 | B1 | 2/2001 | Bonnin |
| 6,419,491 | B1 | 7/2002 | Ricci |
| 6,461,358 | B1 | 10/2002 | Faccioli |
| D490,901 | S | 6/2004 | Schulter et al. |
| D493,890 | S | 8/2004 | Schulter et al. |
| 6,989,003 | B2 | 1/2006 | Wing et al. |
| 7,001,672 | B2 | 2/2006 | Justin et al. |
| D521,642 | S | 5/2006 | Dorahy |
| 7,048,741 | B2 * | 5/2006 | Swanson ............. A61B 17/158 |
| | | | 623/20.14 |
| 7,125,423 | B2 * | 10/2006 | Hazebrouck ........ A61F 2/30721 |
| | | | 606/62 |
| 7,172,627 | B2 | 2/2007 | Fiere et al. |
| D539,426 | S | 3/2007 | Callaghan |
| 7,468,075 | B2 | 12/2008 | Lang et al. |
| D593,202 | S | 5/2009 | Petersen |
| 7,534,246 | B2 | 5/2009 | Reiley |
| 7,534,263 | B2 | 5/2009 | Burdulis, Jr. et al. |
| 7,534,270 | B2 | 5/2009 | Ball |
| D595,853 | S | 7/2009 | Hanson |
| D598,094 | S | 8/2009 | Alber |
| D604,153 | S | 11/2009 | Wantz |
| 7,618,451 | B2 | 11/2009 | Berez et al. |
| 7,632,575 | B2 | 12/2009 | Justin et al. |
| 7,634,119 | B2 | 12/2009 | Tsougarakis et al. |
| 7,666,522 | B2 | 2/2010 | Justin et al. |
| D611,147 | S | 3/2010 | Hanson et al. |
| 7,717,956 | B2 | 5/2010 | Lang |
| D618,800 | S | 6/2010 | Mayon et al. |
| D619,255 | S | 7/2010 | Richter et al. |
| D620,111 | S | 7/2010 | Courtney et al. |
| D623,749 | S | 9/2010 | Horton |
| 7,796,791 | B2 | 9/2010 | Tsougarakis et al. |
| 7,799,077 | B2 | 9/2010 | Lang et al. |
| D626,234 | S | 10/2010 | Otto et al. |
| 7,819,614 | B2 | 10/2010 | Versino et al. |
| D628,344 | S | 11/2010 | Raviv |
| 7,981,158 | B2 | 7/2011 | Fitz et al. |
| 7,981,159 | B2 | 7/2011 | Williams et al. |
| 8,012,216 | B2 | 9/2011 | Metzger |
| 8,062,302 | B2 | 11/2011 | Lang et al. |
| 8,066,708 | B2 | 11/2011 | Lang et al. |
| 8,077,950 | B2 | 12/2011 | Tsougarakis et al. |
| 8,083,745 | B2 | 12/2011 | Lang et al. |
| 8,094,900 | B2 | 1/2012 | Steines et al. |
| 8,105,330 | B2 | 1/2012 | Fitz et al. |
| D653,756 | S | 2/2012 | Courtney et al. |
| 8,122,582 | B2 | 2/2012 | Burdulis, Jr. et al. |
| 8,128,580 | B2 | 3/2012 | Fujimagari et al. |
| 8,142,886 | B2 | 3/2012 | Noble et al. |
| D660,432 | S | 5/2012 | Braido |
| D660,966 | S | 5/2012 | Sheild |
| 8,234,097 | B2 | 7/2012 | Steines et al. |
| D666,298 | S | 8/2012 | Sibhatu et al. |
| 8,262,589 | B2 | 9/2012 | Lupton |
| 8,292,955 | B2 | 10/2012 | Robinson et al. |
| 8,292,965 | B2 | 10/2012 | Walker |
| 8,337,501 | B2 | 12/2012 | Fitz et al. |
| 8,337,507 | B2 | 12/2012 | Lang et al. |
| D675,320 | S | 1/2013 | Oi |
| 8,343,218 | B2 | 1/2013 | Lang et al. |
| 8,366,771 | B2 | 2/2013 | Burdulis, Jr. et al. |
| 8,377,129 | B2 | 2/2013 | Fitz et al. |
| 8,382,755 | B2 | 2/2013 | Austin |
| D681,204 | S | 4/2013 | Farris et al. |
| 8,430,930 | B2 | 4/2013 | Hunt |
| 8,439,926 | B2 | 5/2013 | Bojarski et al. |
| D683,856 | S | 6/2013 | Chin et al. |
| 8,457,930 | B2 | 6/2013 | Schroeder |
| 8,460,304 | B2 | 6/2013 | Fitz et al. |
| 8,480,754 | B2 | 7/2013 | Bojarski et al. |
| 8,485,820 | B1 | 7/2013 | Ali |
| 8,500,740 | B2 | 8/2013 | Bojarski et al. |
| 8,529,568 | B2 | 9/2013 | Bouadi |
| 8,529,630 | B2 | 9/2013 | Bojarski et al. |
| D692,136 | S | 10/2013 | Tyber |
| 8,545,569 | B2 | 10/2013 | Fitz et al. |
| 8,551,099 | B2 | 10/2013 | Lang et al. |
| 8,551,102 | B2 | 10/2013 | Fitz et al. |
| 8,551,103 | B2 | 10/2013 | Fitz et al. |
| 8,551,169 | B2 | 10/2013 | Fitz et al. |
| 8,551,173 | B2 | 10/2013 | Lechmann et al. |
| 8,556,906 | B2 | 10/2013 | Fitz et al. |
| 8,556,907 | B2 | 10/2013 | Fitz et al. |
| 8,556,971 | B2 | 10/2013 | Lang |
| 8,556,983 | B2 | 10/2013 | Bojarski et al. |
| 8,561,278 | B2 | 10/2013 | Fitz et al. |
| 8,562,611 | B2 | 10/2013 | Fitz et al. |
| 8,562,618 | B2 | 10/2013 | Fitz et al. |
| 8,568,479 | B2 | 10/2013 | Fitz et al. |
| 8,568,480 | B2 | 10/2013 | Fitz et al. |
| 8,585,708 | B2 | 11/2013 | Fitz et al. |
| 8,585,767 | B2 | 11/2013 | Ullrich, Jr. et al. |
| 8,617,172 | B2 | 12/2013 | Fitz et al. |
| 8,617,242 | B2 | 12/2013 | Philipp et al. |
| 8,623,026 | B2 | 1/2014 | Wong et al. |
| 8,634,617 | B2 | 1/2014 | Tsougarakis et al. |
| 8,638,998 | B2 | 1/2014 | Steines et al. |
| 8,641,716 | B2 | 2/2014 | Fitz et al. |
| 8,657,827 | B2 | 2/2014 | Fitz et al. |
| D700,700 | S | 3/2014 | Efinger |
| 8,682,052 | B2 | 3/2014 | Fitz et al. |
| 8,690,945 | B2 | 4/2014 | Fitz et al. |
| 8,709,083 | B2 | 4/2014 | Duffield et al. |
| 8,709,089 | B2 | 4/2014 | Lang et al. |
| 8,715,362 | B2 | 5/2014 | Reiley |
| 8,735,773 | B2 | 5/2014 | Lang |
| D708,747 | S | 7/2014 | Curran et al. |
| 8,768,028 | B2 | 7/2014 | Lang et al. |
| 8,771,365 | B2 | 7/2014 | Bojarski et al. |
| 8,775,133 | B2 | 7/2014 | Schroeder |
| D711,537 | S | 8/2014 | Pimenta et al. |
| 8,828,311 | B2 | 9/2014 | Medina et al. |
| 8,840,668 | B1 | 9/2014 | Donahoe et al. |
| 8,843,229 | B2 | 9/2014 | Vanasse et al. |
| 8,882,847 | B2 | 11/2014 | Burdulis, Jr. et al. |
| 8,888,485 | B2 | 11/2014 | Ali |
| 8,906,107 | B2 | 12/2014 | Bojarski et al. |
| 8,926,706 | B2 | 1/2015 | Bojarski et al. |
| 8,932,363 | B2 | 1/2015 | Tsougarakis et al. |
| D722,693 | S | 2/2015 | Kaufmann et al. |

(56)  References Cited

U.S. PATENT DOCUMENTS

| | | | |
|---|---|---|---|
| 8,945,230 | B2 | 2/2015 | Lang et al. |
| 8,951,259 | B2 | 2/2015 | Fitz et al. |
| 8,951,260 | B2 | 2/2015 | Lang et al. |
| 8,965,088 | B2 | 2/2015 | Tsougarakis et al. |
| D724,213 | S | 3/2015 | Tyber |
| 8,974,539 | B2 | 3/2015 | Bojarski et al. |
| 8,998,915 | B2 | 4/2015 | Fitz et al. |
| 9,020,788 | B2 | 4/2015 | Lang et al. |
| 9,023,050 | B2 | 5/2015 | Lang et al. |
| 9,034,237 | B2 | 5/2015 | Sperry et al. |
| 9,055,953 | B2 | 6/2015 | Lang et al. |
| 9,066,728 | B2 | 6/2015 | Burdulis, Jr. et al. |
| D734,460 | S | 7/2015 | Froidevaux |
| 9,072,531 | B2 | 7/2015 | Fitz et al. |
| 9,084,617 | B2 | 7/2015 | Lang et al. |
| D735,860 | S | 8/2015 | Palinchik |
| D736,384 | S | 8/2015 | Palinchik |
| 9,095,353 | B2 | 8/2015 | Burdulis, Jr. et al. |
| 9,095,439 | B2 * | 8/2015 | Lian .................. A61B 17/1682 |
| 9,107,679 | B2 | 8/2015 | Lang et al. |
| 9,107,680 | B2 | 8/2015 | Fitz et al. |
| 9,113,921 | B2 | 8/2015 | Lang et al. |
| 9,125,672 | B2 | 9/2015 | Fitz et al. |
| 9,125,673 | B2 | 9/2015 | Fitz et al. |
| 9,144,500 | B2 | 9/2015 | Harding |
| 9,180,015 | B2 | 11/2015 | Fitz et al. |
| 9,180,029 | B2 | 11/2015 | Hollister et al. |
| 9,186,161 | B2 | 11/2015 | Lang et al. |
| 9,186,254 | B2 | 11/2015 | Fitz et al. |
| 9,186,257 | B2 | 11/2015 | Geisler et al. |
| D745,159 | S | 12/2015 | Lin |
| 9,216,025 | B2 | 12/2015 | Fitz et al. |
| 9,220,516 | B2 | 12/2015 | Lang et al. |
| 9,220,517 | B2 | 12/2015 | Lang et al. |
| D747,485 | S | 1/2016 | Oi |
| 9,241,724 | B2 | 1/2016 | Lang et al. |
| 9,241,725 | B2 | 1/2016 | Lang et al. |
| 9,271,845 | B2 | 3/2016 | Hunt et al. |
| 9,295,481 | B2 | 3/2016 | Fitz et al. |
| 9,295,482 | B2 | 3/2016 | Fitz et al. |
| 9,295,562 | B2 | 3/2016 | Lechmann et al. |
| 9,308,005 | B2 | 4/2016 | Fitz et al. |
| 9,308,053 | B2 | 4/2016 | Bojarski et al. |
| 9,308,060 | B2 | 4/2016 | Ali |
| 9,308,091 | B2 | 4/2016 | Lang |
| 9,308,095 | B2 | 4/2016 | Parisi et al. |
| 9,314,256 | B2 | 4/2016 | Fitz et al. |
| 9,320,620 | B2 | 4/2016 | Bojarski et al. |
| 9,326,780 | B2 | 5/2016 | Wong et al. |
| 9,333,058 | B1 | 5/2016 | Krastev |
| 9,339,279 | B2 | 5/2016 | Dubois et al. |
| 9,358,018 | B2 | 6/2016 | Fitz et al. |
| 9,364,896 | B2 | 6/2016 | Christensen et al. |
| 9,370,426 | B2 | 6/2016 | Gabbrielli et al. |
| 9,375,222 | B2 | 6/2016 | Fitz et al. |
| 9,381,025 | B2 | 7/2016 | Fitz et al. |
| 9,387,079 | B2 | 7/2016 | Bojarski et al. |
| 9,402,726 | B2 | 8/2016 | Linderman et al. |
| 9,408,615 | B2 | 8/2016 | Fitz et al. |
| 9,408,686 | B1 | 8/2016 | Miller et al. |
| 9,415,137 | B2 | 8/2016 | Meridew |
| 9,421,108 | B2 | 8/2016 | Hunt |
| D767,137 | S | 9/2016 | Lin |
| 9,433,510 | B2 | 9/2016 | Lechmann et al. |
| 9,433,707 | B2 | 9/2016 | Swords et al. |
| 9,439,767 | B2 | 9/2016 | Bojarski et al. |
| 9,486,226 | B2 | 11/2016 | Chao |
| 9,488,929 | B2 | 11/2016 | Onishi |
| 9,495,483 | B2 | 11/2016 | Steines et al. |
| 9,517,134 | B2 | 12/2016 | Lang |
| 9,545,317 | B2 | 1/2017 | Hunt |
| 9,549,823 | B2 | 1/2017 | Hunt et al. |
| 9,561,115 | B2 | 2/2017 | Elahinia et al. |
| 9,572,669 | B2 | 2/2017 | Hunt et al. |
| 9,579,110 | B2 | 2/2017 | Bojarski et al. |
| D781,422 | S | 3/2017 | Hahn et al. |
| 9,597,130 | B2 | 3/2017 | Pappalardo et al. |
| 9,597,197 | B2 | 3/2017 | Lechmann et al. |
| 9,603,711 | B2 | 3/2017 | Bojarski et al. |
| 9,610,168 | B2 | 4/2017 | Terrill |
| 9,636,226 | B2 | 5/2017 | Hunt |
| 9,636,229 | B2 | 5/2017 | Lang et al. |
| 9,649,178 | B2 | 5/2017 | Ali |
| 9,662,157 | B2 | 5/2017 | Schneider et al. |
| 9,662,226 | B2 | 5/2017 | Wickham |
| 9,668,863 | B2 | 6/2017 | Sharp et al. |
| 9,675,465 | B2 | 6/2017 | Padovani et al. |
| 9,675,471 | B2 | 6/2017 | Bojarski et al. |
| 9,681,956 | B2 | 6/2017 | Al Hares et al. |
| 9,687,945 | B2 | 6/2017 | Steines et al. |
| 9,688,026 | B2 | 6/2017 | Ho et al. |
| 9,694,541 | B2 | 7/2017 | Pruett et al. |
| 9,700,420 | B2 | 7/2017 | Fitz et al. |
| 9,700,424 | B2 | 7/2017 | Sanders et al. |
| 9,700,971 | B2 | 7/2017 | Lang |
| 9,715,563 | B1 | 7/2017 | Schroeder |
| 9,737,367 | B2 | 8/2017 | Steines et al. |
| 9,750,613 | B2 | 9/2017 | Petteys |
| 9,757,235 | B2 | 9/2017 | Hunt et al. |
| 9,757,245 | B2 | 9/2017 | O'Neil et al. |
| 9,775,680 | B2 | 10/2017 | Bojarski et al. |
| 9,782,270 | B2 | 10/2017 | Wickham |
| 9,788,972 | B2 | 10/2017 | Flickinger et al. |
| 9,848,929 | B2 | 12/2017 | Dacosta |
| 9,849,019 | B2 | 12/2017 | Miller et al. |
| 9,872,773 | B2 | 1/2018 | Lang et al. |
| 9,877,790 | B2 | 1/2018 | Bojarski et al. |
| D809,661 | S | 2/2018 | Mueller et al. |
| D813,394 | S | 3/2018 | Dacosta et al. |
| D814,037 | S | 3/2018 | Dacosta et al. |
| 9,907,670 | B2 | 3/2018 | Deridder et al. |
| 9,910,935 | B2 | 3/2018 | Golway et al. |
| 9,913,723 | B2 | 3/2018 | Fitz et al. |
| 9,918,849 | B2 | 3/2018 | Morris et al. |
| 9,925,054 | B2 | 3/2018 | Siegler |
| D814,634 | S | 4/2018 | Dacosta et al. |
| 9,943,370 | B2 | 4/2018 | Asseln et al. |
| 9,943,627 | B2 | 4/2018 | Zhou et al. |
| 9,949,839 | B2 | 4/2018 | Sander |
| 9,956,047 | B2 | 5/2018 | Bojarski et al. |
| 9,956,048 | B2 | 5/2018 | Bojarski et al. |
| 9,962,209 | B2 | 5/2018 | Dacosta et al. |
| D829,909 | S | 10/2018 | Horton |
| D832,441 | S | 10/2018 | Dacosta et al. |
| 10,085,839 | B2 | 10/2018 | Wong et al. |
| D835,276 | S | 12/2018 | Humphrey |
| D835,277 | S | 12/2018 | Gottlieb |
| D835,278 | S | 12/2018 | Gottlieb |
| D835,788 | S | 12/2018 | Jones et al. |
| D835,977 | S | 12/2018 | Pastorino et al. |
| 10,183,442 | B1 | 1/2019 | Miller |
| D841,168 | S | 2/2019 | Dacosta et al. |
| 10,195,035 | B1 | 2/2019 | Staton et al. |
| 10,245,152 | B2 | 4/2019 | Kloss |
| 10,265,189 | B2 | 4/2019 | Melkent et al. |
| D849,944 | S | 5/2019 | Dacosta |
| 10,278,823 | B1 | 5/2019 | Xue |
| D850,620 | S | 6/2019 | Tyber |
| D855,184 | S | 7/2019 | Predick |
| 10,357,377 | B2 | 7/2019 | Nyahay |
| D857,201 | S | 8/2019 | Predick et al. |
| D858,769 | S | 9/2019 | Barela et al. |
| 10,449,051 | B2 | 10/2019 | Hamzey |
| D870,288 | S | 12/2019 | Dang et al. |
| 10,492,686 | B2 | 12/2019 | Hunter |
| D873,031 | S | 1/2020 | Martensson |
| D875,939 | S | 2/2020 | Dacosta et al. |
| D877,907 | S | 3/2020 | Linder et al. |
| D878,589 | S | 3/2020 | Linder |
| D878,590 | S | 3/2020 | Linder et al. |
| D879,295 | S | 3/2020 | Abbasi |
| D879,961 | S | 3/2020 | Linder et al. |
| D881,665 | S | 4/2020 | Zemel et al. |
| 10,624,746 | B2 | 4/2020 | Jones et al. |

(56)　　　　　　　References Cited

U.S. PATENT DOCUMENTS

| | | |
|---|---|---|
| D884,179 S | 5/2020 | Servidio |
| 10,667,924 B2 | 6/2020 | Nyahay |
| 10,675,159 B2 | 6/2020 | Tipping |
| 10,744,001 B2 | 8/2020 | Sack |
| 10,772,732 B1 | 9/2020 | Miller et al. |
| D898,197 S | 10/2020 | Cain |
| D899,900 S | 10/2020 | Blanco |
| D905,246 S | 12/2020 | Irwin et al. |
| 10,898,206 B2 | 1/2021 | Dacosta et al. |
| 10,940,015 B2 | 3/2021 | Sack |
| D917,697 S | 4/2021 | Reed et al. |
| D920,515 S | 5/2021 | Miller |
| D920,516 S | 5/2021 | Miller |
| D920,517 S | 5/2021 | Miller |
| 11,026,798 B1 | 6/2021 | Miller |
| 11,033,394 B2 | 6/2021 | Hamzey |
| D925,740 S | 7/2021 | Kapitan et al. |
| 11,135,771 B1 | 10/2021 | Reith |
| D938,033 S | 12/2021 | Dang |
| D942,011 S | 1/2022 | Cain |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,324,525 B1 | 5/2022 | Garvey |
| 11,353,277 B2 | 6/2022 | Muceus |
| D962,440 S | 8/2022 | Irwin et al. |
| 11,439,726 B2 | 9/2022 | Spence |
| D967,960 S | 10/2022 | Wang et al. |
| 11,471,203 B2 | 10/2022 | Sutika |
| D968,614 S | 11/2022 | Cain |
| D986,728 S | 5/2023 | Jou et al. |
| 11,648,125 B2 * | 5/2023 | Ng ..................... A61F 2/30734 |
| | | 623/20.15 |
| 11,666,367 B2 | 6/2023 | Goradia |
| 11,666,452 B2 | 6/2023 | Melkent |
| D992,116 S | 7/2023 | Miller et al. |
| 11,744,716 B2 | 9/2023 | Jebsen |
| 11,850,144 B1 * | 12/2023 | Garrigues ........... A61F 2/30749 |
| D1,013,875 S | 2/2024 | Miller et al. |
| D1,013,876 S | 2/2024 | Miller et al. |
| 11,950,822 B2 | 4/2024 | Champagne et al. |
| 11,960,266 B1 | 4/2024 | Kelly et al. |
| D1,030,046 S | 6/2024 | Boey et al. |
| D1,033,648 S | 7/2024 | Finley |
| D1,038,400 S | 8/2024 | Kuyler et al. |
| D1,052,732 S | 11/2024 | Pigue et al. |
| 12,144,738 B2 | 11/2024 | Goldberg et al. |
| 12,226,317 B2 | 2/2025 | Webb et al. |
| D1,071,220 S | 4/2025 | Miller et al. |
| 12,419,753 B2 | 9/2025 | White et al. |
| 2001/0031966 A1 | 10/2001 | Tormala et al. |
| 2003/0045834 A1 | 3/2003 | Wing et al. |
| 2004/0049284 A1 | 3/2004 | German et al. |
| 2004/0049285 A1 | 3/2004 | Haas |
| 2004/0148032 A1 | 7/2004 | Rutter et al. |
| 2004/0230313 A1 | 11/2004 | Saunders |
| 2005/0010302 A1 | 1/2005 | Dietz et al. |
| 2006/0074492 A1 | 4/2006 | Frey |
| 2006/0229730 A1 * | 10/2006 | Railey .................... A61B 17/15 |
| | | 623/23.44 |
| 2006/0249875 A1 | 11/2006 | Robb et al. |
| 2007/0055251 A1 | 3/2007 | Huebner et al. |
| 2007/0100346 A1 | 5/2007 | Wyss |
| 2007/0118243 A1 | 5/2007 | Schroeder et al. |
| 2007/0244563 A1 | 10/2007 | Roche et al. |
| 2008/0091271 A1 | 4/2008 | Bonitati et al. |
| 2008/0119941 A1 | 5/2008 | Seo et al. |
| 2008/0140214 A1 | 6/2008 | Hedley et al. |
| 2008/0206297 A1 | 8/2008 | Roeder et al. |
| 2008/0243260 A1 | 10/2008 | Lee et al. |
| 2009/0062925 A1 | 3/2009 | Samuelson |
| 2009/0093668 A1 | 4/2009 | Marten et al. |
| 2009/0182430 A1 | 7/2009 | Tyber et al. |
| 2010/0055644 A1 | 3/2010 | Arni |

| | | |
|---|---|---|
| 2010/0057216 A1 | 3/2010 | Gannoe et al. |
| 2010/0076567 A1 | 3/2010 | Justin et al. |
| 2010/0131071 A1 | 5/2010 | O'Connor et al. |
| 2010/0137990 A1 | 6/2010 | Apatsidis et al. |
| 2010/0168798 A1 | 7/2010 | Clineff et al. |
| 2010/0286791 A1 | 11/2010 | Goldsmith |
| 2011/0054611 A1 | 3/2011 | Wu et al. |
| 2011/0106268 A1 | 5/2011 | Deffenbaugh et al. |
| 2011/0144752 A1 | 6/2011 | Defelice et al. |
| 2011/0190898 A1 | 8/2011 | Lenz |
| 2011/0224796 A1 | 9/2011 | Weiland et al. |
| 2011/0230974 A1 | 9/2011 | Musani |
| 2011/0251614 A1 | 10/2011 | Piraino |
| 2012/0064288 A1 | 3/2012 | Nakano et al. |
| 2012/0215310 A1 | 8/2012 | Sharp et al. |
| 2012/0239152 A1 | 9/2012 | Ullrich, Jr. et al. |
| 2012/0257507 A1 | 10/2012 | Sato et al. |
| 2012/0259419 A1 | 10/2012 | Brown et al. |
| 2012/0323337 A1 | 12/2012 | Parisi et al. |
| 2013/0046313 A1 * | 2/2013 | Lian ......................... A61F 2/46 |
| | | 606/99 |
| 2013/0068968 A1 | 3/2013 | Daniel |
| 2013/0123935 A1 | 5/2013 | Hunt et al. |
| 2013/0158651 A1 | 6/2013 | Hollister et al. |
| 2013/0184820 A1 | 7/2013 | Schwartz et al. |
| 2013/0197657 A1 | 8/2013 | Anca et al. |
| 2013/0218282 A1 | 8/2013 | Hunt |
| 2013/0245777 A1 | 9/2013 | Jerry |
| 2013/0274890 A1 | 10/2013 | Mckay |
| 2013/0296874 A1 | 11/2013 | Chao |
| 2014/0100779 A1 | 4/2014 | Tuke |
| 2014/0107785 A1 | 4/2014 | Geisler et al. |
| 2014/0107786 A1 | 4/2014 | Geisler et al. |
| 2014/0107799 A1 | 4/2014 | Tuke et al. |
| 2014/0236299 A1 | 8/2014 | Roeder et al. |
| 2014/0277443 A1 | 9/2014 | Fleury et al. |
| 2014/0277452 A1 | 9/2014 | Skaer |
| 2014/0277538 A1 * | 9/2014 | Sander .................. A61F 2/4202 |
| | | 623/20.32 |
| 2014/0288650 A1 | 9/2014 | Hunt |
| 2014/0336680 A1 | 11/2014 | Medina et al. |
| 2014/0350688 A1 | 11/2014 | Michel |
| 2014/0371863 A1 | 12/2014 | Vanasse et al. |
| 2015/0025666 A1 | 1/2015 | Olivieri |
| 2015/0045839 A1 | 2/2015 | Dacosta et al. |
| 2015/0045902 A1 | 2/2015 | Perler |
| 2015/0105858 A1 | 4/2015 | Papay et al. |
| 2015/0282945 A1 | 10/2015 | Hunt |
| 2015/0282946 A1 | 10/2015 | Hunt |
| 2015/0320461 A1 | 11/2015 | Ehmke |
| 2015/0335434 A1 | 11/2015 | Patterson et al. |
| 2015/0343709 A1 | 12/2015 | Gerstle et al. |
| 2015/0351915 A1 | 12/2015 | Defelice et al. |
| 2015/0374411 A1 | 12/2015 | Ehmke et al. |
| 2016/0008139 A1 | 1/2016 | Siegler |
| 2016/0051371 A1 | 2/2016 | Defelice et al. |
| 2016/0089138 A1 | 3/2016 | Early et al. |
| 2016/0151833 A1 | 6/2016 | Tsao |
| 2016/0193055 A1 | 7/2016 | Ries |
| 2016/0199193 A1 | 7/2016 | Willis et al. |
| 2016/0213485 A1 | 7/2016 | Schaufler et al. |
| 2016/0213486 A1 | 7/2016 | Nunley et al. |
| 2016/0213487 A1 | 7/2016 | Wilson et al. |
| 2016/0213488 A1 | 7/2016 | Moore et al. |
| 2016/0220288 A1 | 8/2016 | Dubois et al. |
| 2016/0228255 A1 * | 8/2016 | Samuelson ............ B22D 23/02 |
| 2016/0256279 A1 | 9/2016 | Sanders et al. |
| 2016/0256610 A1 | 9/2016 | Zhou et al. |
| 2016/0270920 A1 | 9/2016 | Dawson et al. |
| 2016/0270931 A1 | 9/2016 | Trieu |
| 2016/0287388 A1 | 10/2016 | Hunt et al. |
| 2016/0303793 A1 | 10/2016 | Ermoshkin et al. |
| 2016/0310189 A1 | 10/2016 | Dacosta et al. |
| 2016/0333152 A1 | 11/2016 | Cook et al. |
| 2016/0374829 A1 | 12/2016 | Vogt et al. |
| 2017/0014169 A1 | 1/2017 | Dean et al. |
| 2017/0018919 A1 | 1/2017 | Chen et al. |
| 2017/0020685 A1 | 1/2017 | Geisler et al. |
| 2017/0036403 A1 | 2/2017 | Ruff et al. |

(56)　　　　　References Cited

U.S. PATENT DOCUMENTS

| | | |
|---|---|---|
| 2017/0042697 A1 | 2/2017 | Mcshane, III et al. |
| 2017/0056178 A1 | 3/2017 | Sharp et al. |
| 2017/0056179 A1 | 3/2017 | Lorio |
| 2017/0066873 A1 | 3/2017 | Gardet |
| 2017/0105844 A1 | 4/2017 | Kuyler et al. |
| 2017/0156880 A1 | 6/2017 | Halverson et al. |
| 2017/0165085 A1 | 6/2017 | Lechmann et al. |
| 2017/0165790 A1 | 6/2017 | Mccarthy et al. |
| 2017/0172758 A1 | 6/2017 | Field et al. |
| 2017/0182222 A1 | 6/2017 | Paddock et al. |
| 2017/0209274 A1 | 7/2017 | Beerens et al. |
| 2017/0216035 A1 | 8/2017 | Hunt |
| 2017/0216036 A1 | 8/2017 | Cordaro |
| 2017/0239054 A1 | 8/2017 | Engstrand et al. |
| 2017/0239064 A1 | 8/2017 | Cordaro |
| 2017/0245998 A1 | 8/2017 | Padovani et al. |
| 2017/0252165 A1 | 9/2017 | Sharp et al. |
| 2017/0258606 A1 | 9/2017 | Afzal |
| 2017/0282455 A1 | 10/2017 | Defelice et al. |
| 2017/0296244 A1 | 10/2017 | Schneider et al. |
| 2017/0319344 A1 | 11/2017 | Hunt |
| 2017/0323037 A1 | 11/2017 | Schroeder |
| 2017/0333205 A1 | 11/2017 | Joly et al. |
| 2017/0354510 A1 | 12/2017 | O'Neil et al. |
| 2017/0354513 A1 | 12/2017 | Maglaras et al. |
| 2017/0355815 A1 | 12/2017 | Becker et al. |
| 2017/0360488 A1 | 12/2017 | Kowalczyk et al. |
| 2017/0360563 A1 | 12/2017 | Hunt et al. |
| 2017/0360578 A1 | 12/2017 | Shin et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0008419 A1 | 1/2018 | Tyber et al. |
| 2018/0012517 A1 | 1/2018 | Ropelato |
| 2018/0022017 A1 | 1/2018 | Fukumoto et al. |
| 2018/0064540 A1 | 3/2018 | Hunt |
| 2018/0085230 A1 | 3/2018 | Hunt |
| 2018/0098858 A1 | 4/2018 | Valderraband |
| 2018/0104063 A1 | 4/2018 | Asaad |
| 2018/0110593 A1 | 4/2018 | Khalil |
| 2018/0110626 A1 | 4/2018 | Mcshane, III et al. |
| 2018/0110627 A1 | 4/2018 | Sack |
| 2018/0117219 A1 | 5/2018 | Yang et al. |
| 2018/0147319 A1 | 5/2018 | Colucci-Mizenko et al. |
| 2018/0196920 A1 | 7/2018 | Liang et al. |
| 2018/0256336 A1 | 9/2018 | Mueller |
| 2018/0280140 A1 | 10/2018 | Jones |
| 2018/0289380 A1 | 10/2018 | Mauldin |
| 2018/0289515 A1 | 10/2018 | Nemes et al. |
| 2019/0091032 A1 | 3/2019 | Pak et al. |
| 2019/0167433 A1 | 6/2019 | Allen |
| 2019/0262101 A1 | 8/2019 | Shanjani et al. |
| 2019/0269527 A1 | 9/2019 | Moore |
| 2019/0302736 A1 | 10/2019 | Chanin |
| 2019/0343652 A1 | 11/2019 | Petersheim et al. |
| 2020/0000595 A1 | 1/2020 | Jones |
| 2020/0030102 A1 | 1/2020 | Mullens et al. |
| 2020/0030108 A1 | 1/2020 | Orphanos et al. |
| 2020/0046512 A1 | 2/2020 | Newman et al. |
| 2020/0085452 A1 | 3/2020 | Siegler |
| 2020/0085585 A1 | 3/2020 | Siegler |
| 2020/0107934 A1 | 4/2020 | Pontius |
| 2020/0107940 A1 | 4/2020 | Murphy et al. |
| 2020/0155321 A1 | 5/2020 | Dikovsky |
| 2020/0171752 A1 | 6/2020 | Rogren |
| 2020/0171753 A1 | 6/2020 | Satko |
| 2020/0253649 A1* | 8/2020 | Langdale ........... A61B 17/0401 |
| 2020/0367910 A1 | 11/2020 | Hafez et al. |
| 2021/0000588 A1 | 1/2021 | Cain |
| 2021/0077276 A1 | 3/2021 | Garvey et al. |
| 2021/0110605 A1 | 4/2021 | Haslam |
| 2021/0113222 A1* | 4/2021 | Khatibi .............. A61B 17/1775 |
| 2021/0121298 A1 | 4/2021 | Walker et al. |
| 2021/0216683 A1 | 7/2021 | Rai |
| 2021/0298908 A1 | 9/2021 | Holmes |
| 2021/0307765 A1* | 10/2021 | Dumpe .................. A61B 34/20 |
| 2021/0340334 A1 | 11/2021 | Portela |
| 2022/0023048 A1 | 1/2022 | Nolens |
| 2022/0087670 A1 | 3/2022 | Selmoune |
| 2022/0134639 A1 | 5/2022 | Allen |
| 2022/0142783 A1 | 5/2022 | Ahmadi |
| 2022/0168109 A1 | 6/2022 | Giordano |
| 2022/0226094 A1 | 7/2022 | Chotkowski et al. |
| 2022/0296386 A1 | 9/2022 | Fang |
| 2022/0401138 A1 | 12/2022 | Finley et al. |
| 2023/0114676 A1 | 4/2023 | Harris et al. |
| 2023/0122922 A1 | 4/2023 | Daudet |
| 2023/0190492 A1 | 6/2023 | Marks et al. |
| 2024/0033092 A1 | 2/2024 | Parthasarathy et al. |
| 2024/0065767 A1 | 2/2024 | Cordonnier et al. |
| 2024/0245523 A1 | 7/2024 | Mermuys et al. |
| 2024/0374291 A1 | 11/2024 | Ogilvie et al. |
| 2025/0099255 A1 | 3/2025 | Hintermann et al. |
| 2025/0152095 A1 | 5/2025 | Hunter |

FOREIGN PATENT DOCUMENTS

| | | |
|---|---|---|
| CN | 110090096 | 8/2019 |
| CN | 306895697 S | 10/2021 |
| DE | 69806985 | 6/2003 |
| EP | 1180989 | 4/2006 |
| EP | 2832321 | 2/2015 |
| EP | 2635239 | 7/2017 |
| EP | 2913030 | 3/2018 |
| EP | 3586800 | 1/2020 |
| FR | 026681-002 S | 2/2003 |
| FR | 3071400 | 3/2019 |
| GB | 4005303 S | 2/2008 |
| JP | 4840886 | 12/2011 |
| KR | 300766315 S | 10/2014 |
| KR | 301007894 | 5/2019 |
| WO | 2014020561 A1 | 2/2014 |
| WO | 2014020562 | 2/2014 |
| WO | 2015054070 | 4/2015 |
| WO | 2020123295 A1 | 6/2020 |
| WO | D211856-003 S | 1/2021 |
| WO | 2023183793 A2 | 11/2023 |

OTHER PUBLICATIONS

Larraona et al., "Radiopaque material for 3D printing scaffolds", XXXV Confreso Anual de la Sociedad Espanola de Ingenieria Biomedica. Bilbao, Nov. 29-Dec. 1, 2017, p. 451-454 (Year: 2017).

Rozema et al., The effects of different steam-sterilization programs on material properties of poly(I-lactide), Journal of Applied Biomaterials, vol. 2, 23-28 (1991) (Year: 1991).

Alt, Sami. "Design for Sterilization Part 1: Steam Sterillization." Material, Material Technology Blog, Jun. 3, 2016, www.material-technology.com/single-post/2016/05/24/Design-for-Sterilization-part-1-Steam-Sterillization.

Ducheyne, Paul. "Comprehensive Biomaterials." Comprehensive Biomaterials, vol. 1, Elsevier, 2011, pp. 135-135.

Anat Ratnovsky et al., Mechanical Properties of Different Airway Stents, Med. Eng'g. Physics, Mar. 2011, at 408., http://www.medengphys.com/article/S1350-4533(15)00042-9/fulltext.

Andrew T. Miller et al., Fatigue of Injection Molded and 30 Printed Polycarbonate Urethane in Solution, 108 Polymer 121 (2017).

Andrew T. Miller et al., Deformation and Fatigue of Tough 30 Printed Elastomer Scaffolds Processed by Fused 3 Deposition Modeling and Continuous Liquid Interface Production, 75 J. Mechanical Behavior Biomedical Materials 1 (2017).

Ortho Spine News, "SeaSpine Announces 25,000th NanoMetalene Implantation", first available Dec. 18, 2019. (https://orthospinenews.com/2019/12/18/seaspine-announces-25000th-nanometalene-implantation/) (Year: 2019).

Restor3d, "Products", first available Sep. 28, 2020. (https://web.archive.org/web/20200928123335/https:/restor3d.com/products) (Year: 2020).

Ortho Spine News, "Nvision Biomedical Technologies: First FDA Clearance for Osteotomy Wedge System", first available Oct. 28,

(56)        References Cited

OTHER PUBLICATIONS 2020. (https://orthospinenews.com/2020/10/28/nvision-biomedical-technologies-first-fda-clearance-for-osteotomy-wedge-system-made-of-peek-optima-ha-enhanced/) (Year: 2020).

Sina, "Application logic of triple periodic minimum surface", first available Oct. 24, 2020. (https://k.sina.com.cn/article_2422410454_90630cd6001 OOtlbm.html?from=science) (Year: 2020).

3D Adept Media, "Johnson & Johnson Medical", first available Sep. 17, 2018. (https://3dadept.com/johnson-johnson-medical-has-acquired-3d-printed-spmplants-special ist-emerging-implant-technologies/) (Year: 2018).

Additive Orthopaedics, "Additive Orthopaedics 3d Printed Cotton Bone Segment", first available Sep. 19, 2020. (https://web.archive.org/web/20200919145251/https://www.additiveorthopaedics.com/our-products/cotton/) (Year: 2020).

Indiamart, "Anterior Cervical Fusion Cage for Spine Surgery", first accessed Dec. 9, 2020. (https://www.indiamart.com/proddetail/ anterior-cervical-fusion-cage-12402896897 .html) (Year: 2020).

Instagram, "restor3d", first available Jul. 21, 2020. (https://www.instagram.com/p/CC6dztOAKcM/?utm_source=ig_web_link) (Year: 2020).

Yan et al., "Ti—6Al—4V triply periodic minimal surface structures for bone implants fabricated via selective laser melting", Jul. 9, 2015, Journal of the mechanical behavior of biomedical materials 51 (2015), 61-73 (Year: 2015).

Yan et al., "Microstructure and mechanical properties of aluminum alloy cellular lattice structures manufactured by direct metal laser sintering", Jan. 31, 2015, Materials Science and Engineering A 628 (2015), 238-246 (Year: 2015).

3D Printing For Orthopedic Implant, publication date Jan. 7, 2021, [online] URL: https://www.eplus3d.com/3d-printing-for-orthopedic-implant.html (Year: 2021).

3D printing implants: A complete guide, publication date Feb. 1, 2023, [online] URL: https://www.ntop.com/resources/blog/3d-printing-implants-a-complete-guide/ (Year: 2023).

Does 3D Printing Add Value In Orthopedics?, publication date Apr. 1, 2019, [online] URL: https://www.odtmag.com/issues/2019-04-01 /view_features/does-3d-printing-add-value-in-orthopedics/ (Year: 2019).

Cera-Metal orthopedic implant coating, ifdesign.com, Published 2006 , Accessed Jul. 24, 2024, https://ifdesign.com/en/wi nner-ranking/projecUcera-metal/27188.

[MTP Hemiarthroplasty Implant Featuring TIDAL Technology™], cdn.prod.website-files.com, Posted: Mar. 2023 [online], site visited: [Jul. 25, 2024], URL: <https://cdn.prod. website-files.com/ 65d612f03cc5c490660ab482/65d612f03cc5c490660ab 7 aa_restor3d-MTP-Sales-Sheet. pdf>. (Year: 2023).

Cotton Wedge Portfolio, cdn.prod.website-files.com, Published Jun. 1, 2023, Accessed Jul. 25, 2024, URL: https://cdn.prod.website-files.com/65d612f03cc5c490660ab482/65d612f03cc5c490660ab7bd_ MKG-010%20 REV01%20JUN2023%20Wedge%20Portfolio% 20Brochure.pdf (Year: 2023).

APEX 3D Total Ankle replacement, Paragon 28, Retrieved from internet: https://paragon28.com/app/uploads/2021/08/DIGITAL-P10-STM-0001-Rev-A_APEX_TAR_SystemOverview.pdf, 2020, 8 pages.

Foot and Ankle Wedge Portfolio with TIDAL Technology™, restor3d, URL: https://www.restor3d.com/wp-content/uploads/2024/07/Foot-Ankle-Wedge-Portfolio-Brochure.pdf, 2023, 2 pages.

Inbone Total Ankle System, Stryker, Retrieved from internet, https:// www.stryker.com/content/dam/stryker/foot-and-ankle/products/inbone/ resources/Inbone-Brochure.pdf, 2022, 6 pages.

Kinos Total Ankle System, restor3d, Retrieved from internet: https:// www.restor3d.com/healthcare-professionals/products/foot-ankle/ total-ankle-replacement/, 2025, 5 pages.

Restor3d | Choose Your Motion, Instagram posted Oct. 3, 2024, Retrieved from internet, https://www.instagram.com/restor3d/p/ DArDUCLSoCj/?img_index=1, 1 page.

Rose, "Paragon 28, Inc. is pleased to announce that the U.S. Food and Drug Administration has cleared the APEX 3D™ Total Ankle Replacement System", P28 News, Retrieved from internet, https:// paragon28.com/paragon-28-inc-is-pleased-to-announce-that-the-u-s-food-and-drug-administration-has-cleared-the-apex-3d-total-ankle-replacement-system/, 2020, 1 page.

TIDAL™ Subtalar Wedge System, restor3d, retrieved from: https:// www.restor3d.com/wp-content/uploads/2024/07/TIDAL®-Subtalar-Wedge-System-Surgical-Technique.pdf, 2022, 10 pages.

Trabecular Metal Total Ankle, Zimmer, Retrieved from internet: https://www.zimmerbiomet.com/content/dam/zb-corporate/en/products/ specialties/foot-&-ankle/trabecular-metal-total-ankle-system/ zimmertrabecularmetaltotalanklebrochure.pdf, 2013, 6 pages.

Vantage Total Ankle, exactech , Retrieved from internet, https:// www.exac.com/wp-content/uploads/2024/09/721-00-10_Rev_D_ Exactech_Vantage_Ankle_Product_Sheet_US_Web.pdf, 2024, 2 pages.

* cited by examiner

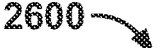
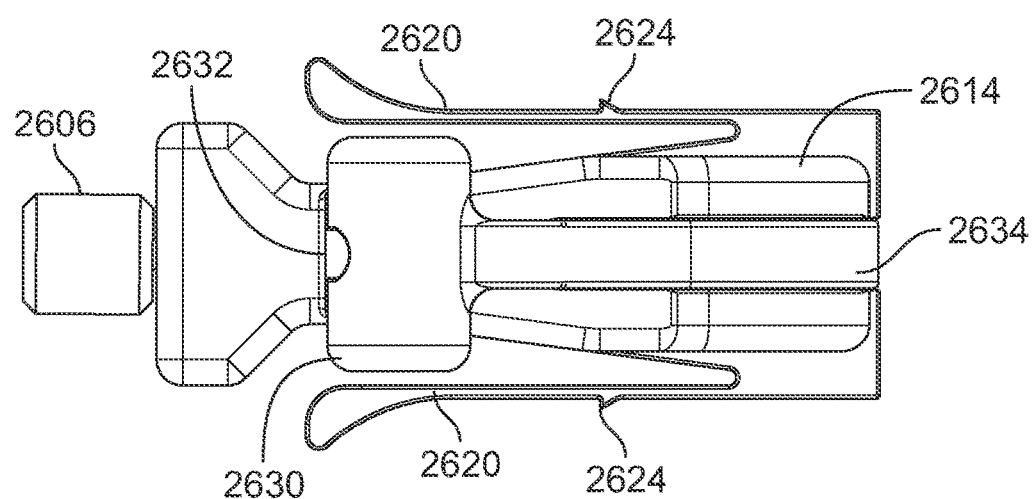
FIG. 67
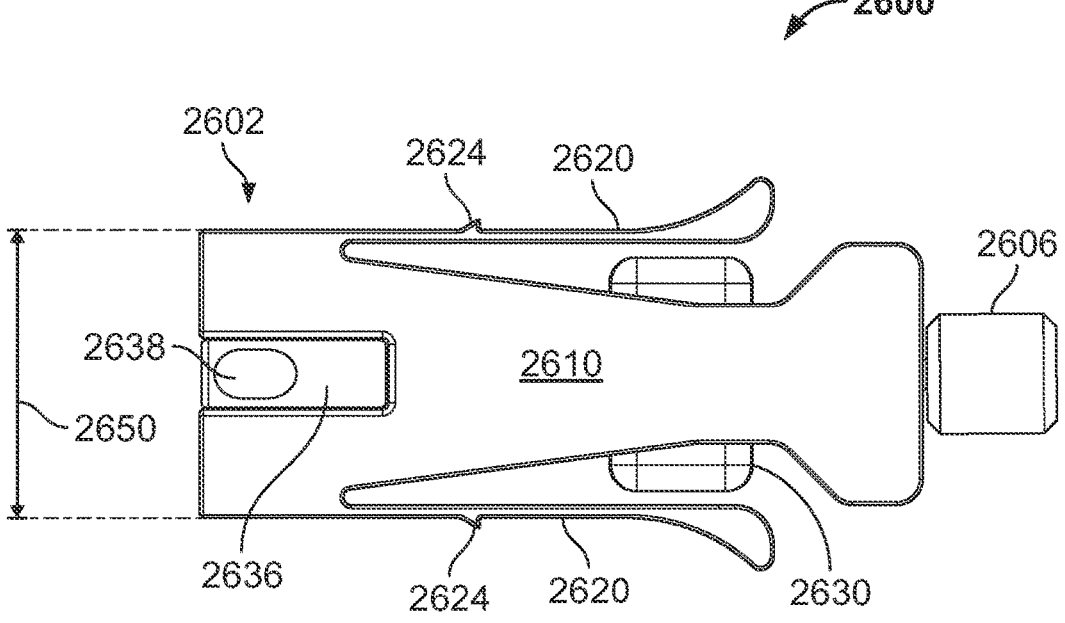
FIG. 68

2900

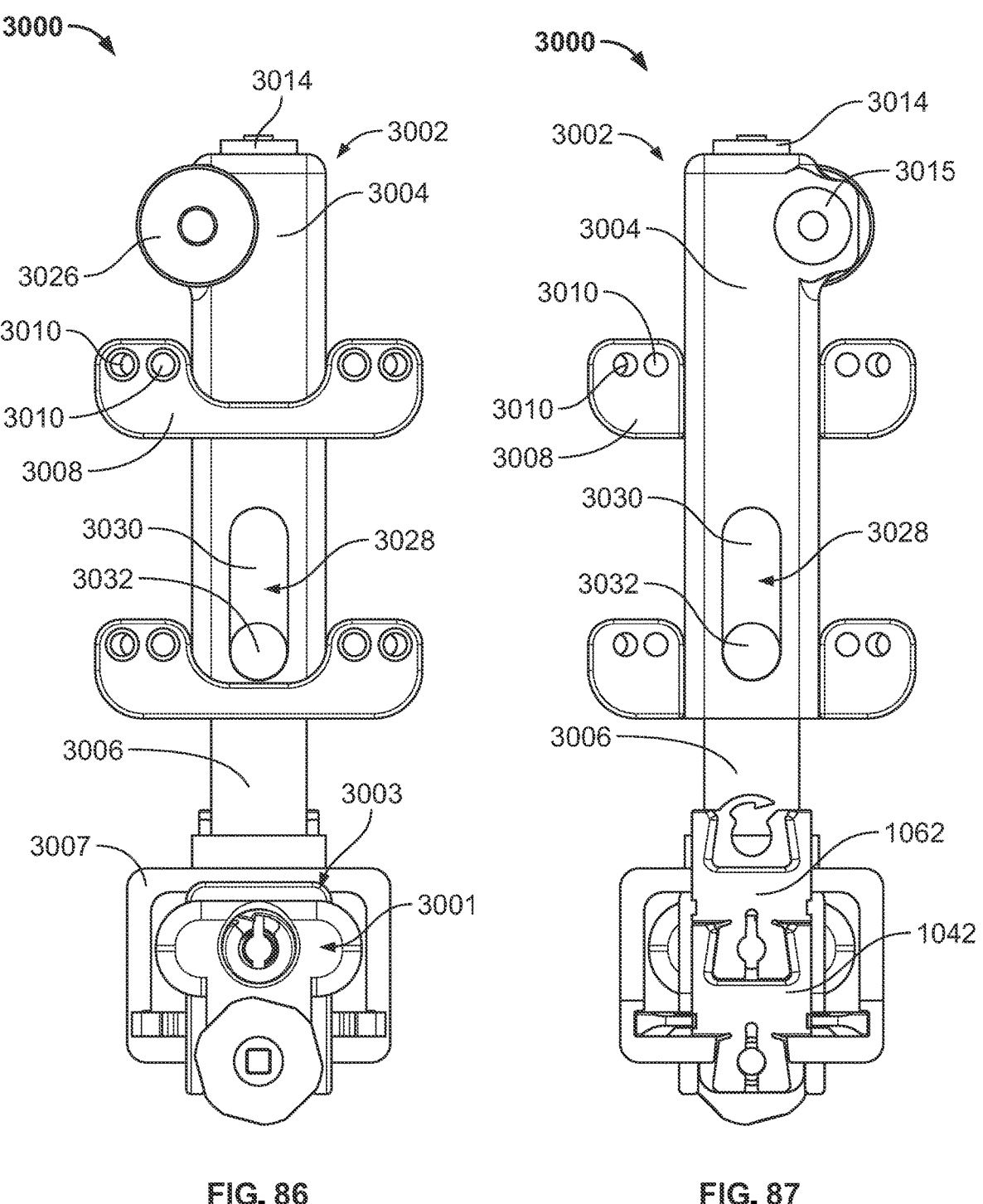
FIG. 86                              FIG. 87

4000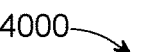

| | |
|---|---|
| Receiving a TAR tool kit | 4005 |
| Making an anterior incision | 4010 |
| Resecting the tibia and the talus | 4015 |
| Inserting a tibial trial on the tibia | 4020 |
| Inserting a sight alignment tool into the tibial trial | 4025 |
| Inserting a distractor into the tibial trial | 4030 |
| Distracting the ankle | 4035 |
| Inserting a drill plate into the tibial trial | 4040 |
| Drilling into the tibial surface using a right angle drill (RAD) | 4045 |
| Inserting a spike broach under the tibial trial | 4050 |
| Impacting the spike broach into the tibial surface | 4055 |
| Inserting a wire guide into the tibial trial | 4060 |
| Inserting a guide wire through the wire guide and spike broach | 4065 |
| Removing the wire guide and spike broach | 4070 |
| Inserting a flexible reamer assembly into the tibial trial | 4075 |
| Reaming over the guide wire into the tibial surface | 4080 |
| Removing one or more tools | 4085 |

FIG. 100

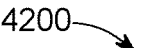

4200

| | |
|---|---|
| Receiving a TAR tool kit | 4205 |
| Making an anterior incision | 4210 |
| Resecting the tibia and the talus | 4215 |
| Inserting a tibial trial on the tibia | 4220 |
| Inserting a sight alignment tool into the tibial trial | 4225 |
| Inserting a distractor into the tibial trial | 4230 |
| Distracting the ankle | 4235 |
| Inserting a drill plate into the tibial trial | 4240 |
| Drilling into the tibial surface using a right angle drill (RAD) | 4245 |
| Inserting a spike broach under the tibial trial | 4250 |
| Impacting the spike broach into the tibial surface | 4255 |
| Inserting a flexible reamer assembly into the tibial trial | 4260 |
| Inserting a guide wire through the flexible reamer assembly | 4265 |
| Reaming over the guide wire into the tibial surface | 4270 |
| Removing one or more tools | 4275 |

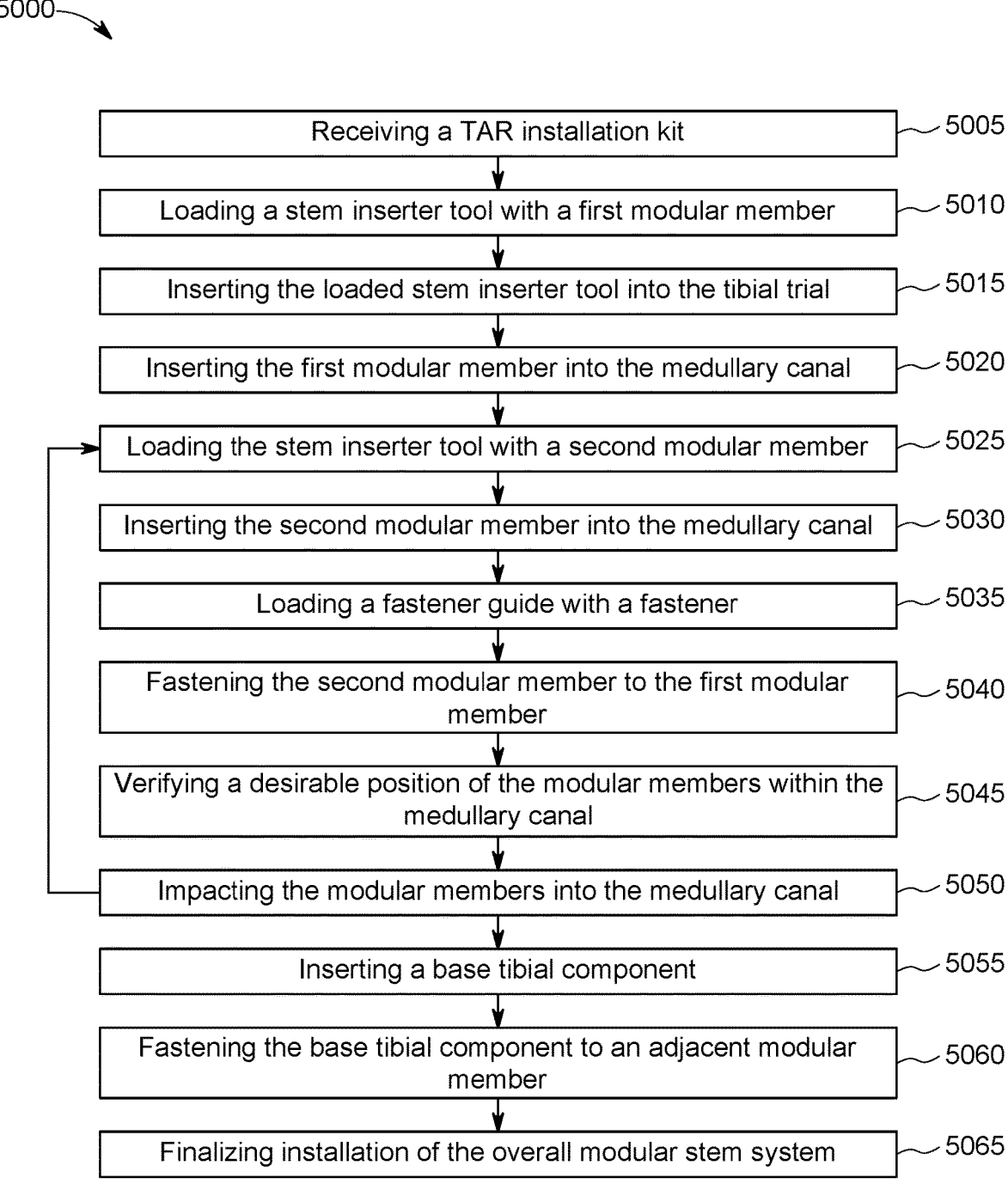

| Receiving a TAR installation kit | 5005 |
| Loading a stem inserter tool with a first modular member | 5010 |
| Inserting the loaded stem inserter tool into the tibial trial | 5015 |
| Inserting the first modular member into the medullary canal | 5020 |
| Loading the stem inserter tool with a second modular member | 5025 |
| Inserting the second modular member into the medullary canal | 5030 |
| Loading a fastener guide with a fastener | 5035 |
| Fastening the second modular member to the first modular member | 5040 |
| Verifying a desirable position of the modular members within the medullary canal | 5045 |
| Impacting the modular members into the medullary canal | 5050 |
| Inserting a base tibial component | 5055 |
| Fastening the base tibial component to an adjacent modular member | 5060 |
| Finalizing installation of the overall modular stem system | 5065 |

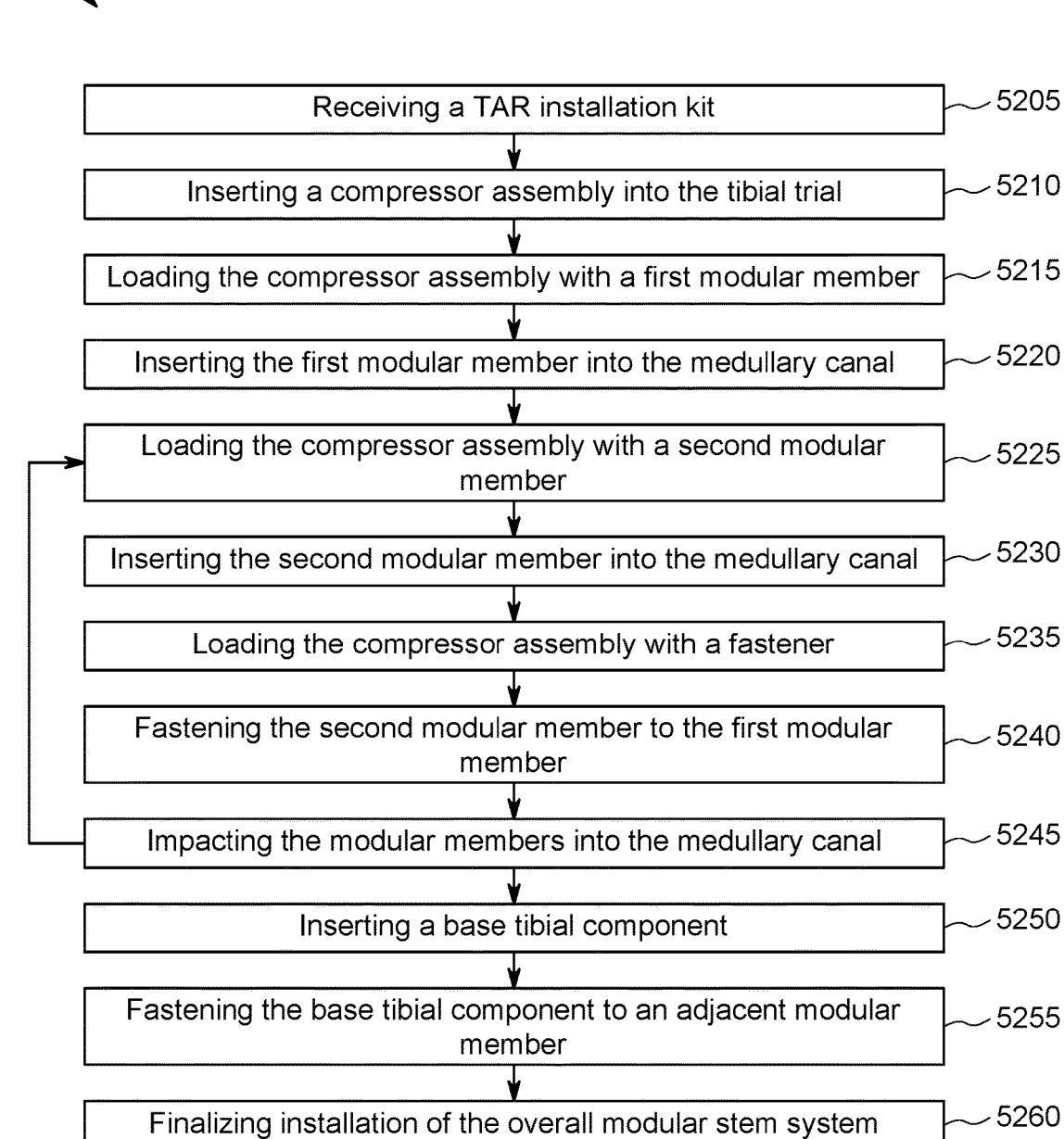

| | |
|---|---|
| Receiving a TAR installation kit | 5205 |
| Inserting a compressor assembly into the tibial trial | 5210 |
| Loading the compressor assembly with a first modular member | 5215 |
| Inserting the first modular member into the medullary canal | 5220 |
| Loading the compressor assembly with a second modular member | 5225 |
| Inserting the second modular member into the medullary canal | 5230 |
| Loading the compressor assembly with a fastener | 5235 |
| Fastening the second modular member to the first modular member | 5240 |
| Impacting the modular members into the medullary canal | 5245 |
| Inserting a base tibial component | 5250 |
| Fastening the base tibial component to an adjacent modular member | 5255 |
| Finalizing installation of the overall modular stem system | 5260 |

FIG. 103

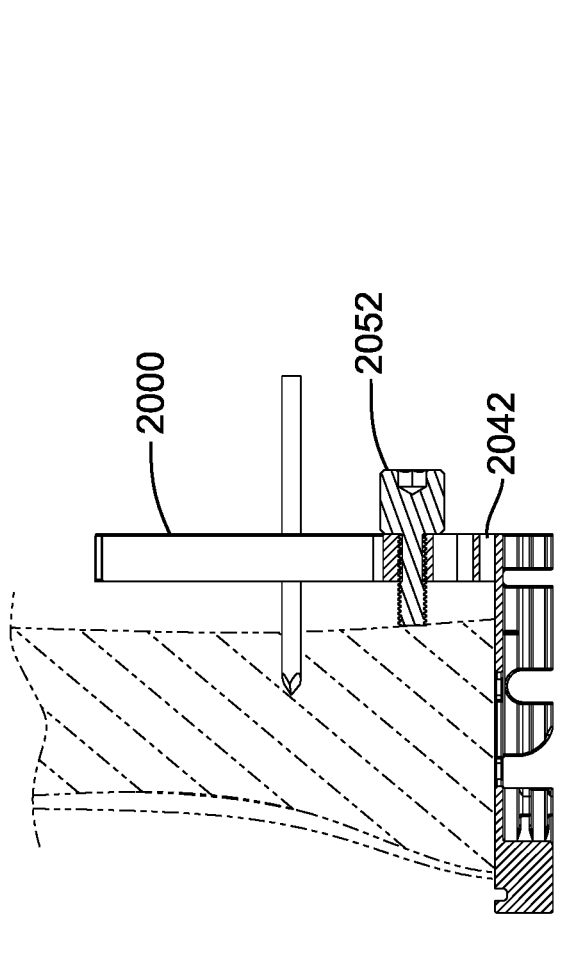
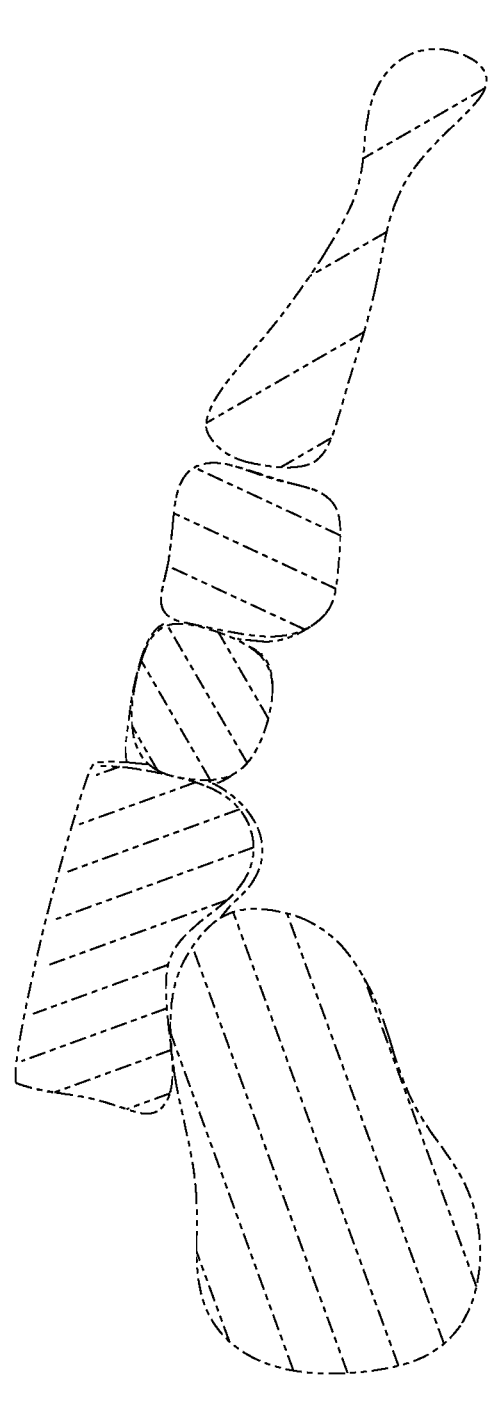
2000
2052
2042
FIG. 106

TOTAL ANKLE REPLACEMENT SYSTEM AND PROCESSES FOR MAKING AND USING THE SAME

CROSS-REFERENCE TO RELATED APPLICATIONS

This application claims priority to U.S. Provisional Patent Application No. 63/518,235, filed Aug. 8, 2023, entitled "RIGHT-ANGLE DRILL" and U.S. Provisional Patent Application No. 63/518,237, filed Aug. 8, 2023, entitled "MODULAR STEM", each of which are incorporated herein by reference in their entireties.

BACKGROUND

Joint replacement surgery involves replacement of an existing joint section in a patient with an artificial joint implant that includes some or all parts of a particular joint and/or surrounding sections of bones. In the case of ankle arthroplasty, or total ankle replacement (TAR) surgery, certain aspects of the ankle joint are removed and replaced with prosthetic components that may simulate natural ankle movement. Further, TAR surgery may be an alternative to an ankle fusion approach (e.g., arthrodesis) because it may preserve the functional range of motion of the ankle, which may lead to better patient health and satisfaction.

BRIEF SUMMARY OF THE DISCLOSURE

Briefly described, aspects of the present disclosure generally relate to devices, systems, and methods pertaining to total ankle replacement (TAR), as well as processes for making and using the same. According to a first aspect, the present disclosure relates to a TAR system comprising a tibial implant comprising a base component comprising a base plate, the base plate having a first surface and a second surface; the first surface including an attachment feature; the second surface including an anchoring member; and a stem component coupled to the anchoring member, the stem component comprising a first modular member.

According to a second aspect, the TAR system of the first aspect, or any other aspect, wherein the first modular member is positioned at an offset angle relative to the second surface.

According to a third aspect, the TAR system of the second aspect, or any other aspect, wherein a first fixation feature of the first modular member engages with the anchoring member.

According to a fourth aspect, the TAR system of the third aspect, or any other aspect, wherein a second fixation feature of the first modular member engages with a first fixation feature of a second modular member.

According to a fifth aspect, the TAR system of the fourth aspect, or any other aspect, wherein each of the first and second modular members includes an opening.

According to a sixth aspect The TAR system of the fifth aspect, or any other aspect, wherein each opening includes at least one anti-backout feature.

According to a seventh aspect, the TAR system of the sixth aspect, or any other aspect, wherein the at least one anti-backout feature includes a flexible pawl, the flexible pawl selectively engaging with one tooth of a fastener.

According to an eighth aspect, the TAR system of the seventh aspect, or any other aspect, wherein the fastener is used to fasten the first modular member to the anchoring member.

According to a ninth aspect, the TAR system of the seventh aspect, or any other aspect, wherein a fastener is used to fasten the second modular member to the first modular member.

According to a tenth aspect, the TAR system of the ninth aspect, or any other aspect, wherein the second fixation feature of the first modular member defines a female portion of a dovetail joint and the first fixation feature of the second modular member defines a male portion of a dovetail joint.

According to an eleventh aspect, the TAR system of the fourth aspect, or any other aspect, wherein the stem component further comprises a terminal modular member such that a second fixation feature of the second modular member engages with a first fixation feature of the terminal modular member.

According to a twelfth aspect, the TAR system of the eleventh aspect, or any other aspect, wherein the terminal modular member includes a tapered end.

According to a thirteenth aspect, the TAR system of the first aspect, or any other aspect, wherein an insert is inserted into the attachment feature.

According to a fourteenth aspect, the TAR system of the thirteenth aspect, or any other aspect, wherein the insert provides a bearing surface between the tibial implant and a talus implant.

According to a fifteenth aspect, the TAR system of the first aspect, or any other aspect, wherein the tibial implant includes one or more regions for osteointegration.

According to a sixteenth aspect, the TAR system of the fifteenth aspect, or any other aspect, wherein the one or more regions comprises a textured structure.

According to a seventeenth aspect, the TAR system of the fifteenth aspect, or any other aspect, wherein the one or more regions comprises a porous structure.

According to an eighteenth aspect, the TAR system of the fifteenth aspect, or any other aspect, wherein the one or more regions comprises a gyroid structure.

The present disclosure also relates to a method for total ankle replacement (TAR) of an ankle of a patient, wherein the ankle includes a tibia having a medullary cavity, the method comprising, according to the nineteenth aspect, or any other aspect, comprising the steps of: making an anterior incision to the ankle; resecting a portion of the tibia to form a prepared tibial surface; positioning a tibial trial on the prepared tibial surface; removably fixing the tibial trial to the tibia; distracting the ankle to form a workspace within the ankle; inserting a right-angle drill into the tibial trial; drilling to begin forming an intramedullary canal; inserting a broach into the workspace; impacting the broach into the prepared tibial surface to continue forming the intramedullary canal; inserting a guide wire into the medullary cavity; inserting a flexible reamer assembly into the tibial trial; reaming into the medullary cavity to continue forming the intramedullary canal; inserting a stem component of a tibial implant into the intramedullary canal; and attaching a base component of the tibial implant to the stem component.

According to a twentieth aspect, the method of the nineteenth aspect, or any other aspect, wherein the step of removably fixing the tibial trial to the tibia further comprises the steps of: inserting a sight alignment tool into the tibial trial, and verifying a desirable position of the tibial trial based on feedback from the sight alignment tool.

According to a twenty-first aspect, the method of the nineteenth aspect, or any other aspect, wherein the step of distracting the ankle to form a workspace within the ankle further comprises the steps of: engaging a distractor, in a first configuration, with the tibial trial; attaching the distractor to the tibial trial; and setting the distractor to a second configuration.

According to a twenty-second aspect, the method of the nineteenth aspect, or any other aspect, further comprising a drill plate, the drill plate comprising a pattern of through-holes, the pattern of through-holes exposing a first portion of the prepared tibial surface when the drill plate is inserted into the tibial trial.

According to a twenty-third aspect, the method of the twenty-second aspect, or any other aspect, wherein the step of drilling to begin forming an intramedullary canal further comprises the steps of: inserting the drill plate into the tibial trial; and drilling through the drill plate to begin forming an intramedullary canal through the first portion of the prepared tibial surface.

According to a twenty-fourth aspect, the method of the nineteenth aspect, or any other aspect, wherein the flexible reamer assembly comprises: a reamer head coupled to a first end of a flexible reamer; a reamer guide configured to house a portion of the flexible reamer; and a reamer lock plate.

According to a twenty-fifth aspect, the method of the twenty-fourth aspect, or any other aspect, wherein the broach comprises a hollow internal channel configured to receive and hold a portion of the guide wire.

According to a twenty-sixth aspect, the method of the twenty-fifth aspect, or any other aspect, further comprising the steps of: inserting a wire guide into the tibial trial; inserting the guide wire into the medullary cavity, wherein the guide wire is inserted through the wire guide and broach; and verifying a desirable position of the guide wire.

According to a twenty-seventh aspect, the method of the twenty-sixth aspect, or any other aspect, wherein the step of inserting a flexible reamer assembly further comprises the steps of: positioning the reamer head over the guide wire; assembling the reamer guide around the flexible reamer; inserting the reamer guide into the tibial trial; and inserting the reamer lock plate into the tibial trial to secure the flexible reamer assembly.

According to a twenty-eighth aspect, the method of the twenty-fourth aspect, or any other aspect, wherein the step of inserting a flexible reamer assembly further comprises the steps of: positioning the reamer head at the medullary cavity; assembling the reamer guide around the flexible reamer; inserting the reamer guide into the tibial trial; inserting the reamer lock plate into the tibial trial to secure the flexible reamer assembly; inserting the guide wire through the flexible reamer assembly; and verifying a desirable position of the guide wire.

According to a twenty-ninth aspect, the method of the twenty-eighth aspect, or any other aspect, wherein the step of verifying a desirable position of the guide wire further comprises the step of inserting a sight alignment tool into the tibial trial.

According to a thirtieth aspect, the method of the nineteenth aspect, or any other aspect, wherein the step of reaming into the medullary cavity to continue forming the intramedullary canal further comprises the step of advancing the guide wire with the flexible reamer assembly.

According to a thirty-first aspect, the method of the nineteenth aspect, or any other aspect, wherein the stem component comprises a first stem portion and a second stem portion.

According to a thirty-second aspect, the method of the thirty-first aspect, or any other aspect, wherein the step of inserting the stem component of a tibial implant into the intramedullary canal comprises the steps of: inserting the first stem portion into the intramedullary canal; attaching the second stem portion to the first stem portion using a fastener; and impacting the first and second stem portions into the intramedullary canal.

According to a thirty-third aspect, the method of the thirty-second aspect, or any other aspect, wherein a stem insertion tool is used to insert the first stem portion into the intramedullary canal.

According to a thirty-fourth aspect, the method of the thirty-second aspect, or any other aspect, wherein a fastener guide is used to attach the second stem portion to the first stem portion.

According to a thirty-fifth aspect, the method of the thirty-second aspect, or any other aspect, wherein an impactor tool is used to impact the first and second stem portions into the intramedullary canal.

According to a thirty-sixth aspect, the method of the nineteenth aspect, or any other aspect, wherein a fastener guide and a fastener are used to attach the base component to the stem component.

The present disclosure also relates to a system for replacing a tibial side of a patient's ankle joint, wherein the tibial side of the ankle joint includes a tibia having a medullary cavity, according to the thirty-seventh aspect, or any other aspect, the system comprising: a tibial implant comprising a stem component and a base component; one or more tools for preparing the tibia for installation of the tibial implant, the one or more tools comprising a tibial trial, a distractor, a right-angle drill, a broach, a reamer assembly, and a guide wire; and one or more instruments for installing the tibial implant into a prepared tibial surface, the one or more instruments comprising a stem inserter and an impactor.

According to a thirty-eighth aspect, the system of the thirty-seventh aspect, or any other aspect, wherein the tibial trial comprises: a trial face having a viewing slot, an alignment slot, and a fastener opening; and a trial base having one or more channels and an access opening.

According to a thirty-ninth aspect, the system of the thirty-eighth aspect, or any other aspect, wherein a sight alignment tool is inserted into the alignment slot to verify a desirable position of the tibial trial.

According to a fortieth aspect, the system of the thirty-ninth aspect, or any other aspect, wherein the tibial trial is secured to the patient's tibia using a fastener and the fastener opening.

According to a forty-first aspect, the system of the thirty-eighth aspect, or any other aspect, wherein the distractor comprises: a distractor frame comprising: a distractor base connected to a support member, the distractor base housing a first rail; and an upright member connected to the support member, the upright member housing a second rail; and a distractor plate coupled to the distractor frame.

According to a forty-second aspect, the system of the forty-first aspect, or any other aspect, wherein the distractor further comprises a guide support.

According to a forty-third aspect, the system of the forty-second aspect, or any other aspect, wherein the guide support engages with the one or more channels.

According to a forty-fourth aspect, the system of the forty-third aspect, or any other aspect, wherein the distractor is set from a first configuration to a second configuration.

According to a forty-fifth aspect, the system of the forty-fourth aspect, or any other aspect, wherein setting the distractor from the first configuration to the second configuration comprises moving the distractor plate relative to the distractor frame.

According to a forty-sixth aspect, the system of the thirty-eighth aspect, or any other aspect, further comprising a drill plate.

According to a forty-seventh aspect, the system of the forty-sixth aspect, or any other aspect, an engagement tab of the drill plate engages with the one or more channels.

According to a forty-eighth aspect, the system of the forty-seventh aspect, or any other aspect, wherein the drill plate comprises a pattern of through-holes exposing a first portion of the prepared tibial surface when the drill plate is inserted into the tibial trial.

According to a forty-ninth aspect, the system of the forty-eighth aspect, or any other aspect, wherein the right-angle drill comprises: a drill bit extending from a drive shaft; a handle coupled to the drive shaft; and a housing enclosing a portion of the drive shaft and drill bit.

According to a fiftieth aspect, the system of the forty-ninth aspect, or any other aspect, wherein the drill bit drills through the pattern of through-holes, the access opening of the tibial trial, and into the medullary cavity to begin forming an intramedullary canal.

According to a fifty-first aspect, the system of the forty-ninth aspect, or any other aspect, wherein the broach is impacted through the access opening to continue forming the intramedullary canal.

According to a fifty-second aspect, the system of the fifty-first aspect, or any other aspect, wherein the flexible reamer assembly comprises: a reamer head coupled to a flexible reamer; a reamer guide enclosing a portion of the flexible reamer; and a reamer lock plate.

According to a fifty-third aspect, the system of the fifty-second aspect, or any other aspect, wherein the broach comprises a hollow internal channel.

According to a fifty-fourth aspect, the system of the fifty-third aspect, or any other aspect, further comprising a wire guide assembly, the wire guide assembly comprising: a wire guide base coupled to a wire guide attachment having one or more engagement tabs; and a knob configured to controllably secure the wire guide attachment to the wire guide base, wherein a guide wire channel extends between a first opening disposed on the wire guide base and a second opening disposed on the wire guide attachment.

According to a fifty-fifth aspect, the system of the fifty-fourth aspect, or any other aspect, wherein the one or more engagement tabs engage with the one or more channels such that the second opening on the wire guide attachment aligns with the hollow internal channel of the broach.

According to a fifty-sixth aspect, the system of the fifty-five aspect, or any other aspect, wherein the guide wire is inserted into the medullary cavity such that the guide wire is inserted through the first opening and the hollow internal channel.

According to a fifty-seventh aspect, the system of the fifty-sixth aspect, or any other aspect, wherein a sight alignment tool is inserted into the alignment slot to verify a desirable position of the guide wire.

According to a fifty-eighth aspect, the system of the fifty-seventh aspect, or any other aspect, wherein the flexible reamer assembly is inserted into the tibial trial such that the flexible reamer is positioned over the guide wire and the reamer guide is assembled around the flexible reamer.

According to a fifty-ninth aspect, the system of the fifty-eighth aspect, or any other aspect, wherein the reamer lock plate engages with the one or more channels.

According to a sixtieth aspect, the system of the fifty-ninth aspect, or any other aspect, wherein the reamer blade is advanced with the guide wire into the medullary cavity to continue forming the intramedullary canal.

According to a sixty-first aspect, the system of the fifty-second aspect, or any other aspect, wherein the flexible reamer assembly is inserted into the tibial trial such that the flexible reamer is positioned over the guide wire and the reamer guide is assembled around the flexible reamer.

According to a sixty-second aspect, the system of the sixty-first aspect, or any other aspect, wherein the guide wire is inserted into the medullary cavity such that the guide wire is inserted through the flexible reamer assembly.

According to a sixty-third aspect, the system of the sixty-second aspect, or any other aspect, wherein the reamer blade is advanced with the guide wire into the medullary cavity continue forming the intramedullary canal.

According to a sixty-fourth aspect, the system of the thirty-seventh aspect, or any other aspect, wherein the stem inserter tool is used to insert the stem component, the stem inserter tool comprising: a body portion; a coupling component; and a stem support, the stem support receiving and holding the stem component.

According to a sixty-fifth aspect, the system of the sixty-fourth aspect, or any other aspect, wherein the coupling component is used to insert the stem component into the prepared tibial surface.

According to a sixty-sixth aspect, the system of the sixty-fifth aspect, or any other aspect, wherein the impactor tool impacts the stem component into the prepared tibial surface.

According to a sixty-seventh aspect, the system of the sixty-sixth aspect, or any other aspect, wherein the base component is attached to the stem component.

The present disclosure also relates to a right-angle drill (RAD) system comprising, according to the sixty-eighth aspect, a right-angle drill comprising: a drive shaft having a drive shaft axis; a drill bit having a drill bit axis, wherein the drill bit is rotationally engaged with the drive shaft and the drive shaft axis is perpendicular to the drill bit axis; a selectively lockable housing enclosing the drive shaft and the drill bit; and a drill plate comprising a pattern of through-holes According to a sixty-ninth aspect, the RAD system of the sixty-eighth aspect, or any other aspect, or any other aspect, wherein the drill bit is rotationally engaged with the drive shaft by a gear.

According to a seventieth aspect, the RAD system of the sixty-ninth aspect, or any other aspect, or any other aspect, wherein the drill bit may be removed from the selectively lockable housing.

According to a seventy-first aspect, the RAD system of the seventieth aspect, or any other aspect, or any other aspect, wherein the selectively lockable housing comprises a swivel door and a lock.

According to a seventy-second aspect, the RAD system of the seventy-first aspect, or any other aspect, or any other aspect, wherein the drill bit extends through complementary semi-circular holes disposed on the swivel door and the lock.

According to a seventy-third aspect, the RAD system of the seventieth aspect, or any other aspect, or any other aspect, wherein the selectively lockable housing comprises a hatch lock.

According to a seventy-fourth aspect, the RAD system of the seventy-third aspect, or any other aspect, or any other aspect, wherein the drill bit extends through a hole disposed on the lock.

According to a seventy-fifth aspect, the RAD system of the sixty-eighth aspect, or any other aspect, or any other aspect, wherein the drill plate engages with the selectively lockable housing such that the though-holes of the drill plate receive and guide the drill bit.

According to a seventy-sixth aspect, the RAD system of the sixty-eighth aspect, or any other aspect, or any other aspect, wherein the drill plate includes an engagement tab.

According to a seventy-seventh aspect, the RAD system of the sixty-eighth aspect, or any other aspect, or any other aspect, wherein the drill bit axis and the drive shaft axis form an angle other than 90 degrees.

The present disclosure also relates to a trial, according to the seventy-eighth aspect, or any other aspect, comprising: a trial face having one or more slots and one or more openings; and a trial base having one or more channels and an access opening, wherein the trial engages with a patient tibia.

According to a seventy-ninth aspect, the trial of the seventy-eighth aspect, or any other aspect, or any other aspect, wherein the one or more slots of the trial face include a viewing slot.

According to an eightieth aspect, the trial of the seventy-ninth aspect, or any other aspect, wherein the viewing slot is designed to reveal one or more portions of the patient tibia.

According to an eighty-first aspect, the trial of the seventy-eighth aspect, or any other aspect, wherein the one or more slots of the trial face include an alignment slot.

According to an eighty-second aspect, the trial of the eighty-first aspect, or any other aspect, wherein the alignment slot is designed to verify alignment of the trial.

According to an eighty-third aspect, the trial of the seventy-eighth aspect, or any other aspect, wherein the one or more openings of the trial face include a fastener opening.

According to an eighty-fourth aspect, the trial of the eighty-third aspect, or any other aspect, wherein the one or more openings of the trial face are designed to receive a fastener such that the fastener secures a position of the trial.

According to an eighty-fifth aspect, the trial of the seventy-eighth aspect, or any other aspect, wherein the one or more channels of the trial base include internally disposed notches.

According to an eighty-sixth aspect, the trial of the seventy-eighth aspect, or any other aspect, wherein the access opening of the trial base forms an "X" pattern.

According to an eighty-seventh aspect, the trial of the seventy-eighth aspect, or any other aspect, wherein the trial base further comprises a reference slot.

According to an eighty-eighth aspect, the trial of the seventy-eighth aspect, or any other aspect, wherein one or more of the trial face and the trial base include a patient-specific mating surface.

The present disclosure also relates to a broach, according to the eighty-ninth aspect, comprising: a spike assembly connected to an arm portion.

According to a ninetieth aspect, the broach of the eighty-ninth aspect, or any other aspect, wherein the spike assembly comprises a central spike and a perimeter spike.

According to a ninety-first aspect, the broach of the ninetieth aspect, or any other aspect, wherein the perimeter spike is arranged around the central spike.

According to a ninety-second aspect, the broach of the ninetieth aspect, or any other aspect, wherein the central spike comprises a hollow internal channel.

According to a ninety-third aspect, the broach of the eighty-ninth aspect, or any other aspect, wherein the arm portion includes a first arm portion and a second arm portion.

According to a ninety-fourth aspect, the broach of the ninety-third aspect, or any other aspect, wherein the second arm portion extends at an offset angle from the first arm portion.

According to a ninety-fifth aspect, the broach of the ninety-fourth aspect, or any other aspect, wherein the offset angle is designed to avoid engaging with patient anatomy.

According to a ninety-sixth aspect, the broach of the eighty-ninth aspect, or any other aspect, wherein an offset impactor is removably attached to the arm portion.

The present disclosure also relates to a reamer system, according to the ninety-seventh aspect, or any other aspect, comprising: a reamer head coupled to a reamer; and a reamer guide enclosing a portion of the reamer, the reamer guide comprising a first guide portion and second guide portion.

According to a ninety-eighth aspect, the reamer system of the ninety-seventh aspect, or any other aspect, wherein the reamer includes a cannulated and flexible shaft.

According to a ninety-ninth aspect, the reamer system of the ninety-eighth aspect, or any other aspect, wherein the shaft comprises one or more discrete, interlocking portions.

According to a one hundredth aspect, the reamer system of the ninety-ninth aspect, or any other aspect, wherein each of the one or more interlocking portions are offset from adjacent interlocking portions.

According to a one hundred and first aspect, the reamer system of the ninety-seventh aspect, or any other aspect, wherein the first guide portion and the second guide portion, when assembled, form a guide channel.

According to a one hundred and second aspect, the reamer system of the one hundred and first aspect, or any other aspect, wherein the guide channel selectively receives and guides a portion of the reamer.

According to a one hundred and third aspect, the reamer system of the one hundred and second aspect, or any other aspect, wherein the reamer guide includes a guide wire attachment, the guide wire attachment selectively receiving and guiding a portion of a guide wire.

According to a one hundred and fourth aspect, the reamer system of the one hundred and second aspect, or any other aspect, wherein the guide channel includes a curved guide portion and straight guide portion.

According to a one hundred and fifth aspect, the reamer system of the one hundred and fourth aspect, or any other aspect, wherein the curved guide portion includes a locating feature.

According to a one hundred and sixth aspect, the reamer system of the one hundred and fifth aspect, or any other aspect, wherein the locating feature selectively engages with the reamer lock plate.

According to a one hundred and seventh aspect, the reamer system of the one hundred and fourth aspect, or any other aspect, further comprising at least one visual indicator.

According to a one hundred and eighth aspect, the reamer system of the one hundred and seventh aspect, or any other aspect, wherein the at least one visual indicator is visible through a slot disposed on the straight guide portion.

According to a one hundred and ninth aspect, the reamer system of the ninety-seventh aspect, or any other aspect, further comprising a reamer lock plate, the reamer lock plate including a locking tab.

The present disclosure also relates to a wire guide, according to the one hundred and tenth aspect, or any other aspect, comprising: a base including an engagement tab; an attachment portion removably coupled to the base; and a guide wire channel defined within an interior of the wire guide.

According to a one hundred and eleventh aspect, the wire guide of the one hundred and tenth aspect, or any other aspect, wherein the engagement tab includes an engagement protrusion.

According to a one hundred and twelfth aspect, the wire guide of the one hundred and eleventh aspect, or any other aspect, wherein the engagement tab further includes a release grip.

According to a one hundred and thirteenth aspect, the wire guide of the one hundred and tenth aspect, or any other aspect, wherein the base includes an attachment cutout, the attachment cutout selectively receiving a mating portion of the attachment portion.

According to a one hundred and fourteenth aspect, the wire guide of the one hundred and tenth aspect, or any other aspect, wherein the mating portion includes a receptacle, the receptable selectively receiving a fastener inserted through a hole in the attachment cutout.

According to a one hundred and fifteenth aspect, the wire guide of the one hundred and tenth aspect, or any other aspect, wherein the base and the attachment portion, when assembled, form the guide wire channel.

According to a one hundred and sixteenth aspect, the wire guide of the one hundred and tenth aspect, or any other aspect, wherein the guide wire channel extends between a channel entrance disposed on the base and a guide wire hole disposed on the attachment portion.

The present disclosure also relates to a joint distractor, according to the one hundred and seventeenth aspect, or any other aspect, comprising: a frame removably attached to a surgical component; and a plate movably coupled to the frame between a first configuration and a second configuration.

According to a one hundred and eighteenth aspect, the joint distractor of the one hundred and seventeenth aspect, or any other aspect, wherein the frame includes: a base; at least one upright member; and at least one lateral support coupled between the base and the at least one upright member.

According to a one hundred and nineteenth aspect, the joint distractor of the one hundred and eighteenth aspect, or any other aspect, wherein the frame includes: a base; at least one upright member; and at least one lateral support coupled between the base and the at least one upright member.

According to a one hundred and twentieth aspect, the joint distractor of the one hundred and eighteenth aspect, or any other aspect, wherein the frame includes: a base; at least one upright member; and at least one lateral support coupled between the base and the at least one upright member.

According to a one hundred and twenty-first aspect, the joint distractor of the one hundred and twentieth aspect, or any other aspect, wherein the frame includes: a base; at least one upright member; and at least one lateral support coupled between the base and the at least one upright member.

According to a one hundred and twenty-second aspect, the joint distractor of the one hundred and seventeenth aspect, or any other aspect, wherein the frame includes: a base; at least one upright member; and at least one lateral support coupled between the base and the at least one upright member.

According to a one hundred and twenty-third aspect, the joint distractor of the one hundred and seventeenth aspect, or any other aspect, wherein the frame includes: a base; at least one upright member; and at least one lateral support coupled between the base and the at least one upright member.

According to a one hundred and twenty-fourth aspect, the joint distractor of the one hundred and seventeenth aspect, or any other aspect, wherein the frame includes: a base; at least one upright member; and at least one lateral support coupled between the base and the at least one upright member.

According to a one hundred and twenty-fifth aspect, the joint distractor of the one hundred and seventeenth aspect, or any other aspect, wherein the frame includes: a base; at least one upright member; and at least one lateral support coupled between the base and the at least one upright member.

According to a one hundred and twenty-sixth aspect, the joint distractor of the one hundred and twenty-fifth aspect, or any other aspect, wherein the frame includes a first release mechanism movably coupled to the frame between a first position and a second position.

According to a one hundred and twenty-seventh aspect, the joint distractor of the one hundred and twenty-sixth aspect, or any other aspect, wherein the first release mechanism engages a notch formed in the first rail when the first release mechanism is in the first position.

According to a one hundred and twenty-eighth aspect, the joint distractor of the one hundred and twenty-seventh aspect, or any other aspect, wherein the first release mechanism disengages the notch formed in the first rail when the first release mechanism moves from the first position to the second position.

According to a one hundred and twenty-nineth aspect, the joint distractor of the one hundred and twenty-fifth aspect, or any other aspect, wherein the frame includes a second release mechanism movably coupled to the frame between a first position and a second position.

According to a one hundred thirtieth aspect, the joint distractor of the one hundred and twenty-sixth aspect, or any other aspect, wherein the second release mechanism engages a notch formed in the second rail when the second release mechanism is in the first position.

According to a one hundred and thirty-first aspect, the joint distractor of the one hundred and twenty-seventh aspect, or any other aspect, wherein the second release mechanism disengages the notch formed in the second rail when the second release mechanism moves from the first position to the second position.

According to a one hundred and thirty-second aspect, the joint distractor of the one hundred and twenty-fifth aspect, or any other aspect, wherein the first rail moves independently to the second rail.

The present disclosure also relates to a system for inserting a modular member into an intramedullary canal formed in a patient's tibia, according to the one hundred and thirty-third aspect, or any other aspect, comprising: an insertion tool comprising: a body, the body including a stem support; a protrusion extending from the stem support; and a hole extending through the body; and a guide comprising: a passage; and one or more wings; and an impacting tool.

According to a one hundred and thirty-fourth aspect, the system of the one hundred and thirty-third aspect, or any other aspect, wherein the guide is integrated with the body of the insertion tool.

According to a one hundred and thirty-fifth aspect, the system of the one hundred and thirty-fourth aspect, or any other aspect, wherein the guide is removably coupled to the body of the insertion tool.

According to a one hundred and thirty-sixth aspect, the system of the one hundred and thirty-third aspect, or any other aspect, wherein the stem support receives the modular member.

According to a one hundred and thirty-seventh aspect, the system of the one hundred and thirty-sixth aspect, or any other aspect, wherein the insertion tool includes a coupling piece removably inserted into the hole.

According to a one hundred and thirty-eighth aspect, the system of the one hundred and thirty-seventh aspect, or any other aspect, wherein the coupling piece is threaded at a first end and includes a knob at a second end.

According to a one hundred and thirty-nineth aspect, the system of the one hundred and thirty-eighth aspect, or any other aspect, wherein the first end of the coupling piece engages and aligns the modular member.

According to a one hundred and fortieth aspect, the system of the one hundred and thirty-nineth aspect, or any other aspect, wherein the one or more wings are disposed around a circumference of the passage.

According to a one hundred and forty-first aspect, the system of the one hundred and fortieth aspect, or any other aspect, wherein a fastener is inserted through the passage to secure a position of the modular member.

According to a one hundred and forty-second aspect, the system of the one hundred and thirty-third aspect, or any other aspect, wherein the impacting tool includes an engagement feature designed to engage a portion of the modular member.

According to a one hundred and forty-third aspect, the system of the one hundred and forty-second aspect, or any other aspect, wherein the impacting tool secures a position of the modular member.

According to a one hundred and forty-fourth aspect, the system of the one hundred and thirty-third aspect, or any other aspect, wherein the impacting tool includes an elbow-bend.

It will be understood by those skilled in the art that one or more aspects of this disclosure can meet certain objectives, while one or more other aspects can lead to certain other objectives. Various modifications to the illustrated embodiments will be readily apparent to those skilled in the art, and the generic principles herein can be applied to other embodiments and applications without departing from embodiments of the disclosure. Other objects, features, benefits, and advantages of the present disclosure will be apparent in this summary and descriptions of the disclosed embodiments, and will be readily apparent to those skilled in the art. Such objects, features, benefits, and advantages will be apparent from the above as taken in conjunction with the accompanying figures and all reasonable inferences to be drawn therefrom.

BRIEF DESCRIPTION OF THE DRAWINGS

Figure 4:
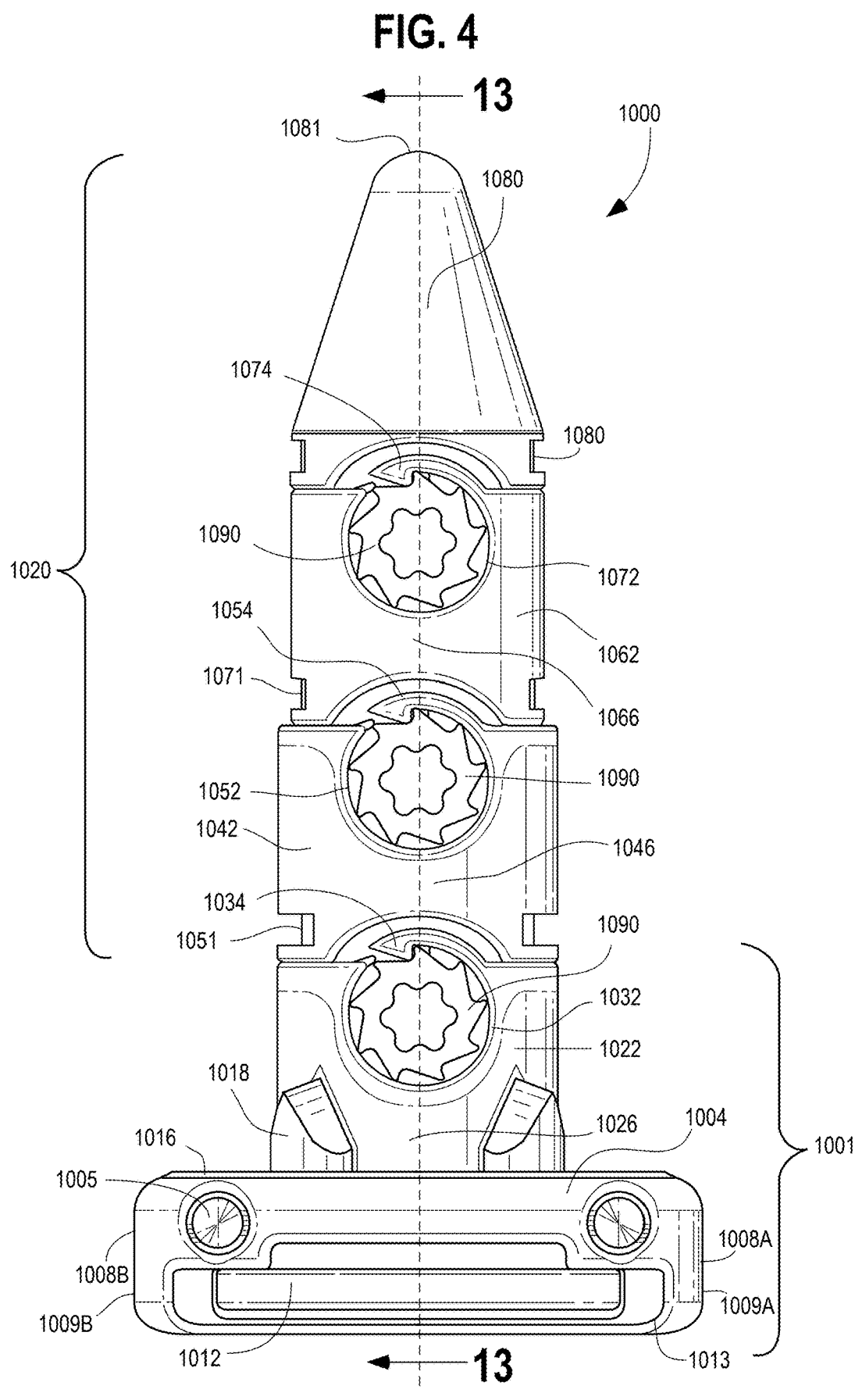

FIG. 4 is a front view of the exemplary modular stem system of FIG. 2;

FIG. 67 is a bottom view of the wire guide of FIG. 65;

FIG. 68 is a top view of the wire guide of FIG. 65;

FIG. 86 is a front view of the compressor assembly of FIG. 84;

FIG. 87 is a back view of the compressor assembly of FIG. 84;

FIG. 100 shows an exemplary method of preparing a surface of a patient's tibia, according to one embodiment;

FIG. 101 shows an exemplary method of preparing a surface of a patient's tibia, according to one embodiment;

FIG. 102 shows an exemplary method of inserting the TAR assembly, according to one embodiment.

FIG. 103 shows an exemplary method of inserting the TAR assembly, according to one embodiment.

FIG. 106 shows an exemplary view of an exemplary TAR assembly for the preparation of a patient tibial surface, according to one embodiment;

FIG. 108 shows an exemplary view of an exemplary TAR assembly for the preparation of a patient tibial surface, according to one embodiment;

FIG. 111 shows an exemplary view of an exemplary TAR assembly for the preparation of a patient tibial surface, according to one embodiment;

FIG. 113 shows an exemplary view of an exemplary TAR assembly for the preparation of a patient tibial surface, according to one embodiment;

FIG. 114 shows an exemplary view of an exemplary TAR assembly for the preparation of a patient tibial surface, according to one embodiment;

FIG. 115 shows an exemplary view of an exemplary TAR assembly for the preparation of a patient tibial surface, according to one embodiment;

FIG. 116 shows an exemplary view of an exemplary TAR assembly for the preparation of a patient tibial surface, according to one embodiment;

FIG. 117 shows an exemplary view of an exemplary TAR assembly for the preparation of a patient tibial surface, according to one embodiment;

FIG. 118 shows an exemplary view of an exemplary TAR assembly for the preparation of a patient tibial surface, according to one embodiment;

FIG. 119 shows an exemplary view of an exemplary TAR assembly for the preparation of a patient tibial surface, according to one embodiment;

FIG. 120 shows an exemplary view of an exemplary TAR assembly for the preparation of a patient tibial surface, according to one embodiment;

FIG. 121 shows an exemplary view of an exemplary TAR assembly for the preparation of a patient tibial surface, according to one embodiment;

FIG. 122 shows an exemplary view of an exemplary TAR assembly for the preparation of a patient tibial surface, according to one embodiment;

FIG. 123 shows an exemplary view of an exemplary TAR assembly for the preparation of a patient tibial surface, according to one embodiment;

FIG. 124 shows an exemplary view of an exemplary TAR assembly for the preparation of a patient tibial surface, according to one embodiment;

Figure 125:
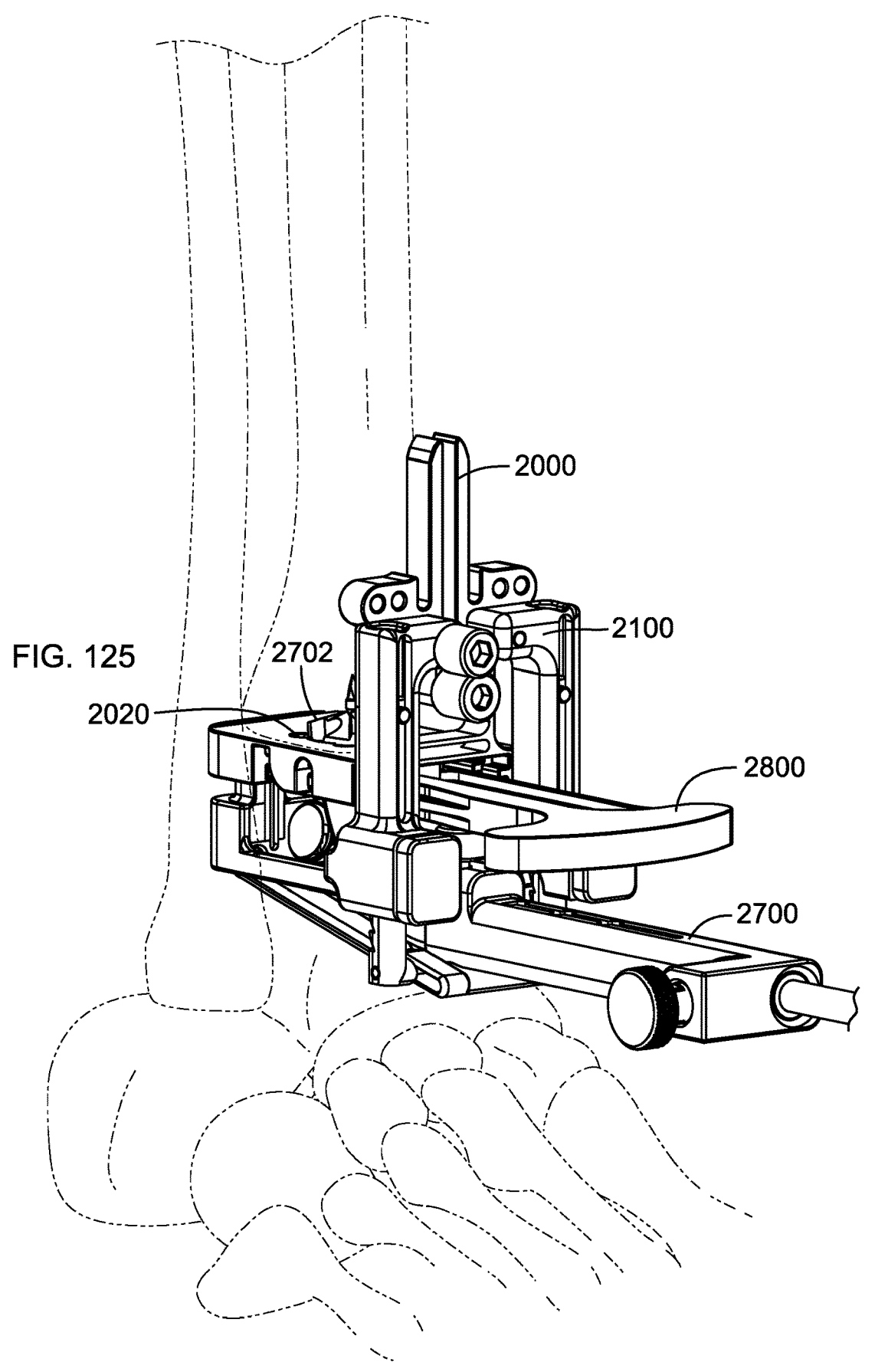
Figure 126:
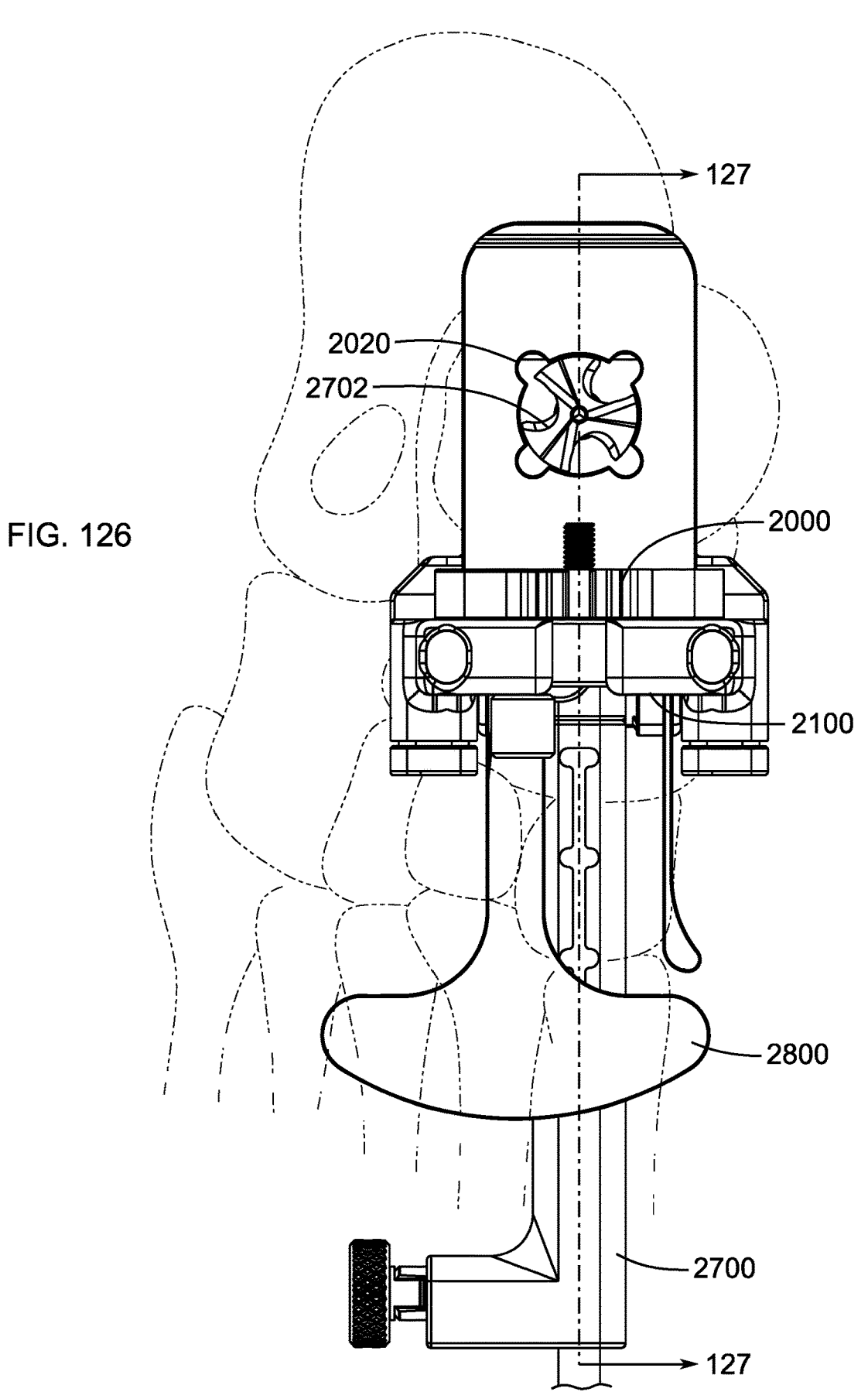
Figure 127:
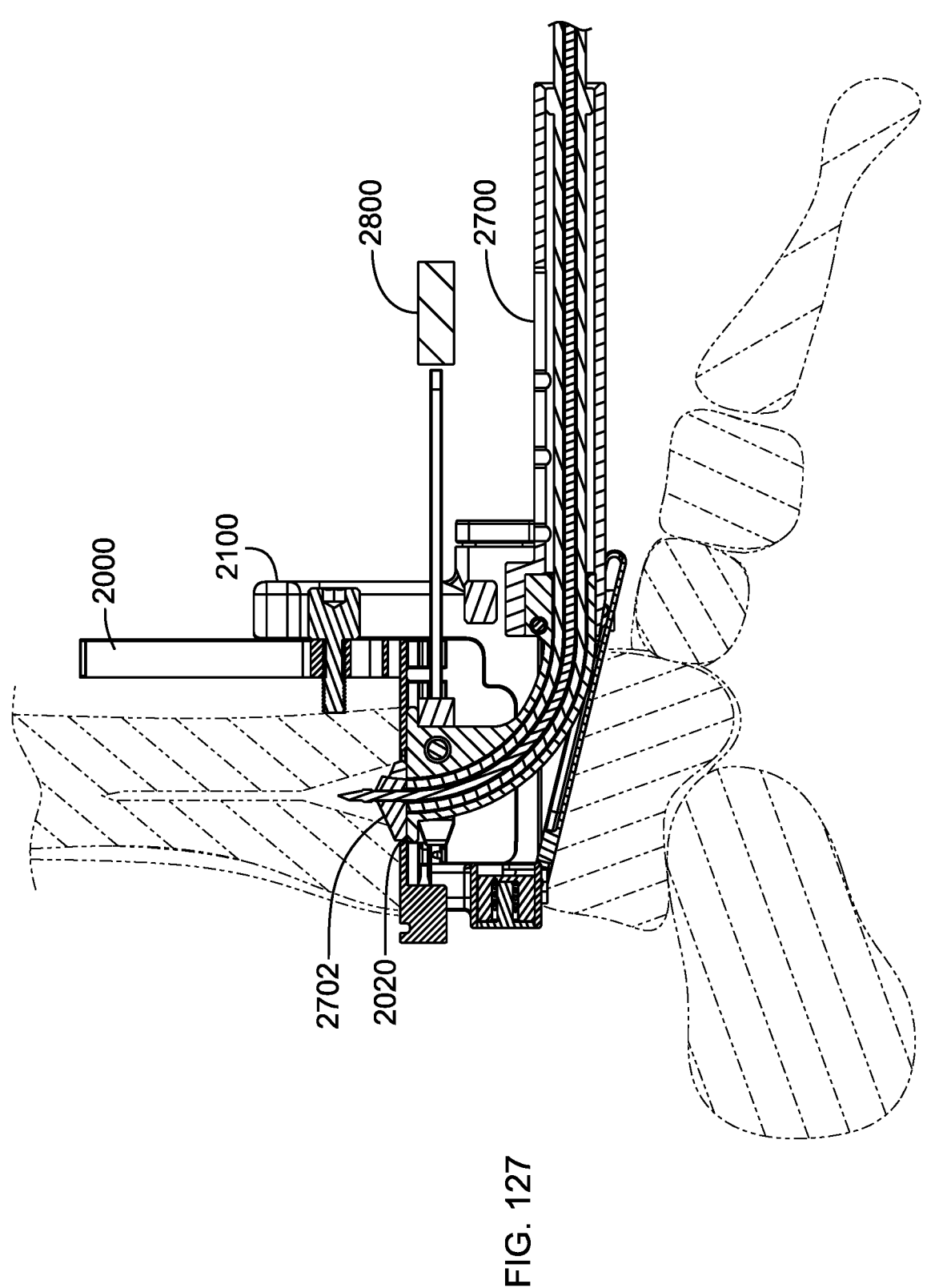
Figure 128:
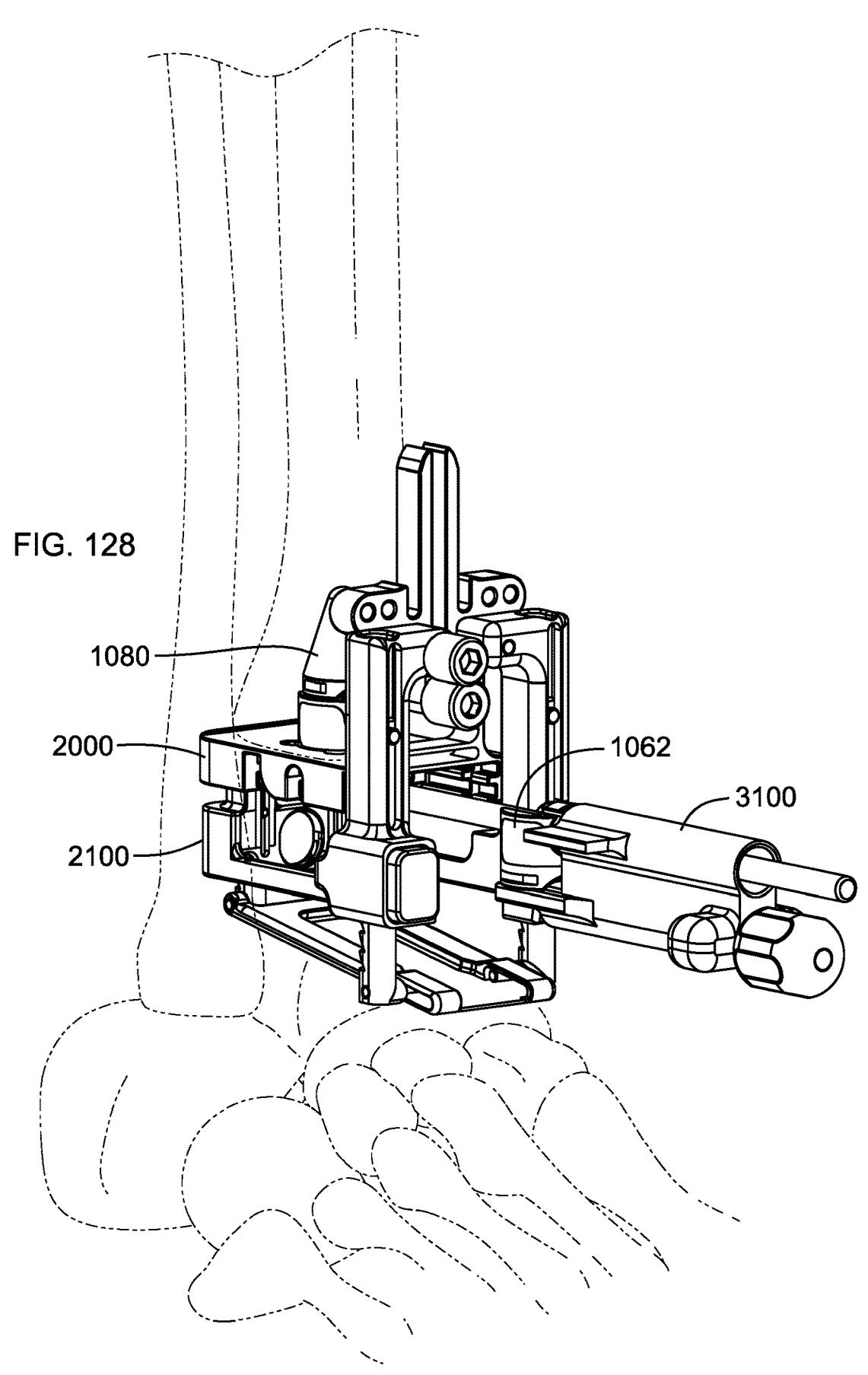
Figure 129:
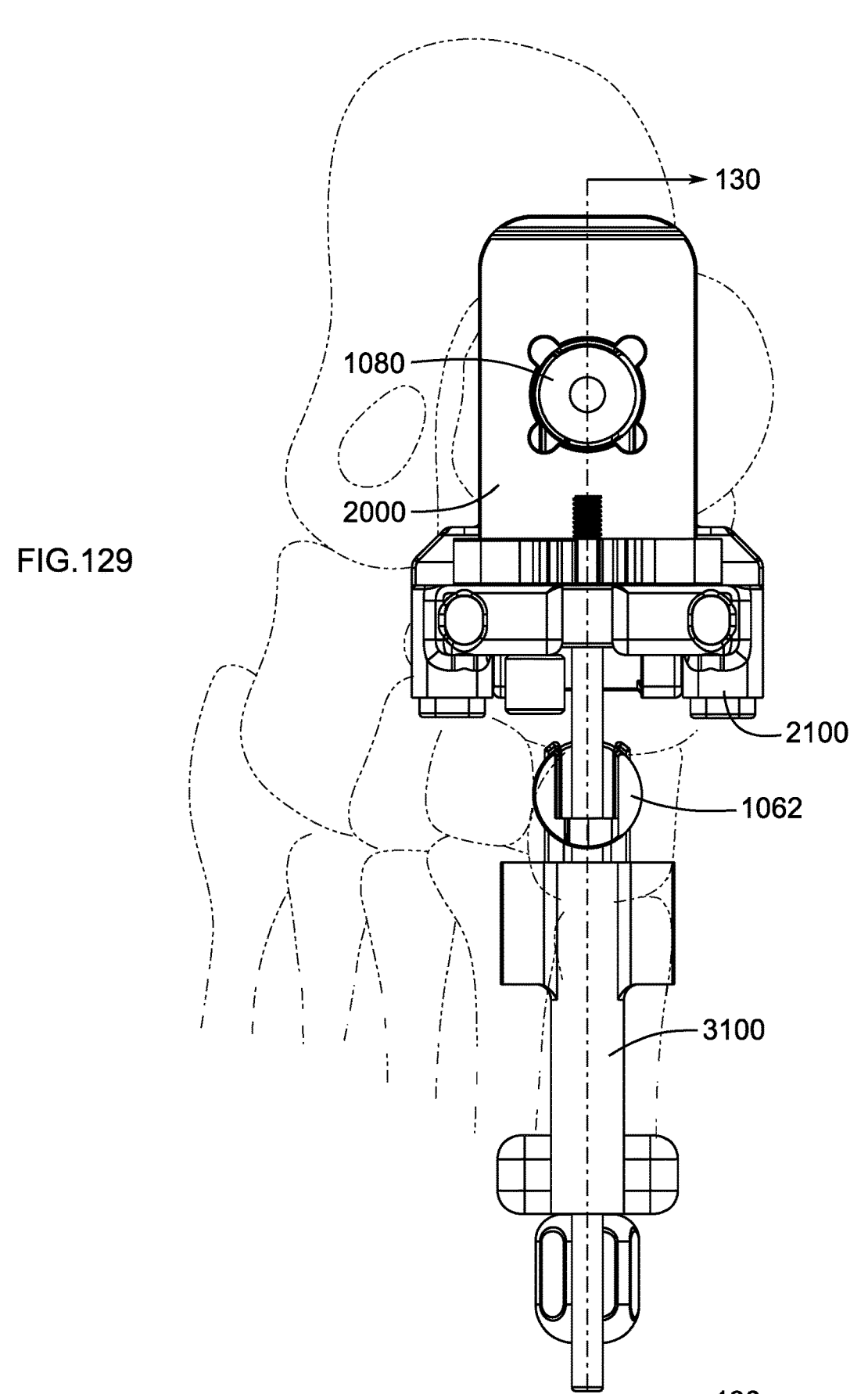
Figure 130:
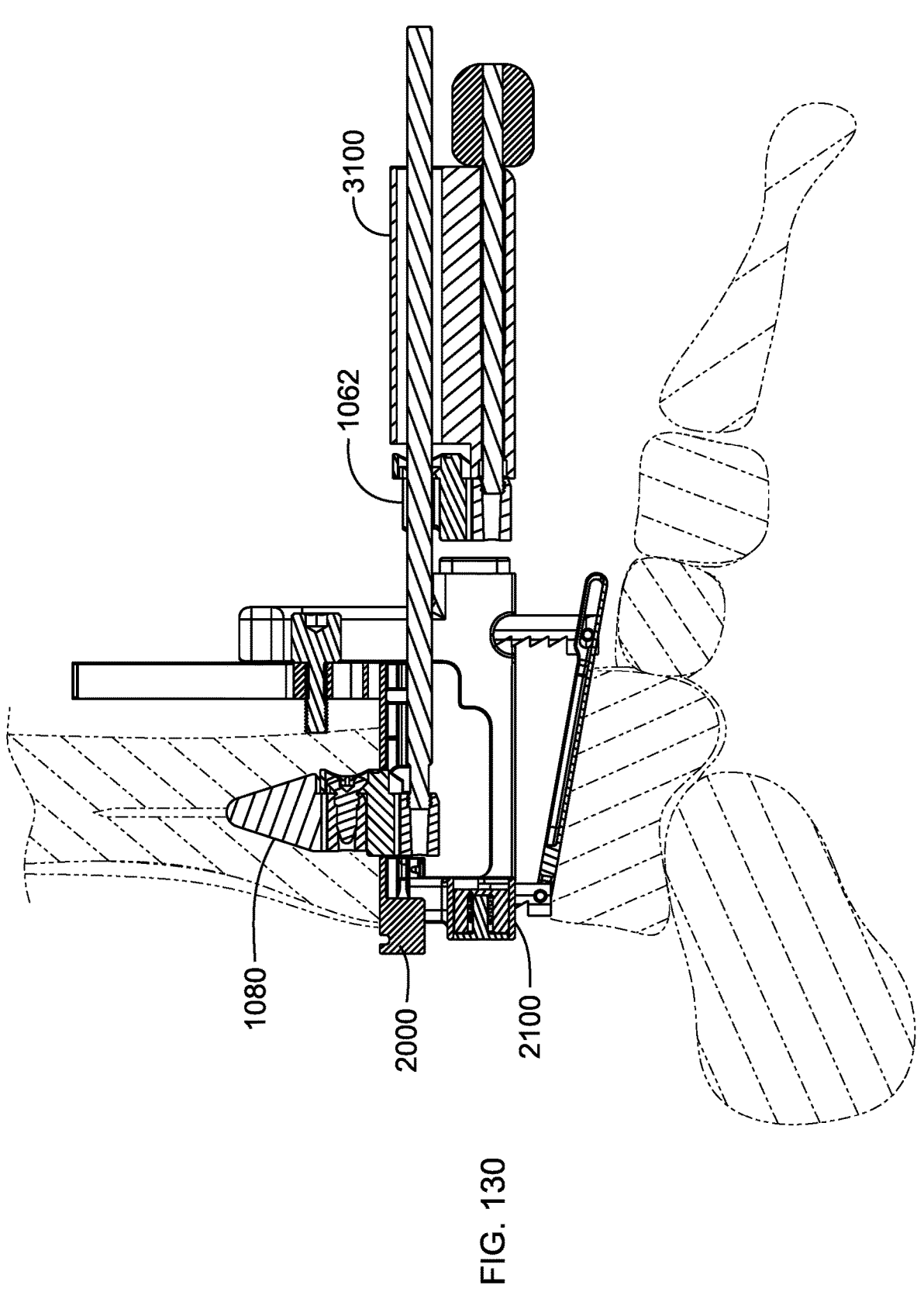
Figure 131:
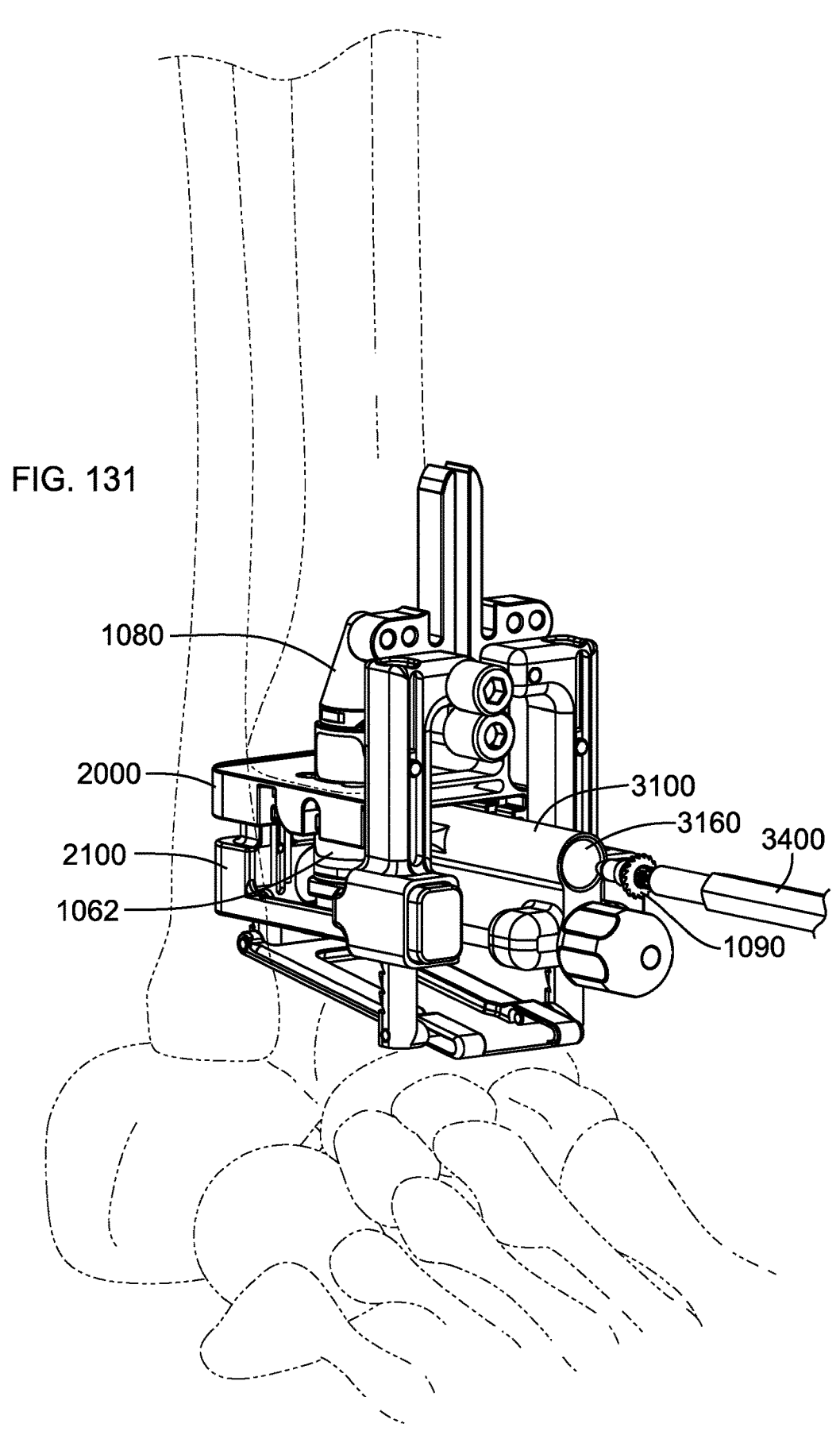
Figure 132:
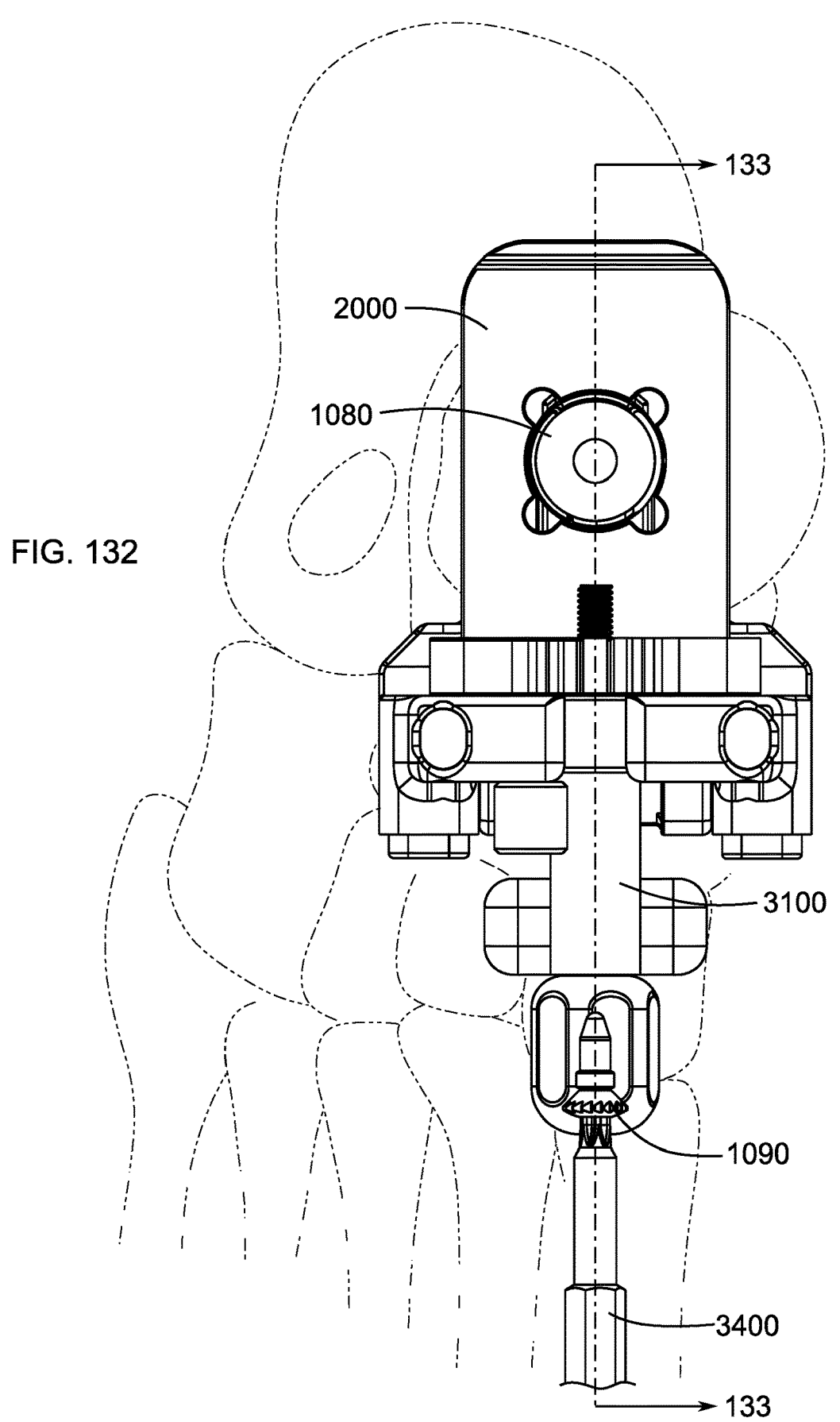
Figure 133:
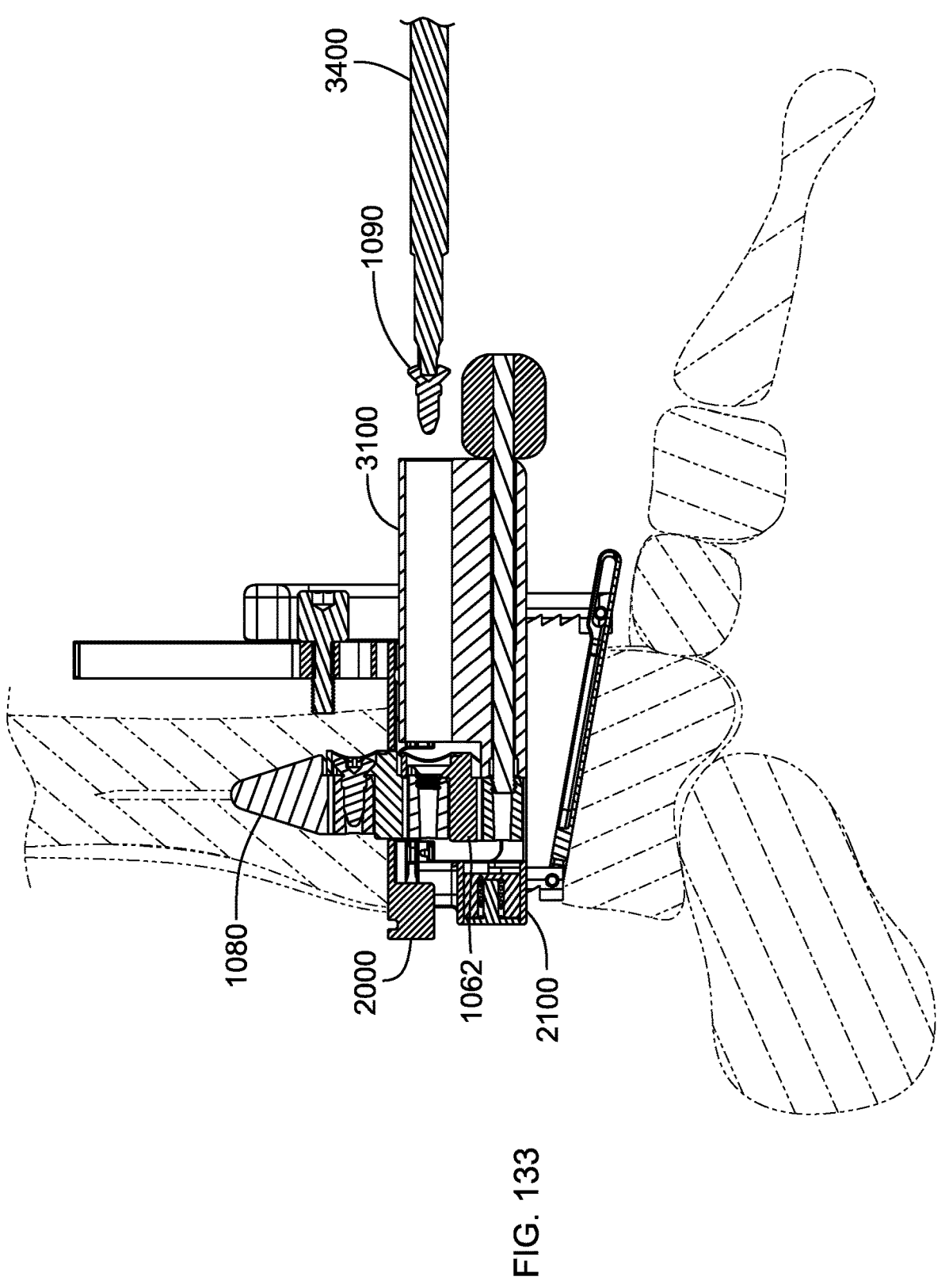
Figure 134:
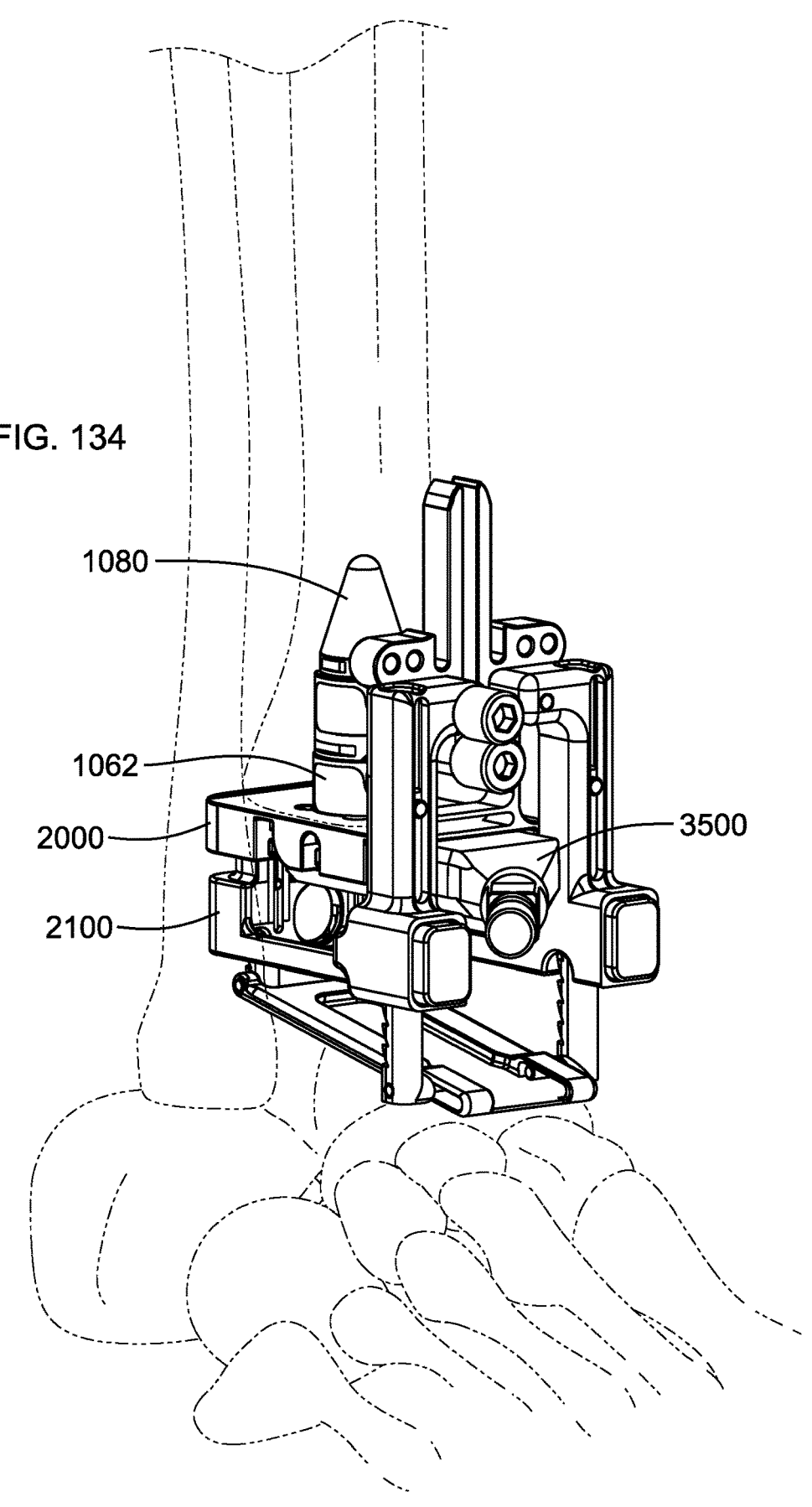
Figure 135:
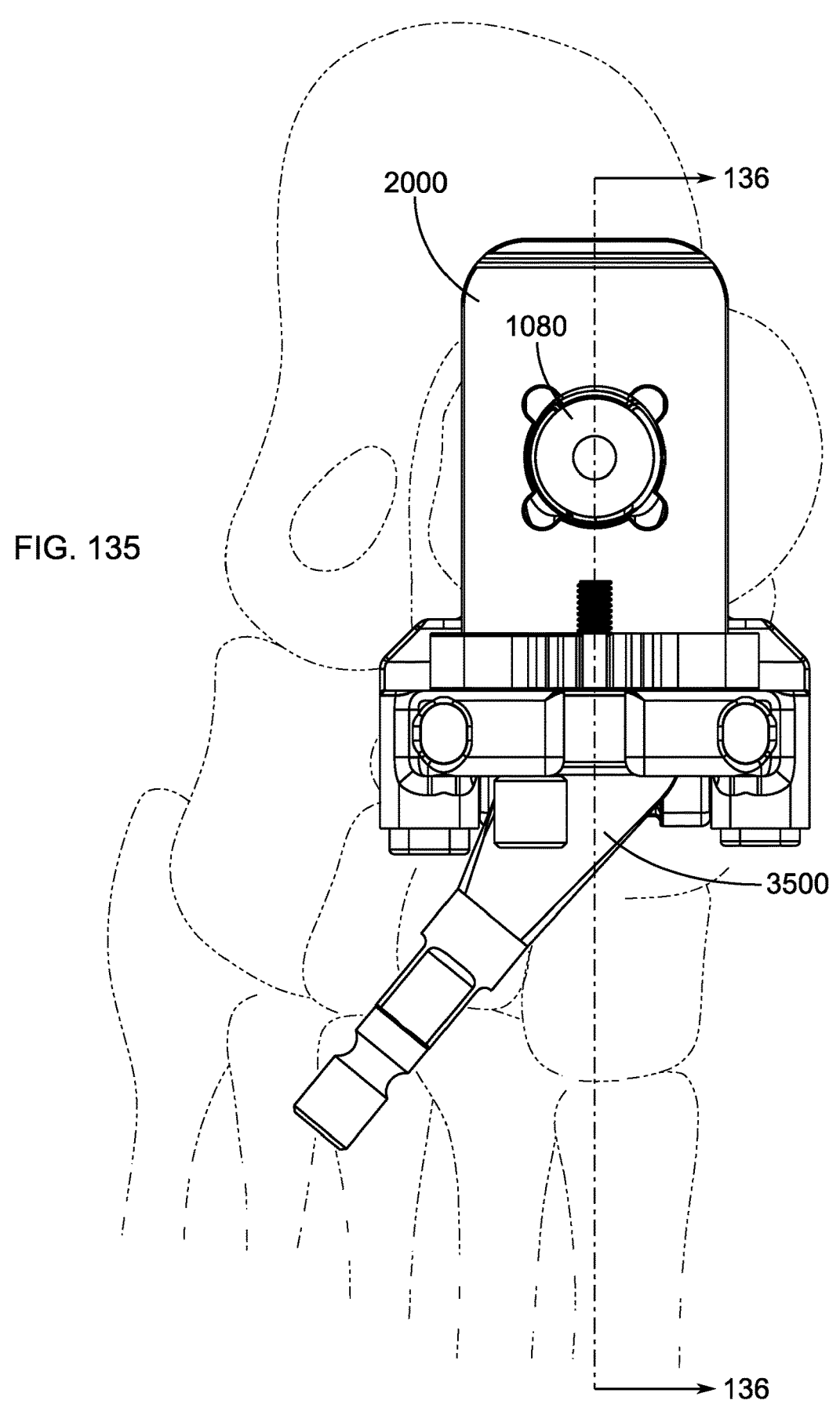
Figure 136:
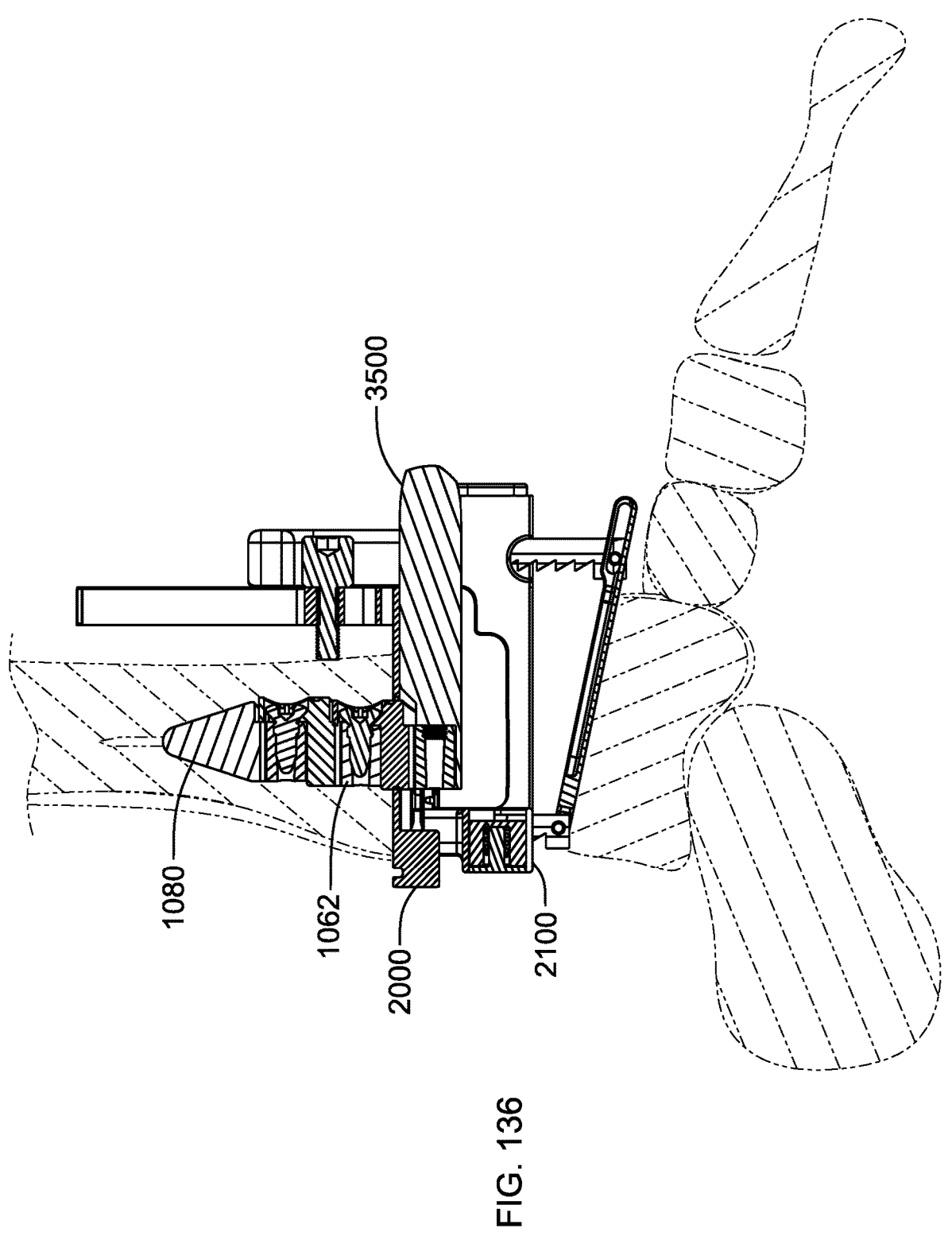
Figure 137:
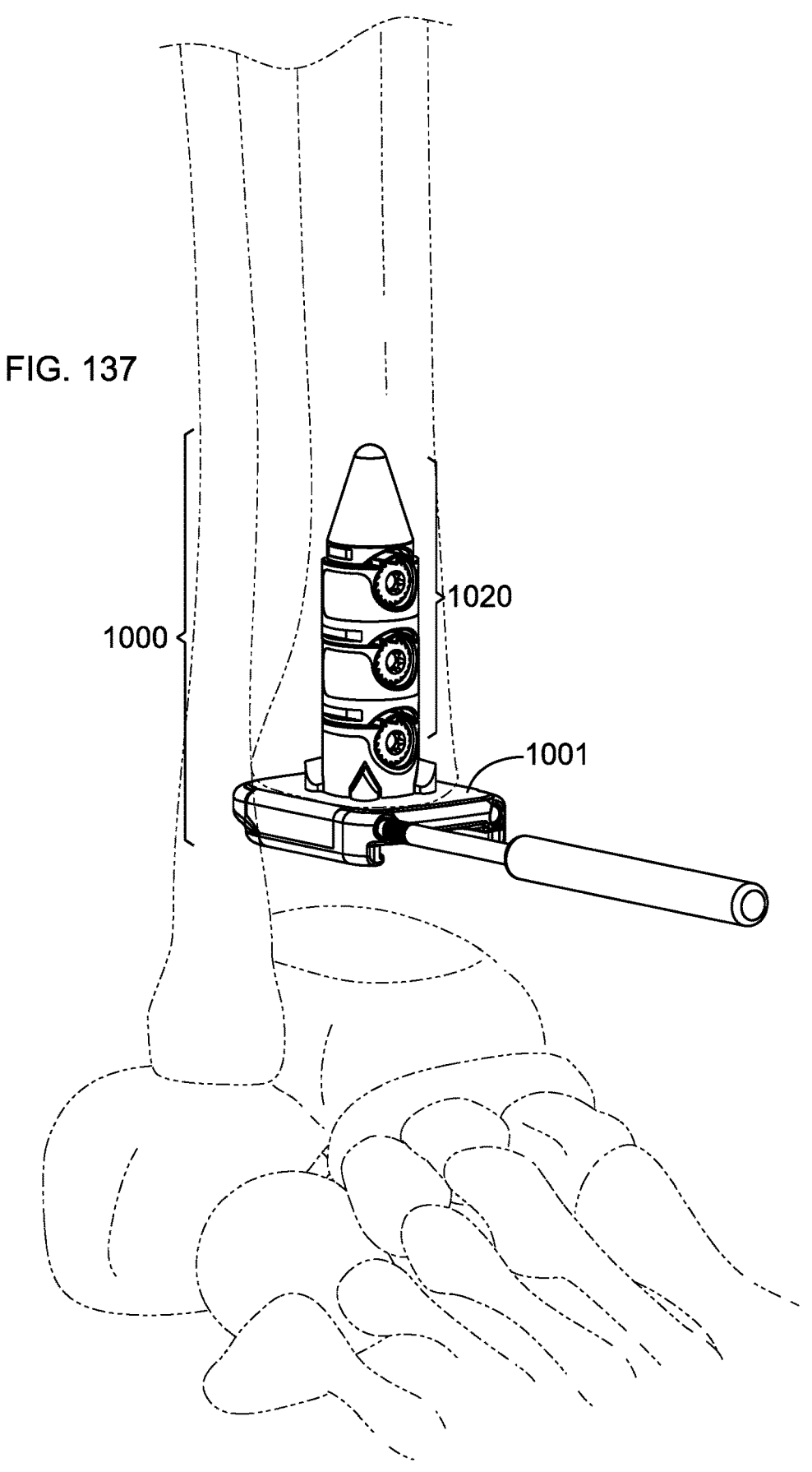
Figure 138:
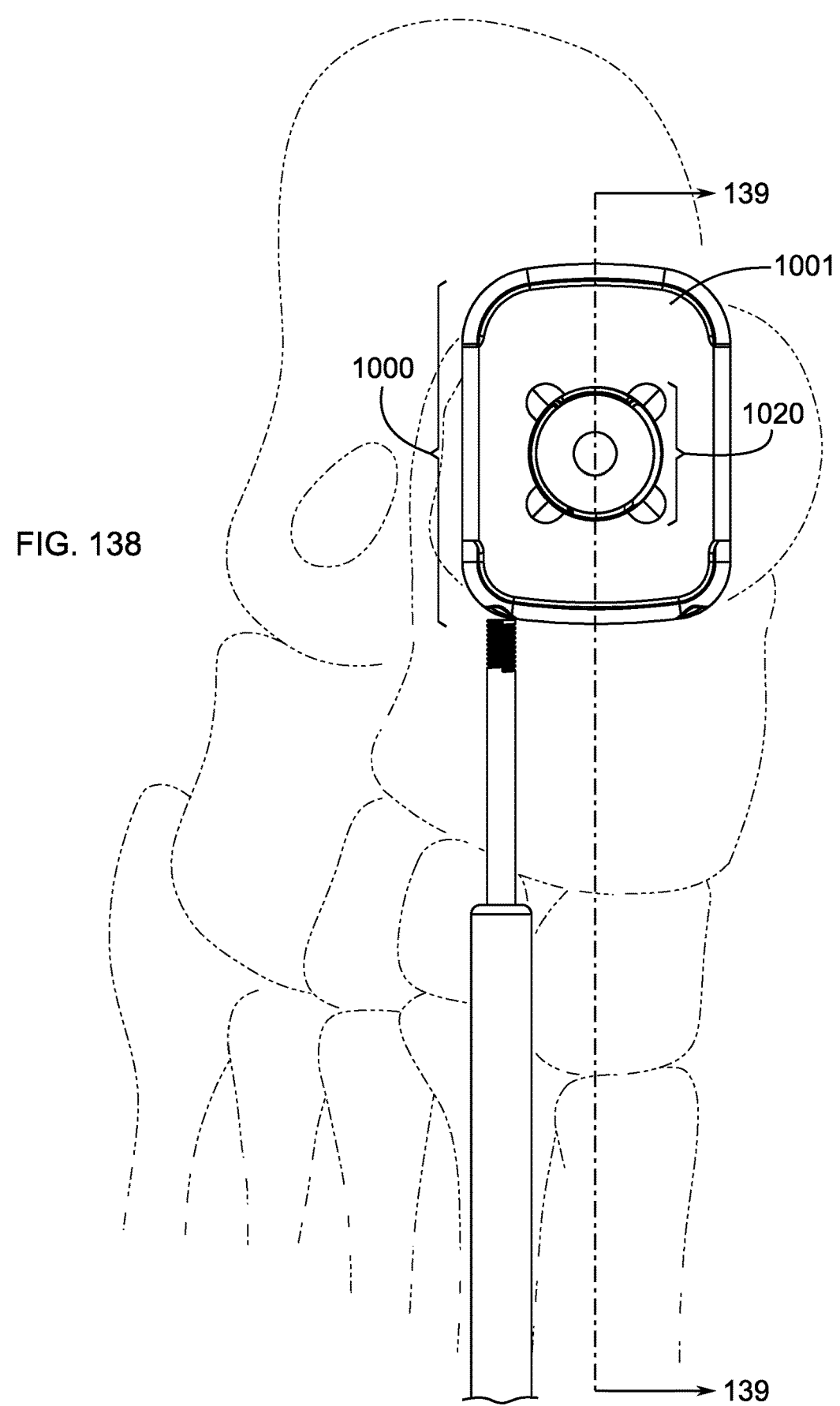
Figure 139:
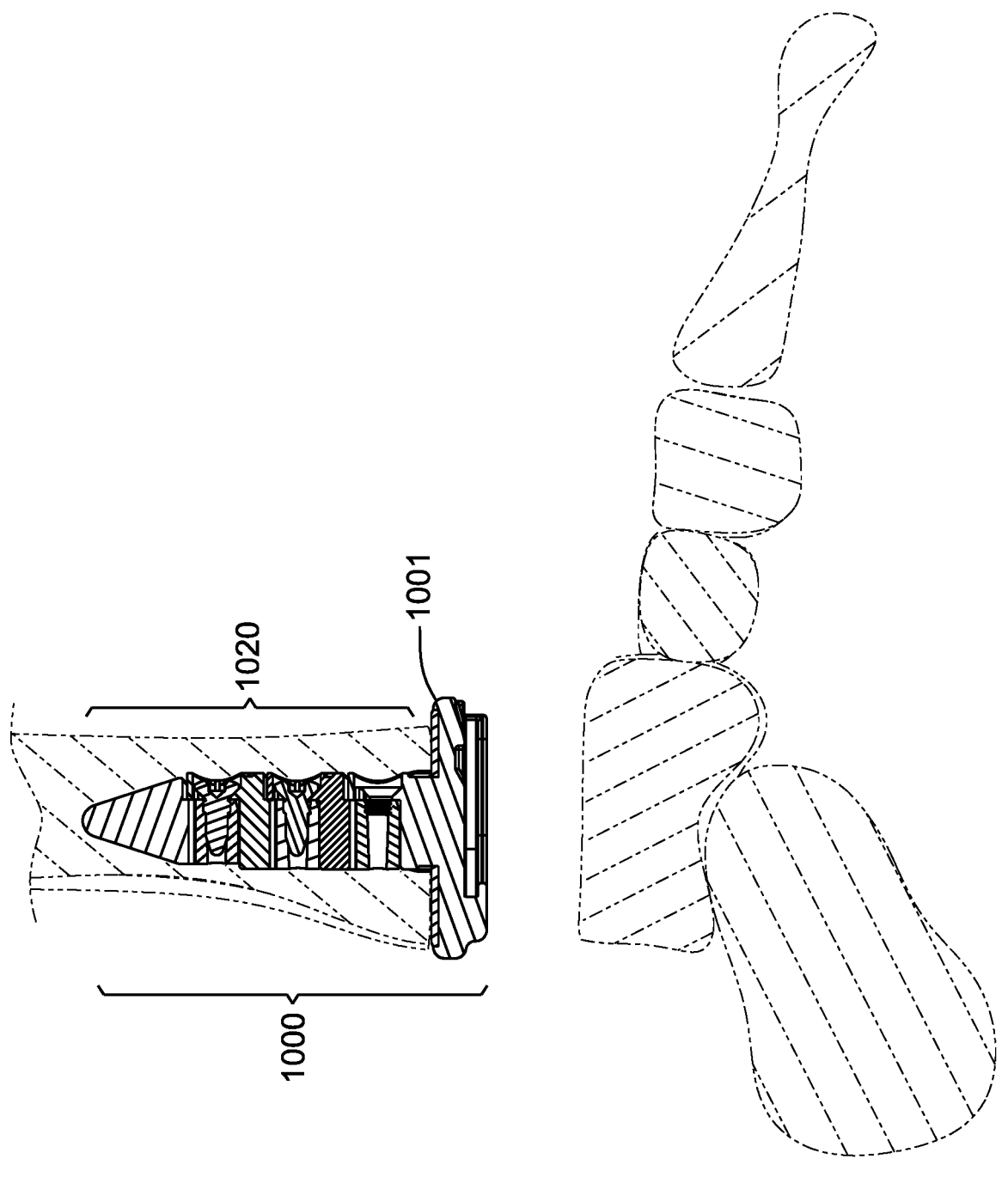

FIG. 125 shows an exemplary view of an exemplary TAR assembly for the preparation of a patient tibial surface, according to one embodiment;

FIG. 126 shows an exemplary view of an exemplary TAR assembly for the preparation of a patient tibial surface, according to one embodiment;

FIG. 127 shows an exemplary view of an exemplary TAR assembly for the preparation of a patient tibial surface, according to one embodiment;

FIG. 128 shows an exemplary view of an exemplary TAR assembly for the insertion of an exemplary tibial component, according to one embodiment;

FIG. 129 shows an exemplary view of an exemplary TAR assembly for the insertion of an exemplary tibial component, according to one embodiment;

FIG. 130 shows an exemplary view of an exemplary TAR assembly for the insertion of an exemplary tibial component, according to one embodiment;

FIG. 131 shows an exemplary view of an exemplary TAR assembly for the insertion of an exemplary tibial component, according to one embodiment;

FIG. 132 shows an exemplary view of an exemplary TAR assembly for the insertion of an exemplary tibial component, according to one embodiment;

FIG. 133 shows an exemplary view of an exemplary TAR assembly for the insertion of an exemplary tibial component, according to one embodiment;

FIG. 134 shows an exemplary view of an exemplary TAR assembly for the insertion of an exemplary tibial component, according to one embodiment;

FIG. 135 shows an exemplary view of an exemplary TAR assembly for the insertion of an exemplary tibial component, according to one embodiment;

FIG. 136 shows an exemplary view of an exemplary TAR assembly for the insertion of an exemplary tibial component, according to one embodiment;

FIG. 137 shows an exemplary view of an exemplary TAR assembly for the insertion of an exemplary tibial component, according to one embodiment;

FIG. 138 shows an exemplary view of an exemplary TAR assembly for the insertion of an exemplary tibial component, according to one embodiment; and FIG. 139 shows an exemplary view of an exemplary TAR assembly for the insertion of an exemplary tibial component, according to one embodiment.

DETAILED DESCRIPTION

According to particular embodiments, this disclosure relates to a total ankle replacement (TAR) procedure and system. The bones of the ankle joint include the tibia (shinbone), fibula (smaller bone in the lower leg), and talus (bone in the foot). During the TAR procedure, a user, such as an orthopedic surgeon, may remove at least a portion of a damaged (e.g., arthritic) patient ankle joint or damaged tibial, fibular, and/or talar surfaces. Generally, the TAR procedure in accordance with the principles of this disclosure involves making an anterior incision on the patient's ankle, removing portions of damaged bone and/or cartilage, and installing the TAR system. The TAR system described herein may include patient-specific prosthetic components that replace the tibial and talar surfaces (e.g., typically metal, such as titanium, stainless steel, etc.), and a bearing insert (e.g., typically plastic) positioned therebetween that serves as a cartilage replacement. The TAR system thus may replace/mimic native joint movement, improve joint function, relieve pain, and/or enhance overall life quality for patients with degenerative ankle joint conditions.

The above features (and others) will be discussed herein in the context of specific implant types (e.g., an ankle implant). However, it will be understood that the concepts discussed here are applicable to any suitable implant used anywhere in a human (or other animal).

Figure 1:
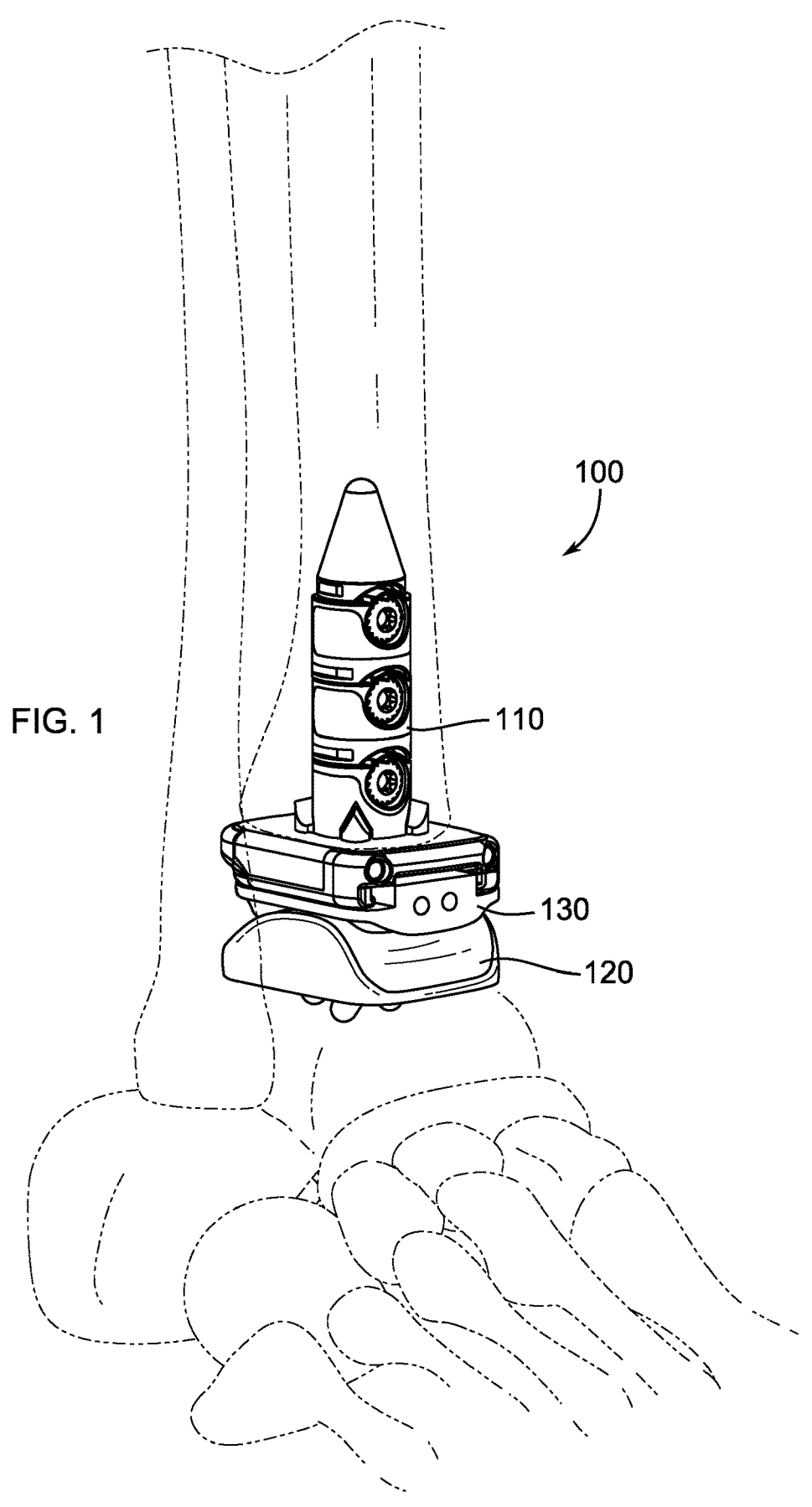
FIG. 1 is a perspective view of an exemplary total ankle replacement system within exemplary patient anatomy, according to one embodiment.
Figure 2:
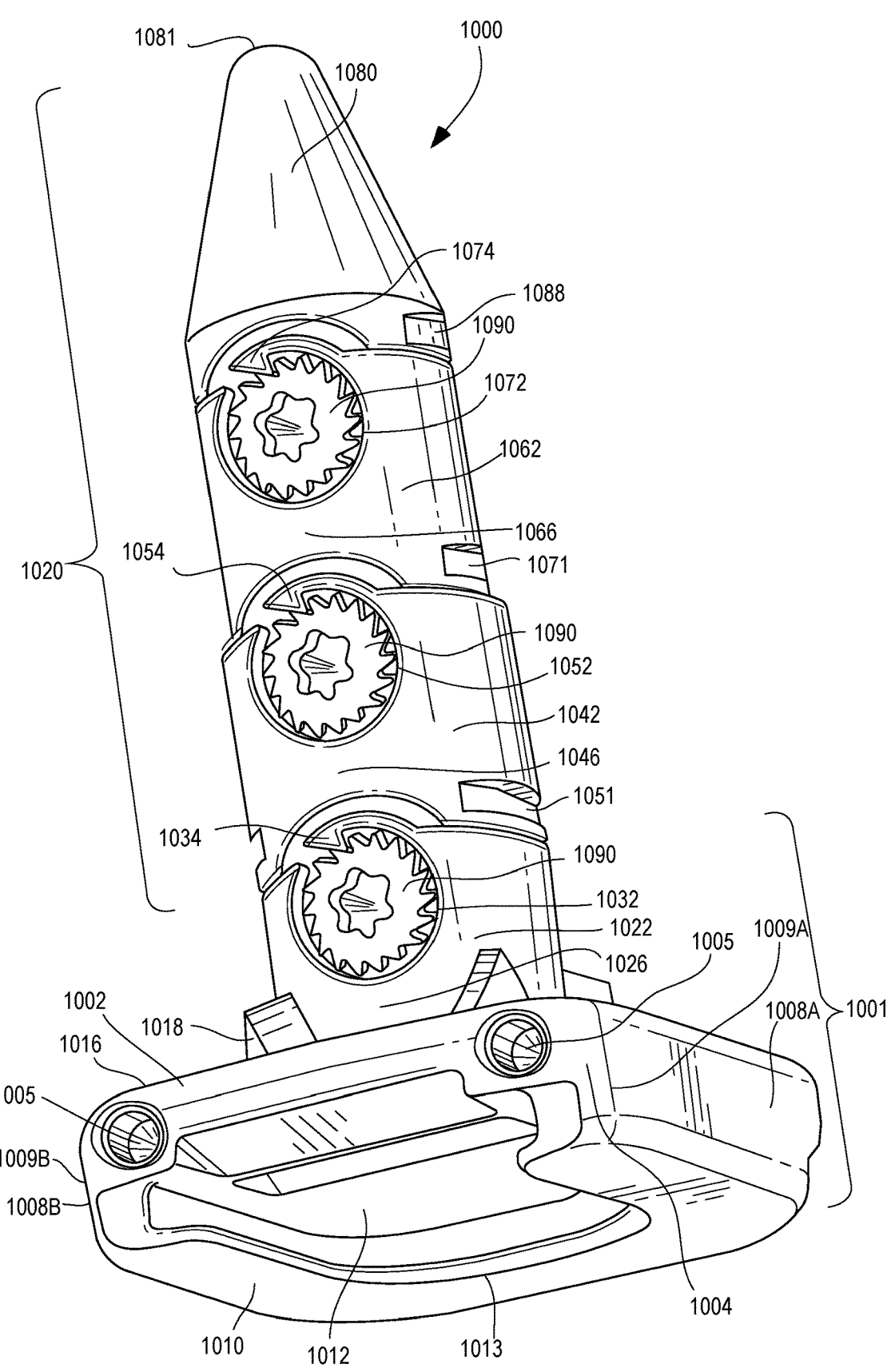
FIG. 2 is a front perspective view of an exemplary modular stem system, according to one embodiment.
Figure 3:
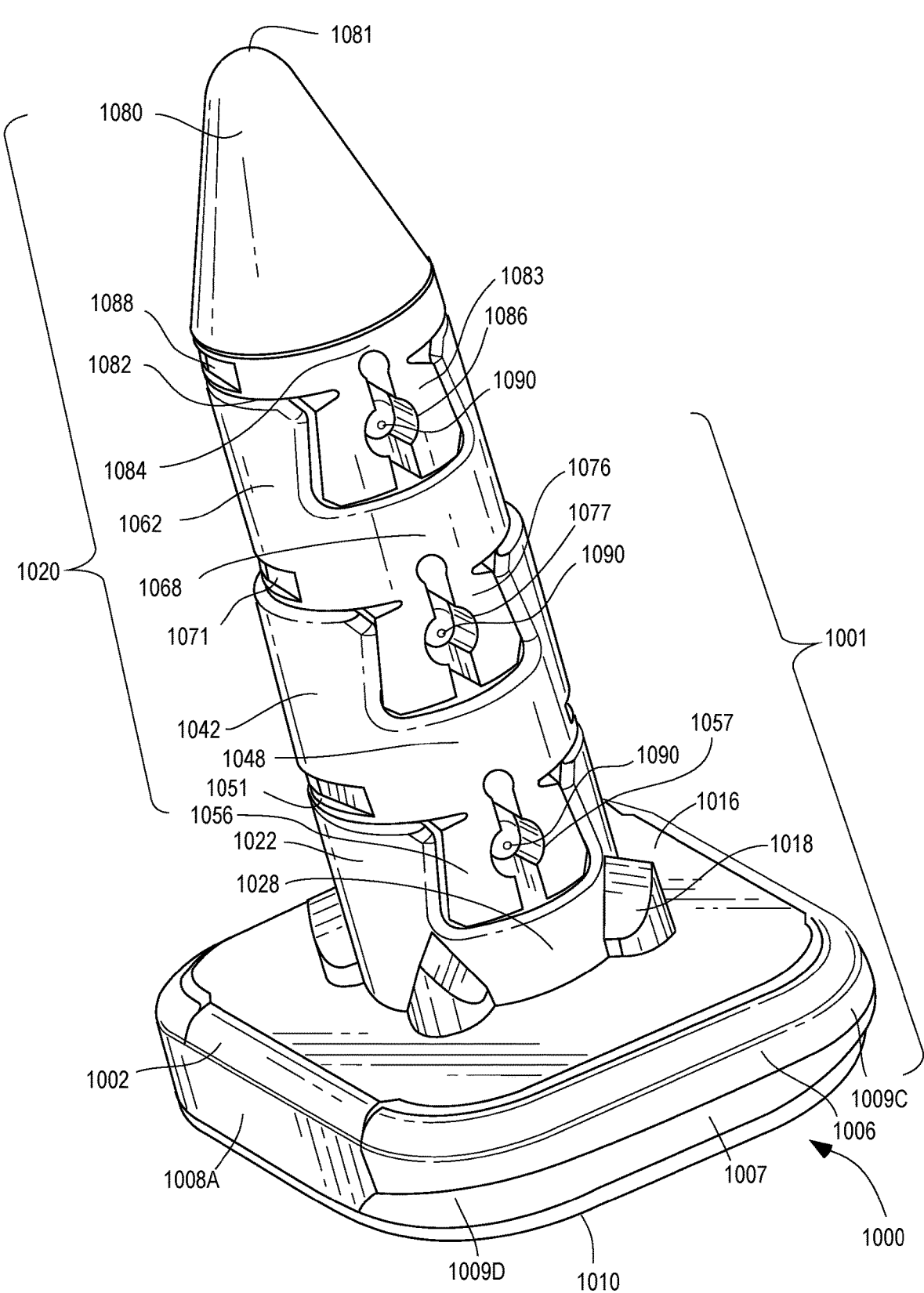
FIG. 3 is a rear perspective view the exemplary modular stem system of FIG. 2.
Figure 5:
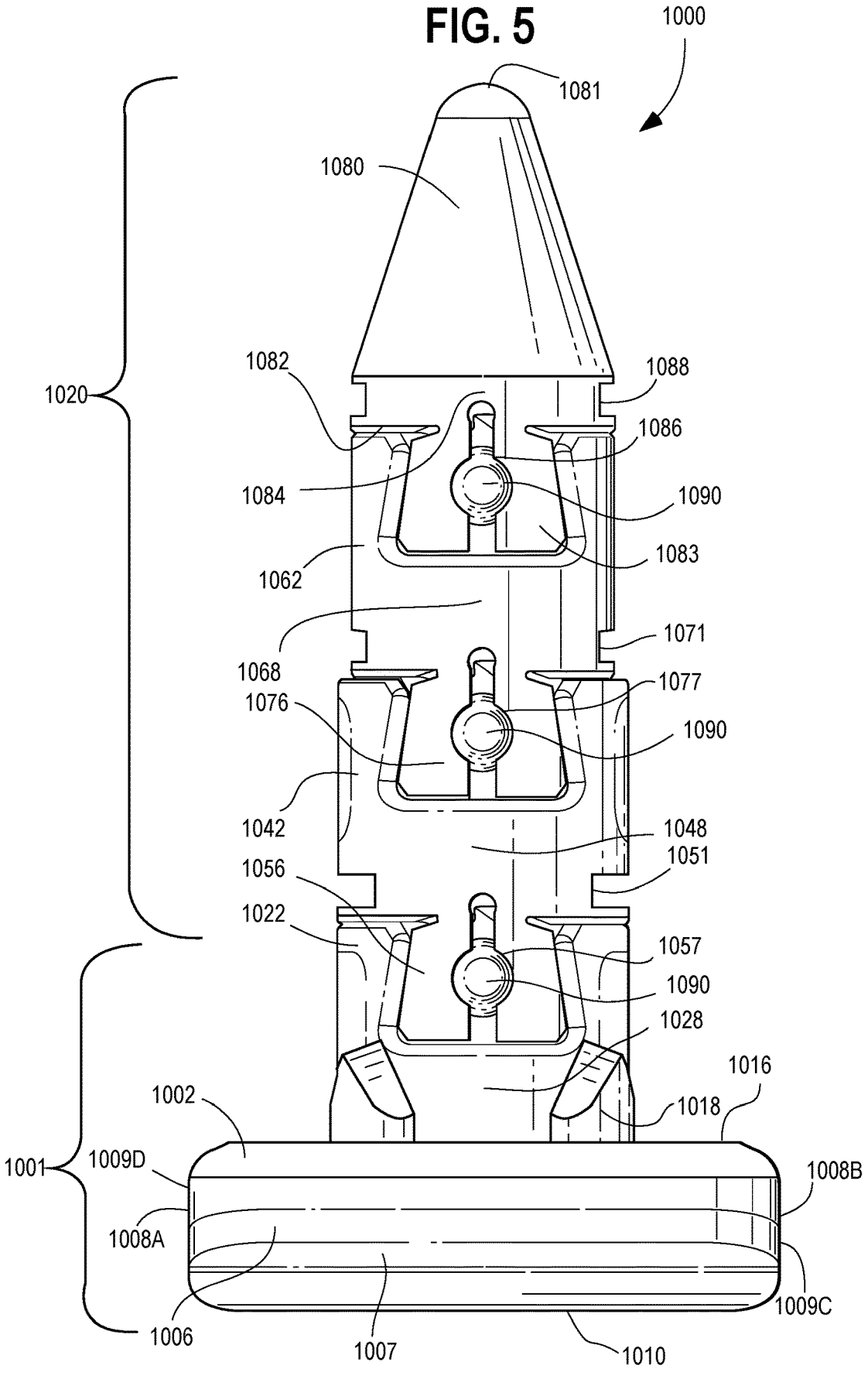
FIG. 5 is a rear view of the exemplary modular stem system of FIG. 2.

Referring now to FIG. 1, one embodiment of an exemplary total ankle replacement (TAR) system 100 installed in a patient, is shown. Generally, a TAR procedure (which will be discussed with reference to FIGS. 100-104) involves removing pieces of bone (e.g., tibia, talus) and replacing them with metal and/or plastic components that combine to form a prosthetic ankle joint. In particular, the metal/plastic components replace the bearing surfaces of the joint. The TAR procedure includes various tools and guides used to prepare joint surfaces and position auxiliary tools to correctly insert the prosthetic components. Additionally, the TAR system 100 includes a tibial component 110 and a talus component 120 with an insert 130, such as a bearing component, disposed between the tibial component and the talus component that may facilitate smooth articulation within the patient's ankle joint. In some embodiments, one or more components of the TAR system 100 may include one or more surfaces having various structures such as, but not limited to, smooth and/or textured structures. As will be understood from discussions herein, a textured surface may include any type of rough surface, including, but not limited to, a porous surface, a gyroid surface, a scored, or other roughened surface. The tibial component 110, talar component 120, and the TAR procedure will each be further described in detail. In some embodiments, the insert 130 may be any suitable bearing component known in the art (e.g., poly-insert, spacer, etc.).

Tibial Component

Referring now to FIGS. 2-8, one embodiment of an exemplary tibial component for use in the TAR procedure, is shown. In particular, the tibial component can be a patient-specific modular stem system 1000 configured to provide a stable fixation component (within the tibia) connected to an artificial, smooth/durable weight-bearing surface of an ankle joint prosthesis. In some embodiments, the modular stem system 1000 may further contribute to the stability of the ankle joint. Further, the modularity of the modular stem system 1000 allows installation of the overall TAR system into the tibia using only anterior access, limiting the total number of access points into the joint space to one such access point. In some embodiments, the modular stem system 1000 includes several components that, when assembled, form the overall tibial component 110 (see FIG. 1) within the TAR system.

According to some embodiments, the modular stem system 1000 includes a base tibial component 1001 and a stem portion 1020. In some embodiments, an inferior surface 1010 of the base tibial component 1001 forms at least a portion of an overall inferior end of the modular stem system 1000. Superior end 1081 of the stem portion 1020 forms at least a portion of an overall superior end of the modular stem system 1000. In some embodiments, the base tibial component 1001 may comprise a base plate 1002 and the stem portion 1020 (when assembled) may comprise a plurality of modular members 1022, 1042, 1062, 1080. In other embodiments, the base tibial component 1001 may comprise the base plate 1002 and modular member 1022 (e.g., as machined, when assembled, etc.), and the stem portion 1020 may complementarily comprise modular members 1042, 1062, 1080.

According to some embodiments, the base plate 1002 includes an anterior surface 1004, a posterior surface 1006, an inferior surface 1010, a superior surface 1016, and side surfaces 1008A-B. In some embodiments, at least a portion of the posterior surface 1006 and/or side surfaces 1008A-B includes patient-specific contouring for improved TAR system stability, integration into patient anatomy, and overall system weight reduction. In some embodiments, the inferior surface 1010 and/or the anterior surface 1004 include an attachment feature 1012 configured to engage with further components of the TAR system. In some embodiments, the anterior surface 1004 further includes one or more holes 1005 that may be used for positioning various components of the TAR system. In some embodiments, holes 1005 may be threaded without departing from the principles of this disclosure. In some embodiments, the anterior surface 1004 and/or a front portion of the superior surface 1016 may include curvature according to patient-specific goals. In some embodiments, one or more of the surfaces 1004, 1006, 1008, 1010, 1016 may include curvature in varying amounts and in any suitable combinations without departing from the principles of this disclosure. In some embodiments, the superior surface 1016 includes an anchoring member 1018 disposed around a base of modular member 1022. In other embodiments, such as the embodiment shown in FIGS. 2-5, the superior surface 1016 further includes at least one portion of modular member 1022 such that the stem portion 1020 complementarily comprises modular members 1042, 1062, 1080.

In certain embodiments, at least one portion of superior surface 1016 is integrally formed with at least one portion of modular member 1022 (e.g., the base tibial component 1001 is 3D-printed as a single component incorporating base plate 1002 and modular member 1022). In other embodiments, at least one portion of the superior surface 1016 is attached to at least one portion of modular member 1022 via mechanical bonding (e.g., soldering, welding, or using fasteners), chemical bonding (e.g., adhesive), or any other suitable means without departing from the principles of this disclosure. Base tibial component 1001 can include any suitable number of modular members positioned on the superior surface 1016 of the base plate 1002, and the stem portion 1020 can include any suitable number of modular members.

In some embodiments, superior surface 1016 can include modular member 1022 at any position of the superior surface 1016, according to patient-specific needs. In one non-limiting example, modular member 1022 can be positioned proximal a center point of the surface 1016 (as shown), or can be positioned on the surface 1016 towards a front, back, or side portion, or any suitable combination thereof to accommodate patient-specific surgical goals (e.g., pertaining to anatomy and/or pathology). Additionally, modular member 1022 can be positioned at any suitable angle relative to the superior surface 1016 according to patient-specific needs (e.g., 0-degree offset from orthogonal, 1-degree offset from orthogonal, 2-degree offset from orthogonal, 5-degree offset from orthogonal, 10-degree offset from orthogonal, etc.). Thus, in some embodiments, depending on how modular member 1022 is positioned on superior surface 1016, the overall stem portion 1020 may follow the same orientation relative to the base plate 1002 to provide increased stability for weaker areas of the patient anatomy.

According to some embodiments, at least a portion of the inferior surface 1010 includes an attachment feature 1012 formed into base plate 1002. In some embodiments, attachment feature 1012 may additionally be disposed on portions of the anterior surface 1004 and/or side surfaces 1008A-B. In some embodiments, the attachment feature 1012 includes a periphery 1013 marking a boundary between a contour of the inferior surface 1010 and the attachment feature 1012. In some embodiments, the attachment feature 1012 may engage with one or more components of the TAR system. In one non-limiting example, the attachment feature 1012 can function as a reference point for various tools and guides that prepare the tibial surface (e.g., for insertion of a bearing component, etc.). In another non-limiting example, the attachment feature 1012 engages with an insert that may facilitate smooth articulation between the tibial component (e.g., modular stem system 1000) and a talar component upon completion of the TAR procedure.

In some embodiments, the attachment feature 1012 may generally be centered on the inferior surface 1010 with respect to the overall modular stem system 1000, while in other embodiments, the attachment feature 1012 may be offset in the anterior-posterior direction and/or the medial-lateral direction. For instance, the attachment feature 1012 may be offset from center by about 1.0 to 2.0 mm, about 2.0 to 3.0 mm, about 3.0 to 4.0 mm, about 4.0 to 5.0 mm, about 5.0 to 6.0 mm, about 6.0 to 7.0 mm, or any suitable amount of offset without departing from the principles of this disclosure. In some embodiments, the attachment feature 1012 further includes various angled walls and/or ridges within periphery 1013 that may stabilize engagement with the bearing component as the patient resumes normal activity levels and range of movement. In some embodiments, the periphery 1013 may be generally U-shaped. In some embodiments, a portion of the inferior surface 1010 can be substantially flat, but in other embodiments, the inferior surface 1010 can be curved or form any suitable contour compatible with patient-specific goals, without departing from the principles of this disclosure.

According to some embodiments, the anterior surface 1004 can be substantially flat, but in other embodiments, the anterior surface 1004 can form any suitable contour, such as convex, concave, generally curved, slanted, etc. without departing from the principles of this disclosure. In some embodiments, at least a portion of the anterior surface 1004 can include one or more holes 1005. In embodiments, the holes 1005 can be blind holes, partial through-holes, or complete through-holes. In some embodiments, the one or more holes 1005 may be threaded whereas in other embodiments, the one or more holes 1005 can provide any suitable means for engagement with one or more tools used during the TAR procedure. In some embodiments, the one or more holes 1005 can function as reference points for various tools and guides that facilitate installation of one or more implants into the patient anatomy. In one non-limiting example, the one or more holes 1005 may be used with at least one tool (e.g., implant inserter, jouster, etc.) during installation of the modular stem system 1000 into the prepared ankle joint space. In another non-limiting example, the one or more holes 1005—and optionally, the attachment feature 1012—can be used with a tool (e.g., bearing inserter) to install a bearing component into the joint space via generation of counter force within the joint space. In some embodiments, a bearing component may provide one or more articulating surfaces extending between the modular system 1000 (e.g., inferior surface 1010) and a talar component of the TAR system by engaging with the attachment feature 1012.

According to some embodiments, the anterior surface 1004, posterior surface 1006, and/or the side surfaces 1008A-B can be substantially flat, but in other embodiments, the anterior surface 1004, posterior surface 1006, and side surfaces 1008A-B can include one or more curves or otherwise form any suitable contour without departing from the principles of this disclosure. In some embodiments, the posterior surface 1006 includes one or more ridges 1007 that may simulate a natural tibial contour, thereby providing stability to the base plate 1002 and overall TAR system, and enhancing comfort of the patient. In some embodiments, the one or more ridges 1007 may allow for reduced materials usage when manufacturing the modular stem system 1000. In some embodiments, the one or more ridges 1007 may be at least partially disposed one or both side surfaces 1008A-B.

According to some embodiments, a plurality of corners 1009A-D may extend between the superior surface 1016 and the inferior surface 1010. In some embodiments, the plurality of corners 1009A-D may connect the anterior and posterior surfaces 1004, 1006 with the side surfaces 1008A-B. In some embodiments, corner 1009A connects anterior surface 1004 with surface 1008A; corner 1009B connects anterior surface 1004 with surface 1008B; corner 1009C connects surface 1008B with posterior surface 1006; and corner 1009D connects posterior surface 1006 with surface 1008A. In some embodiments, one or more of surfaces 1004, 1006, 1008A-B can form at least one convex contour. In some embodiments, one or more of surfaces 1004, 1006, 1008A-B can form at least one concave contour. In some embodiments, one or more of surfaces 1004, 1006, 1008A-B can form at least one straight contour. In some embodiments, at least one of corners 1009A-D can form a right-angle between an adjacent two surfaces. In some embodiments, at least one of corners 1009A-D can form an acutely curved contour between adjacent surfaces. In some embodiments, at least one of corners 1009A-D can form an obtusely curved contour between adjacent surfaces.

According to some embodiments, the superior surface 1016 may include at least one anchoring member 1018 disposed circumferentially about modular member 1022. For instance, the at least one anchoring member 1018 engages with at least a portion of the patient's tibia that may be disposed about a diameter 1120 (see FIG. 10) of modular member 1022. The anchoring member 1018 may engage with bone (e.g., the patient's tibia) to prevent the stem portion 1020 from rotating with respect to the bone once the stem portion 1020 is fully inserted into the bone. In some embodiments, the at least one anchoring member 1018 may further include a fixation feature designed to engage with the stem portion 1020. In some embodiments, at a plurality of anchoring members 1018 can form an "X" pattern when viewed from above. In other embodiments, anchoring members 1018 can form any other suitable shape or may be distributed in any suitable pattern without departing from the principles of this disclosure.

Figures 6, 7:
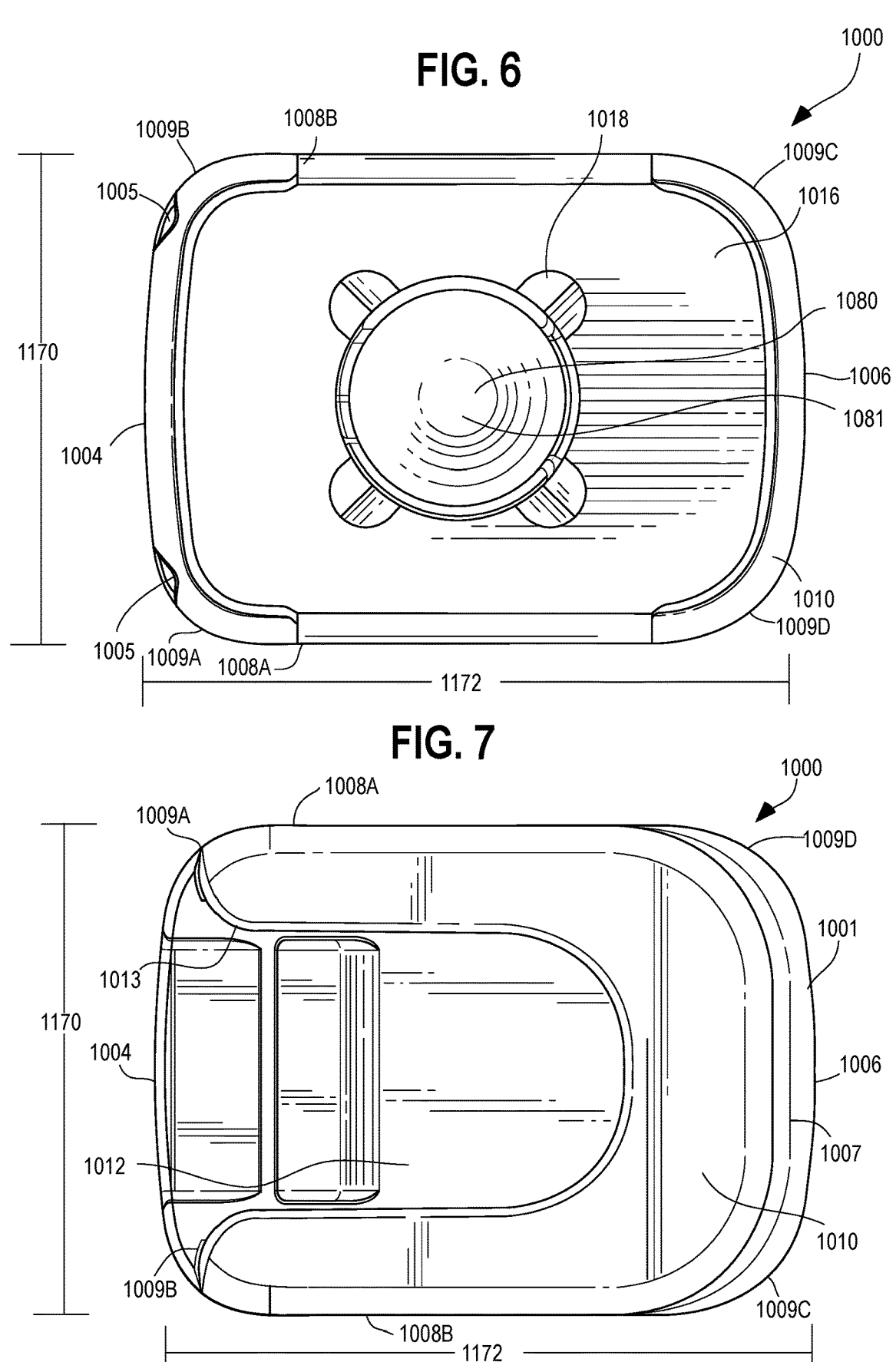
FIG. 6 is a top view of the exemplary modular stem system of FIG. 2.
FIG. 7 is a bottom view of the exemplary modular stem system of FIG. 2.

According to some embodiments, at least some portions of the base tibial component 1001 can include variations in dimensions according to patient-specific interests. With reference to FIGS. 6-7, in some embodiments, the base plate 1002 can include a length 1170 extending between surfaces 1008A-B and measuring about 15.0 to 25.0 mm, about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, about 65.0 to 75.0 mm, or any suitable length in accordance with the principles of this disclosure. In some embodiments, the base plate 1002 can include a length 1172 extending between anterior surface 1004 and posterior surface 1006, measuring about 15.0 to 25.0 mm, about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, about 65.0 to 75.0 mm, or any suitable length in accordance with the principles of this disclosure.

Figure 9:
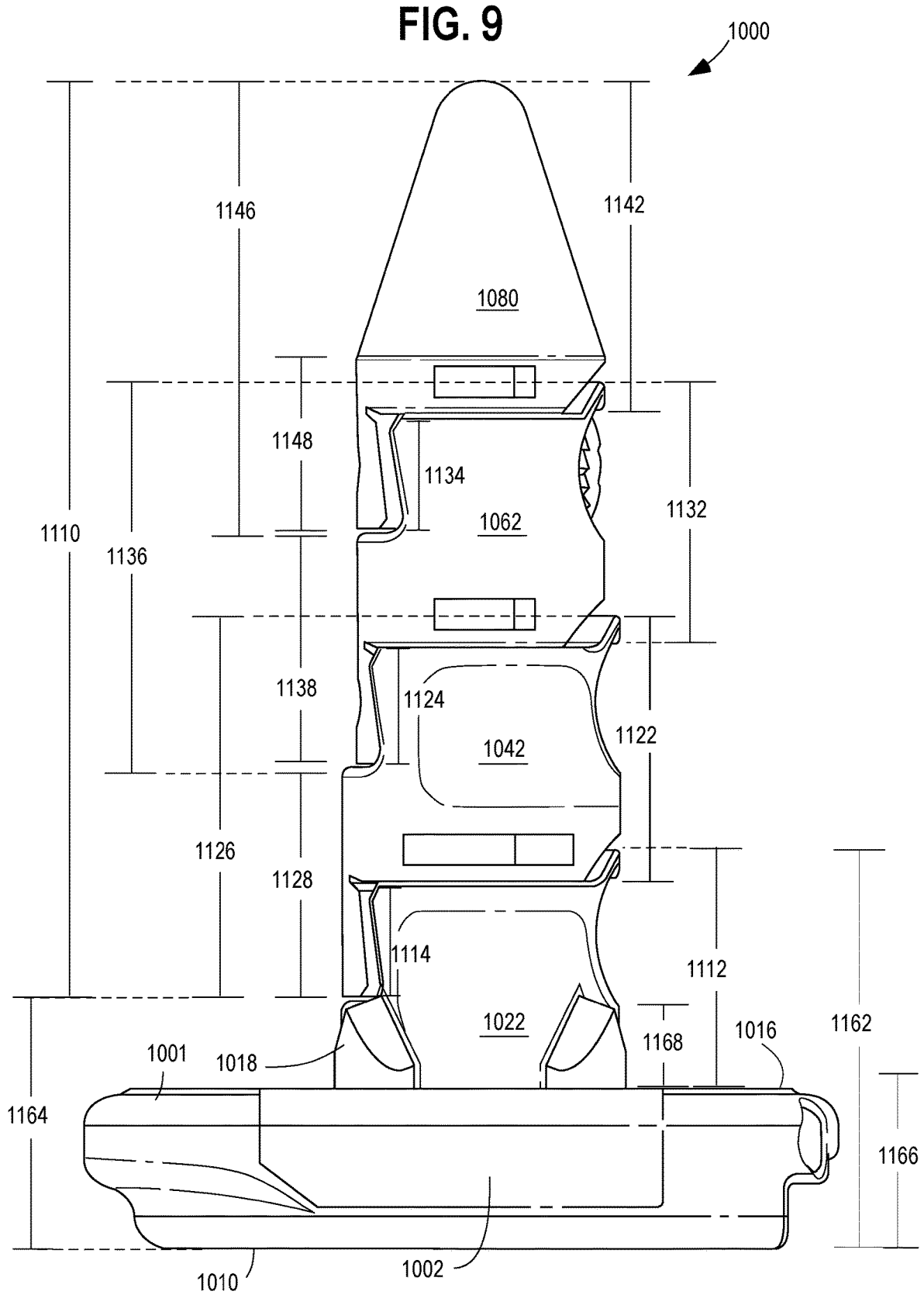
FIG. 9 is a side view of the exemplary modular stem system of FIG. 2.

With reference to FIG. 9, in some embodiments, the base plate 1002 can include a height 1166 measuring about 4.0 to 10.0 mm, about 10.0 to 20.0 mm, about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, or any suitable height/thickness in accordance with the principles of this disclosure. In some embodiments, the at least one anchoring member 1018 can include a height 1168, measuring about 3.0 to 6.0 mm, or about 5.0 to 8.0 mm. In some embodiments, the base plate 1002 and at least one anchoring member 1018 together can include a height 1164, measured from inferior surface 1010 to an end of the at least one anchoring member 1018, measuring about 4.0 to 10.0 mm, about 10.0 to 20.0 mm, about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, or any suitable height/thickness in accordance with the principles of this disclosure. In some embodiments, the base tibial component 1001 (comprising the base plate 1002 and modular member 1022) can include a height 1162, measured from inferior surface 1010 to a top surface of modular member 1024, measuring about 15.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, about 65.0 to 75.0 mm, or any suitable length in accordance with the principles of this disclosure. Variations in any heights and lengths associated with the base tibial component 1001 may, in some embodiments, vary the sizing/depth of the attachment feature 1012. Additionally, heights, lengths, thicknesses may vary on any given portion of the base tibial component 1001.

With reference to FIGS. 2-8, in some embodiments, the stem portion 1020, when assembled, may comprise a plurality of individually manufactured modular members 1022, 1042, 1062, 1080, wherein a variance in size, shape, and number of modular members allows a user to select a customized length, diameter, and thickness for the stem portion 1020 as is desirable for orthopedic surgery. For instance, due to a sequential method of insertion, modular member 1022 may include a larger average diameter and/or a longer length than modular member 1042, and modular member 1042 may include a larger average diameter and/or a longer length than modular member 1062. In some embodiments, the stem portion 1020 may include a fixation feature designed to engage with the fixation feature of the at least one anchoring member 1018. In some embodiments, the stem portion 1020 may comprise any suitable combination of modular members in addition to modular members 1022, 1042, 1062, 1080 to complement the structure (e.g., subcomponents) of the base tibial component 1001. In other embodiments, the stem portion 1020 may be manufactured as a monolithic component for the TAR system.

In some embodiments, modular member 1080 may be disposed such that modular member 1080 is positioned at a superior end (e.g., top surface 1064, see FIG. 8) of modular member 1062. In some embodiments, the superior end 1081 (e.g., overall superior end of the stem portion 1020) of modular member 1080 may include some degree of tapering along its length to aid in the insertion of the stem portion 1020 into a patient's tibia. For example, modular member 1080 may be inserted into an intramedullary canal prior to other modular members, wherein the user forms the intramedullary canal within the medullary cavity of the prepared tibial surface as a result of the TAR procedure. Impaction of modular member 1080 into the intramedullary canal may enable easier insertion and impaction of subsequent modular members 1062, 1042, 1022. Further, modular members 1022, 1042, 1062 can comprise a generally cylindrical shape or any other suitable shape without departing from the principles of this disclosure. Similarly, modular member 1080 can comprise a generally conical shape or any other suitable shape. In some embodiments, at least a portion of modular member 1080 may include cutting teeth, porous or otherwise roughened surfaces (including gyroid surfaces), or any other suitable features without departing from the principles of this disclosure.

Figure 8:
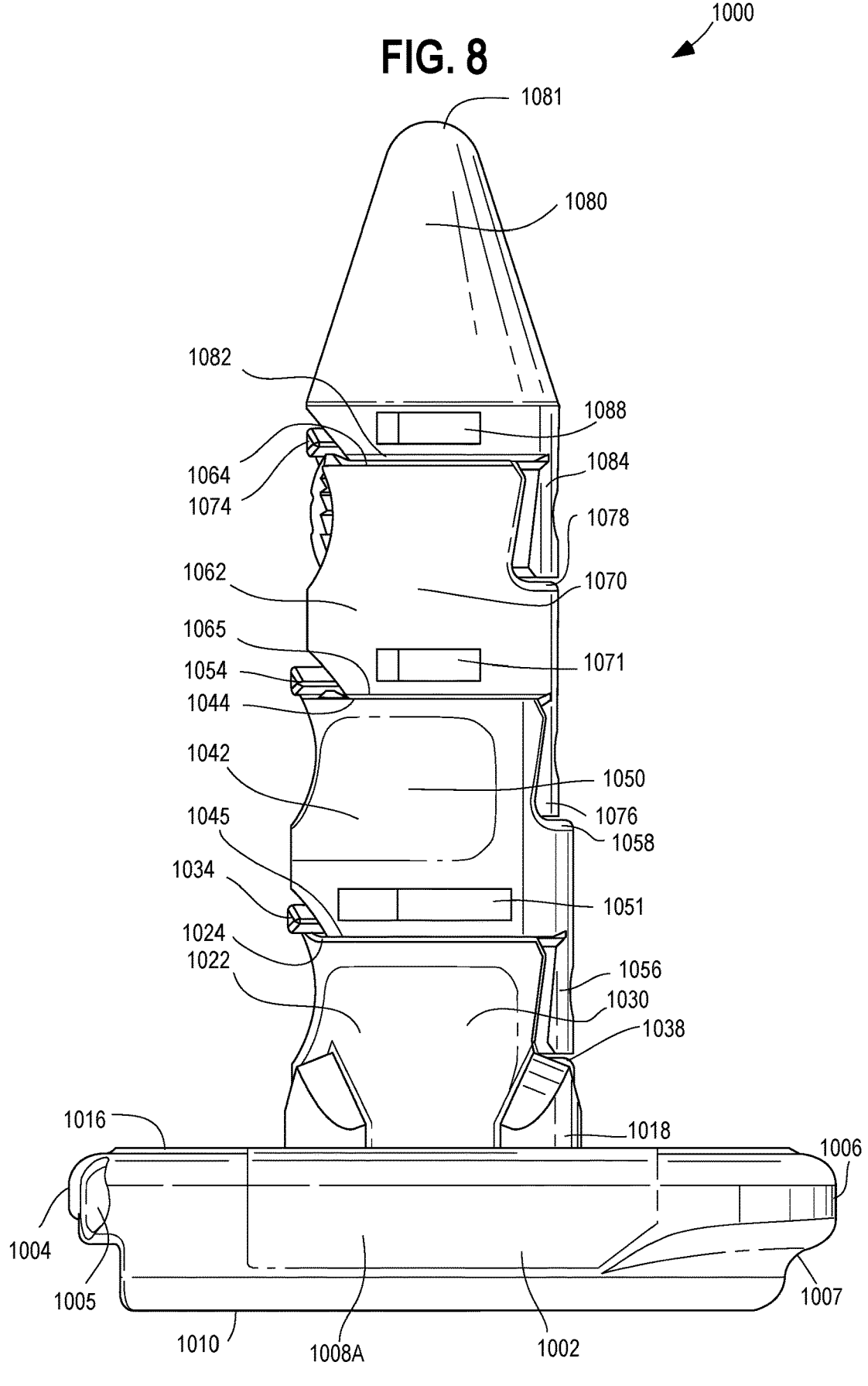
FIG. 8 is a side view of the exemplary modular stem system of FIG. 2.

According to some embodiments, each of the modular members 1022, 1042, 1062, 1080 may include at least one of a top surface or a bottom surface (see FIG. 8). In some embodiments, each of the modular members 1022, 1042, 1062 includes a top surface 1024, 1044, 1064, respectively;

and each of the modular members 1042, 1062, 1080 includes a bottom surface 1045, 1065, 1082, respectively. In some embodiments, each top surface 1024, 1044, 1064 engages with one adjacent bottom surface 1045, (1065, 1082. For example, the top surface 1024 of modular member 1022 selectively engages with the bottom surface 1045 of modular member 1042; the top surface 1044 of modular member 1042 engages with the bottom surface 1065 of modular member 1062; and the top surface 1064 of modular member 1062 engages with the bottom surface 1082 of terminal modular member 1080. In alternative embodiments, each of modular members 1022, 1042, 1062 can include any suitable number of top surfaces and/or bottom surfaces.

In some embodiments, the top surfaces 1024, 1044, 1064 may include various features adapted to enhance engagement with complementary features included with the bottom surfaces 1045, 1065, 1082. For instance, in certain embodiments, at least one area of at least one of the top and/or bottom surfaces of modular members 1022, 1042, 1062, 1080 may include one or more fixation features configured to engage with an adjacent fixation feature, thus stabilizing the stem portion 1020. In some embodiments, adjacent fixation features of adjacent modular members may form joints such as, but not limited to, dovetail joints, box joints, dowel joints, and Knapp joints. In some embodiments, such as the embodiment shown in FIGS. 2-9, a portion of each of bottom surfaces 1045, 1065, 1082 include a male fixation feature 1056, 1076, 1084, respectively, disposed therefrom. In some embodiments, a portion of each of top surfaces 1024, 1044, 1064 include a complementary female fixation feature 1038, 1058, 1078, respectively, disposed therein. In some embodiments, each male fixation feature 1056, 1076, 1084 may selectively engage with one adjacent and complementary female fixation feature 1038, 1058, 1078, thereby preventing vertical separation of the respective adjacent modular members.

For example, male fixation feature 1084 selectively engages with female fixation feature 1078; male fixation feature 1076 selectively engages with female fixation feature 1058; and male fixation feature 1056 selectively engages with female fixation feature 1038. In alternate embodiments, male fixation features 1056, 1076, 1084 can be positioned on any suitable area (e.g., posterior area, medial area, lateral area, central area) of the top surfaces 1024, 1044, 1064 and/or bottom surfaces 1045, 1065, 1082. In alternate embodiments, female fixation features 1038, 1058, 1078 can be positioned on any suitable area (e.g., posterior area, medial area, lateral area, central area) of the top surfaces 1024, 1044, 1064 and/or bottom surfaces 1045, 1065, 1082. In alternate embodiments, there can be any suitable number of male and female fixation features disposed on top surfaces 1024, 1044, 1064 and/or bottom surfaces 1045, 1065, 1082. In accordance with the principles of this disclosure, male fixation features 1056, 1076, 1084 may engage with female fixation features 1038, 1058, 1078 as dovetail connections, or any other suitable method of fixation, to enhancing resistance to separation under tension in the stem portion 1020.

Figures 12A, 12B, 12C:
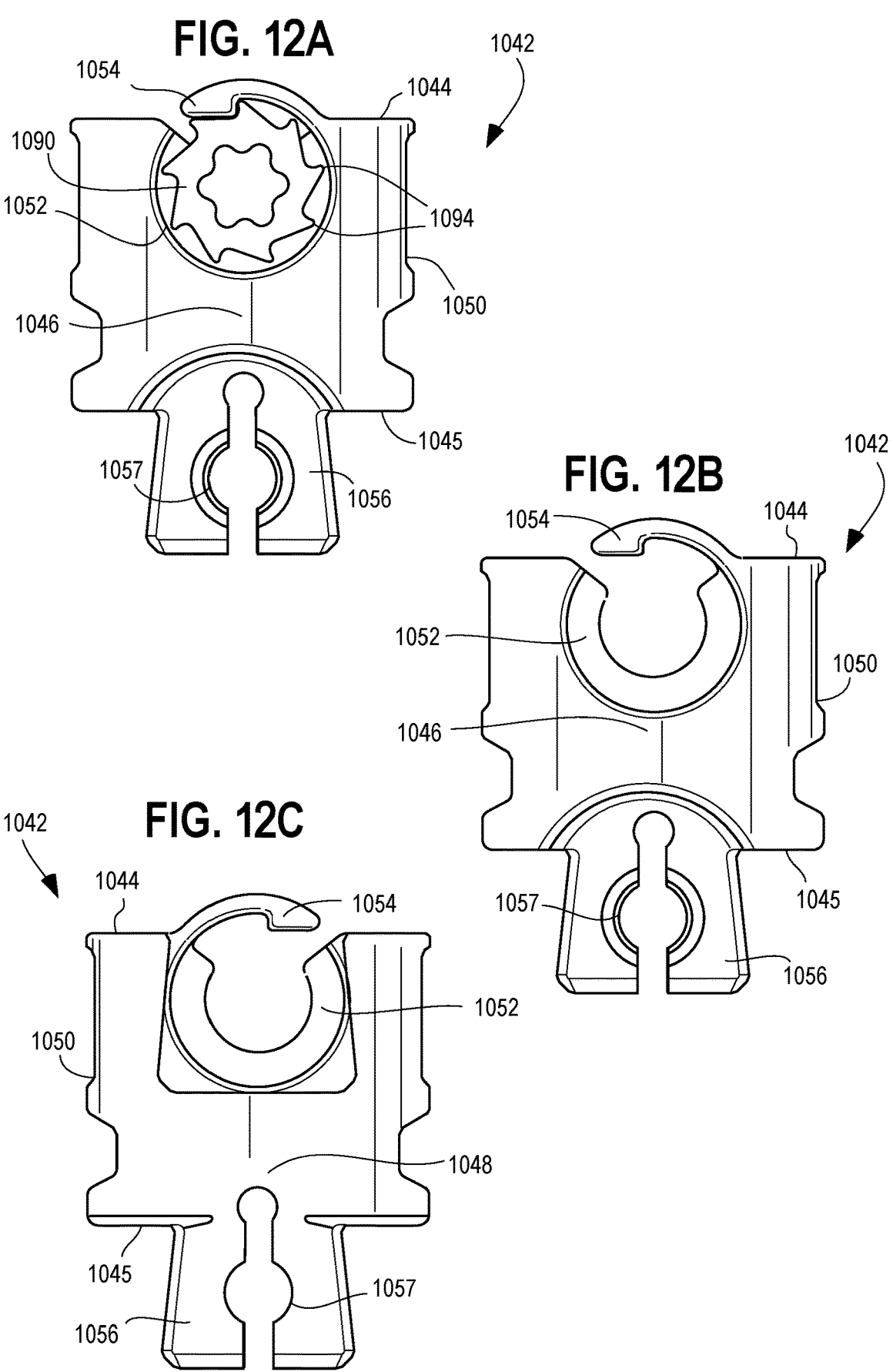
FIG. 12A is a front view of an exemplary modular member of FIG. 2, according to one embodiment.
FIG. 12B is a front view of the exemplary modular member of FIG. 12A, according to one embodiment.
FIG. 12C is a rear view of the exemplary modular member of FIG. 12B.
Figure 13:
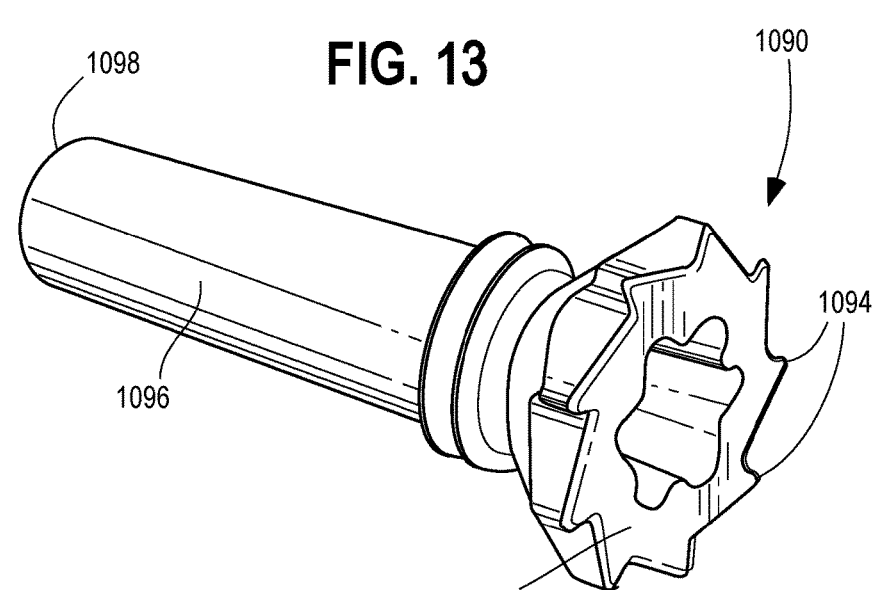
FIG. 13 is a perspective view of an exemplary fastening feature of FIG. 12A, according to one embodiment.
Figure 14:
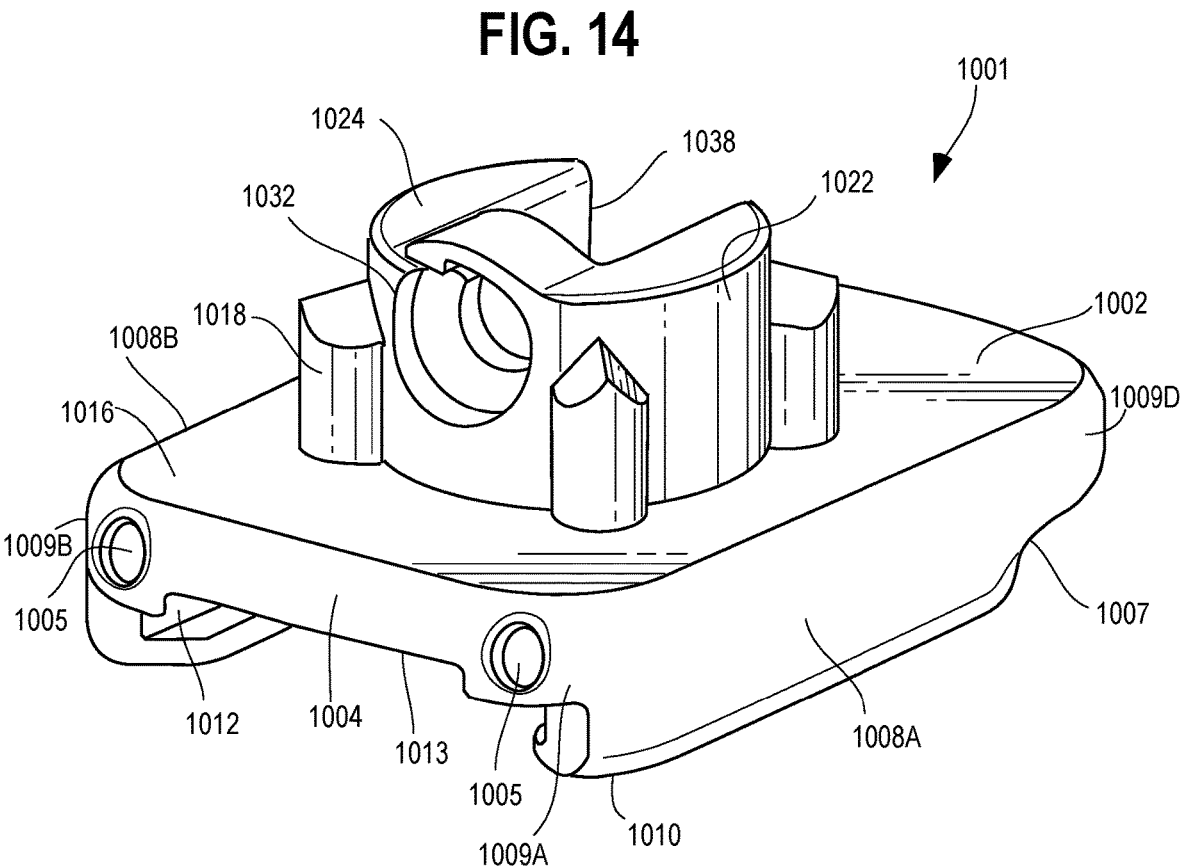
FIG. 14 is a front perspective view of an exemplary base tibial component, according to one embodiment.
Figure 15:
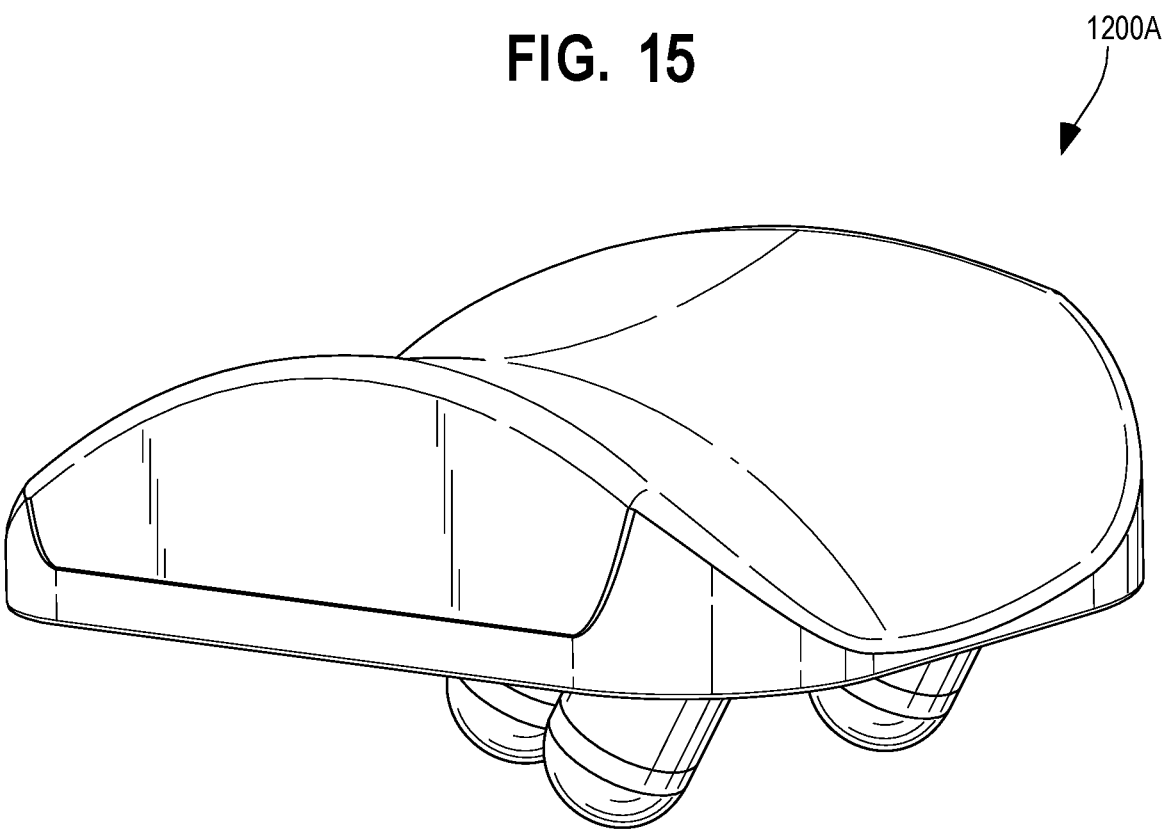
FIG. 15 is a top perspective view of an exemplary talus implant, according to one embodiment.
Figure 16:
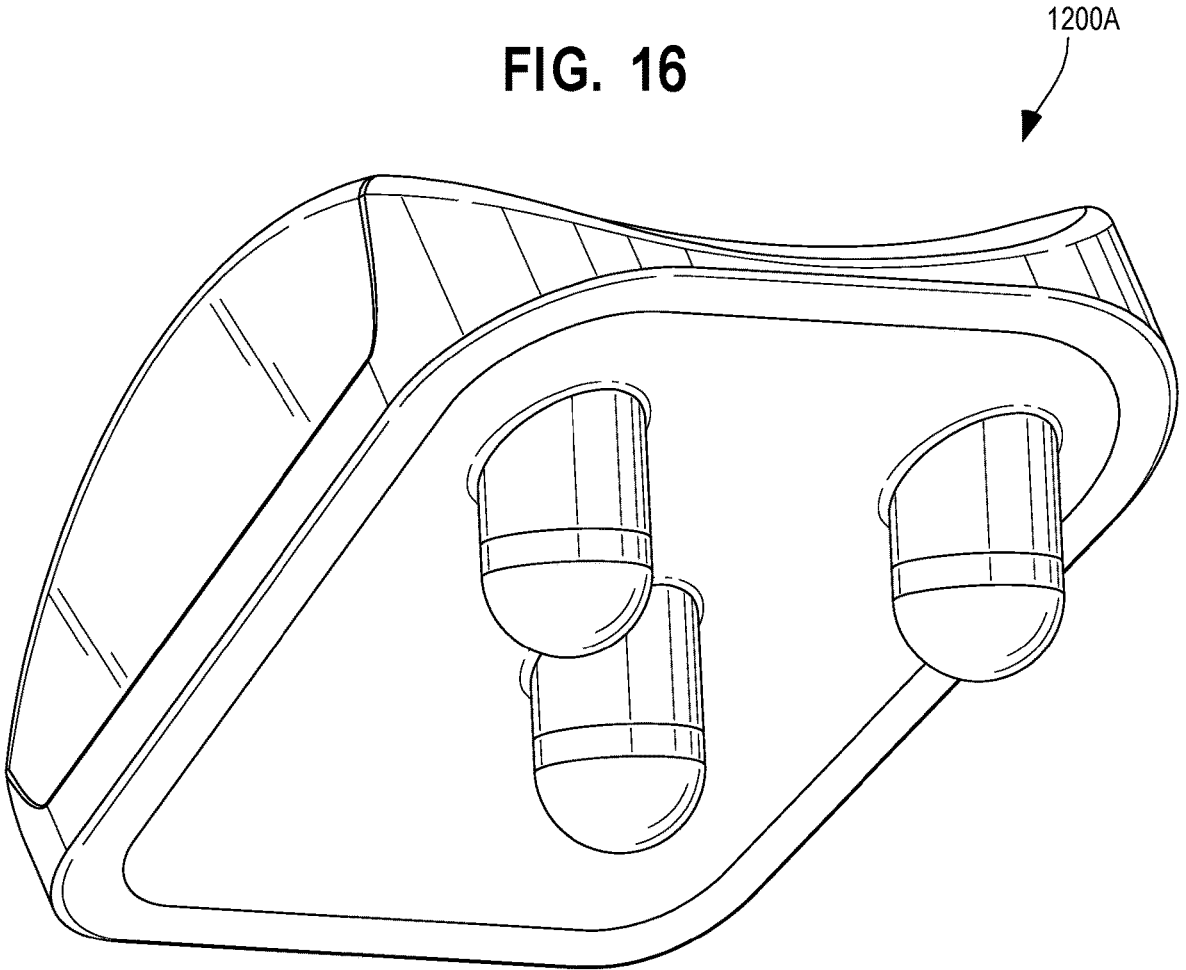
FIG. 16 is a bottom perspective view of the talus implant of FIG. 15.
Figure 17:
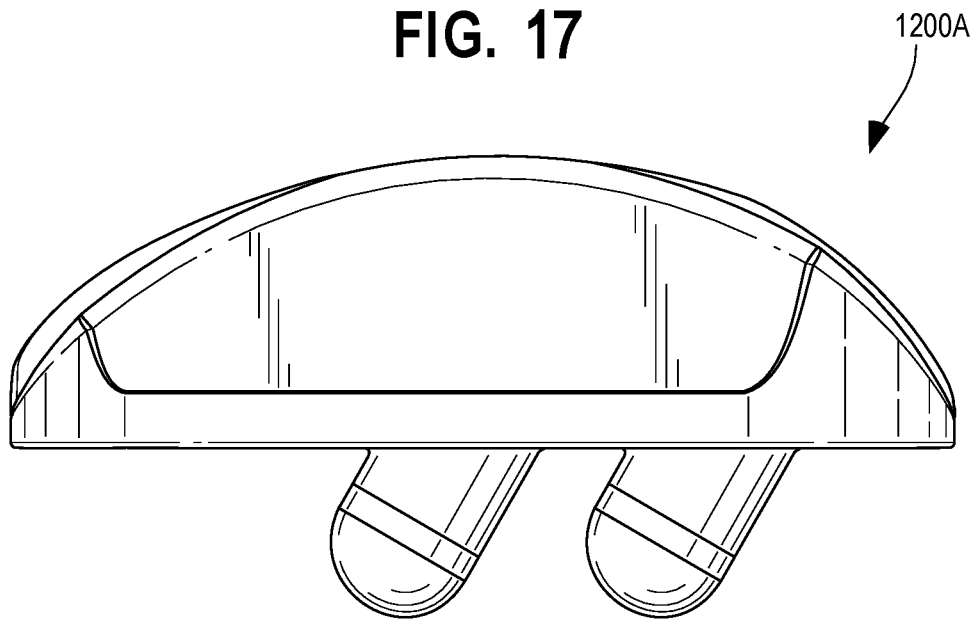
FIG. 17 is a side view of the talus implant of FIG. 15.
Figure 18A:
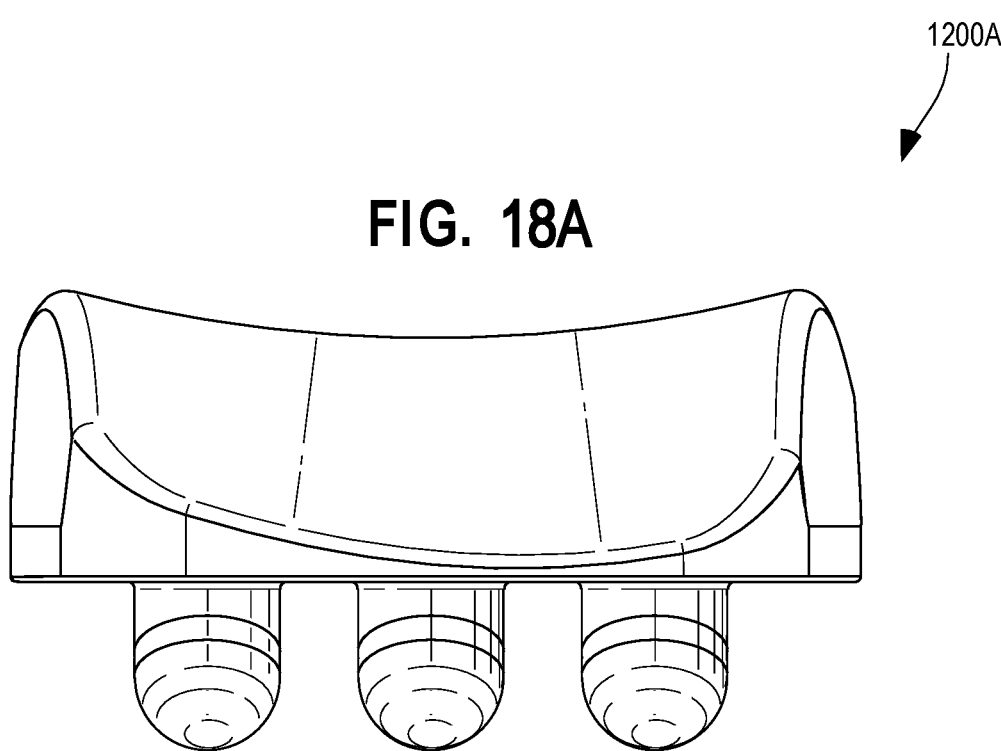
FIG. 18A is a front view of the talus implant of FIG. 15.
Figure 18B:
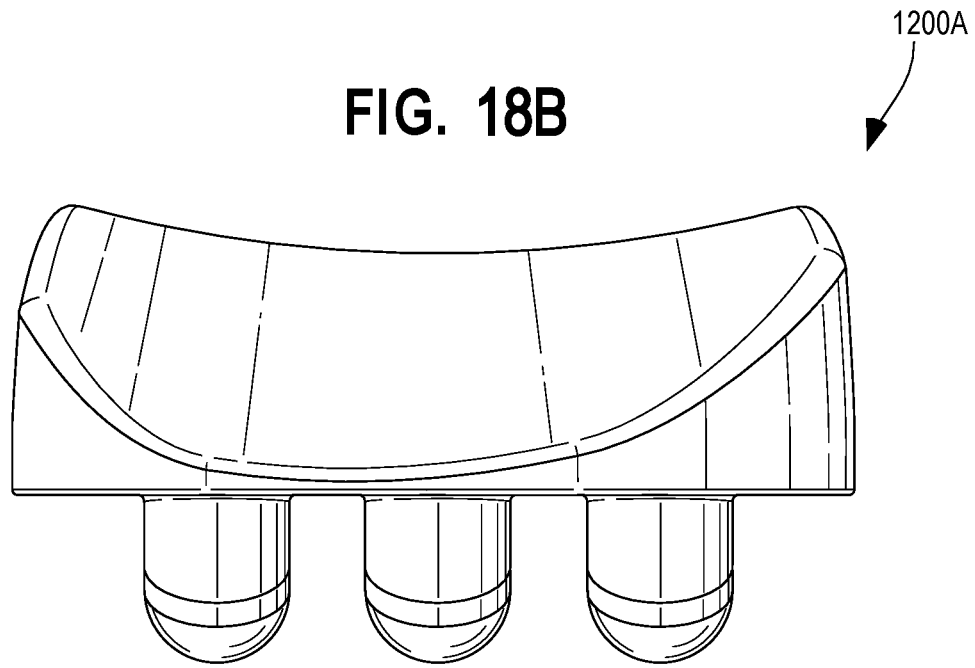
FIG. 18B is a back view of the talus implant of FIG. 15.

According to some embodiments, each of the modular members 1022, 1042, 1062 includes a front surface 1026, 1046, 1066, respectively; and each of the modular members 1022, 1042, 1062, 1080 includes a back surface 1028, 1048, 1068, 1083, respectively. In some embodiments, the front surfaces 1026, 1046, 1066 each include openings 1032, 1052, 1072, respectively, adapted to receive and hold at least a portion of a fastening member, such as fastener 1090 (see FIG. 12). In some embodiments, the back surfaces 1048,

1068, 1083 each include fixation openings 1057, 1077, 1086, respectively, adapted to receive and hold at least a portion of a fastener 1090. Thus, in various embodiments, fastener 1090 may couple each of modular members 1022, 1042, 1062, 1080 to an adjacent modular member.

For example, fastener 1090 selectively couples a portion of modular member 1022 to a portion of male fixation feature 1056 through opening 1032 to opening 1057; fastener 1090 selectively couples a portion of modular member 1042 to a portion of male fixation feature 1076 through opening 1052 to opening 1077; and fastener 1090 selectively couples a portion of modular member 1062 to a portion of male fixation feature 1084 through opening 1072 to opening 1086. In embodiments, fastener 1090 may be externally threaded. In one or more embodiments, at least a portion of openings 1032, 1052, 1072 can be internally threaded from a front surface to a back surface of a modular member. Additionally, in one or more embodiments, at least a portion of openings 1057, 1077, 1086 can be internally threaded. Thus, in some embodiments, use of fasteners 1090 may stabilize the stem portion 1020 and/or by applying compressive force in a horizontal direction (e.g., between an anterior surface of one modular member and a posterior surface of an adjacent modular member).

In certain embodiments, one or more of fasteners 1090 can be screws, nails, or any other suitable means for fastening in accordance with the principles of this disclosure. In some embodiments, one or more of fasteners 1090 may include a head having any suitable driving feature including, but not limited to a Torx®, Phillips, square, or hex pattern. In some embodiments, each modular member 1022, 1042, 1062, 1082 can have one or more resilient tabs disposed on at least one of top surface or a bottom surface that can positively engage corresponding features on an adjacent modular member. In such a case, the one or more resilient tabs can fasten or otherwise secure modular member 1022 to modular member 1042; the one or more resilient tabs can fasten or otherwise secure modular member 1042 to modular member 1062; and the one or more resilient tabs can fasten or otherwise secure modular member 1062 to modular member 1080.

According to some embodiments, and with reference to FIGS. 11 and 12A-C, at least one of the plurality of modular members 1022, 1042, 1062, 1080 may include additional features that further stabilize the engagement of one modular member to an adjacent modular member. For instance, each of openings 1032, 1052, 1072 includes one or more anti-backout features 1034, 1054, 1074, respectively, that—in conjunction with features on fastener 1090—prevents fasteners 1090 from loosening in a horizontal direction once installed. In the embodiment shown in FIGS. 12A-C, the anti-backout feature 1054 can include a flexible pawl that selectively engages at least one tooth 1094 positioned around a circumference of the fastener head 1092. Thus, when fastener 1090 selectively engages with anti-backout feature 1054 of opening 1052, the body 1096 of fastener 1090 is prevented from loosening between opening 1052 and opening 1077 (not shown) where the fastener end 1098 can rest. It will be understood in accordance with the principles of this disclosure that while FIGS. 12A-C pertain to modular member 1042, the figures may detail one or more similar features of at least any of modular members 1022, 1042, 1062, 1080 incorporated in the modular stem assembly 1000. Furthermore, other suitable features may be used in place of or in addition to anti-backout features 1034, 1054, 1074 may be used without departing from the principles of this disclosure.

Referring now to FIG. 8, according to some embodiments, each of the modular members 1042, 1062, 1080 can include one or more indentations that may provide support and stability within the patient (e.g., provide additional surface area for osseointegration), and/or provide suitable surfaces for various tools and guides to reference during the TAR procedure. In some embodiments, modular member 1042 includes one or more indentations 1051; modular member 1062 includes one or more indentations 1071; and terminal modular member 1080 includes one or more indentations 1088. In some embodiments, the one or more indentations 1051, 1071, 1088 may form a rectangular shape, or ovular shape, or any other suitable shape in accordance with the principles of this disclosure. Additionally, in some embodiments, the one or more indentations 1051, 1071, 1088 may include areas of porous structure suited for improved osseointegration within the patient anatomy. In some embodiments, the one or more indentations 1051, 1071, 1088 may provide a suitable surface to engage with one or more tools (e.g., stem inserter, counter torque lock) in the course of the TAR procedure.

With reference to FIG. 9, according to some embodiments, each of the modular members 1022, 1042, 1062, 1080 can have varying lengths measured along a front surface. For example, in some embodiments, front surface 1026 can include a length 1112 measuring about 5.0 to 8.0 mm, about 7.0 to 10.0 mm, or about 9.0 to 12.0 mm. In some embodiments, front surface 1046 can include a length 1122 measuring about 5.0 to 8.0 mm, about 7.0 to 10.0 mm, or about 9.0 to 12.0 mm. In some embodiments, front surface 1066 can include a length 1132 measuring about 5.0 to 8.0 mm, about 7.0 to 15.0 mm, or about 9.0 to 20.0 mm. In some embodiments, terminal modular member 1080 can include a length 1142 measuring about 5.0 to 8.0 mm, about 7.0 to 15.0 mm, or about 9.0 to 20.0 mm.

According to some embodiments, each of the one or more fixation features 1056, 1076, 1084, 1038, 1058, 1078 can have varying lengths. For example, in some embodiments, male fixation feature 1056 can include a length 1128, measuring about 5.0 to 8.0 mm, about 7.0 to 10.0 mm, or about 9.0 to 12.0 mm. In some embodiments, male fixation feature 1076 can include a length 1138, measuring about 5.0 to 8.0 mm, about 7.0 to 10.0 mm, or about 9.0 to 12.0 mm. In some embodiments, male fixation feature 1084 can include a length 1148, measuring about 5.0 to 8.0 mm, about 7.0 to 10.0 mm, or about 9.0 to 12.0 mm. In some embodiments, female fixation feature 1038 can include a length 1114, measuring about 1.0 to 4.0 mm, about 3.0 to 6.0 mm, or about 5.0 to 8.0 mm. In some embodiments, female fixation feature 1058 can include a length 1124, measuring about 1.0 to 4.0 mm, about 3.0 to 6.0 mm, or about 5.0 to 8.0 mm. In some embodiments, female fixation feature 1078 can include a length 1134, measuring about 1.0 to 4.0 mm, about 3.0 to 6.0 mm, or about 5.0 to 8.0 mm.

According to some embodiments, each of the modular members 1022, 1042, 1062, 1080 can have varying lengths measured along an entire length. With reference to FIG. 9, in some embodiments, modular member 1042 can include a length 1126 extending from top surface 1044 and including the length of fixation feature 1056, measuring about 5.0 to 8.0 mm, about 7.0 to 10.0 mm, or about 9.0 to 12.0 mm. In some embodiments, modular member 1062 can include a length 1136 extending from top surface 1064 and including the length of fixation feature 1076, measuring about 5.0 to 8.0 mm, about 7.0 to 10.0 mm, or about 9.0 to 12.0 mm. In some embodiments, terminal modular member 1080 can include a length 1146 extending from the superior end 1081 including the length of fixation feature 1084, measuring about 5.0 to 8.0 mm, about 7.0 to 10.0 mm, or about 9.0 to 12.0 mm.

Figure 10:
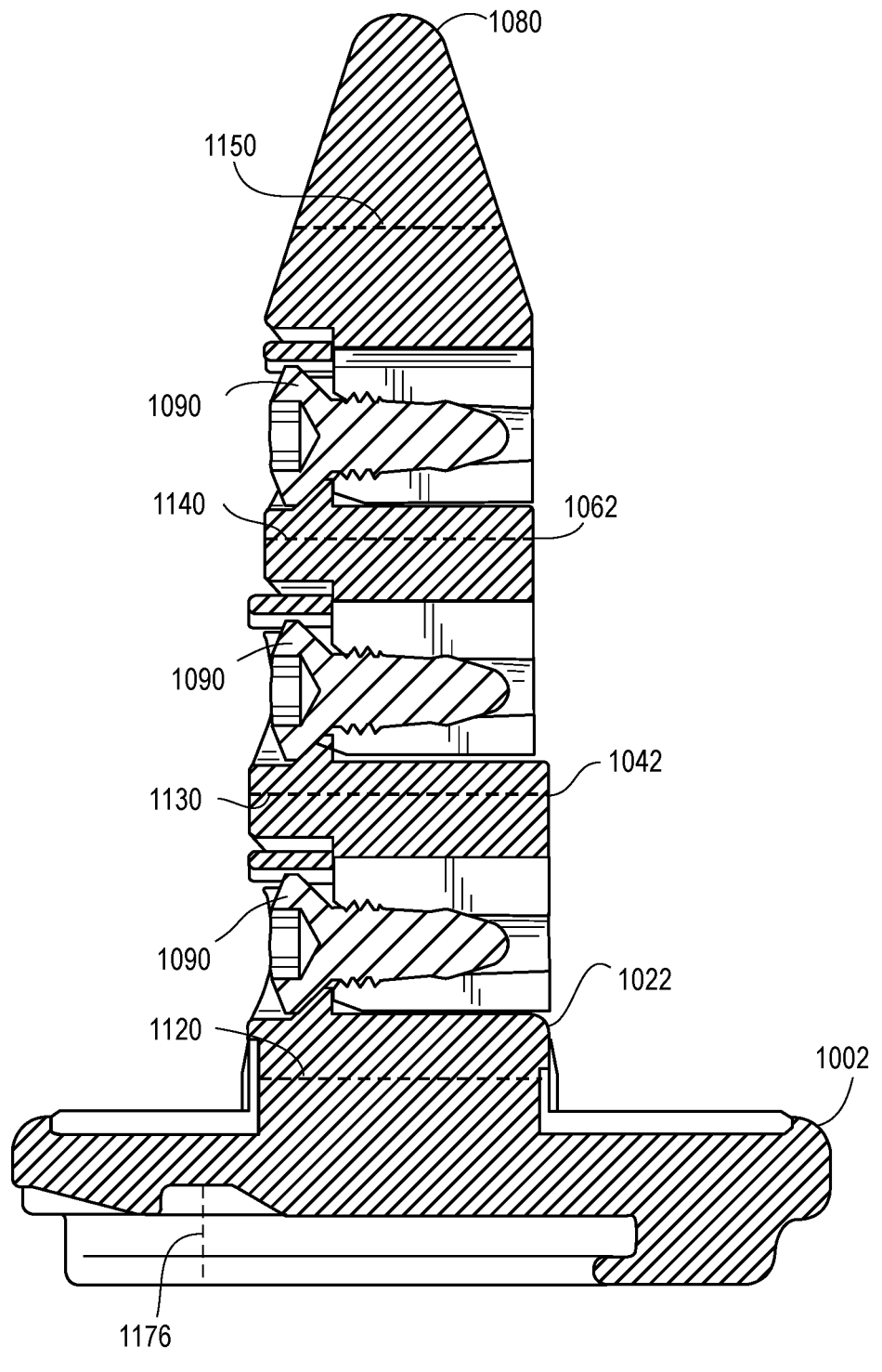
FIG. 10 is a cross-section view of FIG. 4.
Figure 11:
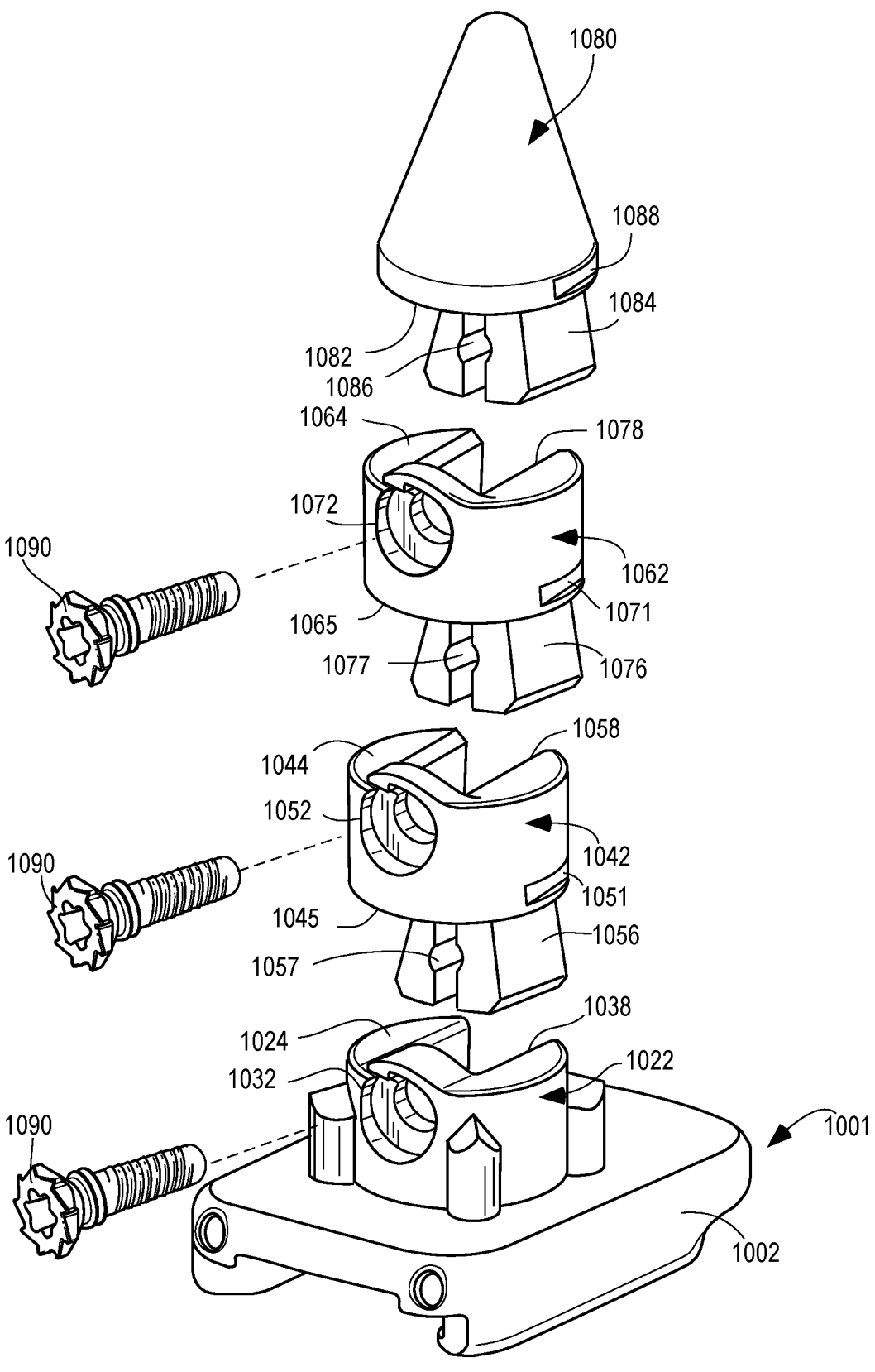
FIG. 11 is an exploded view of the exemplary modular stem system of FIG. 2.

According to some embodiments, with reference to FIG. 10, each of the modular members 1022, 1042, 1062, 1080 can have varying diameters. In some embodiments, modular member 1022 includes a diameter 1120; modular member 1042 includes a diameter 1130; modular member 1062 includes a diameter 1140; and terminal modular member 1080 includes a diameter 1150. By varying each of the diameters 1120, 1130, 1140, 1150 along respective lengths 1112, 1122, 1132, 1142, the assembled modular stem 1000 can taper from a relatively narrow diameter at an overall superior end 1081 of the stem portion 1020 to a relatively wider diameter at an overall inferior end of the stem portion 1020. For instance, in some embodiments, diameter 1120 can measure between about 4.0 to 6.0 mm, about 5.0 to 7.0 mm, or about 6.0 to 8.0 mm; diameter 1130 can measure between about 4.0 to 6.0 mm, about 5.0 to 7.0 mm, or about 6.0 to 8.0 mm; diameter 1140 can measure between about 4.0 to 6.0 mm, about 5.0 to 7.0 mm, or about 6.0 to 8.0 mm; and diameter 1150 can measure between about 2.0 to 4.0 mm, about 3.0 to 5.0 mm, or about 4.0 to 6.0 mm. In other embodiments, each of the diameters 1120, 1130, 1140, 1150 may vary according to patient-specific requirements.

In certain embodiments, some or all of the components of the modular stem system 1000 may be textured or include textured regions that may promote osteo- or other anatomical growth. Some embodiments of the base tibial component 1001 may include one or more portions having at least some textured regions that may increase friction between the modular stem system 1000 and surrounding patient anatomy. In some embodiments, textured regions may promote osteo- or other anatomical ingrowth by, for instance, facilitating ingrowth or ongrowth of bone, soft tissue (e.g., allograft, autograft, etc.), or scar tissue to create mechanically sound functional bonds between the tissue structure and the implant. The depth of the textured region (e.g., porous ingrowth layer) may vary between 100 and 500 micrometers generally wherever surface contact may be expected between the modular stem system 1000 and bone. In certain embodiments, the textured regions may comprise a porous or gyroid structure, wherein the gyroid structure may be a triply periodic minimal surface (TPMS), or any other suitable design without departing from the principles of this disclosure. In at least one embodiment, a gyroid structure is beneficial for tissue ingrowth because its porous microstructure facilitates ingrowth therein. The textured region, certain components of the modular stem, and/or the entire modular stem may be 3D printed in order to obtain a high degree of customizability for different patient applications. In other embodiments, any suitable portion of the modular stem system 1000 may include textured regions, such as the one or more indentations 1051, 1071, 1088; and/or outer surfaces of the modular members 1042, 1062, 1080.

According to some embodiments, one or more indentations 1051, 1071, 1088 may generally accommodate tools/instruments for insertion or removal of some or all components of the modular stem system 1000. For instance, such tool/instruments may be used for any or all of the following steps: insertion into or removal from the patient's tibia bone; insertion and locking or removal and unlocking of modular members; insertion into or removal from a patient's surgical site; and providing counter force during insertion, locking, unlocking or removal, of one or more modular members during the TAR procedure. In some embodiments, the locking and unlocking steps may occur while the modular members (or other implant components) are disposed within the patient's surgical site, within the patient's bony anatomy, or outside the surgical and outside the body (e.g., during assembly or disassembly outside of the patient's body).

Figure 19:
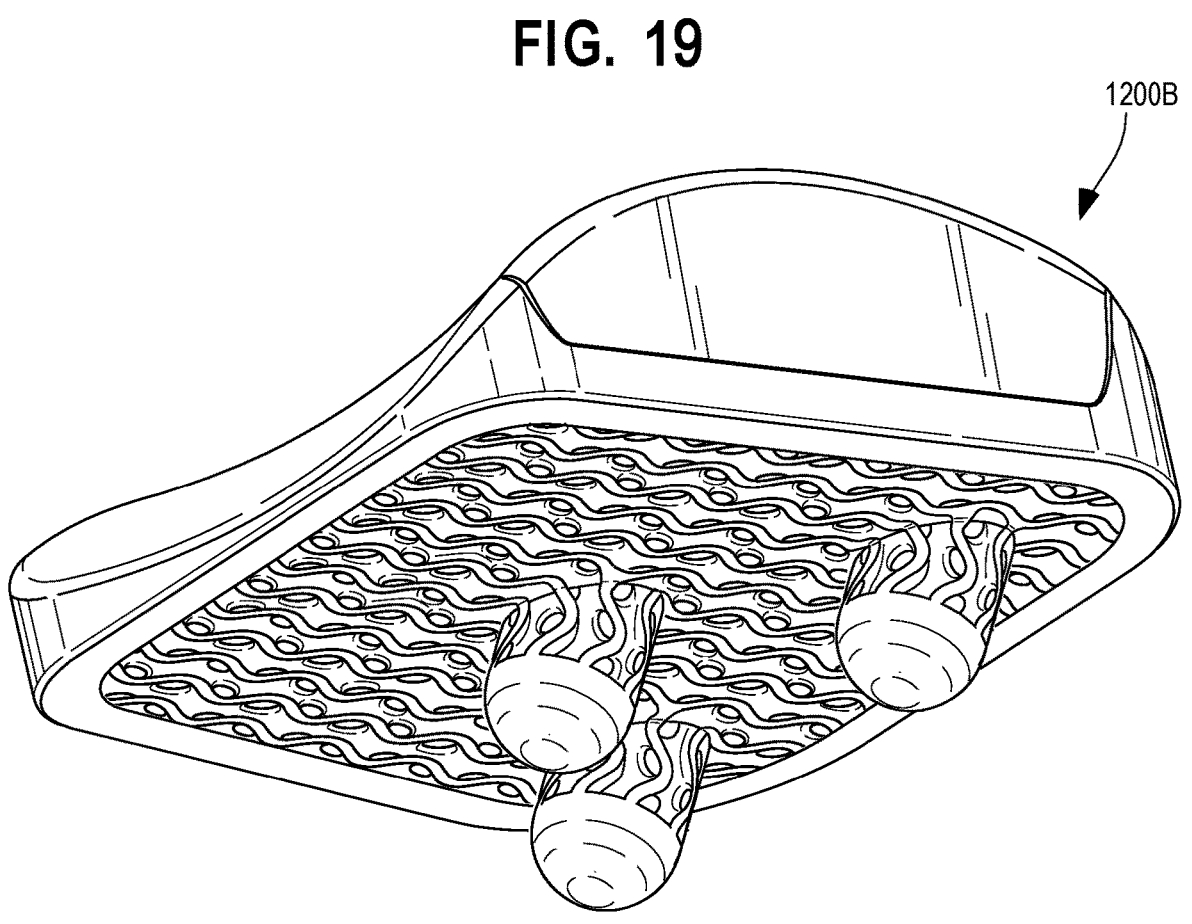
FIG. 19 is a rear perspective view of an exemplary talus implant, according to one embodiment.
Figure 20:
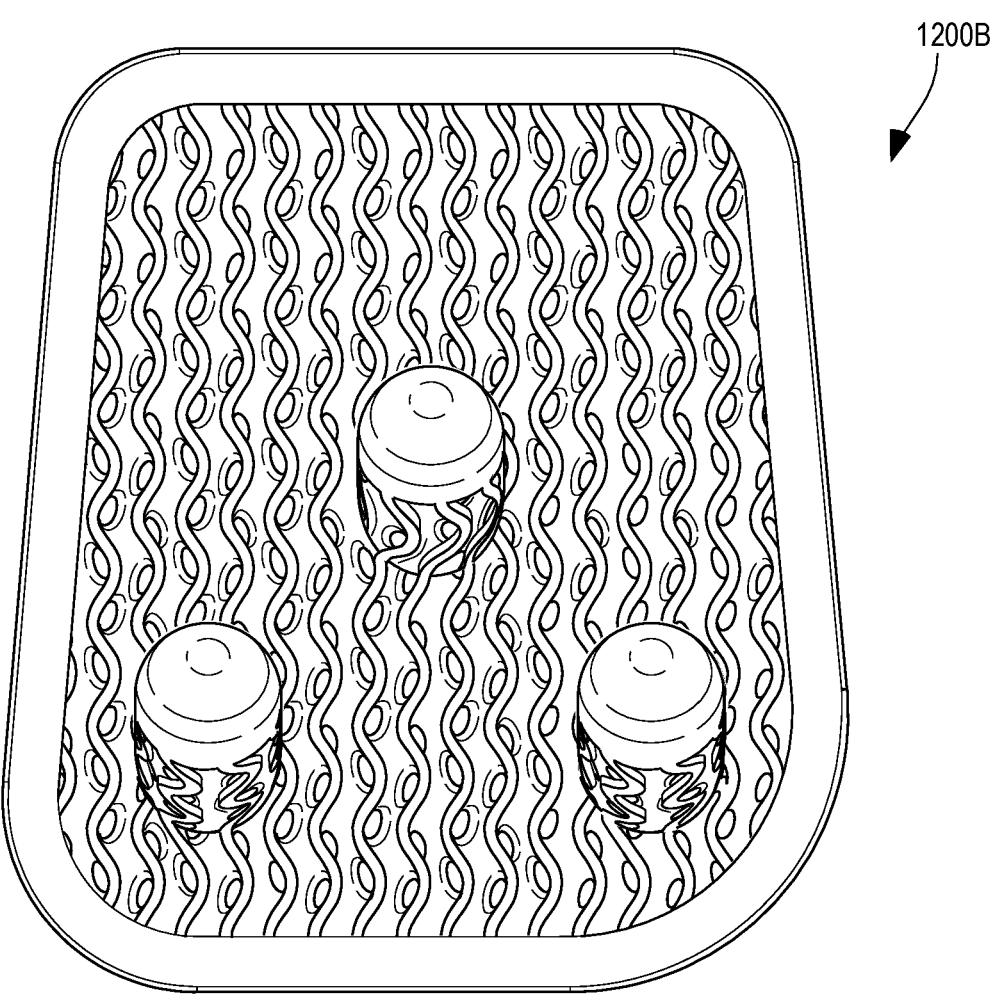
FIG. 20 is a bottom view of the talus implant of FIG. 19.
Figure 21:
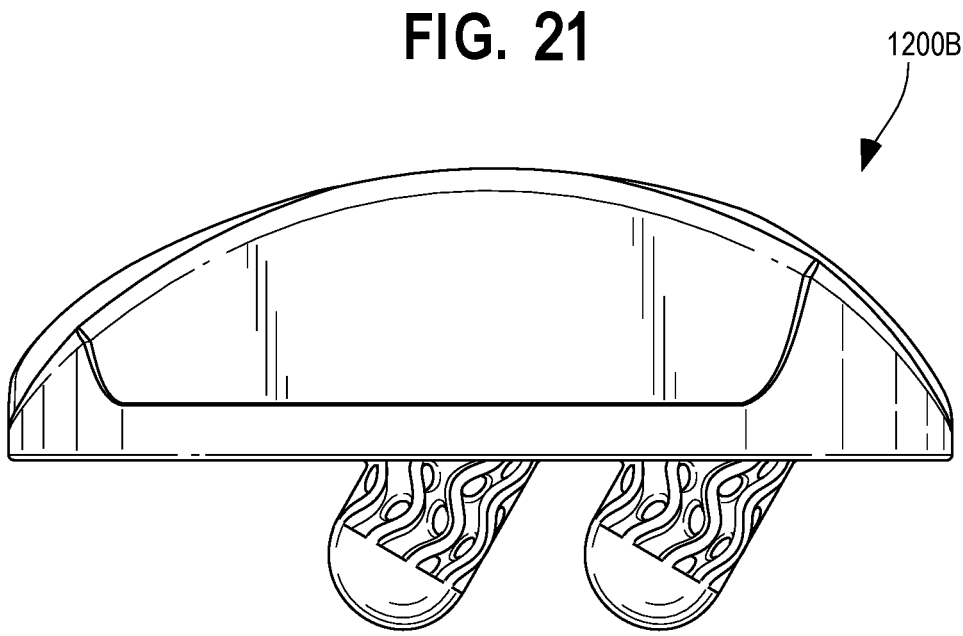
FIG. 21 is a side view of the talus implant of FIG. 19.

Referring now to FIGS. 15-21, exemplary talus implant embodiments are shown. In particular, FIGS. 15-18B pertain to an exemplary talus implant 1200A including generally smooth surfaces. FIGS. 19-21 pertain to an exemplary talus implant 1200B including one or more textured surfaces, where the amount and positioning of the textured surfaces are determined at the pre-operative planning stage. In such embodiments, the textured surfaces may complement the textured surfaces of the modular stem in terms of pattern, sizing, porosity, etc. Exemplary processes for preparing the talar surface and installing a suitable talus implant can be found in the following surgical technique guide incorporated herein by reference as if set forth in its entirety: Kinos Axiom® Total Ankle System with Axiom PSR™ Cut Guides.

Tibial Trial

Turning now to FIGS. 22-28, one embodiment of an exemplary tibial trial 2000 for use in the TAR procedure is shown. Generally, after preliminary resections are made to prepare the tibial surface (e.g., such that the prepared tibial surface includes one or more flat regions), the tibial trial 2000 can then be positioned on and temporarily secured to the prepared tibial surface (using a tibial trial alignment guide, or any other suitable instruments), thereby providing a reference point (e.g., desired alignment relative to a patient's anatomy) for the various tools and instruments of the TAR procedure. In some embodiments, the tibial trial 2000 may comprise a trial base 2002—having a first end 2006, a second end 2008, a superior face 2010, an inferior face 2012, and one or more side faces 2018—and a trial face 2004—having a top end 2034, a bottom end 2036, an anterior face 2014, a posterior face 2016, and one or more arm portions 2038. In some embodiments, the trial base 2002 and the trial face 2004 may be coupled at a junction formed by the first end 2006 and the bottom end 2036. In other embodiments, the trial base 2002 and the trial face 2004 may be formed as a singular component (e.g., via 3D-printing, casting, machining, etc.).

Figures 80, 81, 82:
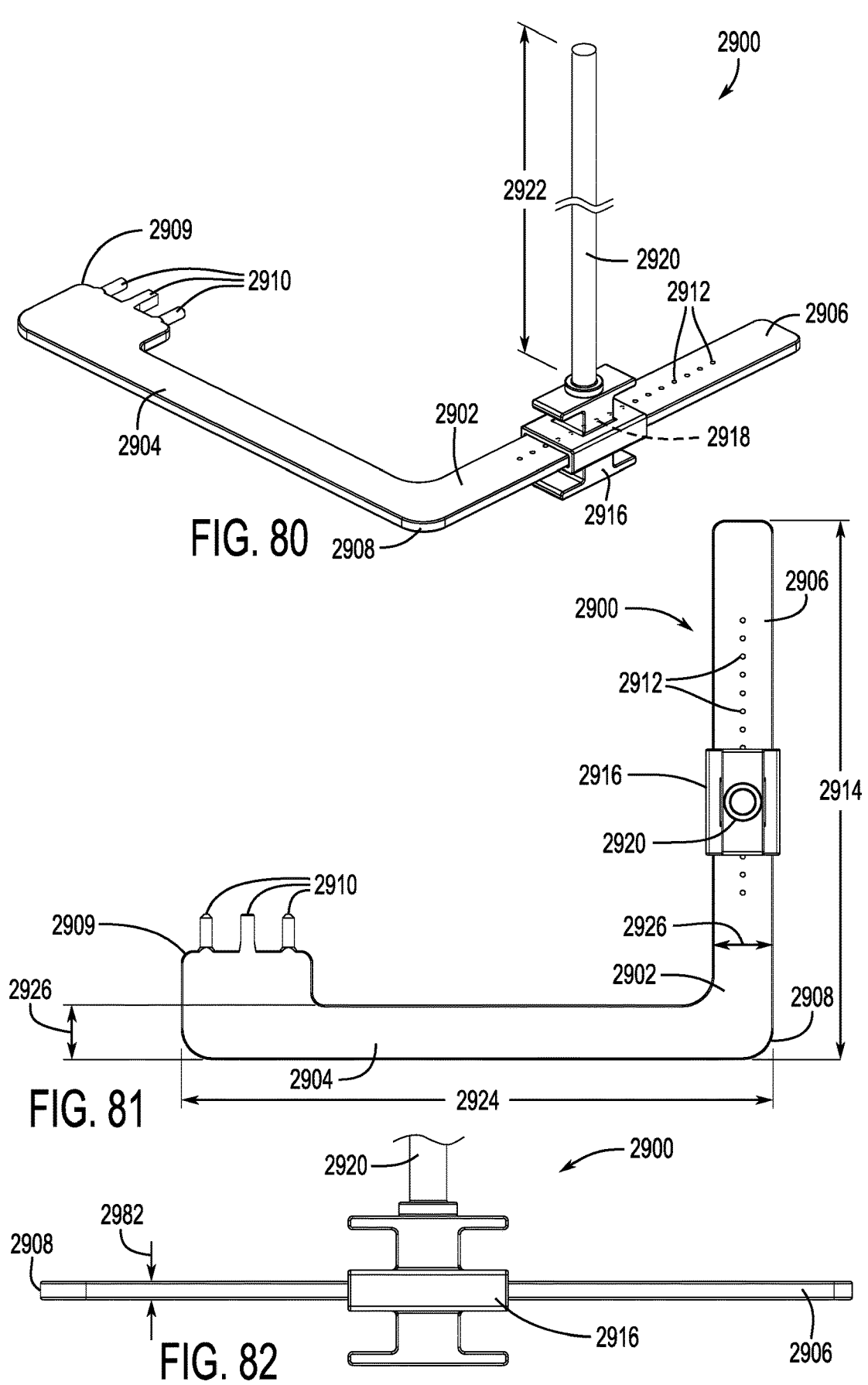
FIG. 80 is a perspective view of an exemplary sight alignment tool, according to one embodiment.
FIG. 81 is a top view of the exemplary sight alignment tool of FIG. 80.
FIG. 82 is a side view of the exemplary sight alignment tool of FIG. 80.
Figure 83:
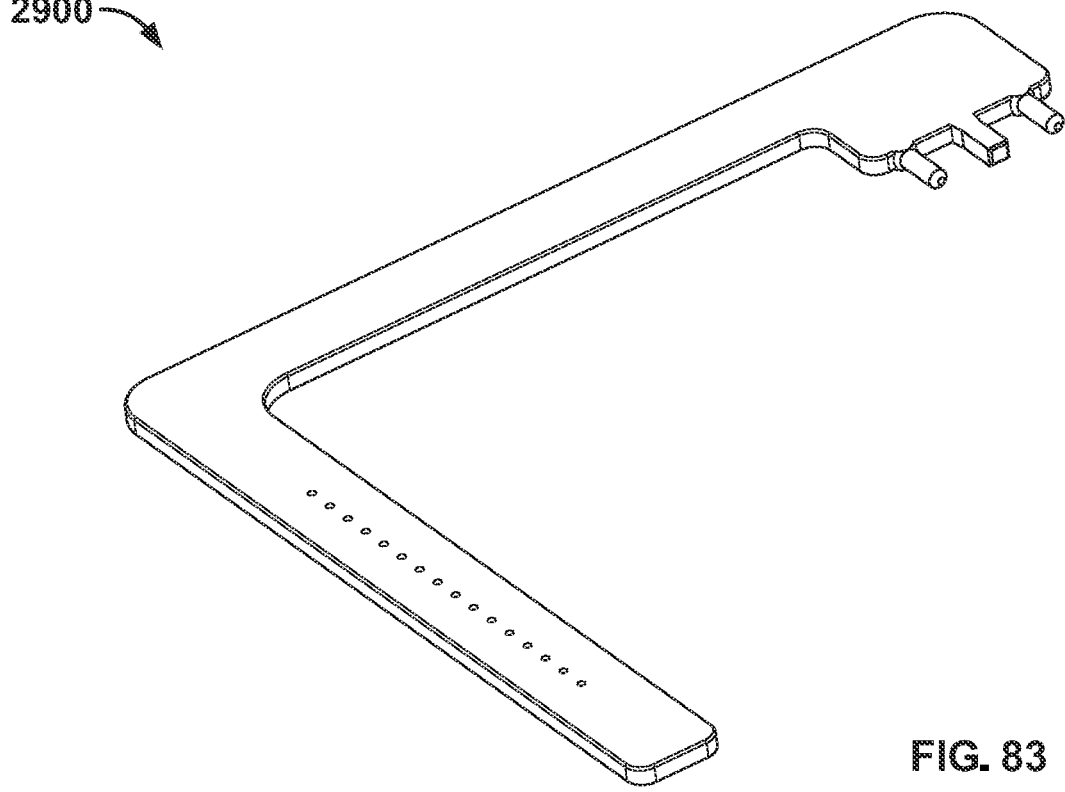
FIG. 83 is a perspective view of an exemplary sight alignment tool, according to one embodiment.
Figure 84:
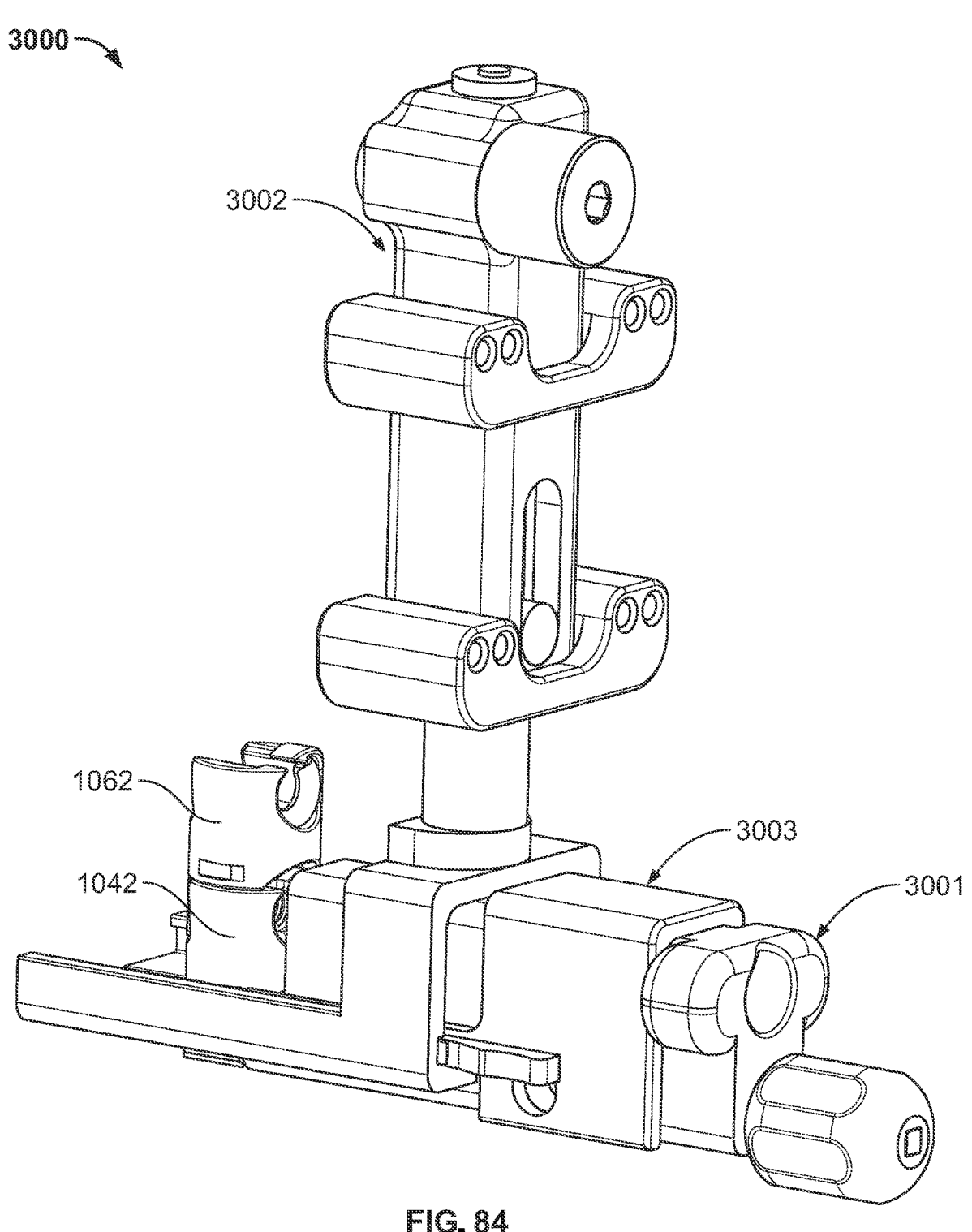
FIG. 84 is a front perspective view of a compressor assembly, according to one embodiment.
Figure 85:
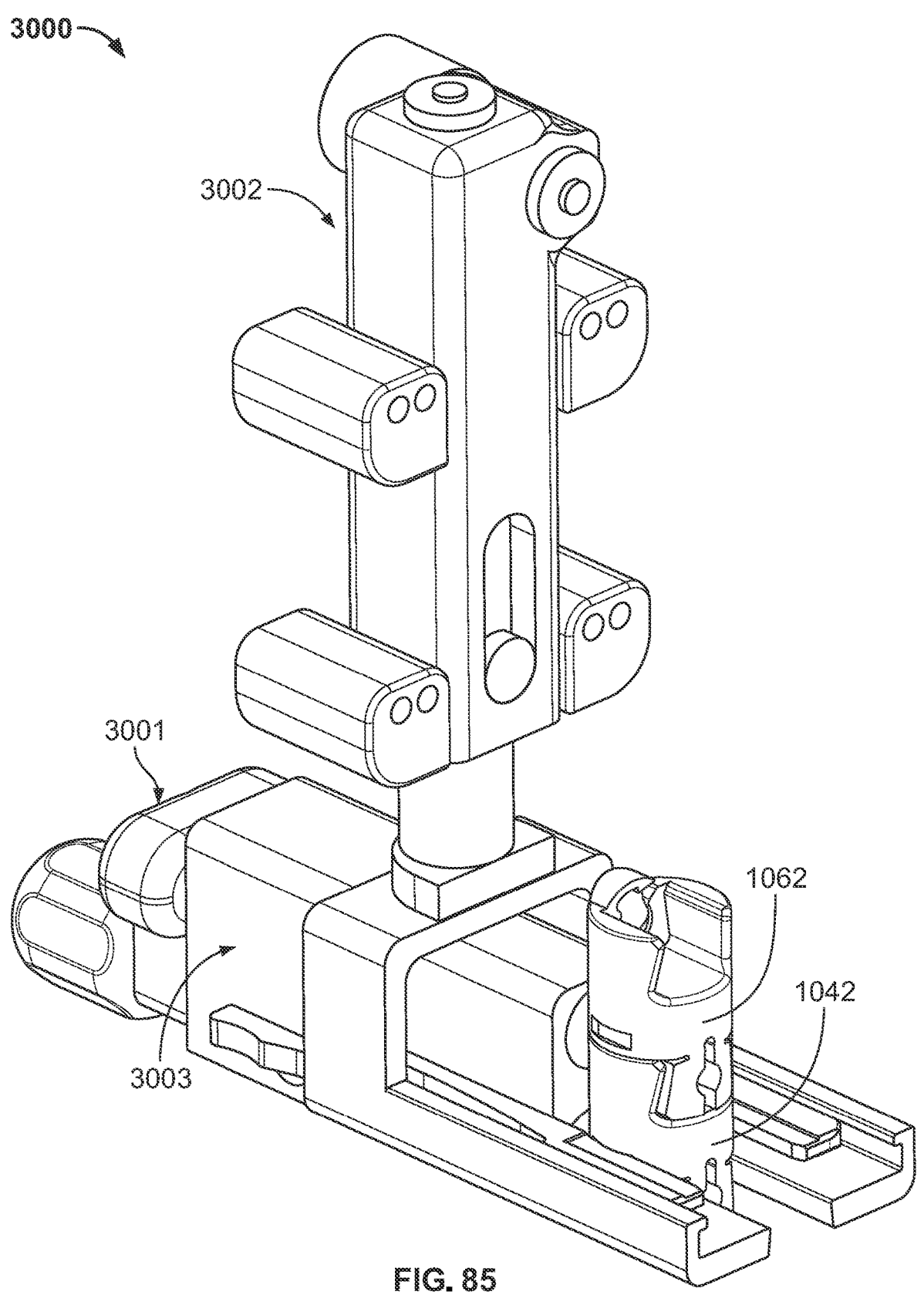
FIG. 85 is a rear perspective view of the compressor assembly of FIG. 84.
Figure 88:
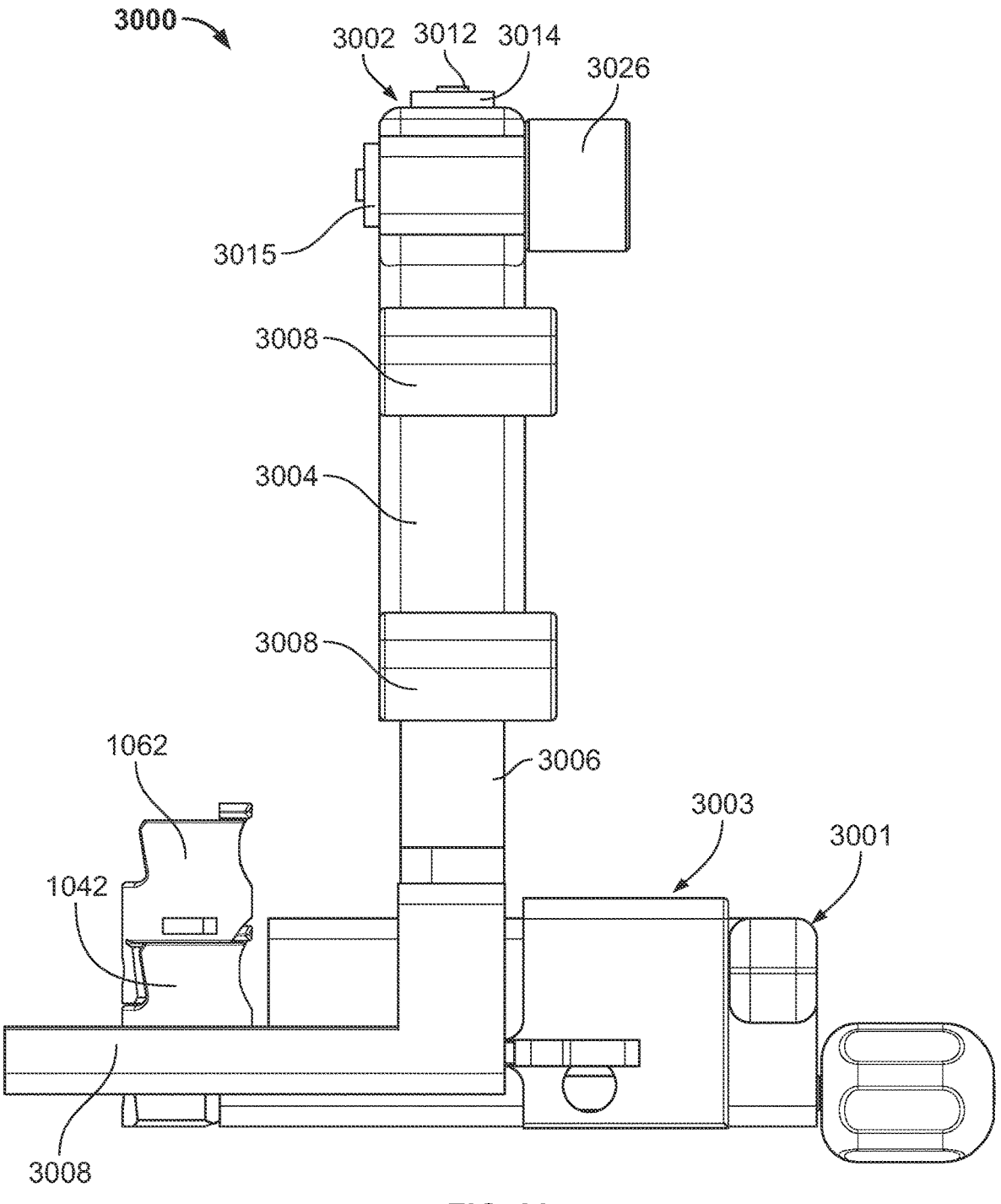
FIG. 88 is a side view of the compressor assembly of FIG. 84.
Figure 89:
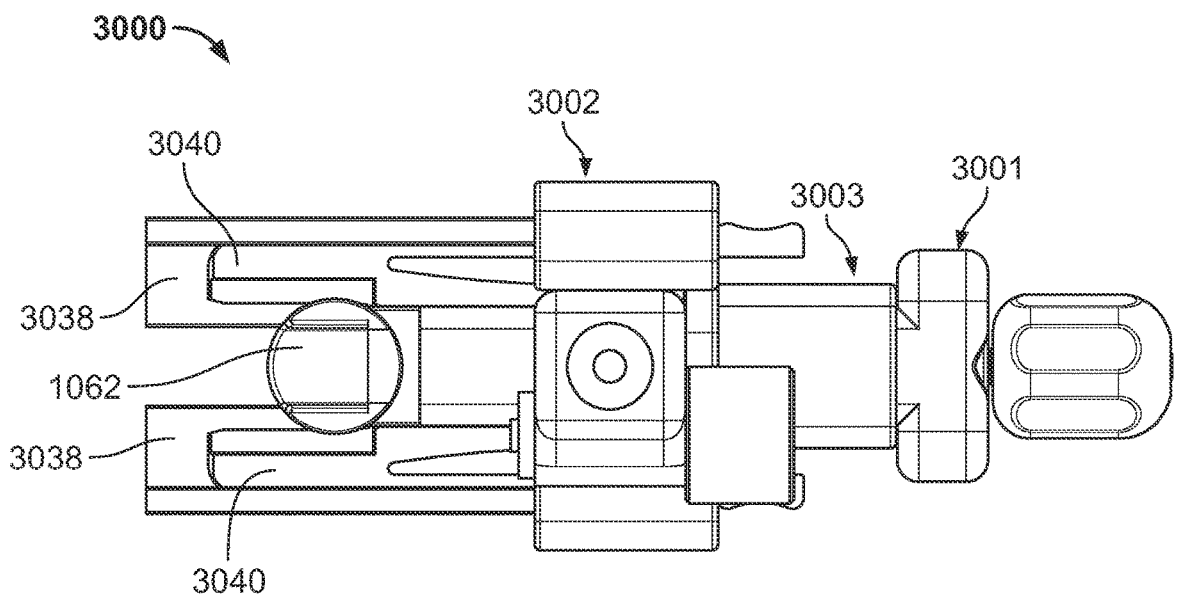
FIG. 89 is a top view of the compressor assembly of FIG. 84.
Figure 90:
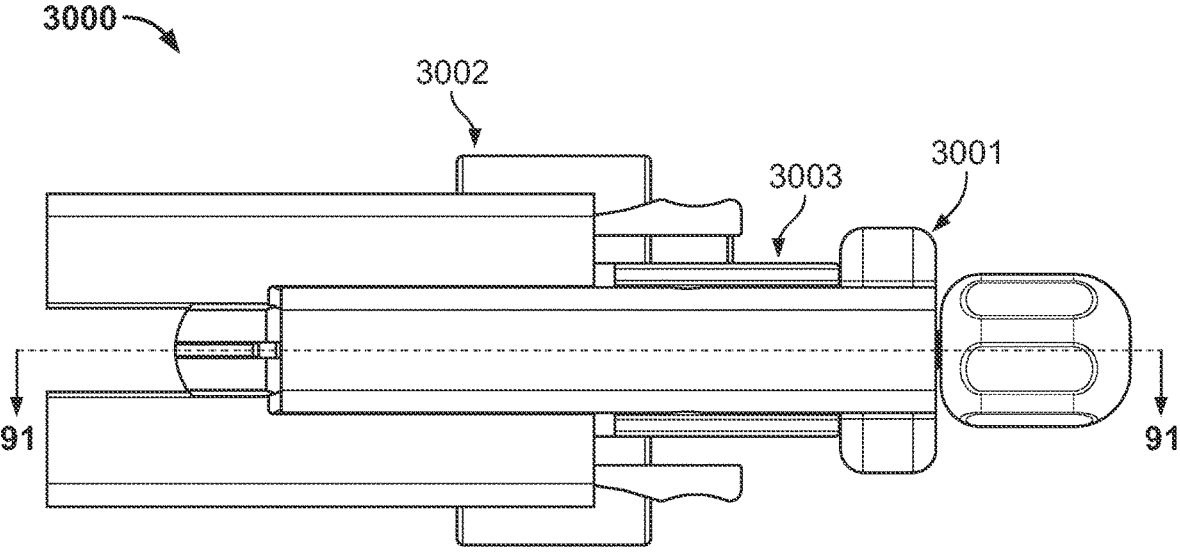
FIG. 90 is a bottom view of the compressor assembly of FIG. 84.

In some embodiments, the second end 2008 of the tibial trial 2000 can be inserted into the prepared joint space such that some or all portions of the one or more side faces 2018, superior face 2010, and/or posterior face 2016 engage with a least a portion of a patient's tibia, and some or all portions of the first end 2006, anterior face 2014, and inferior face 2012 are available to engage with tools of the TAR system. In some embodiments, a sight alignment tool 2900 (as described with reference to FIGS. 80-81) may be used to verify precise alignment of the tibial trial 2000 with respect to the patient's tibia or other suitable landmark. As will be described herein, the tibial trial 2000 may enable alignment in an anterior-posterior direction (while allowing for other degrees of freedom), and each of the trial base 2002 and trial face 2004 may further include various features to facilitate desirable positioning and referencing for other tools of the TAR procedure. Thus, the tibial trial 2000 may provide alignment and temporary fixation for the tools of the TAR system.

According to some embodiments, the trial base 2002 can include a superior face 2010 (see FIGS. 22 and 26) having various through-holes, through-slots, and other features for use with the tools and instruments of the TAR procedure. In some embodiments, the superior face 2010 may include a reference slot 2022 that indicates variable implant component sizes. In other embodiments, the reference slot 2022 may be used to maintain a desired position of the tibial trial 2000 against the prepared tibial surface, or facilitate dynamic positioning of the tibial trial 2000 over the course of the TAR procedure (e.g., by allowing the tibial trial 2000 to move medially-laterally while the trial 2000 maintains a fixed anterior-posterior position). In some embodiments, the superior face 2010 may include a reference, or access opening 2020, which forms a through-hole that enables access to the prepared tibial space (e.g., medullary cavity) in an inferior-superior direction.

In some embodiments, the access opening 2020 may form a generally circular shape, ovular shape, triangular shape, quadrilateral shape, X-shape, any suitable combination thereof, or any other suitable shape without departing from the principles of the disclosure. Additionally, in some embodiments, the access opening 2020 may be generally centered on the superior face 2010 with respect to the overall trial base 2002, while in other embodiments, the access opening 2020 may be offset in the anterior-posterior direction and/or the medial-lateral direction. For example, the access opening 2020 may be offset from center by about 1.0 to 2.0 mm, about 2.0 to 3.0 mm, about 3.0 to 4.0 mm, about 4.0 to 5.0 mm, about 5.0 to 6.0 mm, about 6.0 to 7.0 mm, or any suitable amount of offset without departing from the principles of this disclosure. In some embodiments, the trial base 2002 may include any suitable number of reference or access openings disposed on any suitable portion of the trial base 2002, without departing from the principles of this disclosure. In some embodiments, the access opening 2020 may be positioned based on patient specific anatomy without departing from the principles of this disclosure.

According to some embodiments, the inferior face 2012 (see FIGS. 23 and 27) may include one or more features for various tools and instruments to selectively engage with the tibial trial 2000 and/or provide access to the access opening 2020 mentioned above. For instance, accessible from the first end 2006, a portion of the inferior face 2012 may include a first channel 2024 and a second channel 2026. Various tools and instruments (e.g., distractor, right-angle drill plate, right-angle drill, spike broach, wire guide, reamer assembly, reamer locking tool, counter-torque lock, stem inserter and fastener guide, etc.) may each interact and engage with the first channel 2024 and/or the second channel 2026. For instance, the user may "slide" a tool configured for use with the tibial trial 2000 into one or both of the first channel 2024 and the second channel 2026, and "click" the tool into a desirable position using other features of the inferior face 2012, such as notches 2028 and/or receiving members, 2030, 2032. In some embodiments, the notches 2028 may be used to indicate implant feature sizing/positioning relative to the overall implant sizing/positioning. In some embodiments, a tool configured for use with the tibial trial 2000 may include one or more complementary notches, teeth, or other similar structures to facilitate secure positioning of the tool during the TAR procedure.

According to some embodiments, the side faces 2018 (see FIGS. 22, 23, 27, and 28) can include one or more notches 2028 that provide additional support for tools configured to engage with the first channel 2024 and the second channel 2026. For instance, a larger tool may require additional surface area for positioning or movement within the tibial trial 2000. Alternatively, the one or more notches 2028 may provide additional visibility while using tools of the TAR procedure.

According to some embodiments, the access opening 2020, first channel 2024, and second channel 2026 may be utilized with other instruments such that a user may form an intramedullary canal within a medullary cavity of the tibia as part of the TAR procedure. For instance, the tibial trial 2000 may provide the user with the ability to access a patient tibial shaft at a predetermined angle into the tibia, and/or the ability to rigidly lock accessory guidance instruments for further bone preparation.

In one non-limiting example, a joint distractor (described in detail below) can approach the tibial trial 2000 from the inferior face 2012 and/or first end 2006 and engage with internal portions of the tibial trial 2000 (e.g., first channel 2024; second channel 2026; receiving members 2030, 2032) and other tools (e.g., right-angle drill plate, which will be discussed with reference to FIGS. 57-59). Then, the user can engage portions to the joint distractor to distract the joint space, thus creating a "workspace" for other tools of the TAR procedure to access the access opening 2020.

In another non-limiting example, a drill (e.g., right-angle drill, which will be discussed with reference to FIGS. 40-55) can approach the tibial trial 2000 from the inferior face 2012 and/or first end 2006 and engage with internal portions of the tibial trial 2000 (e.g., first 2024 and second 2026 channels) and other tools (e.g., right-angle drill plate). Then, the user can drill through the access opening 2020 at a 90-degree angle to create one or more holes into the prepared tibial surface. This may be the first step toward forming the intramedullary canal into which a modular stem system 1000 can be inserted.

In another non-limiting example, a broach (e.g., spike broach, which will be discussed with reference to FIGS. 60-64) can approach the tibial trial 2000 from the inferior face 2012 and/or first end 2006 and engage with internal portions of the tibial trial 2000 (e.g., first 2024 and second 2026 channels) and other tools (e.g., wire guide, which will be discussed with reference to FIGS. 65-71). Then, the user can impact the broach upwards through the access opening 2020 and into the prepared tibial surface (over the previously drilled holes) to increase the size of the forming intramedullary canal that may serve as a guide for the next step-reaming.

In another non-limiting example, a reamer (e.g., flexible reamer assembly, which will be discussed with reference to FIGS. 72-78) can approach the tibial trial 2000 from the inferior face 2012 and/or first end 2006 and engage with internal portions of the tibial trial 2000 (e.g., first 2024 and second 2026 channels) and other tools (e.g., reamer locking tool, which will be discussed with reference to FIG. 79). Then, the user can ream upwards through existing cuts to complete formation of the intramedullary canal, verifying the progression of the reamer via other features of the tibial trial 2000 (e.g., viewing slot 2040).

In another non-limiting example, various tools designed for modular stem insertion (e.g., modular stem assembly, which will be discussed with reference to FIGS. 84-91) can approach the tibial trial 2000 from the inferior face 2012 and/or first end 2006 and engage with internal portions of the tibial trial 2000 (e.g., first 2024 and second 2026 channels) and other tools. Then, the user can insert the components of the stem portion 1020 into the prepared intramedullary canal in a step-wise fashion.

Figure 29:
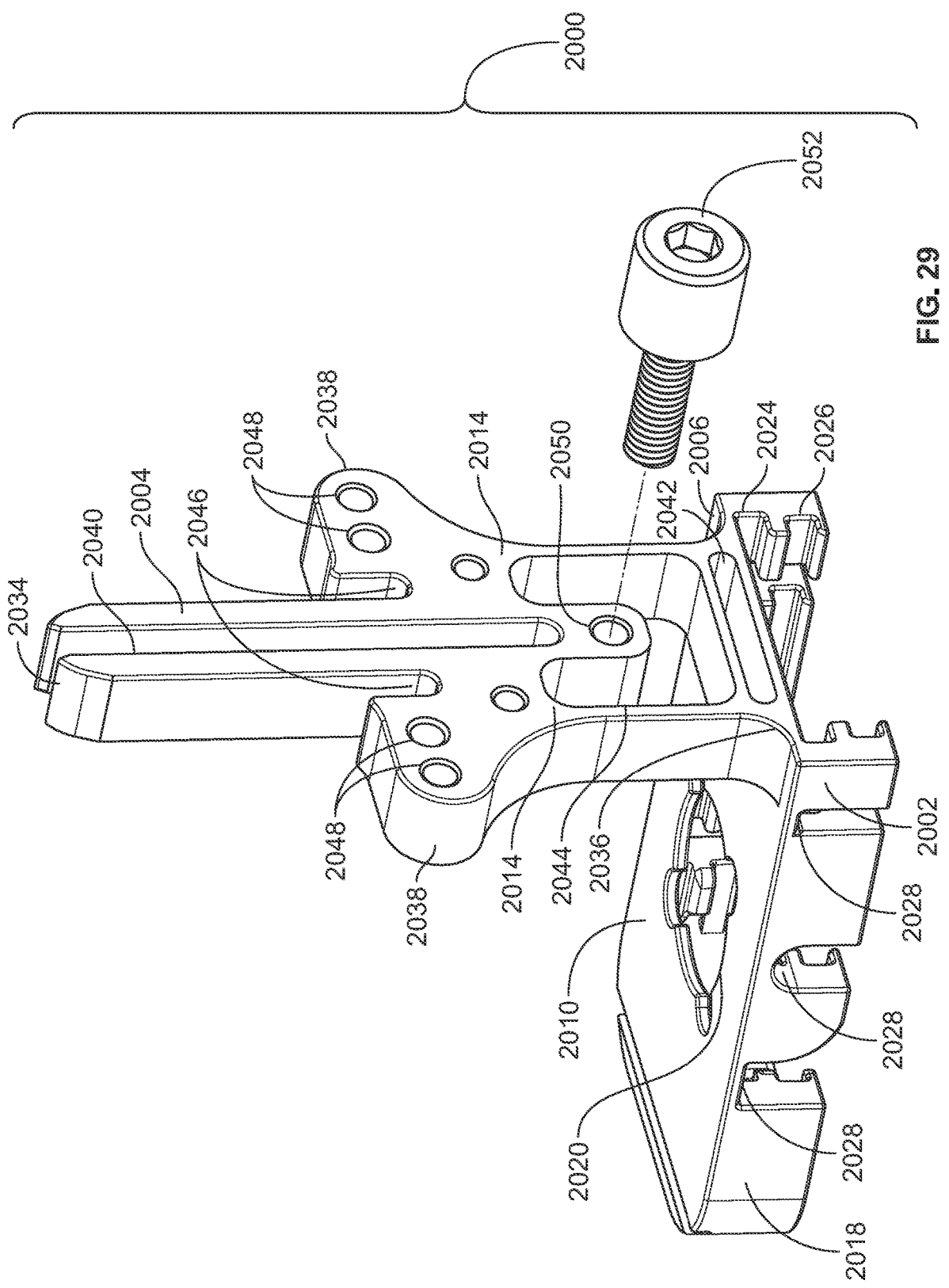
FIG. 29 is an exploded view of the exemplary tibial trial of FIG. 22.

According to some embodiments, the trial face 2004 can include an anterior face 2014 (see FIGS. 23 and 25) and a posterior face 2016 (see FIGS. 22 and 24) having various through-holes, through-slots, and other features for use with the tools and instruments of the TAR procedure. In some embodiments, the trial face 2004 may include a structural opening 2044 that provides visibility and/or access while inserting the tibial trial 2000 into the prepared ankle joint space. In other embodiments, the structural opening 2044 may further provide increased bone surface area for the user to make additional bone resections. In some embodiments, the structural opening 2044 may include a fastener opening 2050 (see FIGS. 22, 24, and 29) sized and configured to receive a fastener 2052. The fastener 2052 may be used to adjust and secure the positioning of the tibial trial 2000 against the underlying patient anatomy in an anterior-posterior direction (e.g., tightening and loosening the fastener 2052 may adjust the position of the tibial trial 2000 against patient anatomy). In some embodiments, the fastener 2052 may be reversibly removal with the fastener opening 2050 (see FIG. 29).

According to some embodiments, the trial face 2004 may include one or more arm portions 2038 disposed between the top end 2034 and the bottom end 2036. In some embodiments, the one or more arm portions 2038 may include one or more apertures 2048 that form through-holes between the anterior face 2014 and posterior face 2016, and that may be used with other tools to position the tibial trial 2000 in a desired orientation relative to a reference point. In one non-limiting example, guide wires, nails, screws, or any other suitable fastener can be inserted through the apertures 2048 to fix the tibial trial 2000 to underlying patient anatomy in a desired position. In some embodiments, the one or more arm portions may further include apertures 2049 that may be used to position other tools (such as a distractor, shown in FIGS. 30-39) in a desired orientation relative to the tibial trial 2000. In one non-limiting example, guide wires, nails, screws, bolts, pins, or any other suitable fastener can be inserted through the apertures 2049 to fix the distractor to the tibial trial 2000.

According to some embodiments, the trial face 2004 may include a viewing slot 2040 extending downwards from the top end 2034 to proximal the bottom end 2036. The viewing slot 2040 may provide ease of access for the user performing the TAR procedure by revealing portions of patient bone in a desired orientation and path relative to a reference point. In one non-limiting example, when viewed under X-ray imaging, the viewing slot 2040 may reveal the progressing path of a reamer, drill bit, guide wire, or any other suitable tool over the course of the TAR procedure. In some embodiments, the trial face 2004 may further include alignment slots 2042, 2046 that are used with other tools and instruments to position the tibial trial 2000 in a desired orientation relative to a reference point. In another non-limiting example, a tool (e.g., sight alignment tool) can mate with the alignment slot 2042 to visually indicate the initial alignment of the tibial trial 2000.

Figures 24, 25:
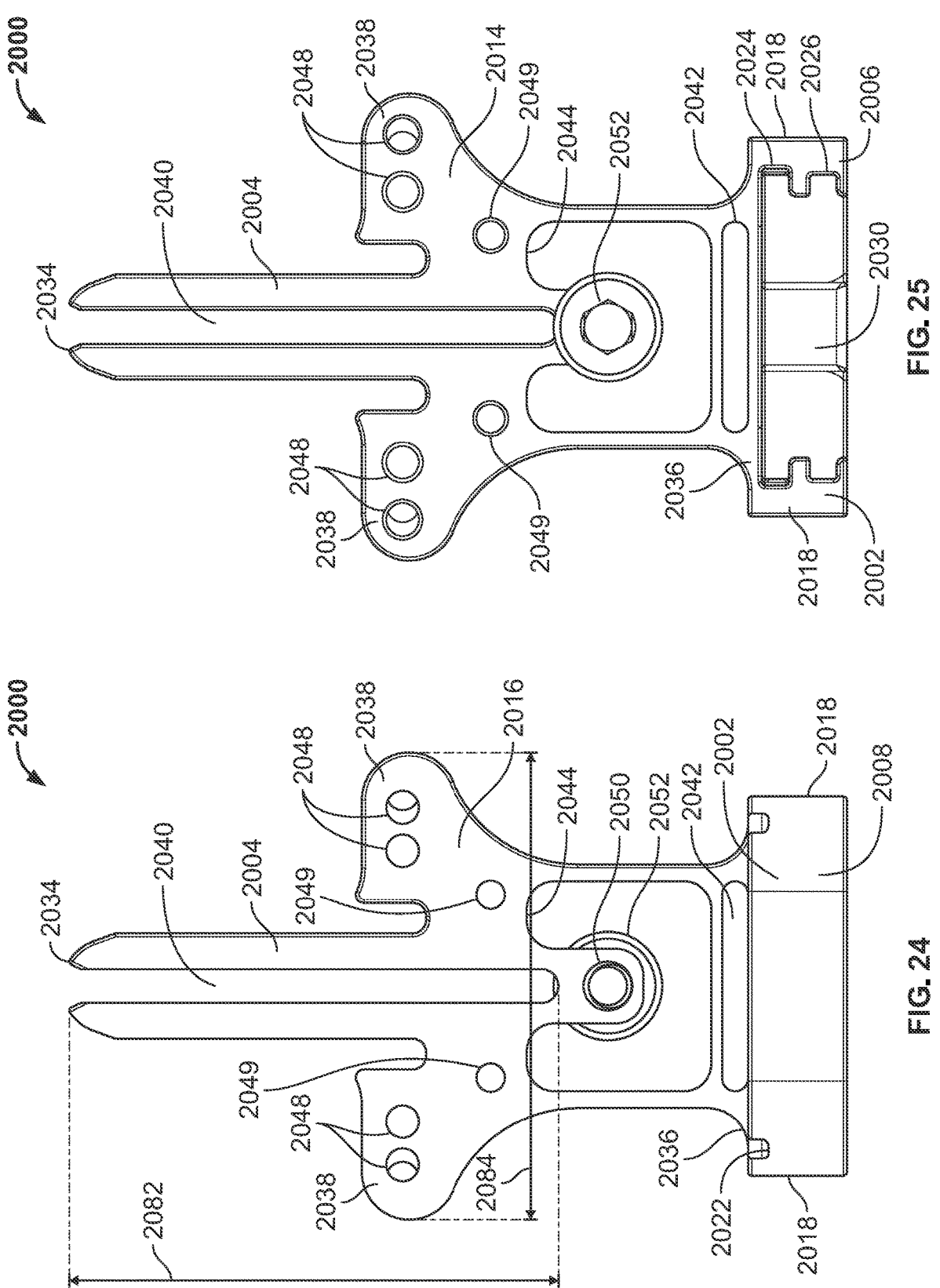
FIG. 24 is a rear view of the exemplary tibial trial of FIG. 22.
FIG. 25 is a front view of the exemplary tibial trial of FIG. 22.

With reference to FIG. 24, in some embodiments, the viewing slot 2040, can include a length 2082 measuring about 15.0 to 20.0 mm, about 20.0 to 25.0 mm, about 25.0 to 30.0 mm, about 30.0 to 35.0 mm, about 35.0 to 40.0 mm, about 40.0 to 50.0 mm, about 45.0 to 55.0 mm, about 50.0 to 60.0 mm, about 55.0 to 65.0 mm, about 60.0 to 70.0 mm, or any suitable length in accordance with the principles of this disclosure. In some embodiments, a length 2084 spanning between the one or more arm portions 2038 can measure about 15.0 to 25.0 mm, about 25.0 to 30.0 mm, about 30.0 to 35.0 mm, about 35.0 to 40.0 mm, about 40.0 to 50.0 mm, about 45.0 to 55.0 mm, about 50.0 to 60.0 mm, about 55.0 to 65.0 mm, about 60.0 to 70.0 mm, or any suitable length in accordance with the principles of this disclosure.

Figures 26, 27:
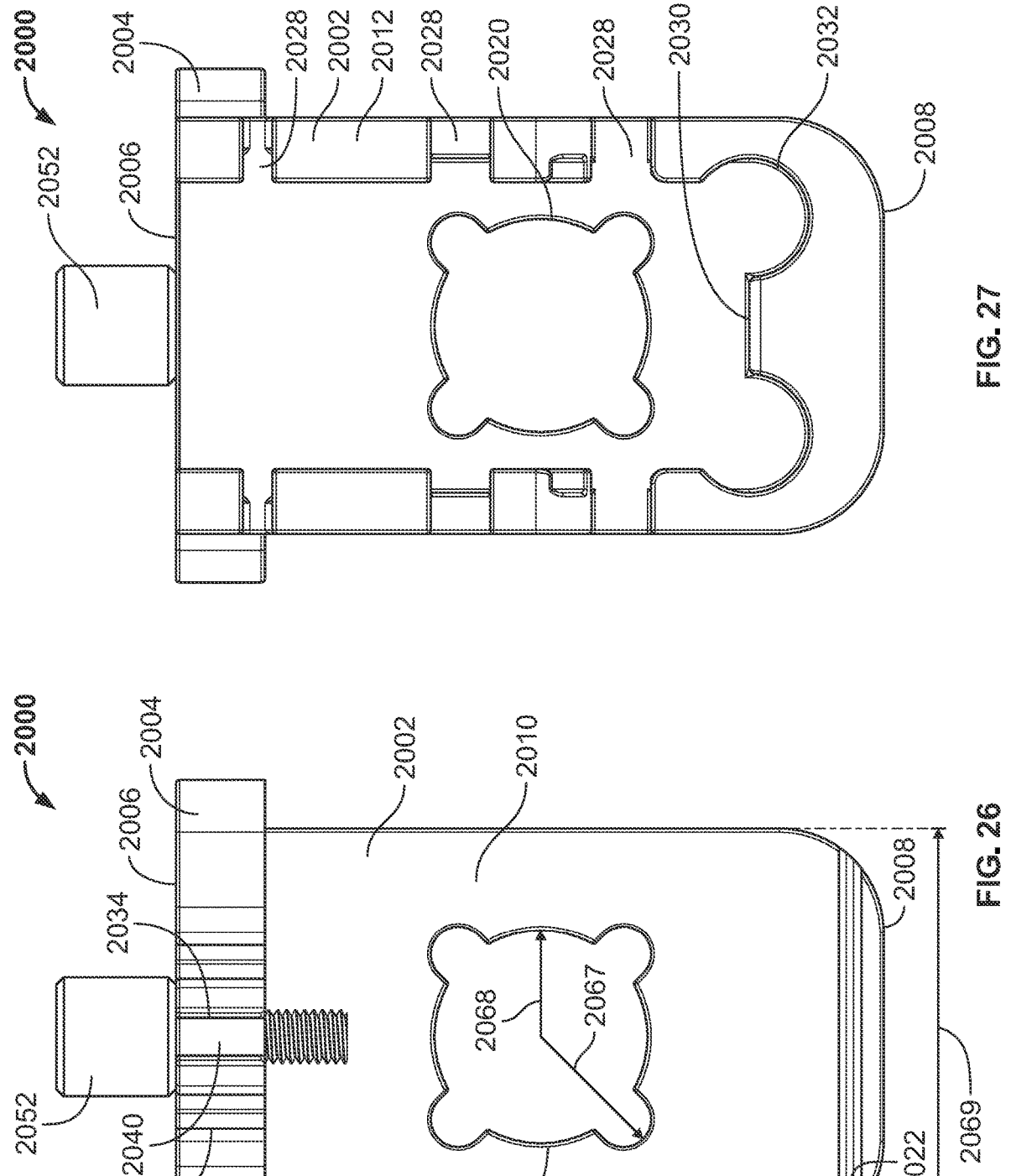
FIG. 26 is a top view of the exemplary tibial trial of FIG. 22.
FIG. 27 is a bottom view of the exemplary tibial trial of FIG. 22.

With reference to FIG. 26, in some embodiments, a first radius 2067 of the access opening 2020 can measure about 4.0 to 7.0 mm, about 6.0 to 9.0 mm, 8.0 to 11.0 mm, about 10.0 to 13.0 mm, about 12.0 to 15.0 mm, about 14.0 to 17.0 mm, about 16.0 to 19.0 mm, or any suitable radius in accordance with the principles of this disclosure. In some embodiments, a second radius 2068 of the access opening 2020 can measure about 2.0 to 5.0 mm, about 4.0 to 7.0 mm, about 6.0 to 9.0 mm, 8.0 to 11.0 mm, about 10.0 to 13.0 mm, about 12.0 to 15.0 mm, or any suitable radius in accordance with the principles of this disclosure. In some embodiments, a width 2069 of the trial base 2002 can measure about 10.0 to 15.0 mm, about 15.0 to 20.0 mm, about 20.0 to 25.0 mm, about 25.0 to 30.0 mm, about 35.0 to 40.0 mm, about 40.0 to 45.0 mm, about 45.0 to 50.0 mm, or any suitable length in accordance with the principles of this disclosure.

Figure 28:
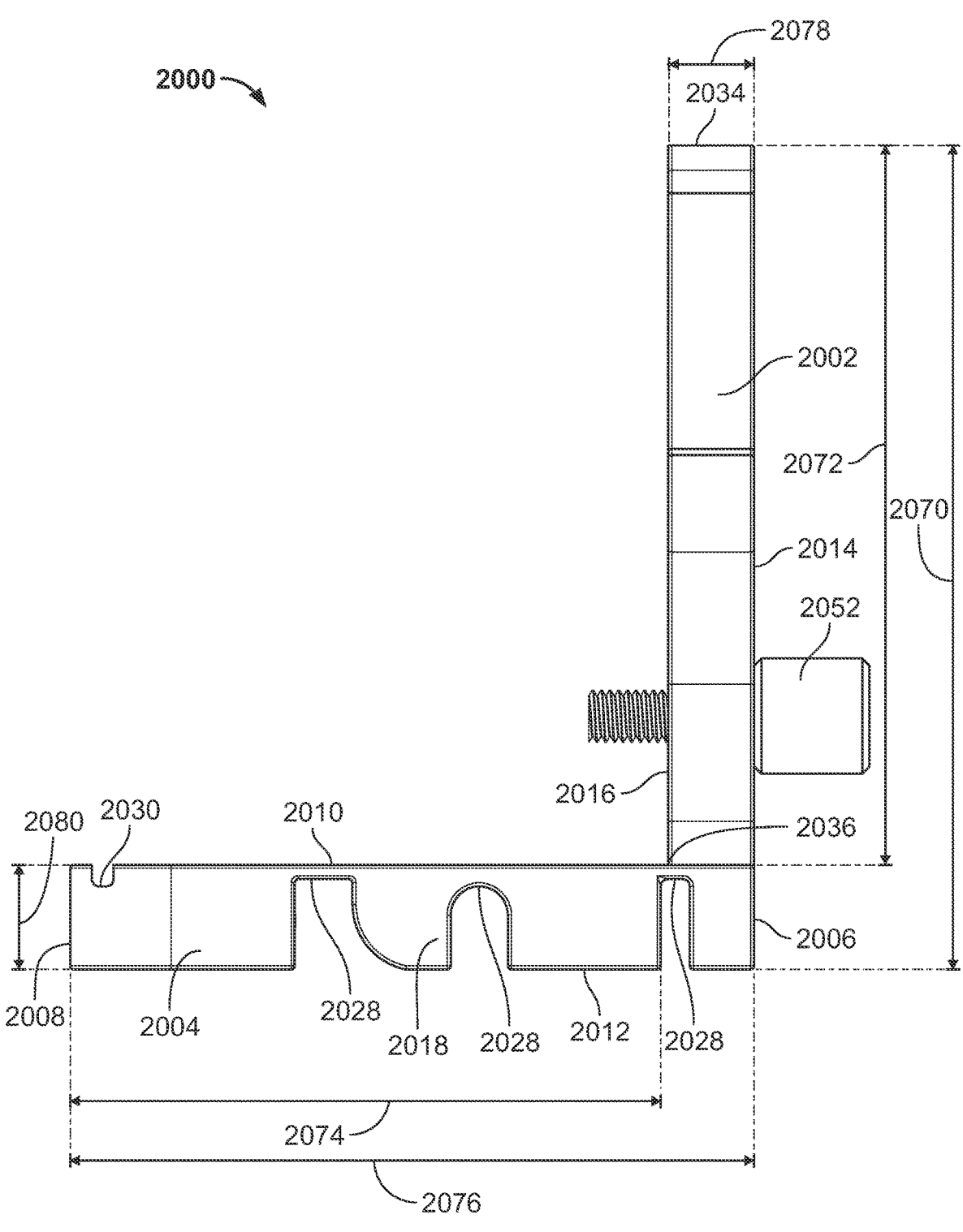
FIG. 28 is a side view of the exemplary tibial trial of FIG. 22.

With reference to FIG. 28, in some embodiments, the overall tibial trial 2000, measured from top end 2034 to a distal end of the inferior face 2012, can include an overall height 2070 measuring about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, about 65.0 to 75.0 mm, about 70.0 to 80.0 mm, or any suitable length in accordance with the principles of this disclosure. In some embodiments, the trial face 2004 can include a length 2072 from the top end 2034 to the bottom end 2036, measuring about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, or any suitable length in accordance with the principles of this disclosure. In some embodiments, trial face 2004 can include a thickness 2078 measured from a proximal end of the anterior face 2014 to a distal end of the posterior face 2016, measuring about 3.0 to 8.0 mm, about 5.0 to 10.0 mm, about 13.0 to 18.0 mm, about 15.0 to 20.0 mm, or any suitable length in accordance with the principles of this disclosure.

In some embodiments, the overall tibial trial 2000, measured from the first end 2006 to the second end 2008, can include an overall length 2074 measuring about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, or any suitable length in accordance with the principles of this disclosure. In some embodiments, the superior face 2010 includes a length 2076 measuring about 20.0 to 30.0 mm, about 25.0 to 35.0 mm, about 30.0 to 40.0 mm, about 35.0 to 45.0 mm, about 40.0 to 50.0 mm, about 45.0 to 55.0 mm, about 50.0 to 60.0 mm, about 55.0 to 65.0 mm, about 60.0 to 70.0 mm, or any suitable length in accordance with the principles of this disclosure. In some embodiments, the trial base 2002 can include a height 2080 measuring about 3.0 to 8.0 mm, about 5.0 to 10.0 mm, about 13.0 to 18.0 mm, about 15.0 to 20.0 mm, or any suitable height in accordance with the principles of this disclosure.

Distractor

Turning now to FIGS. 30-39, an exemplary distractor 2100 for use in the TAR procedure is shown, according to one embodiment. Generally, once the tibial trial 2000 is positioned on and secured to the prepared tibial surface, the user can install the distractor 2100 on the tibial trial 2000 to displace, or distract, the talus bone from the prepared tibial surface, thereby providing a "workspace" when using various tools and instruments of the TAR procedure. In embodiments, the distractor 2100 may comprise one or more materials including, but not limited to, various metals and/or polymers. In some embodiments, the distractor used for the TAR procedure may be static, wherein one or more components of the distractor are fixed in position. In other embodiments, the distractor may be dynamic such that the one or more components may change in position, according to user preference. In certain embodiments, use of the distractor may be optional for the TAR procedure (e.g., larger cuts made in the patient bone surfaces, smaller sized instrumentation, etc.).

In some embodiments, the distractor 2100 may comprise a distractor frame 2102 and a distractor plate 2104 coupled to the distractor frame 2102. As shown in the illustrated embodiment, the distractor frame 2102 may comprise a base 2106, first and second lateral supports 2108, 2110, and first and second upright members 2112, 2114. The base 2106 may be disposed at the posterior end 2116 of the distractor 2100, and the first and second uprights 2112, 2114 may be disposed at the anterior end 2118 of the distractor 2100. The distractor plate 2104 may include a superior surface 2120 (see FIGS. 30, 32-34, 37, and 39) and an inferior surface 2122 (see FIGS. 31, 33, 35, and 36).

Figure 30:
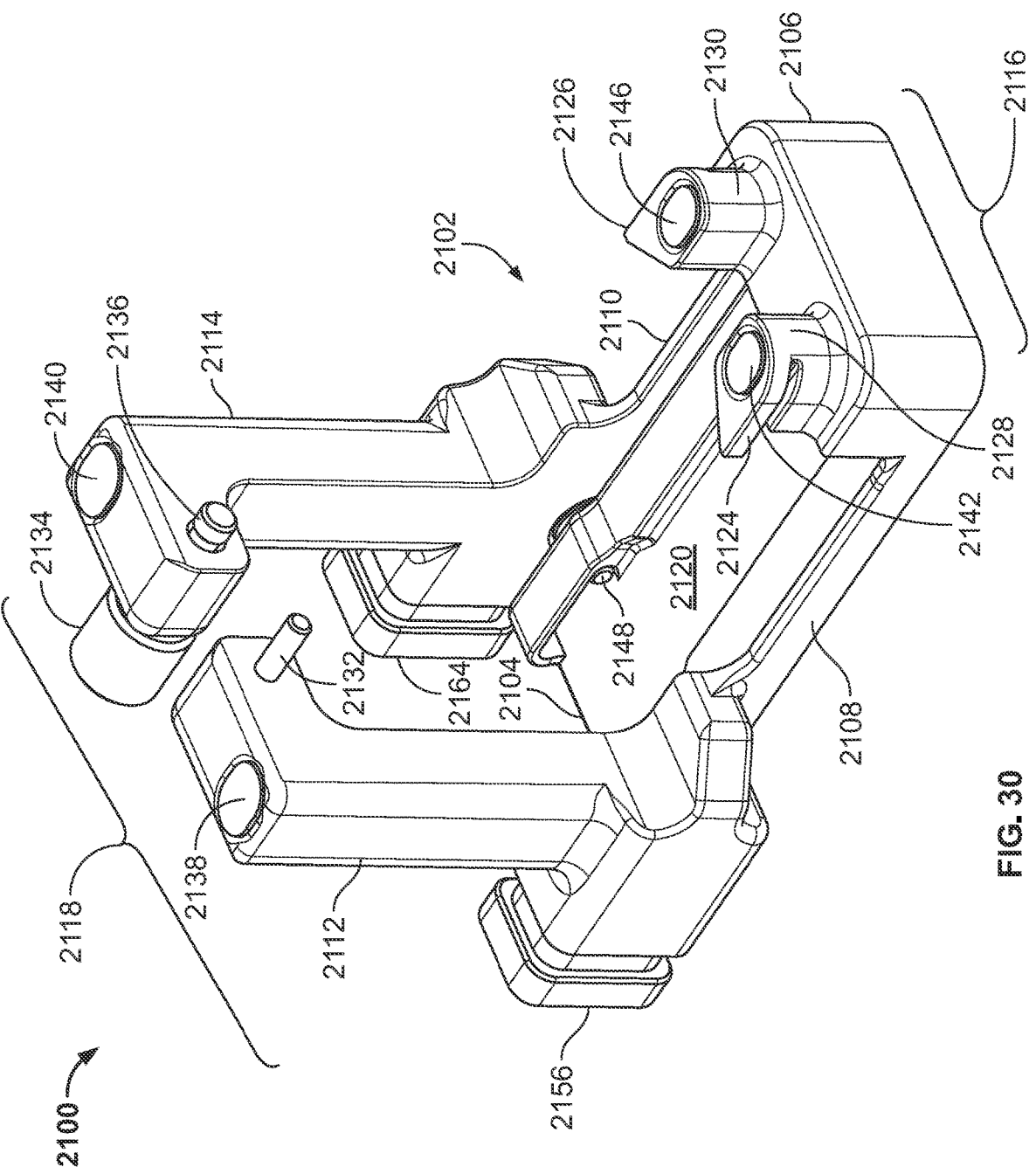
FIG. 30 is a rear perspective view of an exemplary distractor, in a first position, according to one embodiment.

With reference to FIG. 30, in some embodiments, the first upright 2112 may be connected to the base 2106 by the first lateral support 2108 such that the first upright 2112 extends from an anterior end of the first lateral support 2108. Similarly, the second upright 2114 may be connected to the base 2106 by the second lateral support 2110 such that the second upright 2114 extends from an anterior end of the second lateral support 2110. In some embodiments, the base 2106, the lateral supports 2108, 2110, and the uprights 2112, 2114 may be integrally formed such that the distractor frame 2102 is a single component. In other embodiments, one or more of the components of the distractor frame 2102 may be individually formed and subsequently connected to one or more other components to assemble the distractor frame 2102.

In some embodiments, the distractor frame 2102 may further comprise one or more locating components that are used to secure the distractor 2100 to the tibial trial 2000. For instance, the distractor frame 2102 may include first and second guide rails 2124, 2126 that are respectively supported by first and second guide rail supports 2128, 2130. As shown, the first and second guide rail supports 2128, 2130 extend from the base 2106. In some embodiments, the first and second guide rails 2124, 2126 may engage with or slide into the one or more channels 2024, 2026 of the tibial trial 2000 in order for the user to install the distractor 2100 onto the tibial trial 2000. In some embodiments, after engaging the first and second guide rails 2124, 2126 the one or more channels 2024, 2026, the distractor 2100 can be secured to the tibial trial 2000 with a snap-fit connection. For example, the user can position the first and second guide rail supports 2128, 2130 against receiving members 2030, 2032 on the trial base 2002 to form a snap-fit connection between the guide rail supports 2128, 2130 and the trial base 2002. In some embodiments, the first and second guide rails 2124, 2126 are alternatively arranged to engage and slide within the first channel 2024 of the tibial trial 2000 when installing the distractor 2100 onto the tibial trial 2000.

In some embodiments, the distractor frame 2102 may further comprise one or more locating pins 2132 that are used to prevent the distractor 2100 from moving relative to the tibial trial 2000. With reference to FIG. 30, the one or more locating pins 2132 may extend from the uprights 2112, 2114. In this regard, as the first and second guide rails 2124, 2126 slide into the one or more channels 2024, 2026, the one or more locating pins 2132 engage with the one or more corresponding holes and/or slots disposed on the trial face 2004 (e.g., apertures 2048, 2049). Thus, the one or more locating pins 2132 may prevent translation and/or rotation of the distractor 2100 relative to the tibial trial 2000.

In some embodiments, the distractor frame 2102 may be fastened to the trial face 2004. For example, with reference to FIG. 30, the distractor frame 2102 may include a threaded rod 2136 (or any other suitable fastener) extending from the first and/or second uprights 2112, 2114. In this regard, as the first and second guide rails 2124, 2126 engage with the one or more channels 2024, 2026, the threaded rod 2136 may engage with corresponding openings (e.g., apertures 2048, 2049) on the trial face 2004 to fasten the distractor 2100 to the tibial trial 2000. In one non-limiting example, the corresponding openings (e.g., apertures 2048, 2049) on the trial face 2004 may include female threads while the threaded rod 2136 may include complementary male threads. Thus, by turning a knob portion 2134 coupled to the threaded rod 2136 and disposed on an anterior side of the first and/or second uprights 2112, 2114, the user may selectively fasten the threaded rod 2136 with the openings on the trial face 2004 and coupled to the threaded rod 2136 to fasten the threaded rod 2136 to the female threads formed in the trial face 2004. For example, the user may turn the knob 2134 using a hexagonal wrench (see FIG. 31), a Phillips head screwdriver, a Torx® wrench, a flathead screwdriver, or any other type of fastening tool. In some embodiments, the distractor frame 2102 may comprise one or more other types of fasteners that can be used to fasten the distractor 2100 to the tibial trial 2000.

In some embodiments, when the distractor 2100 is installed on the tibial trial 2000, the inferior surface 2122 of the distractor plate 2104 contacts and/or engages the prepared talar surface such that the distractor plate 2104 is disposed between the prepared talar surface and the prepared tibial surface. Furthermore, while the distractor 2100 is installed on the tibial trial 2000, the workspace within which the user can access the prepared tibial surface (e.g., via the access opening 2020) may be defined as the space between the inferior face 2012 of the tibial trial 2000 and the superior surface 2120 of the distractor plate 2104. As will be described in more detail herein, in some embodiments, the distractor plate 2104 can be moved between a first position, or configuration, shown in FIGS. 30 and 31 and a second position, or configuration, shown in FIGS. 32 and 33 to distract the prepared tibial and talar surfaces.

In one non-limiting example, while the distractor plate 2104 is in the first, or closed, configuration (see FIGS. 30 and 31), the size of the workspace may be relatively narrow. In this regard, it may be difficult for the user to insert and articulate various surgical tools within the relatively small workspace while performing the TAR procedure. Accordingly, in some embodiments, the user can move the distractor plate 2104 from the closed configuration to the second, or open, configuration (see FIGS. 32 and 33) to increase the size of the workspace. In doing so, the user releases the distractor plate 2104 from distractor frame 2102 such that distractor plate 2104 pushes, or distracts, the prepared talar surface from the prepared tibial surface, thereby increasing the size of the workspace. For instance, FIG. 32 illustrates an increased size of the opening 2178 into the workspace.

According to some embodiments, the distractor plate 2104 may be coupled to the distractor frame 2102 by a plurality of rails that allow for the distractor plate 2104 to move relative to the distractor frame 2102. For example, with reference to FIGS. 32, 33, and 39, the distractor plate 2104 may be coupled to the distractor frame 2102 by one or more of a first anterior rail 2138, a second anterior rail 2140, a first posterior rail 2142, and a second posterior rail 2144. As will be described in more detail herein, notches may be formed in the posterior-facing surfaces of each of the anterior rails 2138, 2140 and the posterior rails 2142, 2144. For example, a plurality of notches 2139 may be formed in the posterior-facing surface of the first anterior rail 2138, a plurality of notches 2141 may be formed in the posterior-facing surface of the second anterior rail 2140, a plurality of notches 2143 may be formed in the posterior-facing surface of the first posterior rail 2142, and a plurality of notches 2145 may be formed in the posterior-facing surface of the second posterior rail 2144. In some embodiments, a length of the first and second anterior rails 2138, 2140 may be longer than a length of the first and second posterior rails 2142, 2144. In other embodiments, the length of the anterior rails 2138, 2140 may be approximately equal to the length of the posterior rails 2142, 2144.

In some embodiments, the first anterior rail 2138 may be coupled to the anterior end of the distractor plate 2104 using a first pin 2146 and the second anterior rail 2140 may be coupled to the anterior end of the distractor plate 2104 using a second pin 2148. Similarly, the first posterior rail 2142 may be coupled to the posterior end of the distractor plate 2104 using a third pin 2150 and the second posterior rail 2144 may be coupled to the posterior end of the distractor plate 2104 using a fourth pin 2152. As will be described in more detail herein, in some embodiments, the anterior end of the distractor plate 2104 may slide relative to the first and second pins 2146, 2148 and the posterior end of the distractor plate 2104 may rotate about the third and fourth pins 2150, 2152. In some embodiments, the distractor plate 2104 can be coupled to the anterior rails 2138, 2140 and posterior rails 2142, 2144 using a different type of coupling mechanism.

In some embodiments, while the distractor plate 2104 is in the first configuration (see FIGS. 30 and 31), the first anterior rail 2138 is housed, or contained, within an interior of the first upright 2112 and the second anterior rail 2140 is housed, or contained, within an interior of the second upright 2114. Similarly, while the distractor plate 2104 is in the first configuration (see FIGS. 30 and 31), the first posterior rail 2142 is housed, or contained, within an interior of the base 2106 and the first guide rail support 2128 and the second posterior rail 2144 is housed, or contained, within an interior of the base 2106 and the second guide rail support 2130.

In some embodiments, when the distractor plate 2104 moves from the first configuration to the second configuration (see FIGS. 32 and 33), the anterior rails 2138, 2140 release from the inferior ends of the uprights 2112, 2114 and move in the inferior direction relative to the distractor frame 2102. In this regard, as the anterior rails 2138, 2140 move in the inferior direction, the anterior end of the distractor plate 2104 is also moved in the inferior direction by the anterior rails 2138, 2140. Similarly, when the distractor plate 2104 moves from the first configuration to the second configuration, the posterior rails 2138, 2140 are respectively released from the base 2106 and move in the inferior direction relative to the distractor frame 2102. In this regard, as the anterior rails 2138, 2140 move in the inferior direction, the posterior end of the distractor plate 2104 is also driven in the inferior direction by the posterior rails 2142, 2144. In some embodiments, movement of the anterior rails 2138, 2140 may be independent from the movement of the posterior rails 2142, 2144.

In some embodiments, the anterior end of the distractor plate 2104 may be slide relative to the first and second pins 2146, 2148, and the posterior end of the distractor plate 2104 may rotate about the third and fourth pins 2150, 2152. In this regard, as the anterior rails 2138, 2140 and posterior rails 2142, 2144 move in the inferior direction, the distractor plate 2104 may rotate about the third and fourth pins 2150, 2152 and slide relative to the first and second pins 2146, 2148 such that the anterior end of the distractor plate 2104 moves further into the inferior direction than the posterior end of the distractor plate 2104. For example, with reference to FIG. 33 that shows the distractor plate 2104 in the open configuration, the anterior end of the distractor plate 2104 is displaced from the distractor frame 2102 further in the inferior direction than the posterior end of the distractor plate 2104. By rotating the distractor plate 2104 about the third and fourth pins 2150, 2152 and sliding the anterior end of the distractor plate 2104 further into the inferior direction along the first and second pins 2146, 2148, the path of the distractor plate 2104 corresponds to flexion of the ankle joint according to a normal ankle joint range of motion. In this regard, moving the distractor plate 2104 to the open configuration may distract the prepared talar surface from the prepared tibial surface in accordance with normal flexion of the ankle joint. In other embodiments, the pin configuration of the distractor 2100 may be reversible such that the distractor plate 2104 may rotate about the first and second pins 2146, 2148 and slide relative to the third and fourth pins 2150, 2152 such that the posterior end of the distractor plate 2104 moves further into the inferior direction than the anterior end of the distractor plate 2104.

In some embodiments, the distractor 2100 may comprise one or more release mechanisms that release the anterior rails 2138, 2140 from the uprights 2112, 2114 and/or release the posterior rails 2142, 2144 from the base 2106 and guide rail supports 2128, 2130. For example, with reference to FIGS. 38 and 39, the distractor 2100 may include a first anterior rail release 2154 configured to control the release of the first anterior rail 2138 from the first upright 2112. In some embodiments, the first anterior rail release 2154 can include a first pad 2156, a first arm 2158, a first pawl 2159, a first spring pin 1260, and a first spring 2161. As shown in FIG. 39, the first arm 2158 couples the first release pad 2156 to the first pawl 2159. Additionally, the first spring pin 2160 extends laterally outward from the posterior surface of the first pawl 2159. In some embodiments, the first release pad 2156, the first arm 2158, the first pawl 2159, and the first spring pin 2160 may be integrally formed as a single component. In other embodiments, one or more of the first release pad 2156, the first arm 2158, the first pawl 2159, and the first spring pin 2160 may be individually formed and coupled to one or more other components to assemble the first anterior rail release 2154.

Figure 38:
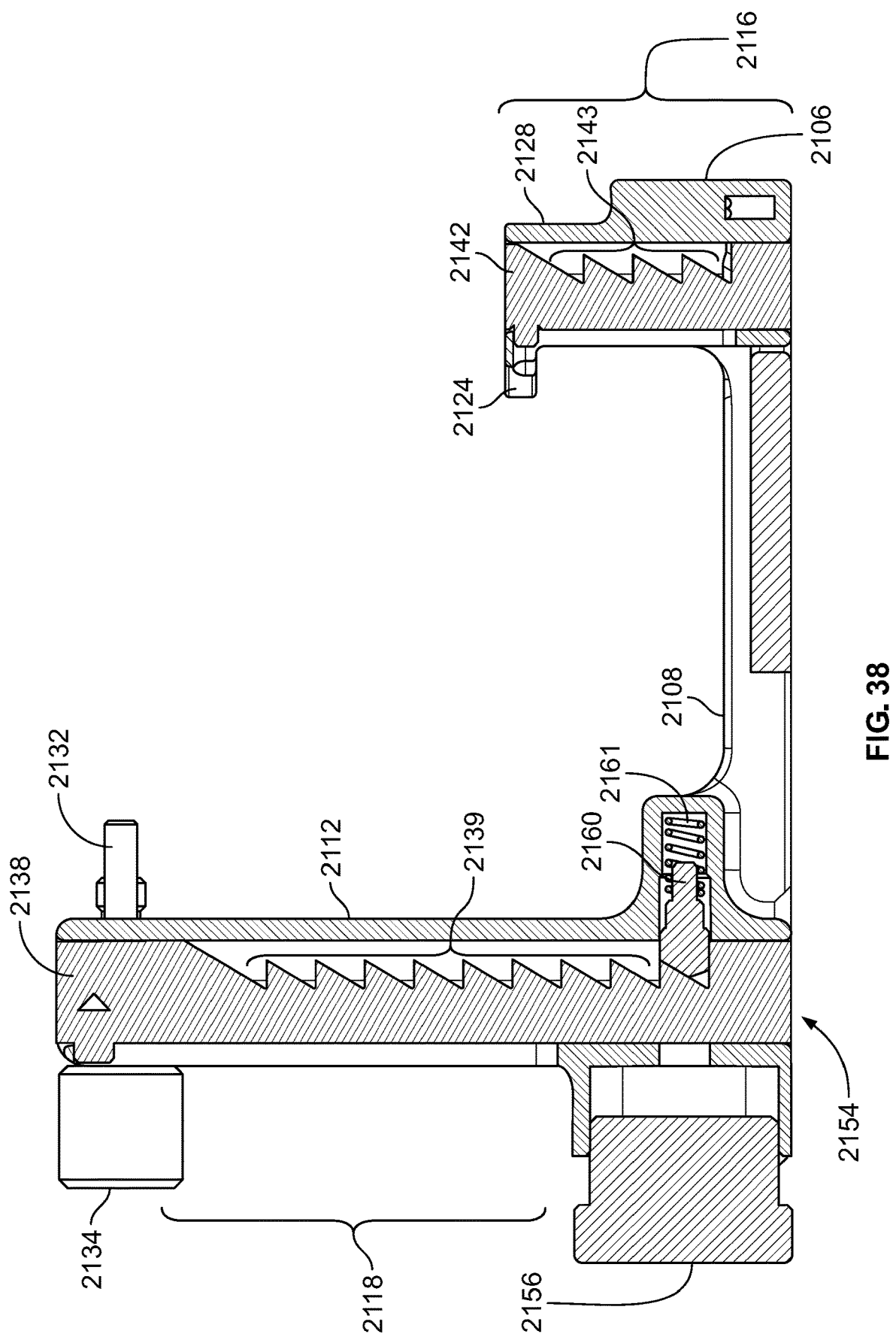
FIG. 38 is a cross-section view of the exemplary distractor of FIG. 37.
Figure 39:
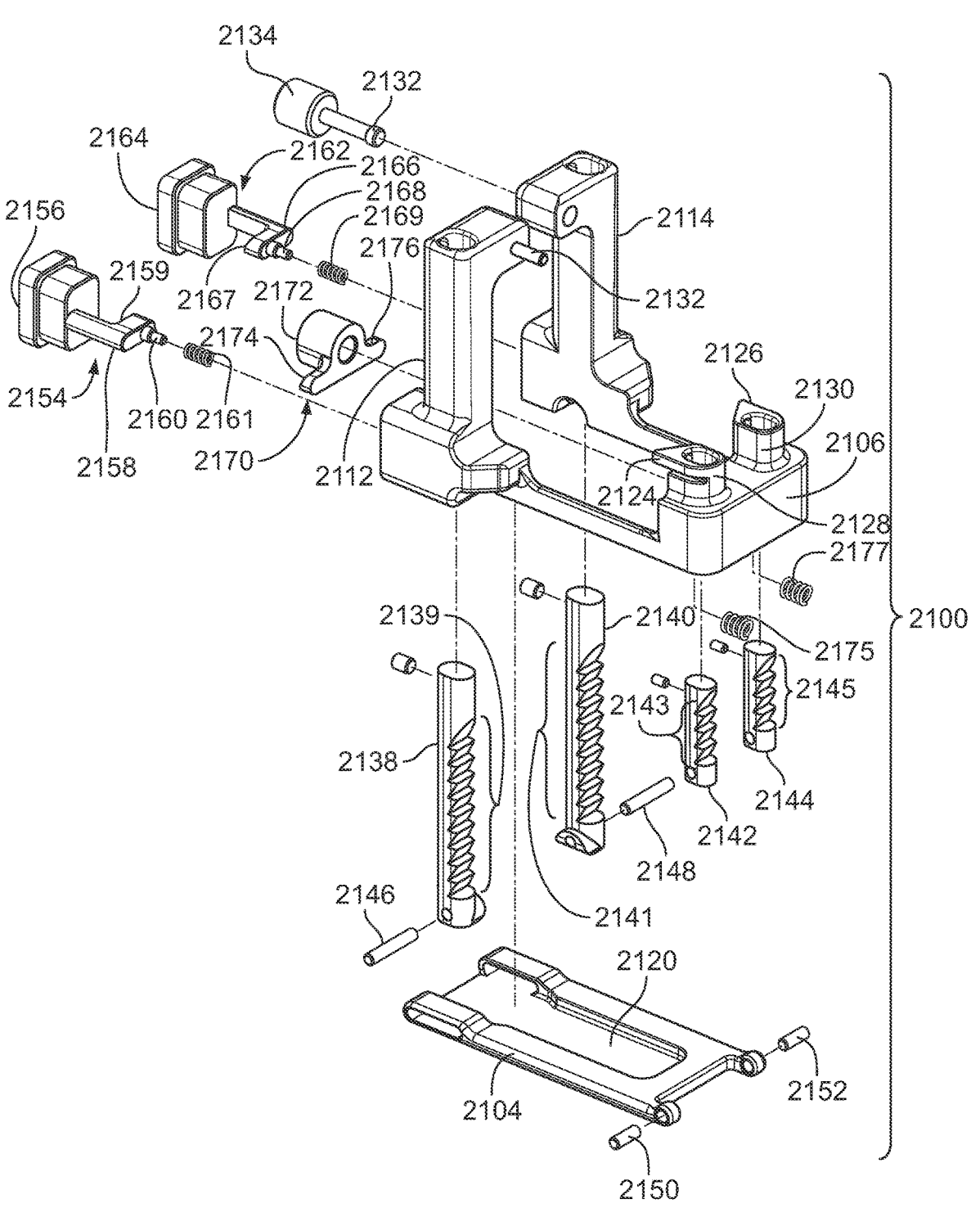
FIG. 39 is an exploded view of the exemplary distractor of FIG. 30.
Figure 40:
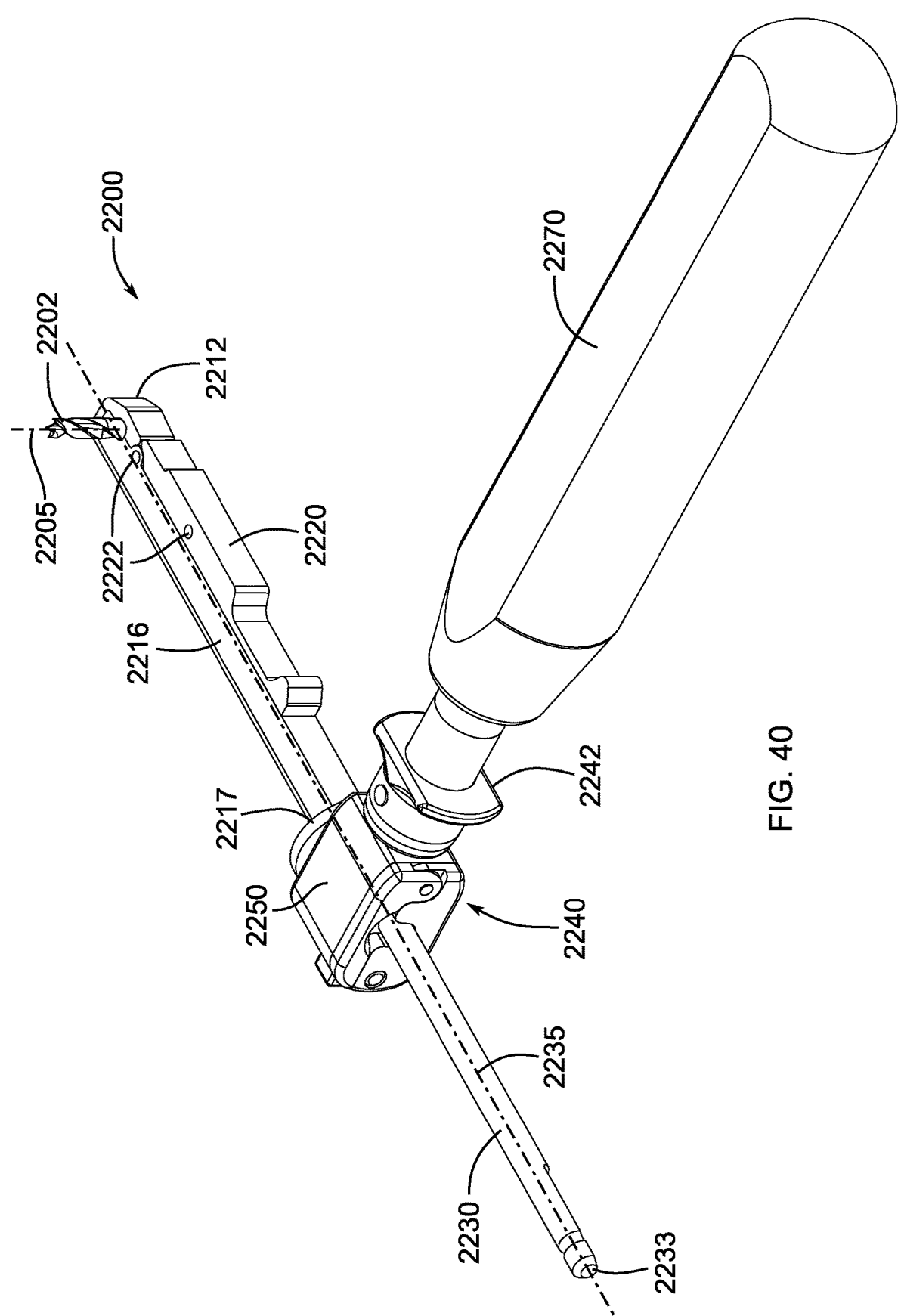
FIG. 40 is a rear perspective view of an exemplary right-angle drill, according to one embodiment.

FIG. 38 illustrates the first anterior rail release in a rest state, wherein no force is applied to the first release pad 2156. In some embodiments, the first release pad 2156 may be disposed on the anterior side of the first upright 2112 such that the first arm 2158 extends into the interior of the first upright 2112. In this regard, the first pawl 2159, which is connected to the posterior end of the first arm 2158, may reside within the interior of the first upright 2112. In some embodiments, while the first anterior rail release 2154 is in the rest state, the first spring 2161 may engage and apply a compressive force in the anterior direction to the first spring 2160, thereby biasing the first pawl 2159 in the anterior direction. In this regard, while in the rest state, the first pawl 2159 may engage a notch 2139 formed in the posterior-facing surface of the first anterior rail 2138, thereby preventing the first anterior rail 2138 from releasing from the bottom of the first upright 2112. To disengage the first pawl 2159 from the notch 2139 and release the first anterior rail 2138 from the bottom of the first upright 2112, the user may apply force to the first release pad 2156. This may cause the first pawl 2159 to move in the posterior direction and disengage the notch 2139, thereby allowing the first anterior rail 2138 to move in the inferior direction unimpeded by the first pawl 2159. Once the first anterior rail 2138 releases from the bottom of the first upright 2112 to a desired depth, the user may disengage the first release pad 2156 such that the compressive force of the first spring 2161 causes the first pawl 2159 to move in the anterior direction and re-engage a notch 2139 formed in the posterior-facing surface of the first anterior rail 2138. When the first pawl 2159 re-engages with a notch 2139 formed in the posterior-facing surface of the first anterior rail 2138, the first anterior rail 2138 may again be prevented from moving in the inferior and superior directions.

In some embodiments, the distractor 2100 may further comprise a second anterior rail release 2162 that is configured to control the release of the second anterior rail 2140 from the second upright 2114. In some embodiments, the second anterior rail release 2162 may be similar in construction and operation to the first anterior rail release 2154. For example, with reference to FIG. 39, the second anterior rail release 2162 can include a second release pad 2164, a second arm 2166, a second pawl 2167, a second spring pin 1268, and a second spring 2169. In some embodiments, the second arm 2166 couples the second release pad 2164 to the second pawl 2167. In some embodiments, the second spring pin 2168 extends laterally from the posterior surface of the second pawl 2167. In some embodiments, the second release pad 2164, the second arm 2166, the second pawl 2167, and the second spring pin 2168 may be integrally formed as a single component. In other embodiments, one or more of the second release pad 2164, the second arm 2166, the second pawl 2167, and the second spring pin 2168 may be individually formed and coupled to one or more other components to assemble the second anterior rail release 2162.

Figure 31:
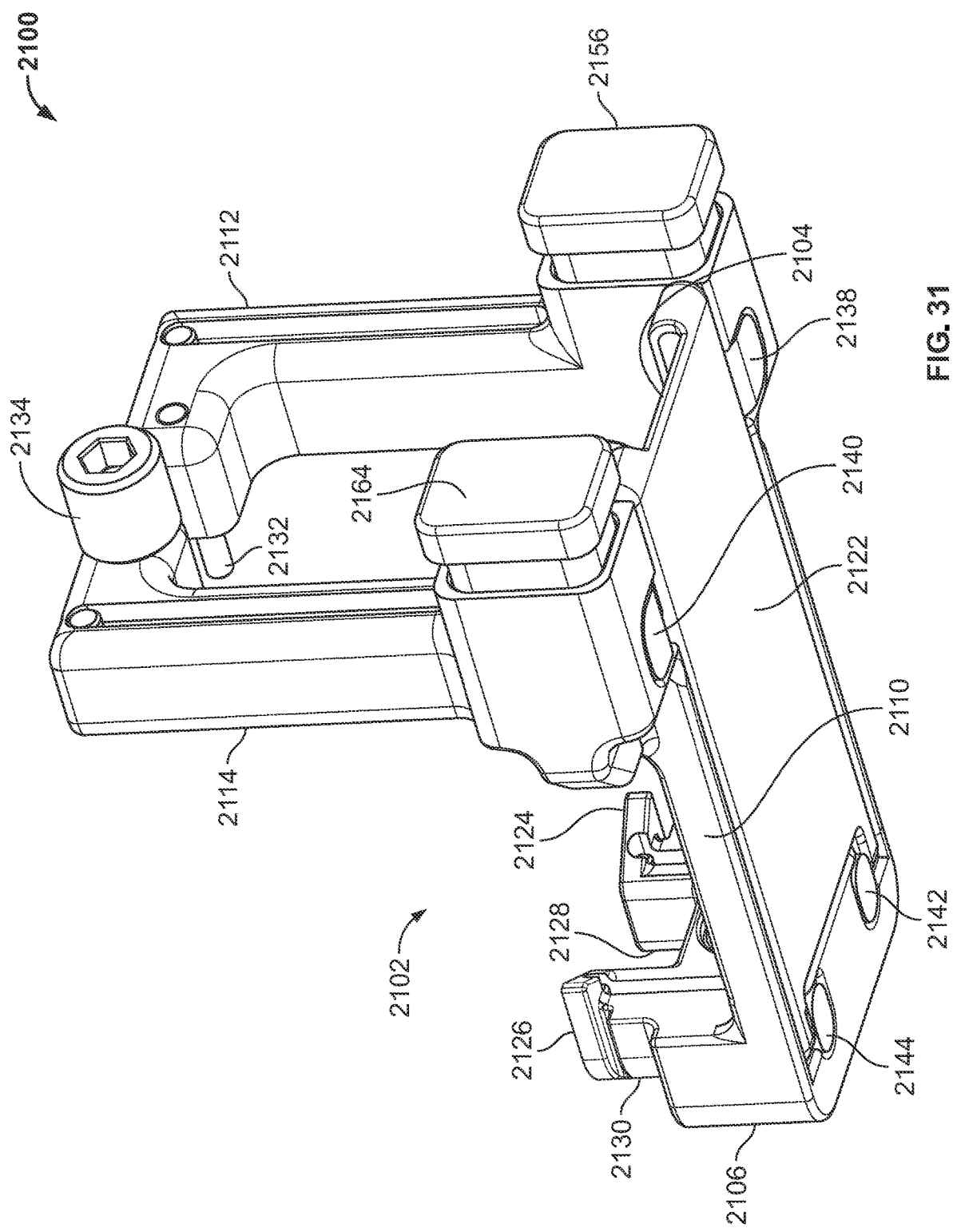
FIG. 31 is a front perspective view of the exemplary distractor of FIG. 30.
Figure 32:
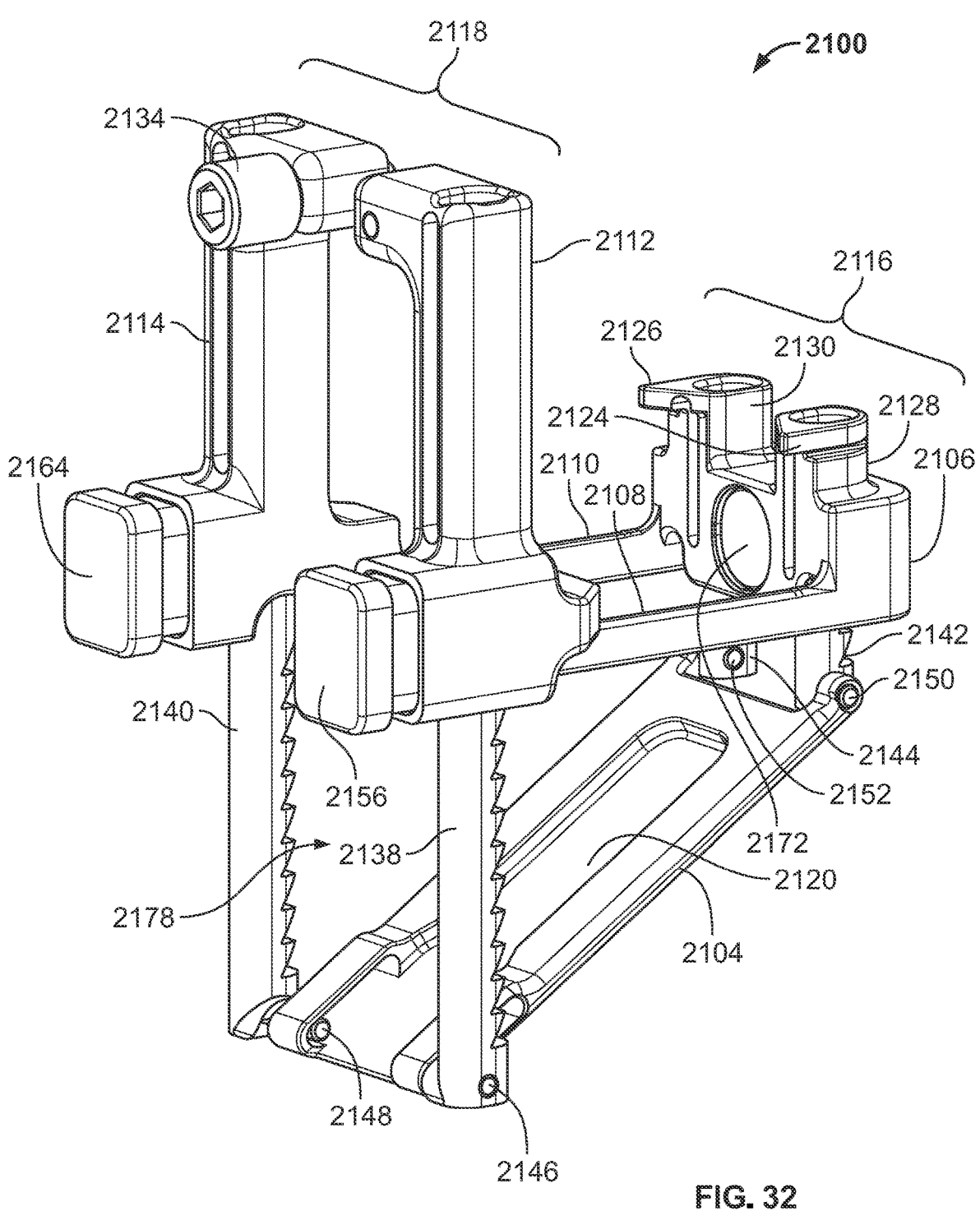
FIG. 32 is a front perspective view of the exemplary distractor, in a second position, according to one embodiment.

With reference to FIGS. 30 and 31, in some embodiments, the second release pad 2164 may be disposed on the anterior side of the second upright 2114 such that the second arm 2166 extends in the posterior direction into the interior of the second upright 2114. In this regard, the second pawl 2167, which is connected to the posterior end of the second arm 2166, resides within the interior of the second upright 2114. When the second anterior rail release 2162 is in a rest state, in which no force is applied to the second release pad 2164 in the posterior direction, the second spring 2169 engages and applies a compressive force in the anterior direction to the second spring 2168, thereby biasing the second pawl 2167 in the anterior direction. In this regard, while the second anterior rail release 2162 is in the rest state, the second pawl 2167 engages a notch 2141 formed in the posterior-facing surface of the second anterior rail 2140 thereby preventing the second anterior rail 2140 from releasing from the bottom of the second upright 2114. To disengage the second pawl 2167 from the notch 2141 and release the second anterior rail 2140 from the bottom of the second upright 2114, the user can apply force to the second release pad 2164 to move the second pawl 2167 in the posterior direction and disengage the notch 2141, thereby allowing the second anterior rail 2140 to move vertically in the inferior direction unimpeded by the first pawl 2167. Once the second anterior rail 2140 has been released from the bottom of the second upright 2114 to a desired depth, the user can disengage the second release pad 2164 such that the compressive force of the second spring 2169 causes the second pawl 2167 to move in the anterior direction and re-engage a notch 2141 formed in the posterior-facing surface of the second anterior rail 2140. When the second pawl 2167 is re-engaged with a notch 2141 formed in the posterior-facing surface of the second anterior rail 2140, the second anterior rail 2140 is once again prevented from moving vertically in the inferior and superior directions.

As described herein, in some embodiments, the distractor 2100 may include a first anterior rail release 2154 configured to release the first anterior rail 2138 from the bottom of the first upright 2112, and a second anterior rail release 2162 configured to release the second anterior rail 2140 from the bottom of the second upright 2114. However, in other embodiments, the distractor 2100 may include a single anterior rail release that can be used to release both the first anterior from the bottom of the first upright 2112 and the second anterior rail 2140 from the bottom of the second upright 2114. For example, in some embodiments, the distractor 2100 may include a single release pad that, when pressed, releases the first anterior rail 2138 from the bottom of the first upright 2112 and the second anterior rail 2140 from the bottom of the second upright 2114.

Figures 34, 35:
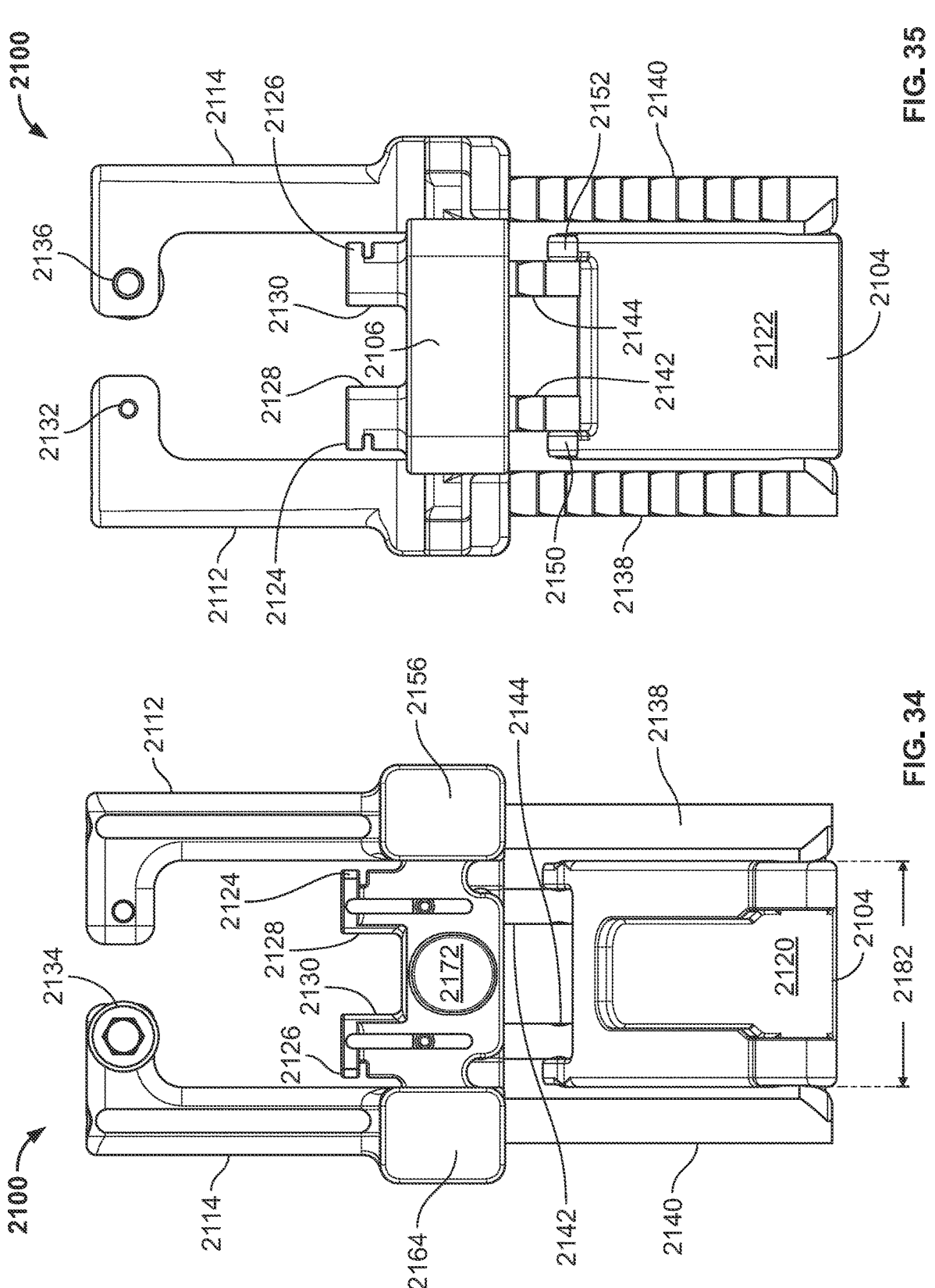
FIG. 34 is a rear view of the exemplary distractor of FIG. 32.
FIG. 35 is a front view of the exemplary distractor of FIG. 32.
Figure 36:
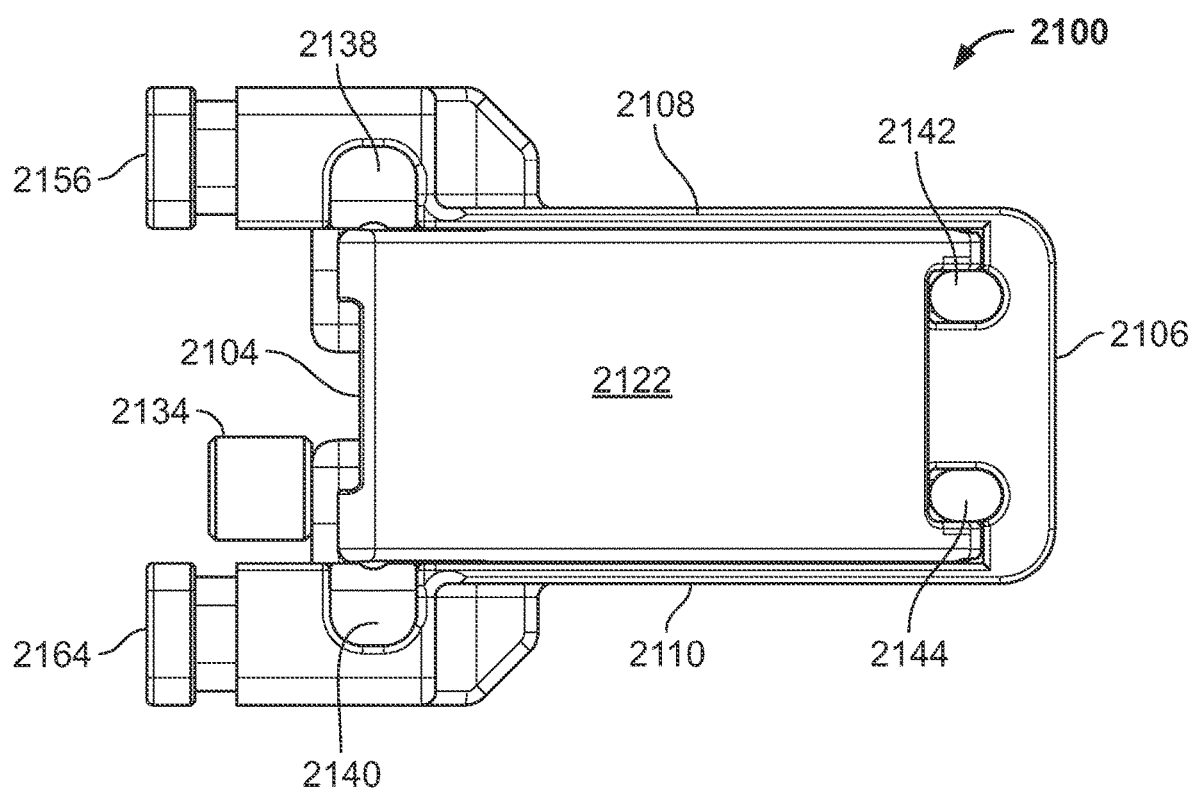
FIG. 36 is a bottom view of the exemplary distractor of FIG. 32.
Figure 37:
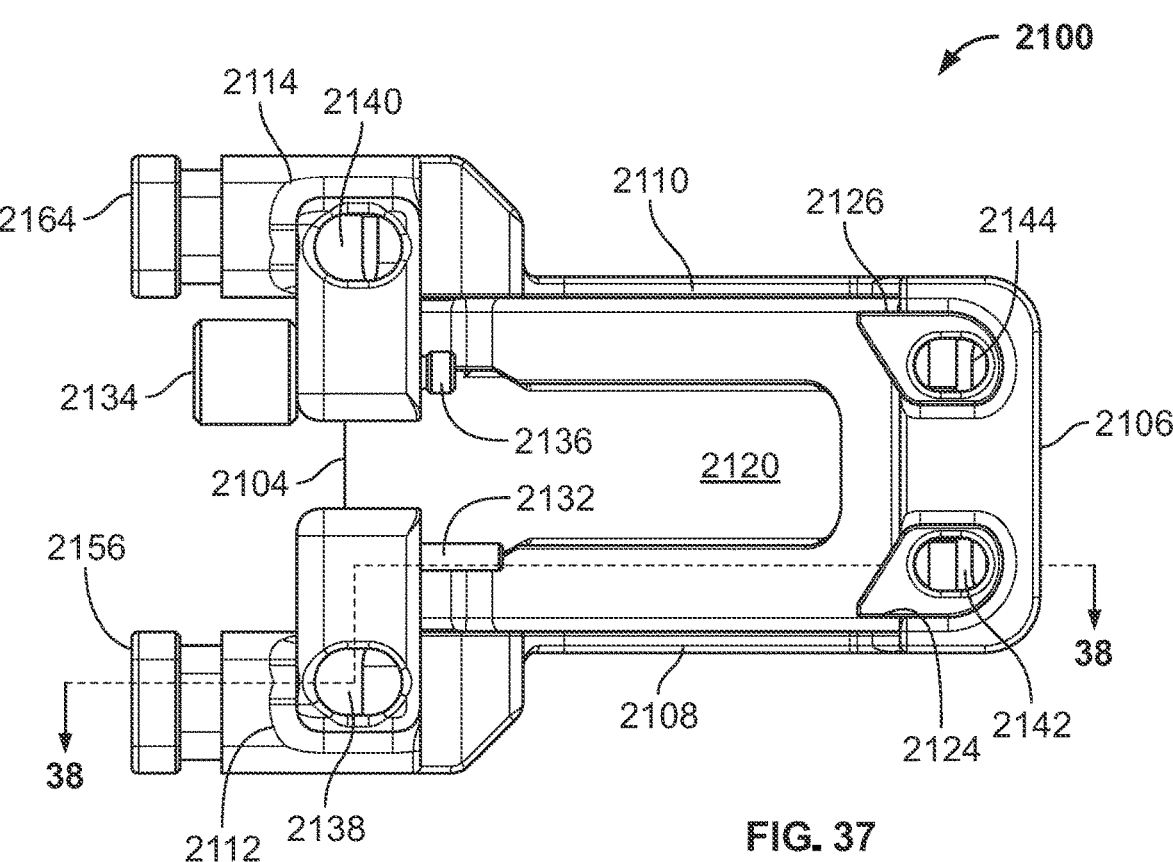
FIG. 37 is a top view of the exemplary distractor of FIG. 32.

In some embodiments, the distractor 2100 may further comprise a posterior rail release 2170 configured to control the release of the first and second posterior rails 2142, 2144 from the bottom of the base 2106. For example, with reference to FIG. 39, the posterior rail release 2170 can include a button 2172, a third pawl 2174, a third spring 2175, a fourth pawl 2176, and a fourth spring 2177. In some embodiments, the third pawl 2174 and the fourth pawl 2176 are coupled to the button 2172, extending laterally in opposite directions. In some embodiments, the button 2172, the third pawl 2174, and the fourth pawl 2176 can be integrally formed as a single component. In other embodiments, one or more of the button 2172, the third pawl 2174, and the fourth pawl 2176 can be individually formed and coupled to one or more other components to assemble the posterior rail release 2170. With reference to FIGS. 32 and 34, the button 2172 may be accessible through the anterior-facing surface of the base 1206. For example, an opening may be formed in the anterior-facing surface of the base 2106 to expose the button 2172 to the exterior of the base 1206.

In some embodiments, when the posterior rail release 2170 is in a rest state (e.g., wherein no force is applied to the button 2172 in the posterior direction), the third spring 1275 may engage and apply a compressive force in the anterior direction to the third pawl 2174, thereby biasing the third pawl 2174 in the anterior direction. Similarly, when the posterior rail release 2170 is in the rest state, the fourth spring 1277 may engage and apply a compressive force in the anterior direction to the fourth pawl 2176, thereby biasing the fourth pawl 2176 in the anterior direction. In this regard, while in the rest state, the third pawl 2174 may engage a notch 2143 formed in the posterior-facing surface of the first posterior rail 2142 thereby preventing the first posterior rail 2142 from releasing from the bottom of the base 2106. Similarly, while in the rest state, the fourth pawl 2176 engages a notch 2145 formed in the posterior-facing surface of the second posterior rail 2144 thereby preventing the second posterior rail 2144 from releasing from the bottom of the base 2106. To disengage the third pawl 2174 from the notch 2143 and the fourth pawl 2176 from the notch 2145, the user may apply force to the button 1272 in the posterior direction. This may cause the third and fourth pawls 2174, 2176 to disengage the notches 2143, 2145, respectively, thereby allowing the first and second posterior rails 2142, 2144 to move in the inferior direction.

In some embodiments, once the posterior rails 2142, 2144 have been released from the bottom of the base 2106 to a desired depth, the user can disengage the button 1272 such that the compressive force of the third spring 2175 causes the third pawl 2174 to re-engage a notch 2143 formed in the posterior-facing surface of the first posterior rail 2142 and the compressive force of the fourth spring 2177 causes the fourth pawl 2176 to re-engage a notch 2145 formed in the posterior-facing surface of the second posterior rail 2144. When the third pawl 2174 is re-engaged with a notch 2143 formed in the posterior-facing surface of the first posterior rail 2142 and the fourth pawl 2176 is re-engaged with a notch 2145 formed in the posterior-facing surface of the second posterior rail 2144, the posterior rails 2142, 2144 may be prevented from moving in the inferior and superior directions.

As described herein, in some embodiments, the distractor 2100 may include a single posterior rail release 2170 configured to release the first and second posterior rails 2142, 2144 from the bottom of the base 2106. However, in other embodiments, the distractor 2100 may include a first posterior rail release configured to release the first posterior rail 2142 from the bottom of the base 2106 and a second, separate, posterior rail release configured to release the second posterior rail 2144 from the bottom of the base 2106. For example, in some embodiments, the distractor 2100 may include a first button that, when pressed, releases the first posterior rail 2142 from the bottom of the base 2106 and a second button that, when pressed, releases the second posterior rail 2144 from the bottom of the base 2106. In other embodiments, the distractor 2100 may include a single rail release that can be used to release the first anterior from the bottom of the first upright 2112, the second anterior rail 2140 from the bottom of the second upright 2114, and the posterior rails 2142, 2144 from the bottom of the base 2106. For example, in some embodiments, the distractor 2100 may include a single release pad that, when pressed, releases the first anterior rail 2138 from the bottom of the first upright 2112, releases the second anterior rail 2140 from the bottom of the second upright 2114, and releases the posterior rails 2142, 2144 from the bottom of the base 2106.

As described herein, in some embodiments, a user may (1) apply force to the first release pad 2156 to release the first anterior rail 2138 from the bottom of the first upright 2112; (2) apply force to the second release pad 2164 to release the second anterior rail 2140 from the bottom of the second upright 2114; and (3) apply force to the button 2172 to release the posterior rails 2142, 2144 from the bottom of the base 2106. In this regard, the user can move the distractor plate 2104 from the first configuration (see FIGS. 30 and 31) to the second configuration (see FIGS. 32 and 33) by applying force to one or more of the first release pad 2156, the second release pad 2164, and the button 2172. Thus, the user may distract the prepared talar surface from the prepared tibial surface with the distractor plate 2104. In some embodiments, the user may set the distractor plate 2104 to one or more intermediate configurations between the first configuration and the second configuration. For example, the user may apply force to one or more of the first release pad 2156, the second release pad 2164, and the button 2172 to move the distractor plate 2104 to a position that is between the first configuration and the second configuration. Subsequently, the user may disengage the one or more of the first release pad 2146, the second release pad 2164, and the button 2172 to set the distractor plate 2104 in the position that is between the first configuration and the second configuration. In some embodiments, the position of the distractor plate 2104 may be fixed and/or rigid relative to the distractor frame 2102.

Figure 33:
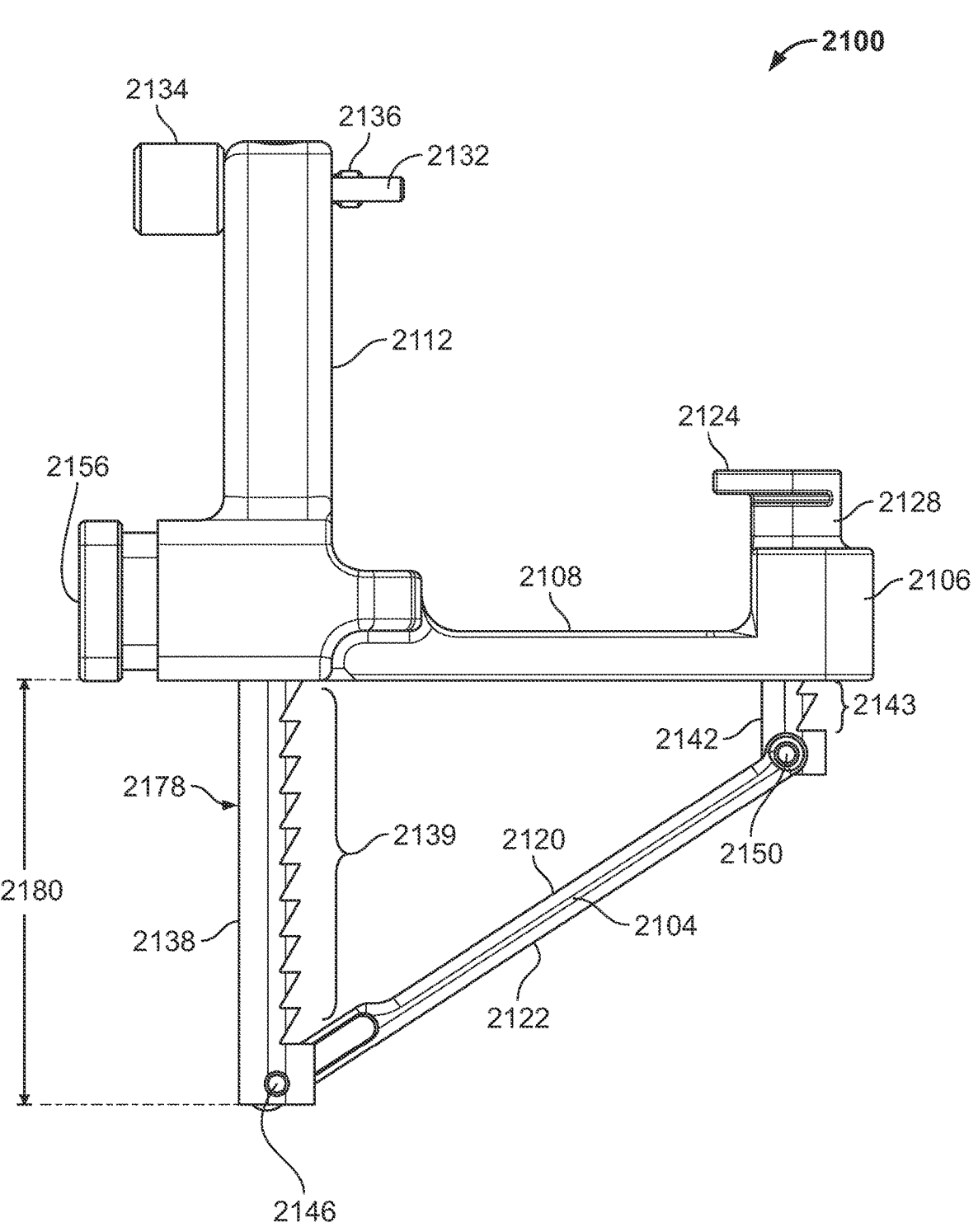
FIG. 33 is a side view of the exemplary distractor of FIG. 32.

With reference to FIG. 33, in some embodiments, the length of the opening 2178 into the workspace defined between the inferior surface of the tibial trial 2000 and the superior surface 2120 of the distractor plate 2104 can be extended by a length 1280 measuring about 15.0 to 20.0 mm, about 20.0 to 25.0 mm, about 25.0 to 30.0 mm, about 30.0 to 35.0 mm, about 35.0 to 40.0 mm, about 40.0 to 50.0 mm, about 45.0 to 55.0 mm, about 50.0 to 60.0 mm, about 55.0 to 65.0 mm, about 60.0 to 70.0 mm, or any other suitable length in accordance with the principles of this disclosure when the distractor plate 2104 is moved from the first configuration to the second configuration.

With reference to FIG. 34, in some embodiments, the opening 2178 into the workspace defined between the inferior surface of the tibial trial 2000 and the superior surface 2120 of the distractor plate 2104 can have a width 1282 measuring about 10.0 to 15.0 mm, about 15.0 to 20.0 mm, about 20.0 to 25.0 mm, about 25.0 to 30.0 mm, about 30.0 to 35.0 mm, about 35.0 to 40.0 mm, about 40.0 to 50.0 mm, about 45.0 to 55.0 mm, about 50.0 to 60.0 mm, about 55.0 to 65.0 mm, about 60.0 to 70.0 mm, about 70.0 to 80.0 mm, or any other suitable length in accordance with the principles of this disclosure. The width 1282 corresponds to, for example, the lateral distance between the first anterior rail 2138 and the second anterior rail 2140.

Right-Angle Drill

Referring now to FIGS. 40, 41A, 42-47, one embodiment of a right-angle drill for use in the TAR procedure is shown. Generally, the right-angle drill may permit a user to drill one or more holes into the prepared tibial surface at regions that may be difficult to reach using a traditional drill. For example, the user may use the right-angle drill to begin forming the intramedullary canal in the distal end of the medullary cavity of the prepared tibial surface. In particular, FIGS. 40, 41A, 42-47 show one embodiment of a swivel door right-angle drill 2200 in accordance with the principles of this disclosure.

Figure 46:
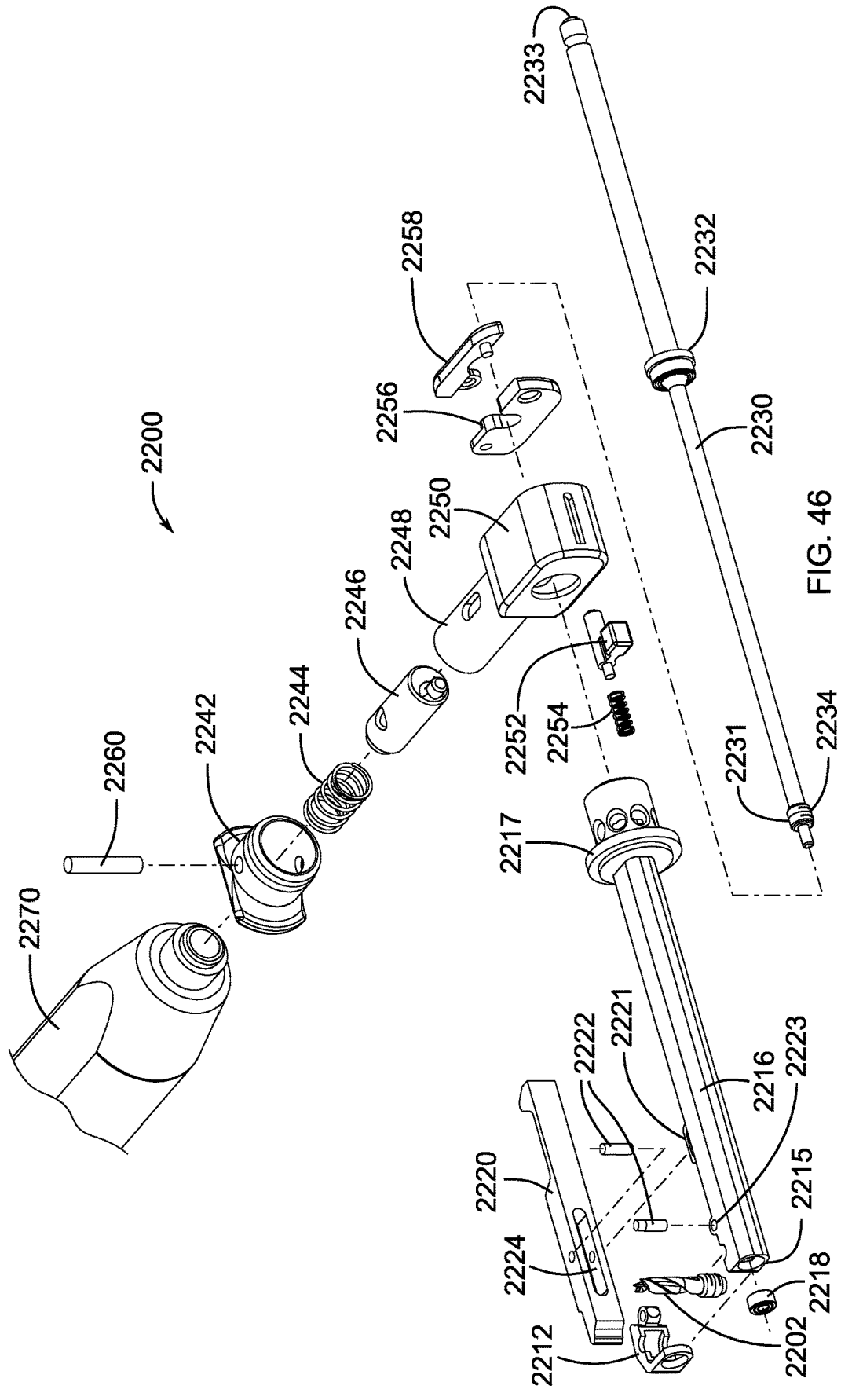
FIG. 46 is an exploded view of the exemplary right-angle drill of FIG. 40.
Figure 47:
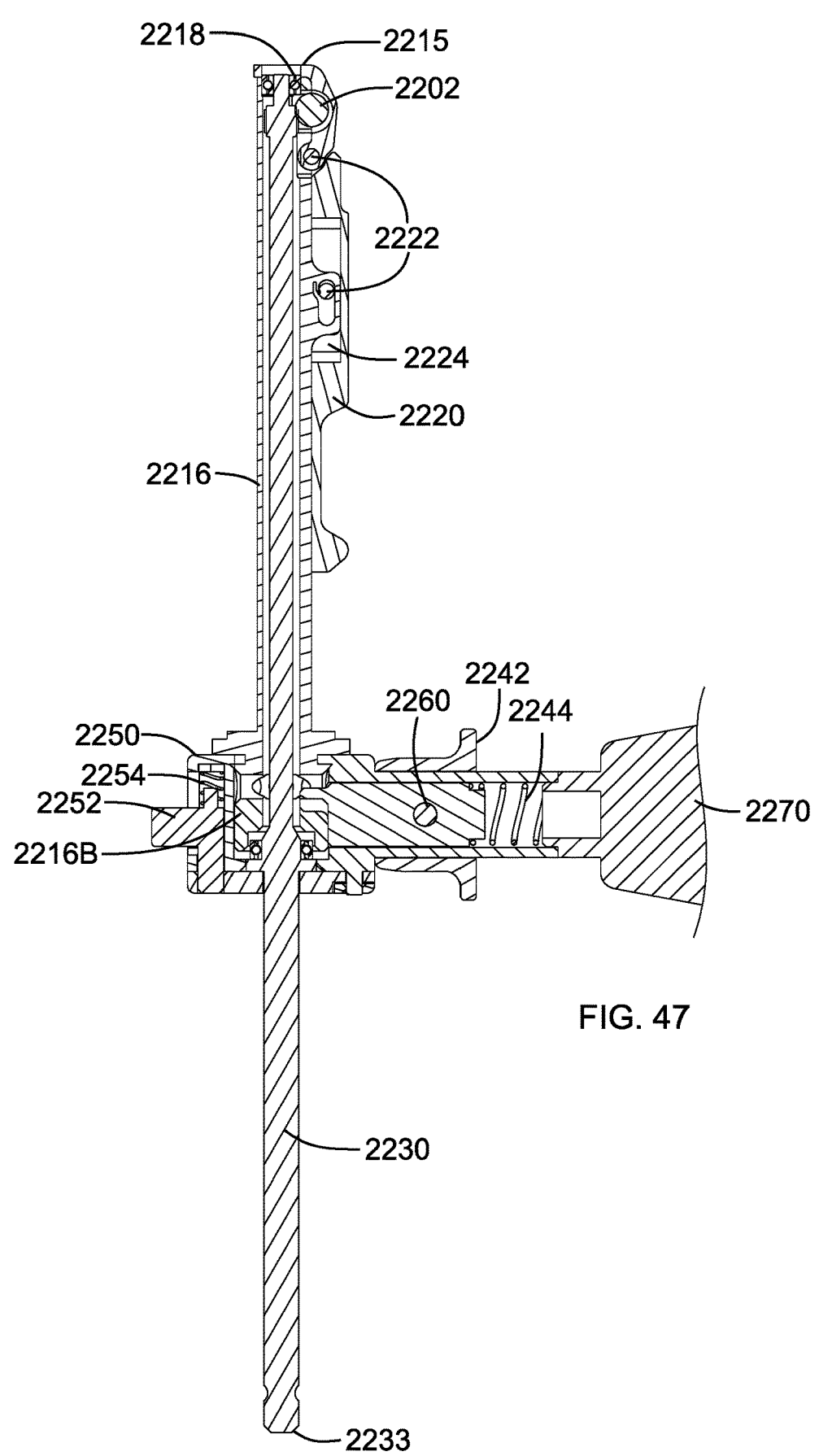
FIG. 47 is a cross-section view of the exemplary right-angle drill of FIG. 42.

According to some embodiments, the swivel door right-angle drill 2200 may include a drive shaft 2230 having a drive shaft axis 2235, a handle 2270, a swivel door housing 2216, and a swivel door 2212. The drive shaft 2230 may be removably coupled to a motor (not shown) on a first end 2233. As shown in FIGS. 46 and 47, a surface 2234, near the second end 2215 of the swivel door right-angle drill 2200 and opposite the first end 2233, may sit in a bearing 2218 that supports the second end 2215 and allows it to freely rotate. A drive shaft gear 2231 is disposed adjacent to the second end 2215. The drive shaft gear 2231 may engage with a drill bit gear 2204 disposed on the end of the drill bit 2202 (see FIG. 48). In the embodiment shown, the drill bit 2202 includes a drill bit axis 2205 and is disposed perpendicularly to drive shaft 2230. Thus, the interface between the drive shaft gear 2231 and drill bit gear 2204 may translate torque transmitted by the motor through the drive shaft 2230 into the drill bit 2202 perpendicular to the drive shaft 2230. Although the embodiment shown has the drill bit 2202 disposed perpendicularly to the drive shaft 2230, the drill bit 2202 (and the drill bit axis 2205) may be disposed in any suitable orientation or angle in relation to the drive shaft 2230 (and the drive shaft axis 2235) without departing from the principles of this disclosure.

In some embodiments, the handle 2270 may be coupled to the drive shaft 2230 via handle clasp 2240. As shown in FIG. 46, the drive shaft 2230 may be held longitudinally in place relative to the handle 2270 by an interface between a stopper 2232, a lower cap 2256, and an upper cap 2258 on one side, and the swivel door housing end cap 2217 within the handle clasp housing 2250 on the other side. In use, the lower cap 2256 and the upper cap 2258 may be coupled together by a slide 2252 and a spring 2254. When the slide 2252 is pushed towards the spring 2254, the lower cap 2256 may swing downwards, allowing the drive shaft 2230 to be moved relative the handle 2270. Further, the handle 2270 may be locked in a variety of orientations with respect to the drill bit 2202 through a spring positioning system comprising a spring adjustment housing 2248, a locking piece 2246, a spring 2244, and a finger handle 2242, each of which are coupled to one another by a pin 2260. The locking piece 2246 may extend into one or more holes on the swivel door housing end cap 2217 when the swivel door right-angle drill 2200 is in use, thereby holding the handle 2270 axially in place. When the user wishes to change the axial position of the handle 2270, the user may pull the finger handle 2242 to compress the spring 2244 and pull the locking piece 2246 from the swivel door housing end cap 2217. The handle 2270 may then be rotated. When in a desired position, the finger handle 2242 may be released, causing locking piece 2246 to enter a hole on the swivel door housing end cap 2217.

In some embodiments, the swivel door housing 2216 may enclose the drive shaft 2230 from the second end 2215 to the handle clasp 2240. The swivel door housing end cap 2217 may be coupled to the first end of the swivel door housing 2216, which may be equipped with a groove to couple with one end of the handle clasp 2240. A second end of the swivel door housing 2216 may include a bearing hole at the second end 2215 that couples with and supports bearing 2218.

In some embodiments, the swivel door housing 2216 may also include a protrusion 2221 with a slot as well as a hole 2223 near the second end 2215. The protrusion 2221 may be surrounded by chamber 2224 of the swivel door lock 2220 and coupled to the swivel door lock 2220 via one or more pins 2222, allowing the swivel door lock 2220 to slide longitudinally along the swivel door housing 2216. When in a locked position, the swivel door 2212 may wrap around the second end of the drive shaft 2230. A semicircular cutout, complementary with a semicircular cutout in the swivel door housing 2216, may surround and support a portion of the drill bit 2202. In some embodiments, one end of the swivel door lock 2220 presses against the swivel door 2212 to hold it in the locked position. Once the swivel door 2212 is secured in the locked position, the swivel door right-angle drill 2200 is ready for use. Further, if a drill bit having a different length or width is desired, the previous drill bit can be removed by sliding the swivel door lock 2220 away from the swivel door 2212. Thus, the swivel door 2212 may swing open and a different drill bit can be inserted.

In some embodiments, the swivel door housing 2216, measured from the swivel door housing end cap 2217 to the second end 2215, can include a length 2388 measuring about 40.0 to 50.0 mm, about 50.0 to 60.0 mm, about 60.0 to 70.0 mm, about 70.0 to 80.0 mm, about 80.0 to 90.0 mm, about 90.0 to 100.0 mm, about 100.0 to 110.0 mm, about 110.0 to 120.0 mm, about 120.0 to 1300.0 mm, or any suitable length in accordance with the principles of this disclosure.

In some embodiments, the swivel door housing 2216 can include a height 2287 measuring about 3.5 to 4.0 mm, about 4.0 to 4.5 mm, about 4.5 to 5.0 mm, about 5.5 to 6.0 mm, about 6.0 to 6.5 mm, about 6.5 to 7.0 mm, about 7.0 to 7.5 mm, about 7.5 to 8.0 mm, about 8.0 to 8.5 mm, or any suitable length in accordance with the principles of this disclosure.

In some embodiments, the drill bit protrusion height 2299 can include a height measuring about 8.5 to 9.0 mm, about 9.0 to 10.5 mm, about 10.5 to 11.0 mm, about 11.5 to 12.0 mm, about 12.0 to 12.5 mm, about 12.5 to 13.0 mm, about 13.0 to 13.5 mm, about 13.5 to 14.0 mm, about 14.0 to 14.5 mm, about 14.5 mm to 15 mm, about 15.0 to 15.5 mm, about 15.5 to 16.0 mm, or any suitable length in accordance with the principles of this disclosure.

Figure 41:
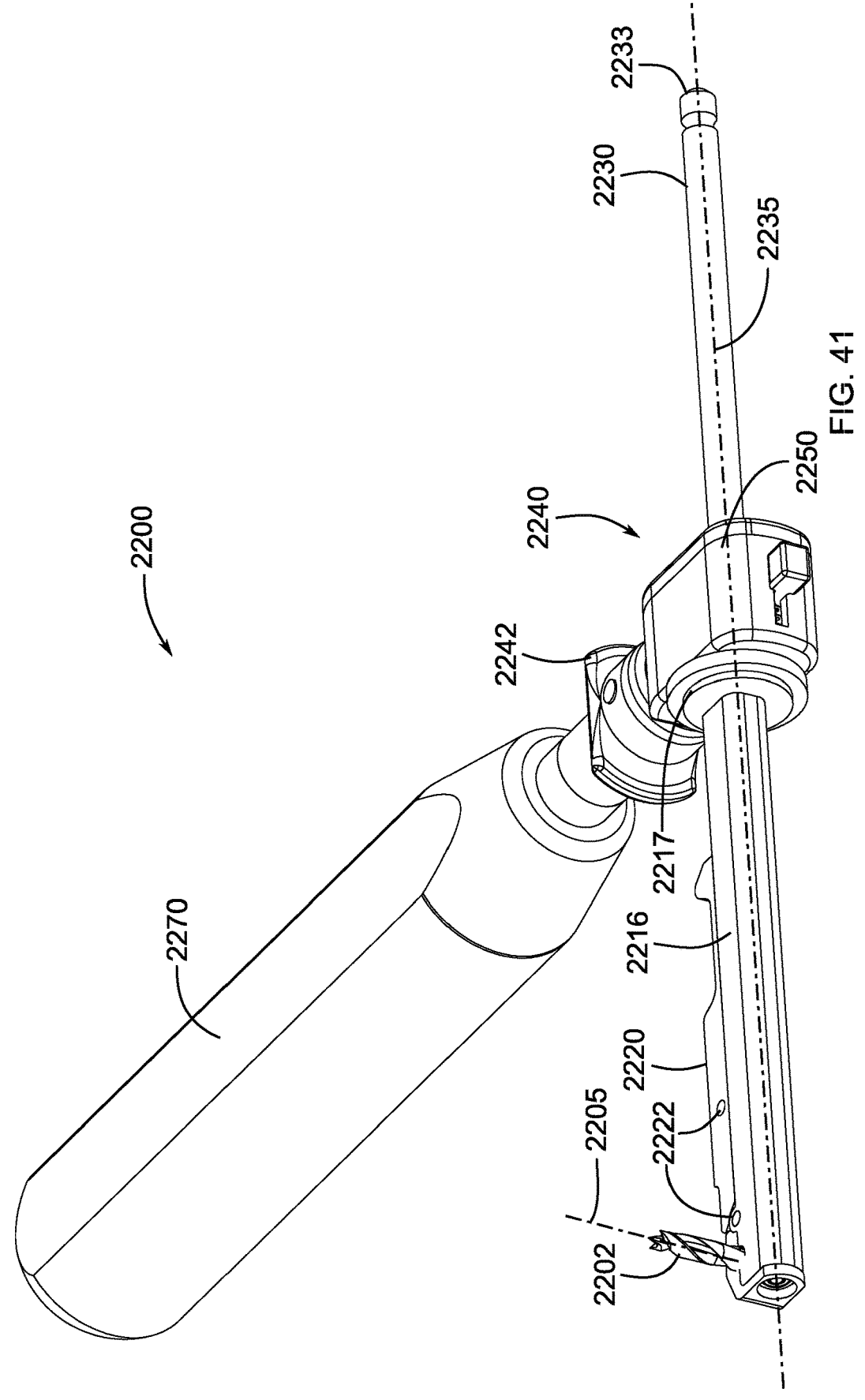
FIG. 41 is a front perspective view of the exemplary right-angle drill of FIG. 40.
Figure 41A:
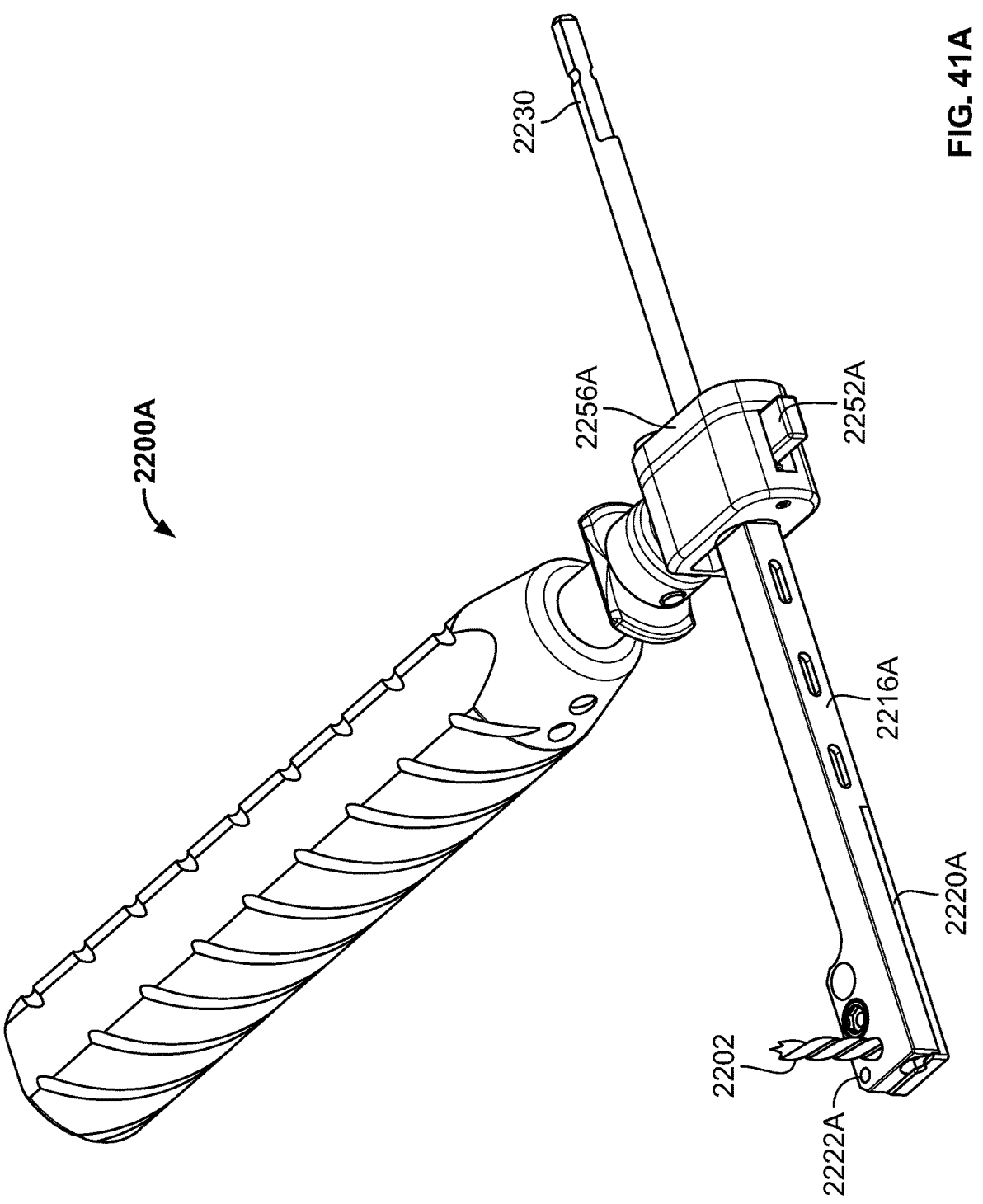
FIG. 41A is a front perspective view of an exemplary right-angle drill.
Figure 43:
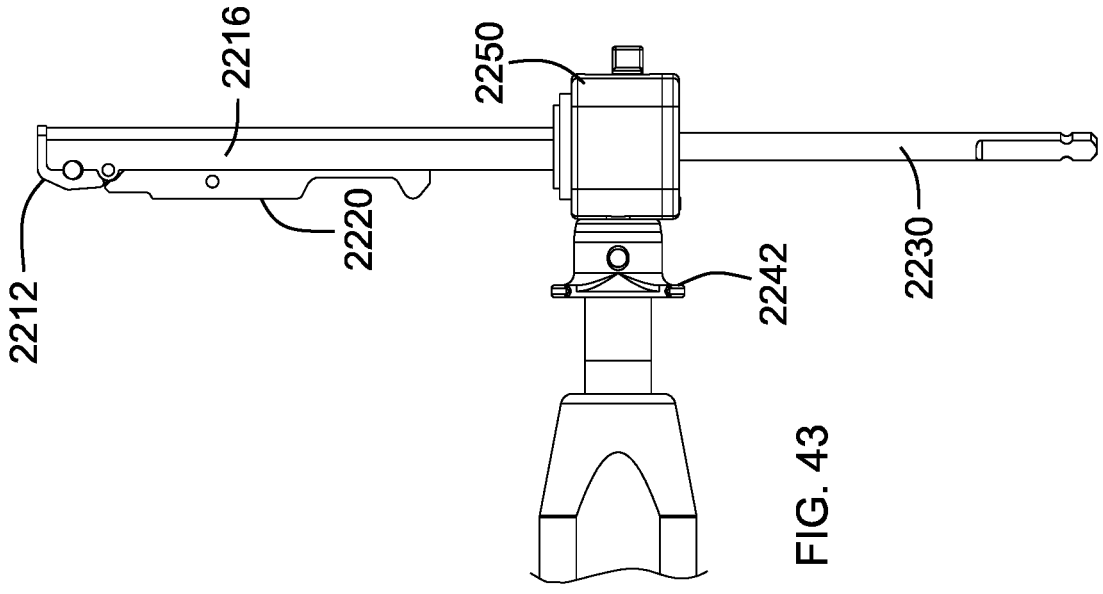
FIG. 43 is a bottom view of the exemplary right-angle drill of FIG. 40.
Figure 42:
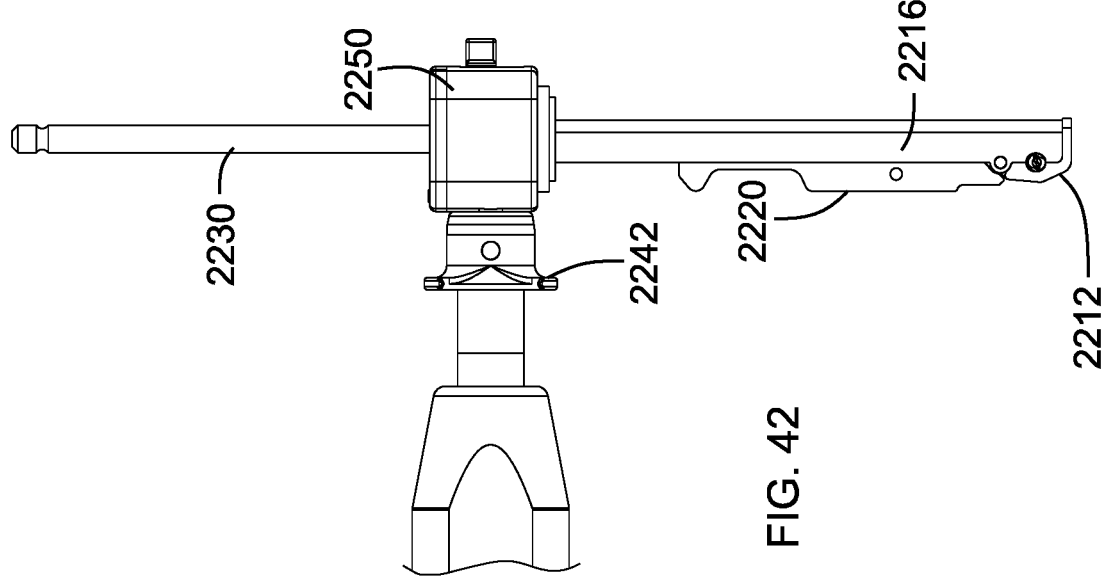
FIG. 42 is a top view of the exemplary right-angle drill of FIG. 40.
Figures 44, 45:
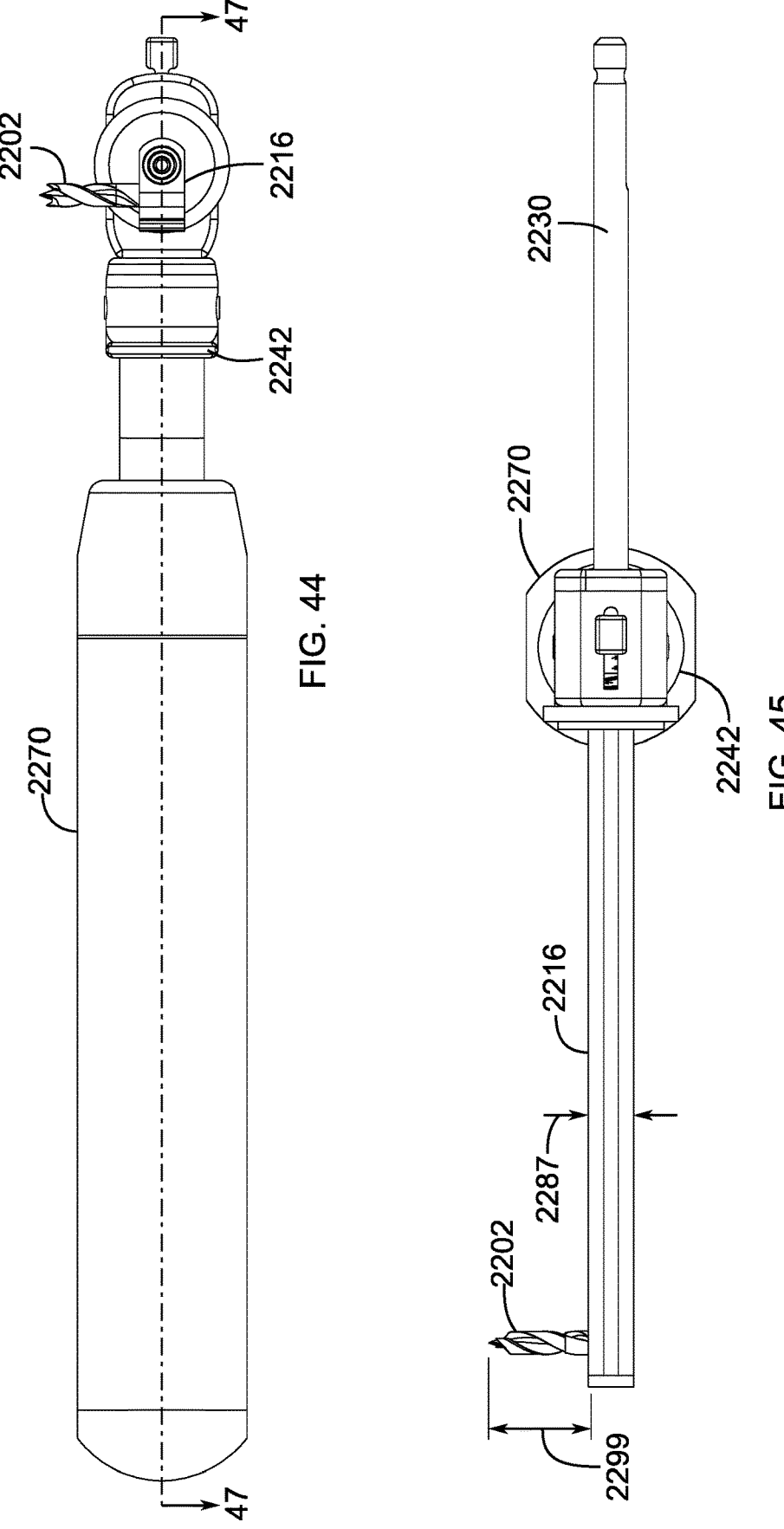
FIG. 44 is a front view of the exemplary right-angle drill of FIG. 40.
FIG. 45 is a back view of the exemplary right-angle drill of FIG. 40.

Referring now to FIG. 41A, one embodiment of the swivel door right-angle drill 2200A is shown, having an alternate configuration for the swivel door housing 2216A and swivel door lock 2220A enclosing the drive shaft 2230 and drill bit 2202. In this embodiment, the user may press a button 2252A to open a cap 2256A and insert the drive shaft 2230. The user may then unscrew one or more fasteners positioned on the swivel door lock 2220A to unlock the swivel door. Then, the user may rotate the lock 2220A about the housing 2216A and insert the drill bit 2202 (e.g., insert in the inferior direction while the drill is facing downwards). The user may then secure the drill bit 2202 by closing and securing the lock 2220A over the housing 2216 (e.g., via on or more bolts). In some embodiments, the swivel door lock 2220A may be coupled to a distal portion of the swivel door housing 2216A. For instance, the lock 2220A may be coupled to the housing 2216A via a hinge using one or more pins 2222A, while in other embodiments, the lock 2220A may be coupled to the housing 2216A via a snap-fit connection. In embodiments using a hinged connection, the lock 2220A may swing in a medial-lateral direction or in a superior-inferior direction to enclose and support the drill bit 2202.

Figure 48:
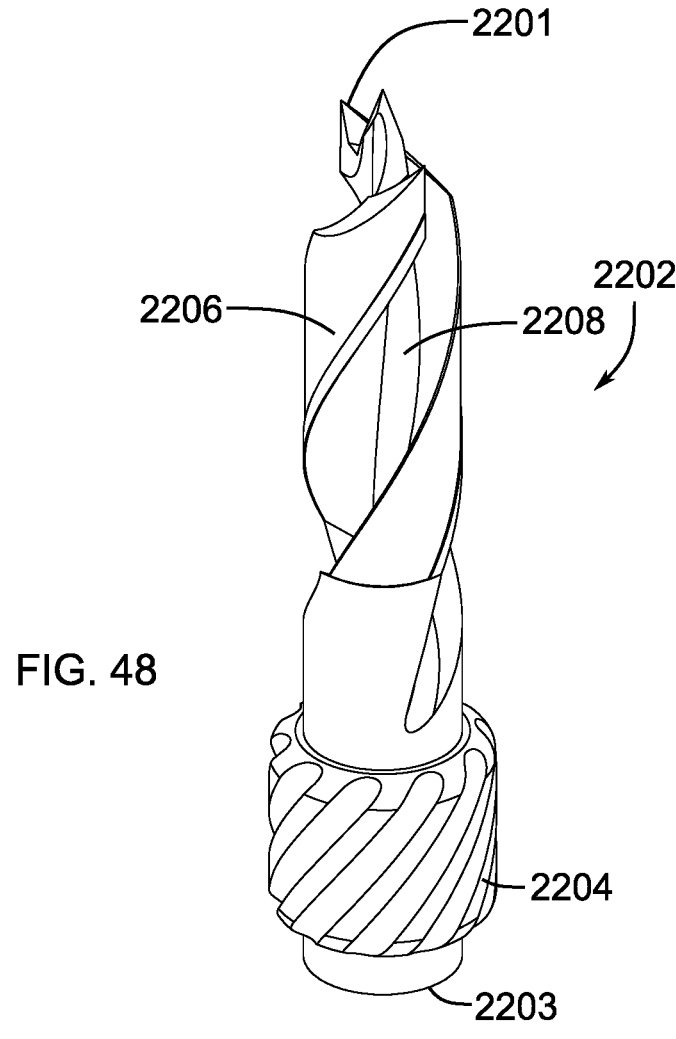
FIG. 48 is a rear perspective view of an exemplary right-angle drill, according to one embodiment.
Figure 49:
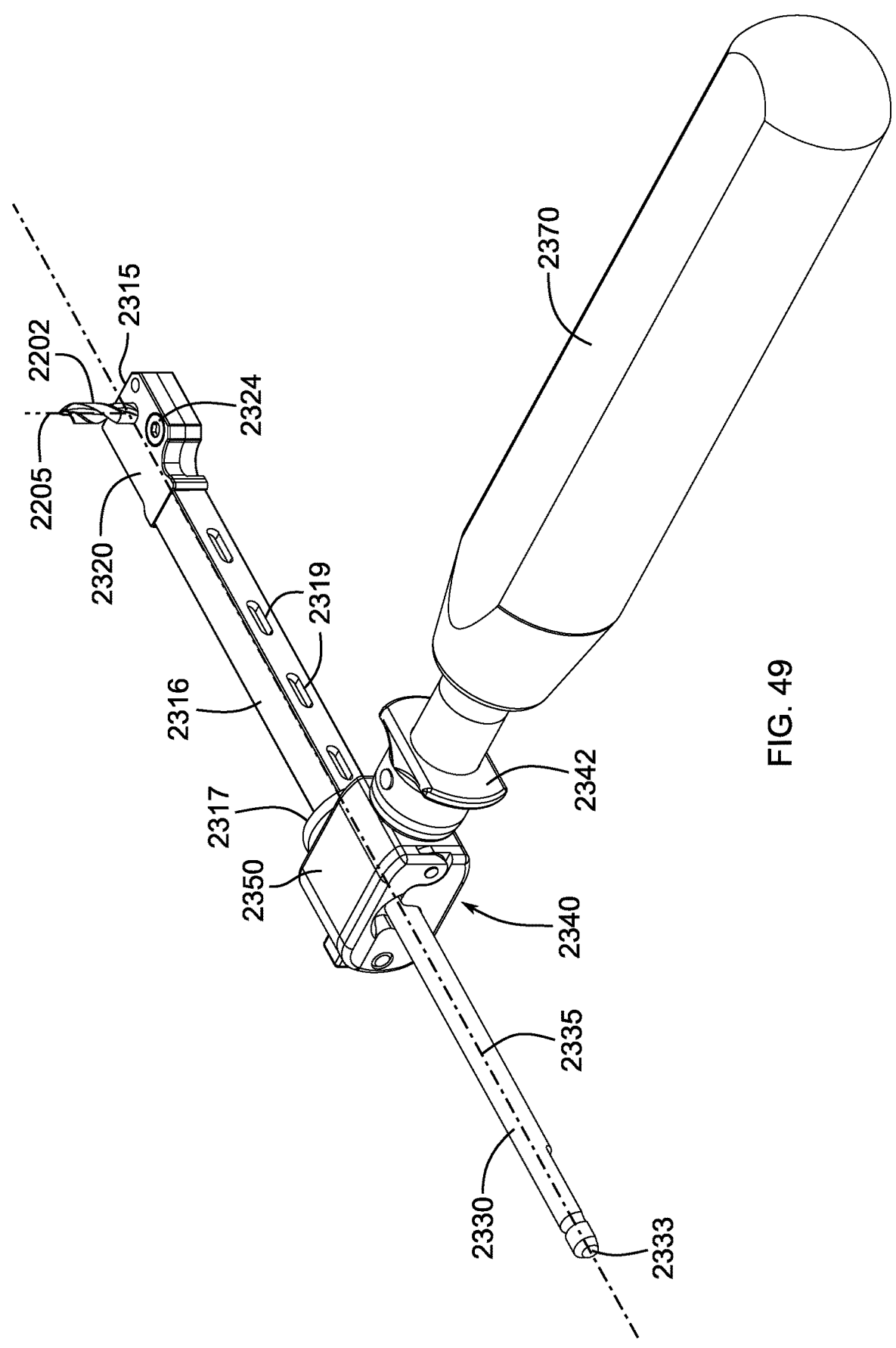
FIG. 49 is a front perspective view of the exemplary right-angle drill of FIG. 48.
Figure 50:
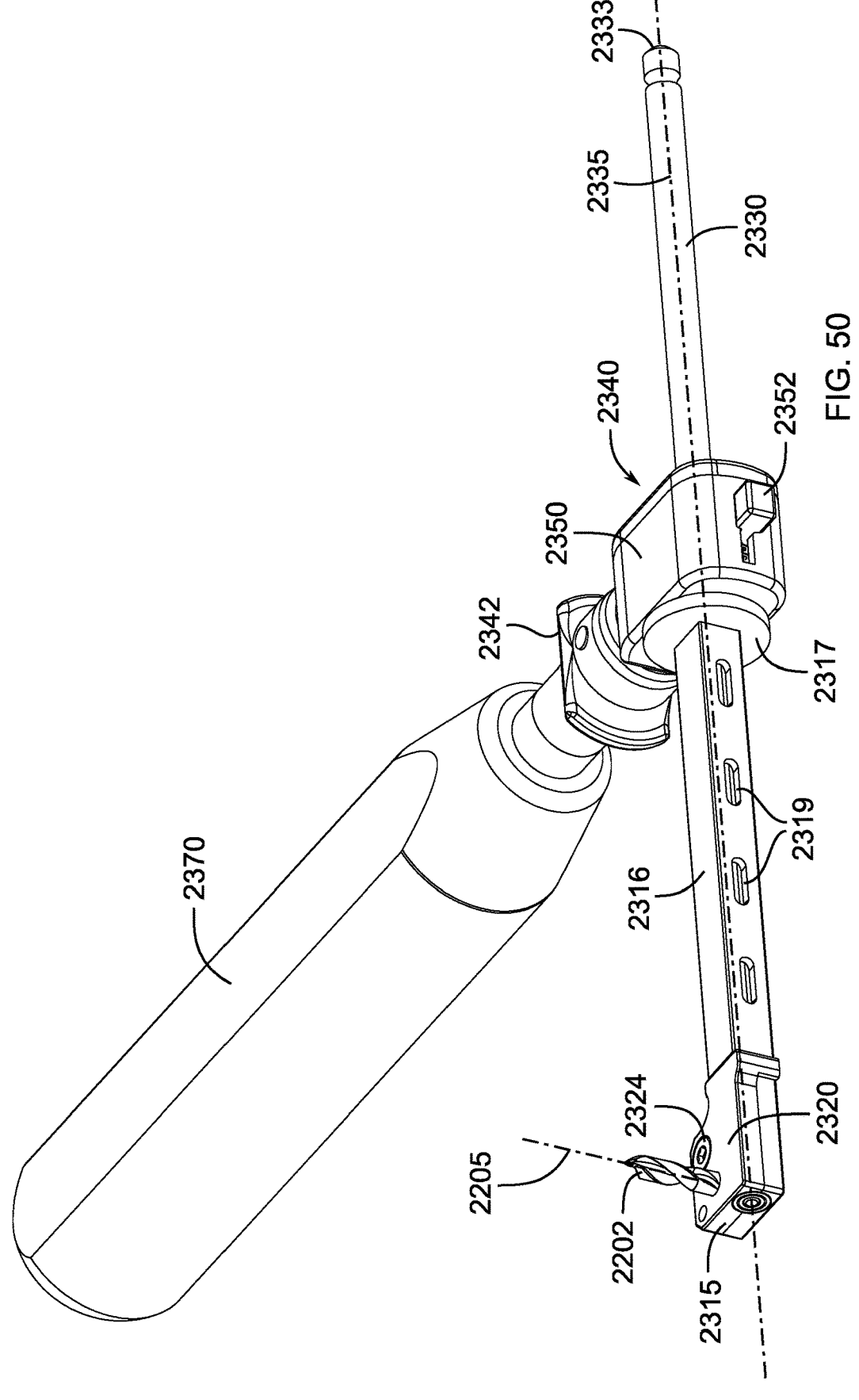
FIG. 50 is a top view of the exemplary right-angle drill of FIG. 48.
Figure 52:
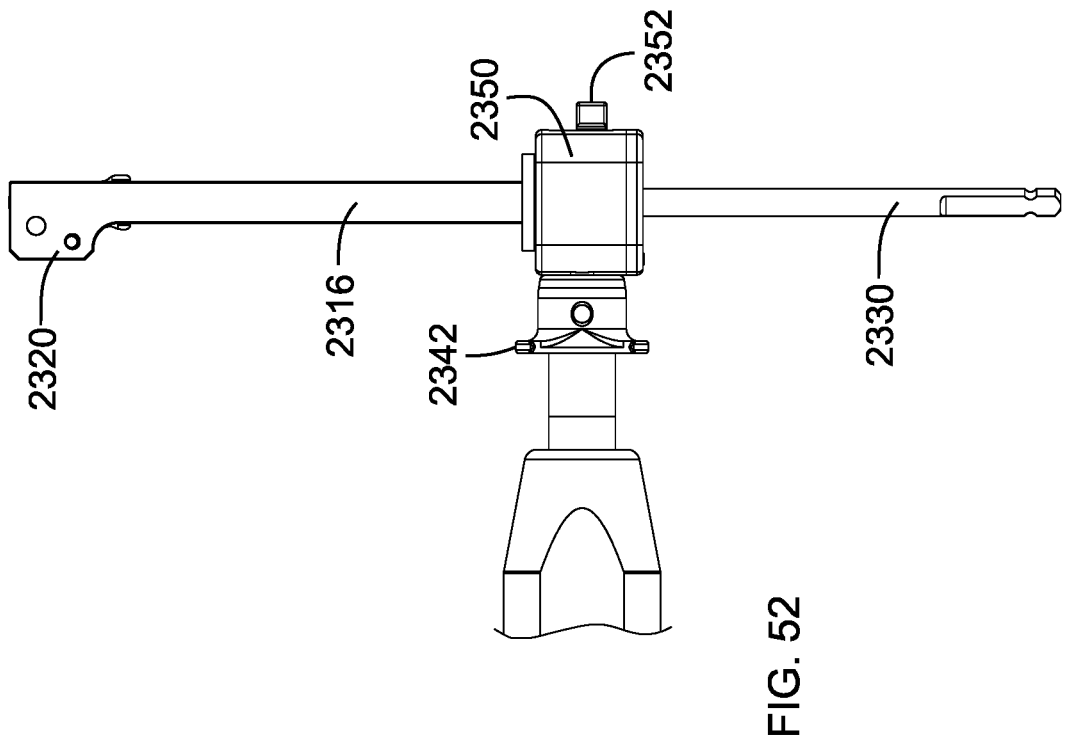
FIG. 52 is a front view of the exemplary right-angle drill of FIG. 48.
Figure 51:
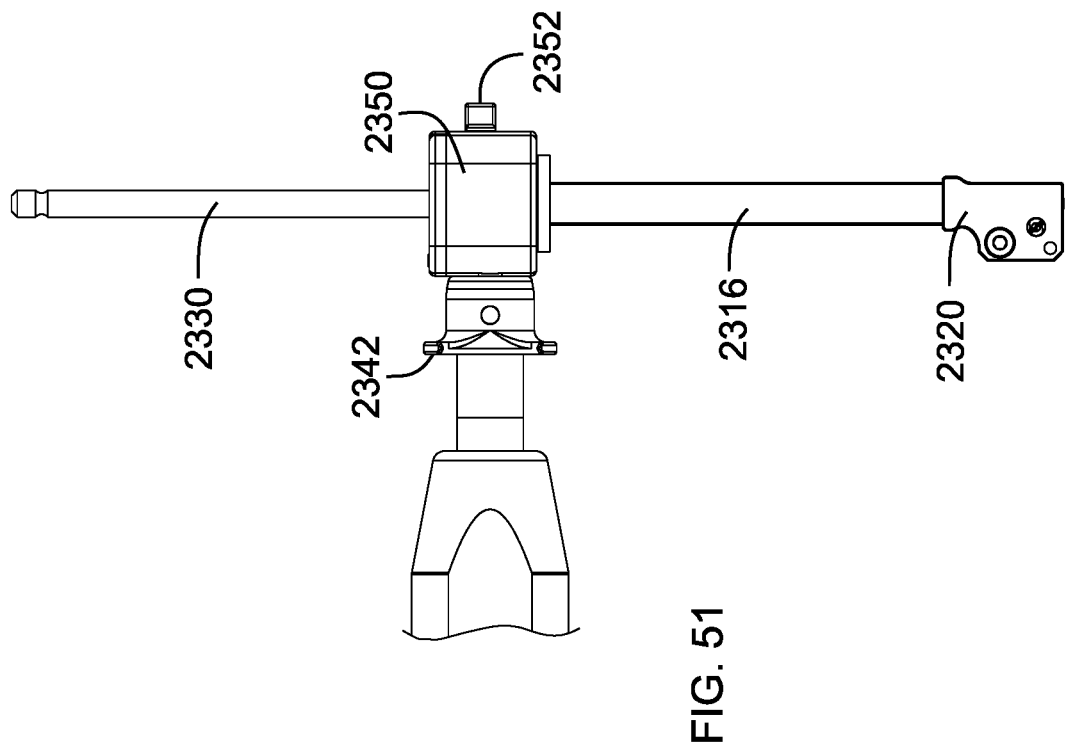
FIG. 51 is a bottom view of the exemplary right-angle drill of FIG. 48.
Figures 53, 54:
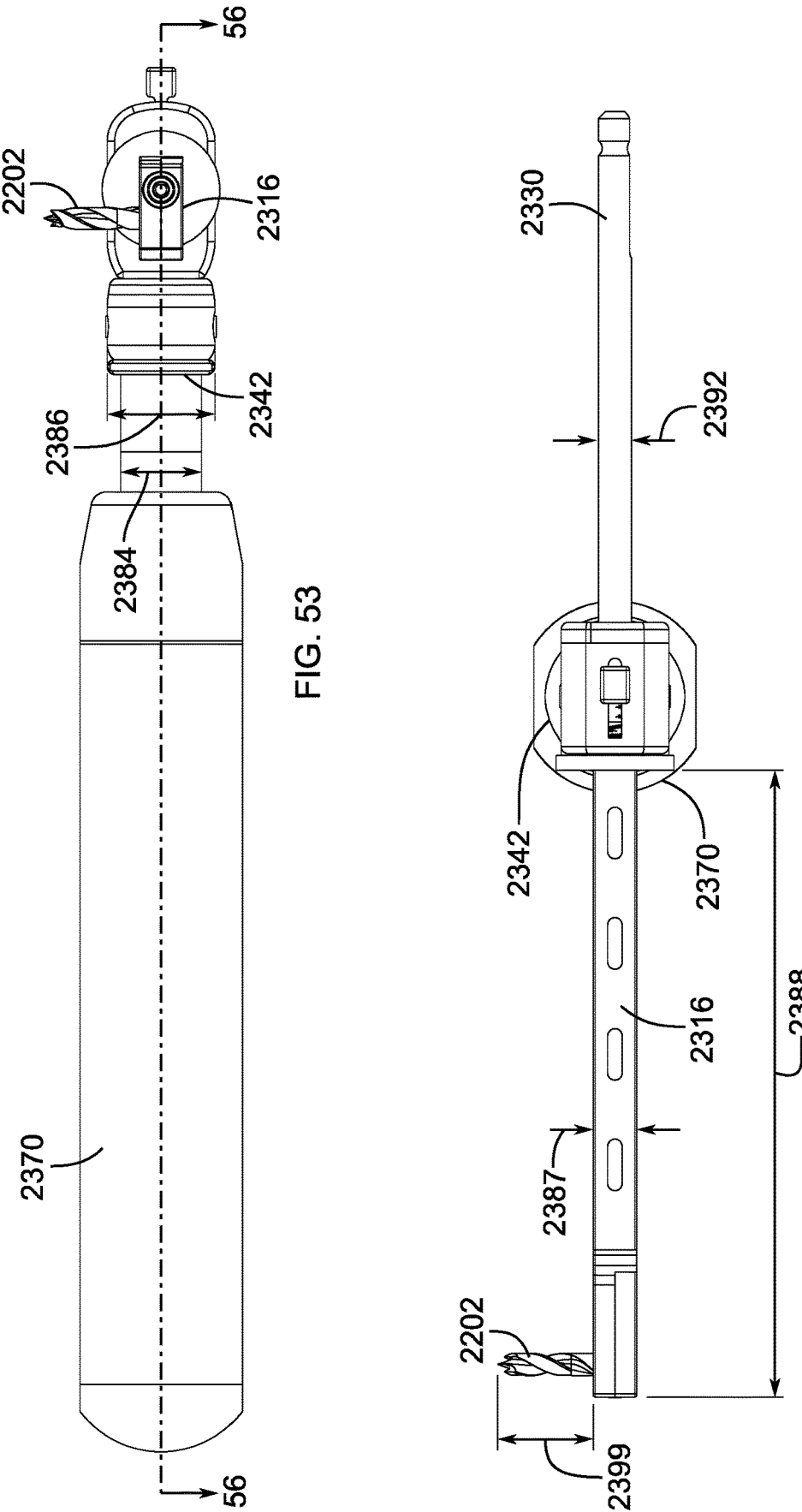
FIG. 53 is a back view of the exemplary right-angle drill of FIG. 48.
FIG. 54 is an exploded view of the exemplary right-angle drill of FIG. 48.
Figure 55:
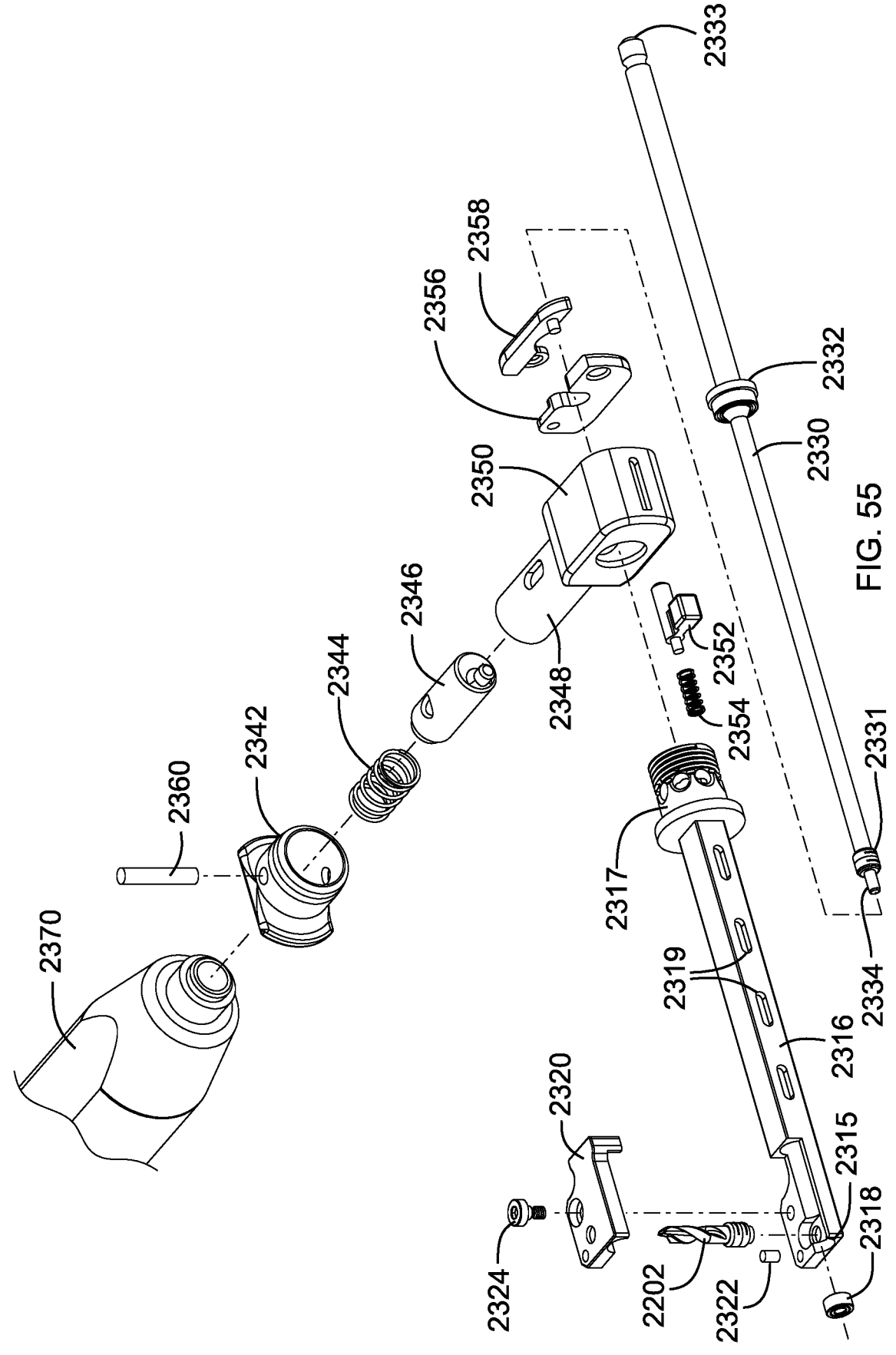
FIG. 55 is a cross-section view of the exemplary right-angle drill of FIG. 50.
Figure 56:
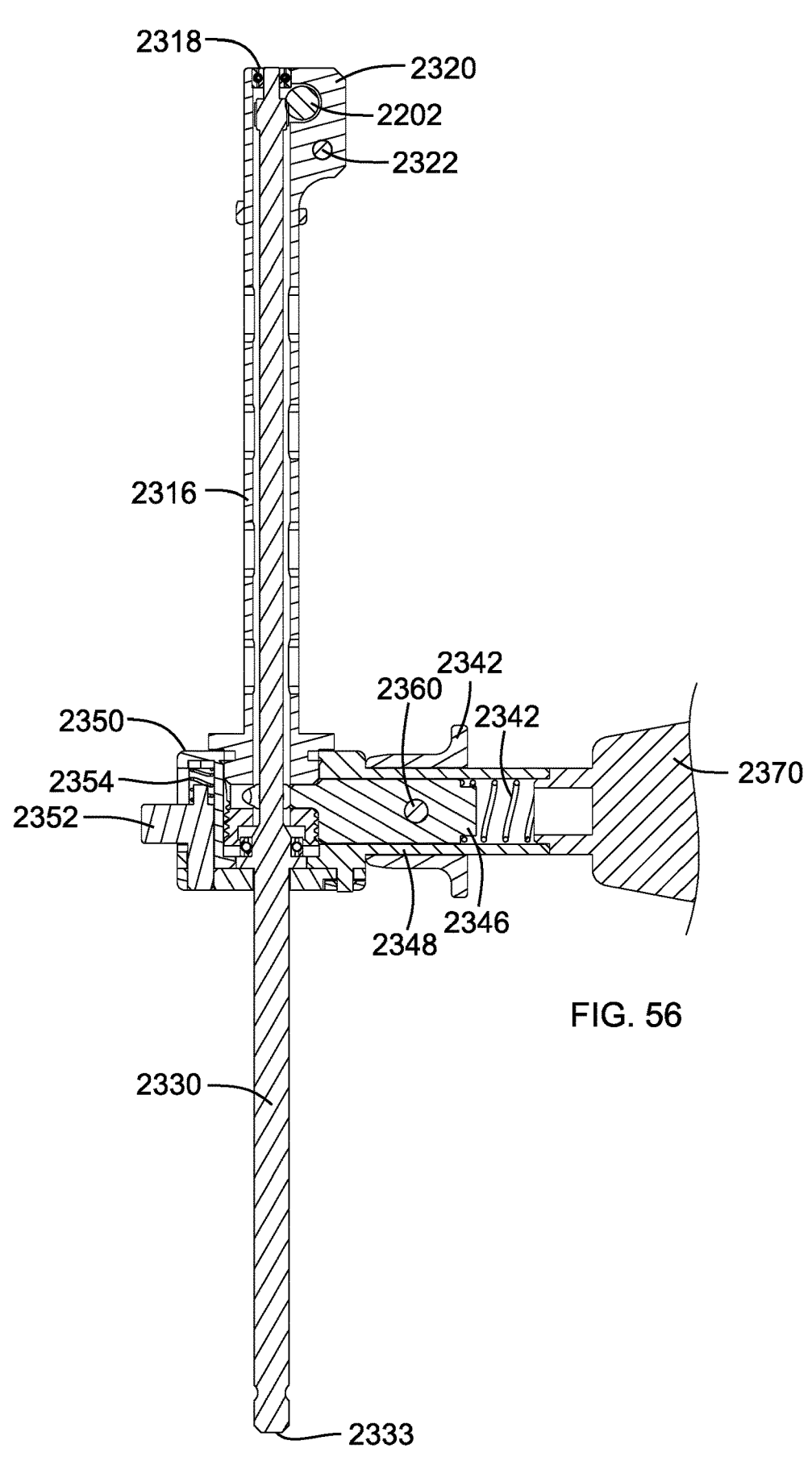
FIG. 56 is a perspective view of an exemplary drill bit, according to one embodiment.

Referring now to FIG. 48, one embodiment of the drill bit 2202 in accordance with the principles of this disclosure is shown. Depending on user preference and/or patient specific considerations, one or more features of the drill bit 2202 may be selected. For instance, in some embodiments, the drill bit 2202 may vary features such as, but not limited to, lengths, diameters, flute patterns, point style, or any other suitable features or combinations thereof. In one non-limiting example, FIG. 48 shows a drill bit 2202 having a point 2201 comprising one or more separate tips in different positions (e.g., about near a center of the drill bit 2202, about near an outer diameter at an end of each land 2206). In other embodiments, other point designs may be used, including, but not limited to, standard point and split point designs without departing from the principles of this disclosure.

In some embodiments, the shank 2203 may include a drill bit gear 2204 configured to interface with one or more complementary drive shaft gears 2231 on the drive shaft 2230 of the right-angle drill 2200. In the embodiment shown, the drill bit gear 2204 may include a helical shape or any other suitable shape permitting a translation of rotational movement to a different orientation. In some embodiments, the drill bit gear 2204 may be formed as an integral part of the drill bit 2202 or can be manufactured separately and coupled to the shank 2203. In some embodiments, when the drill bit 2202 is installed on the right-angle drill 2200, a portion of the shank 2203 may engage with a corresponding region of the right-angle drill 2200 configured to align and hold the drill bit 2202.

According to some embodiments, the drill bit 2202 may be compatible with any other suitable drill or right-angle drill. In particular, FIGS. 49-56 depict one embodiment of a hatch lock right-angle drill 2300 in accordance with the principles of this disclosure that may accommodate drill bit 2202.

In some embodiments, the hatch lock right-angle drill 2300 may include a drive shaft 2330 having a drive shaft axis 2335, a handle 2370, a hatch lock housing 2316, and a hatch lock 2320. The drive shaft 2330 may be removably coupled to a motor (not shown) on a first end 2333. The drive shaft 2330 may include bearing surface 2334 positioned near a second end 2315 of the hatch lock right-angle drill 2300, opposite the first end 2333. In certain embodiments, bearing surface 2334 may rotationally engage a bearing 2318 that supports the second end 2315, allowing drive shaft 2330 to freely rotate. A drive shaft gear 2331 may be adjacent to the second end 2315 such that the drive shaft gear 2331 couples with the drill bit gear 2204 disposed on the end of the drill bit 2202, which includes a drill bit axis 2205. Thus, the interface between the drive shaft gear 2331 and the drill bit gear 2204 may translate the torque transmitted by the motor through the drive shaft 2330 into the drill bit 2202 at a right-angle to the drive shaft 2330. Although the embodiment shown has the drill bit 2202 disposed perpendicularly to the drive shaft 2330, the drill bit 2202 (and the drill bit axis 2205) may be disposed in any suitable orientation or angle in relation to the drive shaft 2330 (and the drive shaft 2335) without departing from the principles of this disclosure.

In some embodiments, the handle 2370 may be coupled to the drive shaft 2330 via the handle clasp 2340. The drive shaft 2330 may be held longitudinally in place relative to the handle 2370 by an interface between a stopper 2332 and a lower cap 2356 and an upper cap piece 2358 on one side, and the hatch lock housing end cap 2317 on the other side within the handle clasp housing 2350. In use, the lower cap 2356 and the upper cap 2258 may be coupled together by a slide 2352 and a spring 2354. When a user slides the slide 2352 towards spring 2354, lower cap 2356 is released, allowing it to swing downwards, thereby allowing the drive shaft 2330 to be moved relative the handle 2370. The handle 2370 can be locked in variety of orientations with respect to the drill bit 2202 through the spring positioning system consisting of spring adjustment housing 2348, locking piece 2346, spring 2344, and finger handle 2342, each of which is coupled to one another by pin 2360. When the hatch lock right-angle drill 2300 is in use, the locking piece 2346 may extend into one of the holes on the hatch lock housing end cap 2317, holding the handle 2370 axially in place. When a user wishes to change the axial position of the handle 2370, the user can pull the finger handle 2342 to compress the spring 2344 and pull the locking piece 2346 out of the hole on the hatch lock housing end cap 2317. The handle 2370 can then be rotated. When in the desired position, the finger handle 2343 may be released, allowing the locking piece to enter a hole disposed on the hatch lock housing end cap 2317.

In some embodiments, the hatch lock housing 2316 may enclose the drive shaft 2330 from the second end to the handle clasp 2340. The hatch lock housing end cap 2317 may be coupled to the first end of the hatch lock housing 2316, and the hatch lock housing end cap 2317 may be equipped with external threads to couple with internal threads in the handle clasp 2340. In the embodiment of FIGS. 49-56, the hatch lock housing 2316 may include a rectangularly-shaped cross section for a portion of its length, but in other embodiments, the housing 2316 may include any suitably shaped cross section. Further, one or more slits 2319 may be disposed on the sides of the hatch lock housing 2316. In some embodiments, a second end of the hatch lock housing 2316 may include a bearing hole 2315 that couples with and supports a bearing 2318. The second end may further include an area where the drive shaft 2330 is exposed to couple with the hatch lock 2320. This area may further include one or more holes in which the drill bit 2202, pin 2322, and locking screw 2324 are coupled.

In some embodiments, the user can select and insert a drill bit 2202 into the relevant hole in the hatch lock housing 2316. The user may then place the hatch lock 2320 over the drill bit 2202 to secure it within hatch lock housing 2316. A locking screw 2324 may then inserted and tightened through the hatch lock 2320 and hatch lock housing 2316 to hold the drill bit 2202 in place. Then, the user may use the hatch lock right-angle drill 2300. If a drill bit 2202 with a different length or width is required, the previous drill bit can be removed and a new drill bit can be inserted.

In some embodiments, the hatch lock housing 2316, measured from the hatch lock housing end cap 2317 to the second end 2315, can include a length 2388 measuring about 40.0 to 50.0 mm, about 50.0 to 60.0 mm, about 60.0 to 70.0 mm, about 70.0 to 80.0 mm, about 80.0 to 90.0 mm, about 90.0 to 100.0 mm, about 100.0 to 110.0 mm, about 110.0 to 120.0 mm, about 120.0 to 1300.0 mm, or any suitable length in accordance with the principles of this disclosure.

In some embodiments, the hatch lock housing 2316 can include a height 2387 measuring about 3.5 to 4.0 mm, about 4.0 to 4.5 mm, about 4.5 to 5.0 mm, about 5.5 to 6.0 mm, about 6.0 to 6.5 mm, about 6.5 to 7.0 mm, about 7.0 to 7.5 mm, about 7.5 to 8.0 mm, about 8.0 to 8.5 mm, or any suitable length in accordance with the principles of this disclosure.

In some embodiments the drill bit protrusion height 2399 (see FIG. 54) can measure about 4.0 to 8.5 mm, about 8.5 to 9.0 mm, about 9.0 to 10.5 mm, about 10.5 to 11.0 mm, about 11.5 to 12.0 mm, about 12.0 to 12.5 mm, about 12.5 to 13.0 mm, about 13.0 to 13.5 mm, about 13.5 to 14.0 mm, about 14.0 to 14.5 mm, about 14.5 mm to 15 mm, about 15.0 to 15.5 mm, about 15.5 to 16.0 mm, or any suitable length in accordance with the principles of this disclosure.

In some embodiments, the right-angle drill 2200, 2300 may be motorized such that, when in use, the drive shaft 2230, 2330 may move in the anterior-posterior and/or medial-lateral directions without manual user action. For instance, the user may press a button disposed on the handle 2270, 2370 to control the movement of the drive shaft 2230, 2330, and thus drill bit 2202, towards or away from the prepared tibial surface. Additionally, in some embodiments, the right-angle drill 2200, 2300 may be compatible with one or more drill guides that assist the user with initial positioning of the right-angle drill 2200, 2300 with relation to patient anatomy.

Drill Plate

Figure 57:
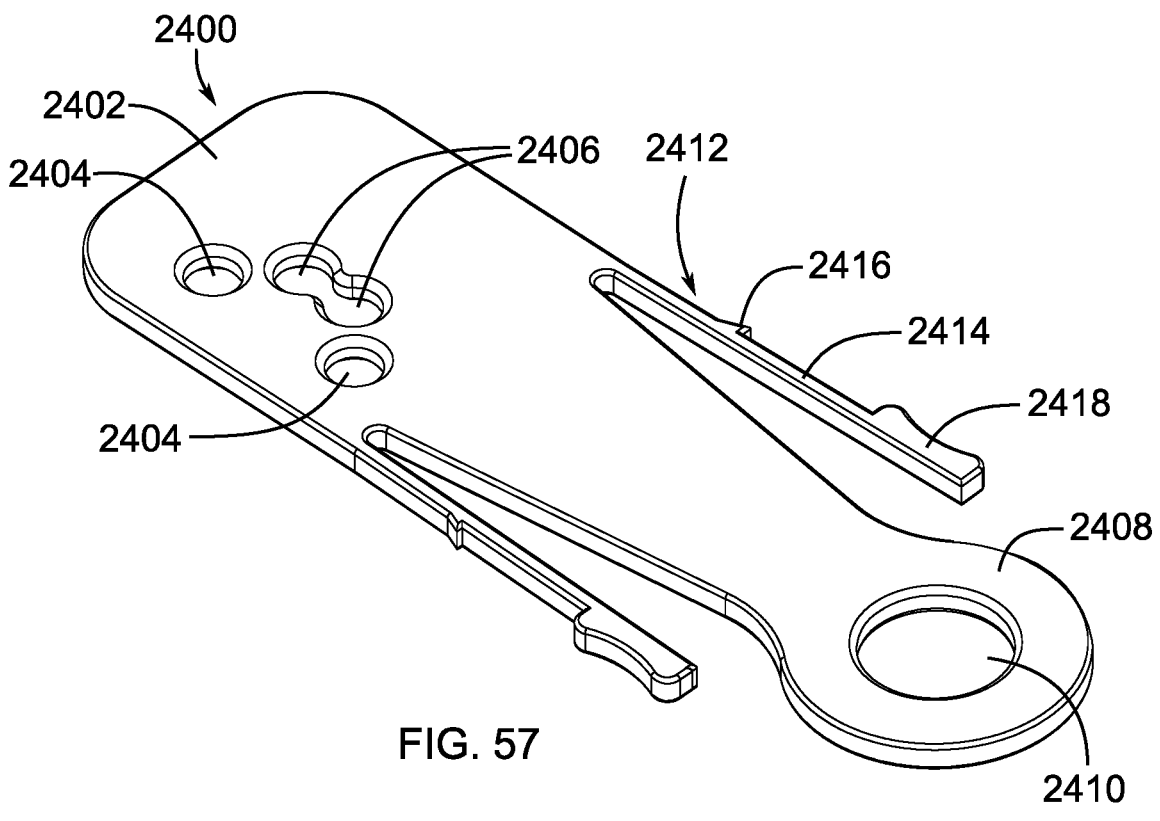
FIG. 57 is a perspective view of an exemplary drill plate, according to one embodiment.
Figure 58:
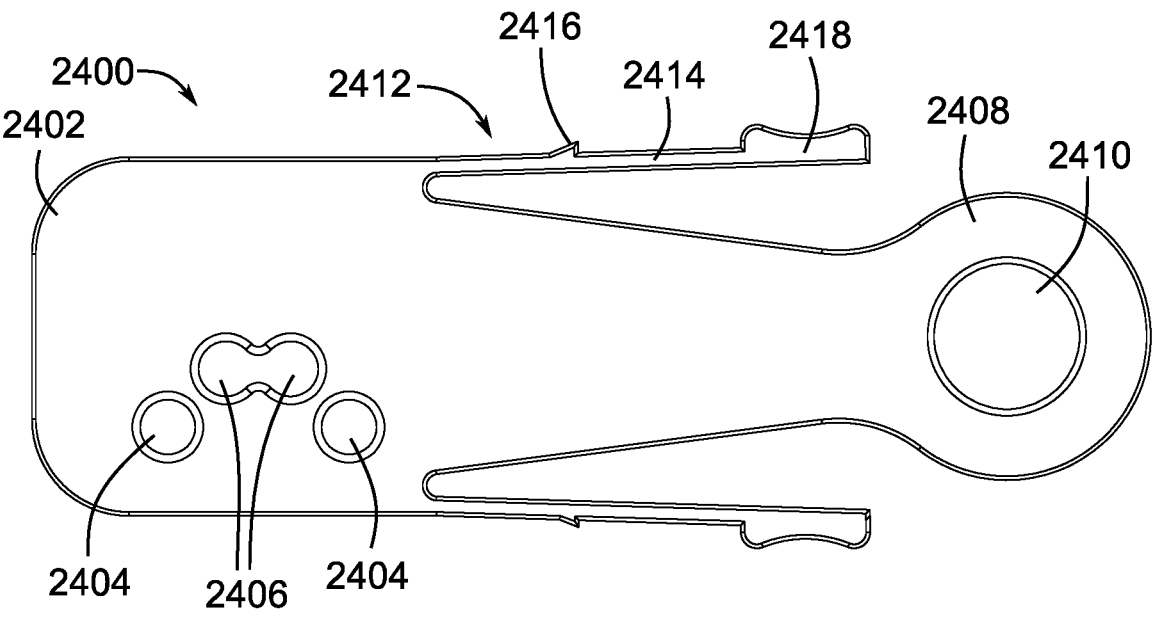
FIG. 58 is a top view of the exemplary drill plate of FIG. 57.

Referring now to FIGS. 57 and 58, one embodiment of a drill plate 2400 is shown. In some embodiments, the drill plate 2400 may be used with the right-angle drill 2200, 2300 (see FIGS. 40-56), or any other suitable drill or similar tool. In some embodiments, the drill plate 2400 comprises a body 2402, a pull tab 2408, and locking mechanisms 2412. In some embodiments, corner holes 2404 and/or center holes 2406 may form one or more through-holes disposed on a portion of the body 2402. The corner holes 2404 and/or center holes 2406 may guide a corresponding portion of a drill (e.g., drill bit 2202) as the user drills into the prepared tibial surface to begin forming the intramedullary canal. In some embodiments, the body 2402 may further include a pull tab 2408 having a hole 2410 that the user may use when inserting and/or removing the drill plate 2400 into the tibial trial 2000. For instance, the pull tab 2408 and/or the hole 2410 may provide a gripping surface for the user.

As shown, the center holes 2406 and corner holes 2404 may be asymmetrical relative to a centerline (not shown) of the drill plate 2400 (and thus may form an asymmetric pattern of through-holes on the drill plate 2400). In some embodiments, such asymmetry may improve the structural strength of the drill plate 2400 (i.e., the drill plate 2400 may be less likely to deform when in use) and improve the accuracy/alignment when the user drills into the prepared tibial surface. In some embodiments, the user may insert the drill plate 2400 into the tibial trial 2000 with a first side facing upwards when initially drilling into the prepared tibial surface, using corner holes 2404 and center holes 2406. Then, the user may remove and reverse the drill plate 2400 such that a second side faces upwards, thus allowing the user to subsequently drill into different portions of the prepared tibial surface using corner holes 2404 and center holes 2406. In some embodiments, the drill plate 2400 may be repositioned after the user drills initial holes into the prepared tibial surface. In other embodiments, the drill plate 2400 may include additional holes such that the pattern of through-holes is symmetric, thus reducing the need to reposition the drill plate during drilling of the prepared tibial surface.

In some embodiments, the drill plate 2400 may be configured for insertion into the one or more channels 2024, 2026 using at least one trial engagement tab 2412. In some embodiments, the trial engagement tab 2412 may be positioned on either side of the body 2402. Each of the trial engagement tabs 2412 may include an arm 2414, an engagement protrusion 2416 positioned along the arm 2414, and a release grip 2418 positioned near an end of the arm 2414. When inserted into the tibial trial 2000, the engagement protrusion 2416 may engage with a corresponding notch 2028 of the one or more channels 2024, 2026, thus maintaining a fixed position of the drill plate 2400 relative to the tibial trial 2000. In one non-limiting example, a user can squeeze or compress the release grips 2418 to disengage the engagement protrusions 2416 from the notches 2028 of the one or more channels 2024, 2026. The user can then remove, invert, and/or reinsert the drill plate 2400 into the one or more channels 2024, 2026. In certain embodiments at least a portion of the arm 2414 may be resilient to allow elastic deflection of the engagement protrusions 2416 in relation to the notches 2028.

Figure 59:
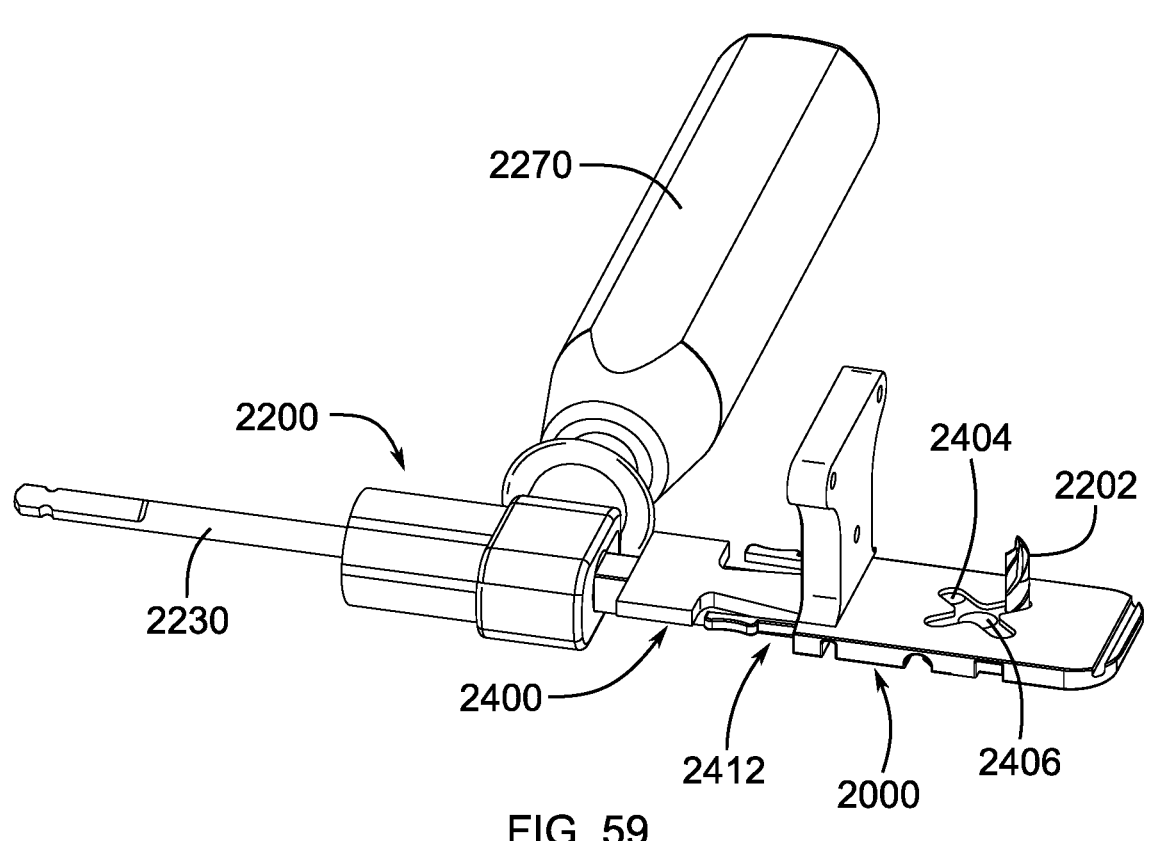
FIG. 59 is a perspective view of an exemplary TAR assembly, according to one embodiment.

FIG. 59 illustrates one embodiment of the TAR assembly, using the drill plate 2400 with the right-angle drill 2200 and the tibial trial 2000. As shown, the drill plate 2400 can be inserted into the tibial trial 2000 (via the one or more channels 2024, 2026) such that the center holes 2406 and corner holes 2404 are positioned with respect to the access opening 2020 of the tibial trial 2000. Here, the drill bit 2202 of the right-angle drill 2200 may move through the center holes 2406 and corner holes 2404 as desired by the user to drill into the prepared tibial surface. In some embodiments, the user may grip the handle 2270 to move the right-angle drill 2200 into position to perform the drilling, while in other embodiments, the user may control movement of the right-angle drill 2200 and drill bit 2202 through the drill plate 2400 electronically (e.g., via button action). In still other embodiments, use of the drill plate 2400 may be omitted such that the user drills through only the access opening 2020 to reach the prepared tibial surface.

In one non-limiting example, the user may select a drill bit 2202 to use with the desired right-angle drill (e.g., right-angle drill 2200 or right-angle drill 2300). The user may then insert the drill bit 2202 such that a helical gear portion of the drill's drive shaft is coupled with a corresponding gear portion of the drill bit 2202. The user may then secure the drill bit 2202 (e.g., using the hatch lock 2312 or the swivel door 2212). The user may then insert the drill plate 2400 into the tibial trial 2000 so that the locking mechanisms 2412 engage with the one or more channels 2024, 2026, securing the position of the drill plate 2400. Next, the user may align the drill bit 2202 with one or more holes 2404, 2406 disposed on the body of the drill plate 2400 and begin drilling into the prepared tibial surface. The user may remove the drill and drill plate 2400, reverse the drill plate 2400, and re-insert it into the tibial trial 2000 to continue drilling into the prepared tibial surface.

Spike Broach

Turning now to FIGS. 60A, 61-64, an exemplary broach, or "spike" broach 2500, is shown according to one embodiment. Generally, the spike broach 2500 can be used to increase space within the medullary cavity for installing an implant during a surgical procedure. In particular, with respect to the TAR procedure described herein, the spike broach 2500 may be used to continue forming the intramedullary canal for installation of the modular stem system 1000.

In some embodiments, the spike broach 2500 may include a first arm 2502 connected to a second arm 2504. In some embodiments, the first arm 2502 may support and/or include a spike assembly 2506, and the second arm 2504 may support and/or include a surface 2508. For example, during the TAR procedure, the user may insert the first arm 2502 into the workspace defined between the inferior face 2012 of the tibial trial 2000 and the superior surface 2120 of the distractor plate 2104. The user may then align the spike assembly 2506 with the access opening 2020 of the tibial trial 2000 such that the spike assembly 2506 engages with the prepared tibial surface. Then, the user may strike or otherwise impact the surface 2508 of the spike broach 2500, thus driving the spike assembly 2506 into the prepared tibial surface to form the intramedullary canal. In some embodiments, the user may use an impactor tool or other suitable tool to strike the surface 2508, while in other embodiments, the user may manually impact the spike broach 2500. In other embodiments, an offset impactor may be removably attached to the surface 2508, and the user may strike a distal end (e.g., anvil surface) to impact the spike broach 2500 from a direction co-linear with the spike assembly 2506. In some embodiments, the user may use the spike broach 2500 to continue forming the intramedullary canal over the one or more holes drilled by the right-angle drill (e.g., drill 2200, drill 2300). In this regard, the user may position the spike assembly 2506 near the one or more drilled holes before impacting the spike broach 2500 into the prepared tibial surface.

In some embodiments, the first arm 2502 may be connected with the second arm 2504 at a non-zero offset angle. In some embodiments, the offset angle may be about 10 to 20-degrees, about 15 to 25-degrees, about 20 to 30-degrees, about 25 to 35-degrees, about 30 to 40-degrees, about 35 to 45-degrees, 40 to 60-degrees, about 50 to 70-degrees, about 60 to 80-degrees, about 70 to 90-degrees, about 80 to 100-degrees, or any other suitable offset angle. In this regard, when the spike broach 2500 is inserted into the workspace, the second arm 2504 may extend outward from the workspace at the offset angle. However, in other embodiments, the offset angle may be 0-degrees such that the first arm 2502 is not offset from the second arm 2504; in this case, the spike broach 2500 may include a generally straight contour. Additionally, in some embodiments, the first arm 2502, the second arm 2504, the spike assembly 2506, and/or the anvil surface 2508 may be integrally formed such that the spike broach 2500 is a single component. In other embodiments, one or more of the first arm 2502, the second arm 2504, the spike assembly 2506, and/or the anvil surface 2508 may be individually formed and subsequently coupled to other components to assemble the spike broach 2500.

In some embodiments, the spike assembly 2506 may include one or more perimeter spikes 2512 disposed around a central spike 2510. For example, in the illustrated embodiment, the spike assembly 2506 can include a central spike 2510 and four perimeter spikes 2512A-2512D arranged around the perimeter of the central spike 2510. In some embodiments, the central spike 2510 may have a cone shape, cylindrical shape, triangular prism shape, or any other suitable shape. In some embodiments, the spike assembly 2506 may include less than or more than four perimeter spikes 2512 arranged around the perimeter of the central spike 2510. In some embodiments, the perimeter spikes 2512 may be arranged around the perimeter of the central spike 2510 such that the perimeter spikes 2512 form an "X" pattern (e.g., when viewed from the superior direction). For instance, with reference to FIG. 61, the four perimeter spikes 2512A-2512D may be arranged in an "X" pattern around the perimeter of the central spike 2510. In some embodiments, the perimeter spikes 2512 are arranged around the perimeter of the central spike 2510 such that the combined outer perimeter of the central spike 2510 and the perimeter spikes 2512 generally align with the size/shape of the access opening 2020 in the trial base 2002. Thus, the spike assembly 2506 may be driven in the superior direction through the access opening 2020 and into the prepared tibial surface. In some embodiments, the spike assembly 2506 may comprise a central spike 2510 without perimeter spikes 2512.

Figures 60, 61, 62:
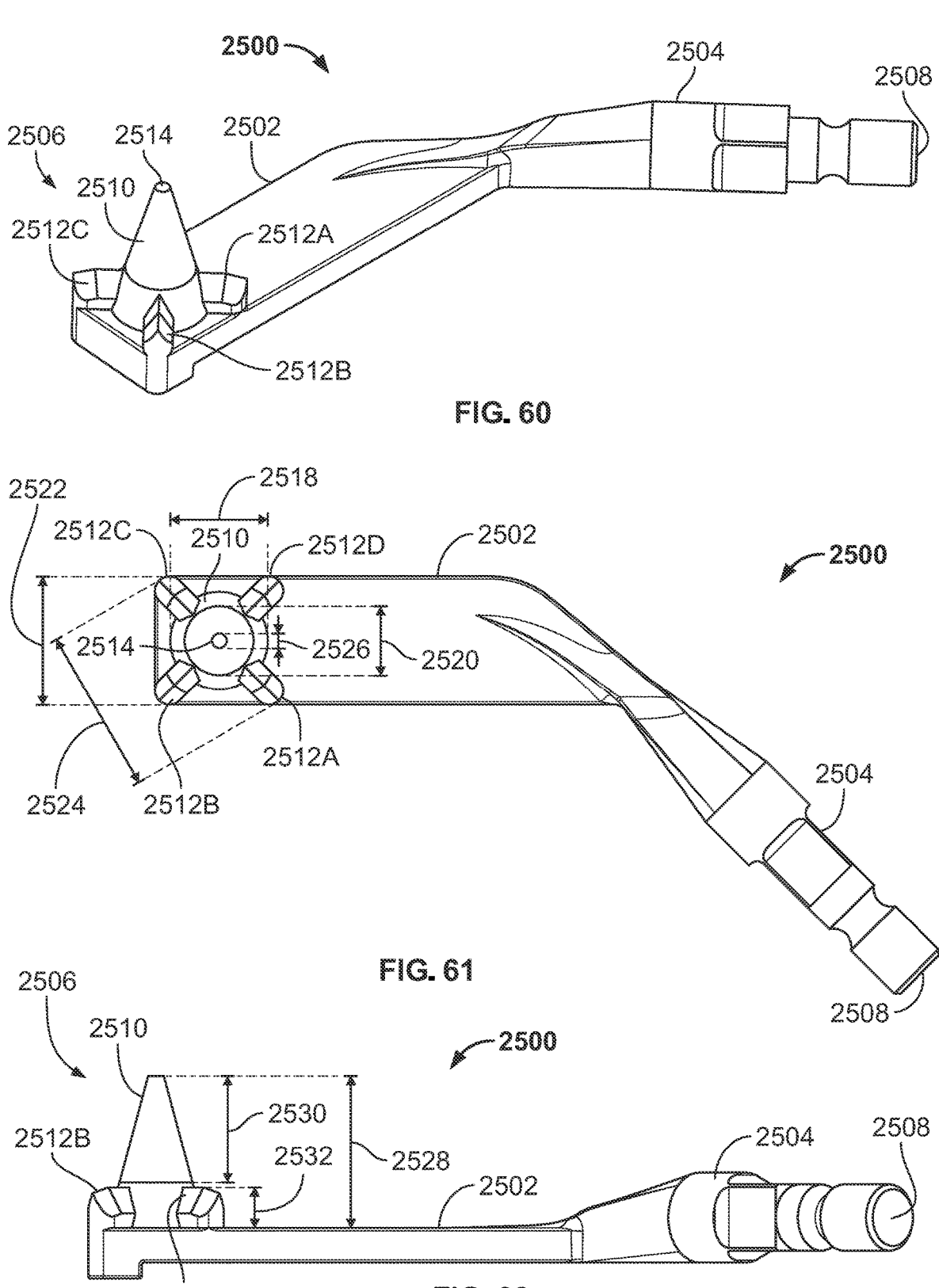
FIG. 60 is a perspective view of a spike broach, according to one embodiment.
FIG. 61 is a top view of the spike broach of FIG. 60.
FIG. 62 is a side view of the spike broach of FIG. 60.

With reference to FIG. 62, in some embodiments, the central spike 2510 may include a first height 2530 and the perimeter spikes 2512 may include a second height 2532. Thus, the central spike 2510 may contact the prepared tibial surface prior to the perimeter spikes 2512 when the spike assembly 2506 is initially driven by a distance substantially similar to the first height 2530. Then, the perimeter spikes 2512 may contact the prepared tibial surface when the spike assembly 2506 is further driven by a distance substantially similar to the first height 2530 and the second height 2532. In some embodiments, the first height 2530 may be longer than the second height 2532 such that the central spike 2510 may extend further than the perimeter spikes 2512. For instance, in some embodiments, the first height 2530 may be greater in length than the second height 2532 by about 0 to 10%, about 5 to 15%, about 10 to 20%, about 15 to 25%, about 20 to 30%, about 25 to 35%, about 30 to 40%, about 35 to 45%, about 40 to 50%, about 45 to 55%, about 50 to 75%, about 65 to 90%, about 75 to 100%, or any other suitable proportions. Additionally, the first height 2530 and the second height 2532 can be sized according to patient-specific parameters.

In some embodiments, the spike assembly 2506 may be cannulated. With respect to FIGS. 60 and 64, a tip of the central spike 2506 may include a central opening 2514 and a guide wire channel 2516. As shown, the guide wire channel 2516 may extend from the central opening 2514, through interior portions of the central spike 2510, to an opening disposed on an inferior side of the spike broach 2500. In this regard, once the user drives the spike broach 2500 into the prepared tibial surface to continue forming the intramedullary canal, the spike broach 2500 can remain in place while the user inserts a guide wire through the spike assembly 2506 (via the guide wire channel 2516) and further into the medullary cavity. In particular, the user may insert the guide wire into the opening disposed on the inferior side of the spike broach 2500, through the guide wire channel 2516, out the central opening 2514, and into the medullary cavity. Next, the user may remove the spike broach 2500 from the workspace without removing the guide wire by "sliding" the spike assembly 2506 along the inserted guide wire away from the patient. Thus, in some embodiments, the guide wire channel 2516 may direct the guide wire into the prepared tibial surface while the spike assembly 2506 is disposed within the medullary cavity, thus controlling the intended target trajectory of the guide wire over a greater distance. In other embodiments, the spike assembly 2506 may not be cannulated. In such embodiments, other tools of the TAR procedure may be used to insert the guide wire (e.g., flexible reamer assembly).

According to some embodiments, after insertion into the prepared tibial surface, the user may attach one or more additional instruments to the spike assembly 2506, wherein the additional instruments contain a channel following a trajectory of the spike assembly 2506. This may increase the length along which the guide wire is guided on its intended trajectory. In some embodiments, increasing the length along the intended trajectory of the guide wire may increase the likelihood that the guide wire will be inserted along the intended target trajectory. In some embodiments, the intended trajectory may include a portion of a curve tangent to a straight guided section.

With reference to FIG. 61, in some embodiments, when measured at the base of the central spike 2510 (e.g., at the superior surface of the first arm 2502), the central spike 2510 may have a first diameter 2518 measuring about 8.0 to 10.0 mm, about 10.0 to 12.0 mm, about 12.0 to 14.0 mm, about 14.0 to 16.0 mm, or any other suitable length in accordance with the principles of this disclosure. In some embodiments, when measured at a height along the central spike 2510 that is displaced from the superior surface of the first arm 2502 (e.g., at approximately the second height of the perimeter spikes 2512), the central spike 2510 may have a second diameter 2520 measuring about 4.0 to 6.0 mm, about 6.0 to 8.0 mm, about 8.0 to 10.0 mm, about 10.0 to 12.0 mm, or any other suitable length in accordance with the principles of this disclosure. In some embodiments, the central spike 2510 may taper in diameter from the base to the tip such that the first diameter 2518 may be larger than the second diameter 2520. For embodiments in which the spike assembly 2506 is cannulated, the central opening 2514 may have a diameter 2526 measuring about 0.5 to 1.0 mm, about 1.0 to 1.5 mm, about 1.5 to 2.0 mm, about 2.0 to 2.5 mm, or any other suitable length in accordance with the principles of this disclosure.

With further reference to FIG. 61, in some embodiments, when measured from an outer tip of a first perimeter spike 2512 (e.g., perimeter spike 2512B) to an outer tip of an adjacent second perimeter spike 2512 (e.g., perimeter spike 2512C), the spike assembly 2506 may have a width 2522 measuring about 8.0 to 10.0 mm, about 10.0 to 12.0 mm, about 12.0 to 14.0 mm, about 14.0 to 16.0 mm, or any other suitable length in accordance with the principles of this disclosure. In some embodiments, when measured from an outer tip of a first perimeter spike 2512 (e.g., perimeter spike 2512A) to an outer tip of a second perimeter spike 2512 (e.g., perimeter spike 2512C) disposed on an opposite side of the central spike 2510, the spike assembly 2506 may have a diagonal cross-section length 2524 measuring about 10.0 to 14.0 mm, about 14.0 to 18.0 mm, about 18.0 to 22.0 mm, about 22.0 to 26.0 mm, or any other suitable length in accordance with the principles of this disclosure.

With reference to FIG. 62, in some embodiments, when measured from the superior surface of the first arm 2502 to the tip of the central spike 2510, the spike assembly 2506 may include a total height 2528 measuring about 10.0 mm, to 15.0 mm, about 15.0 to 20.0 mm, about 20.0 to 25.0 mm, about 25.0 to 30.0 mm, about 30.0 to 35.0 mm, or any other suitable height in accordance with the principles of this disclosure. In some embodiments, the first height 2530 may measure about 6.0 to 8.0 mm, 8.0 to 10.0 mm, about 10.0 to 12.0 mm, about 12.0 to 14.0 mm, about 14.0 to 16.0 mm, about 16.0 to 18.0 mm, or any other suitable height difference in accordance with the principles of this disclosure. In some embodiments, the perimeter spikes 2512 may include a second height measuring about 2.0 to 4.0 mm, about 3.0 to 5.0 mm, about 4.0 to 6.0 mm, about 5.0 to 7.0 mm, or any other suitable height in accordance with the principles of this disclosure. In some embodiments, the total height 2528 may include the first height 2530 and the second height 2532.

Figure 60A:
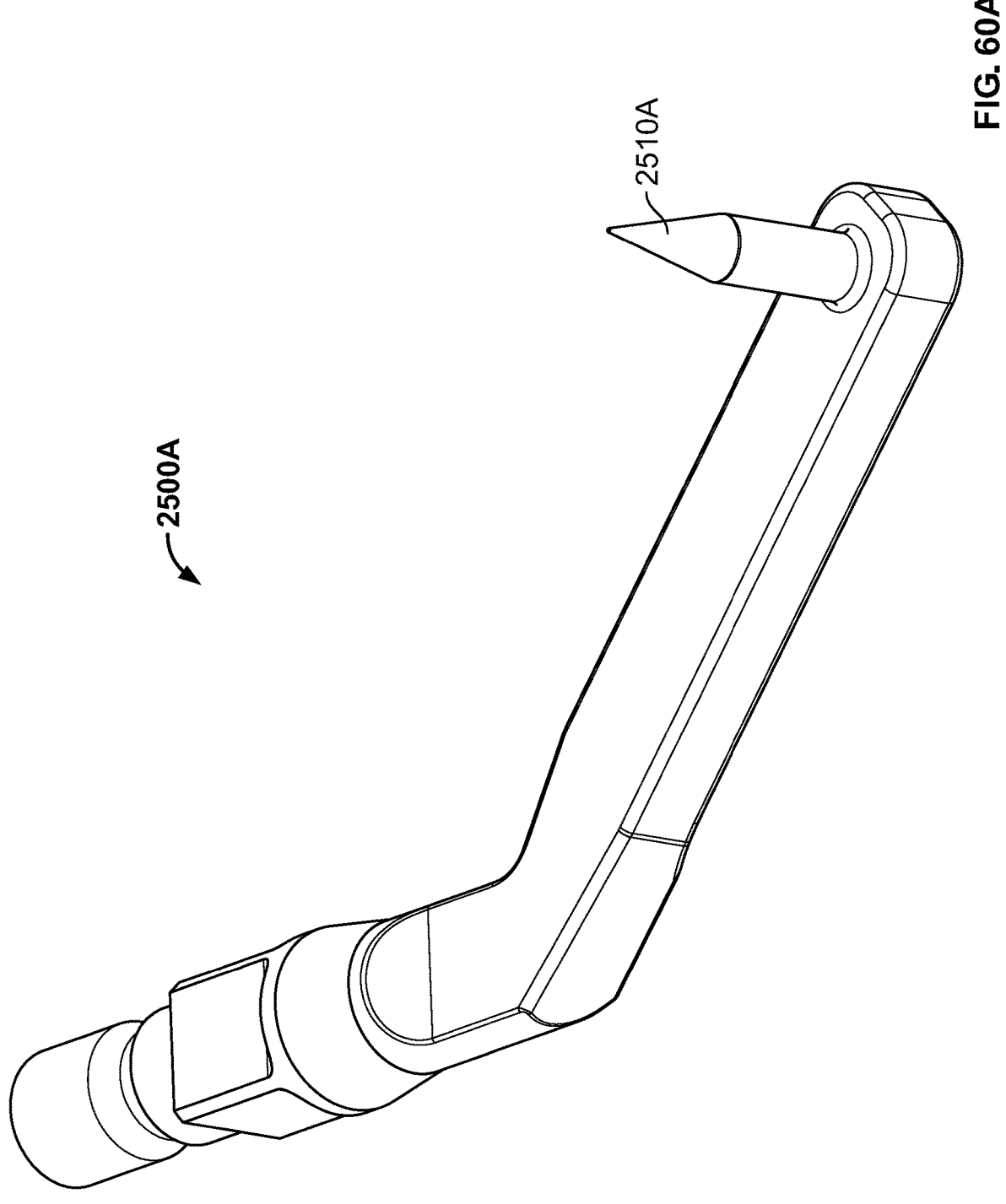
FIG. 60A is a perspective view of a spike broach, according to one embodiment.
Figures 63, 64:
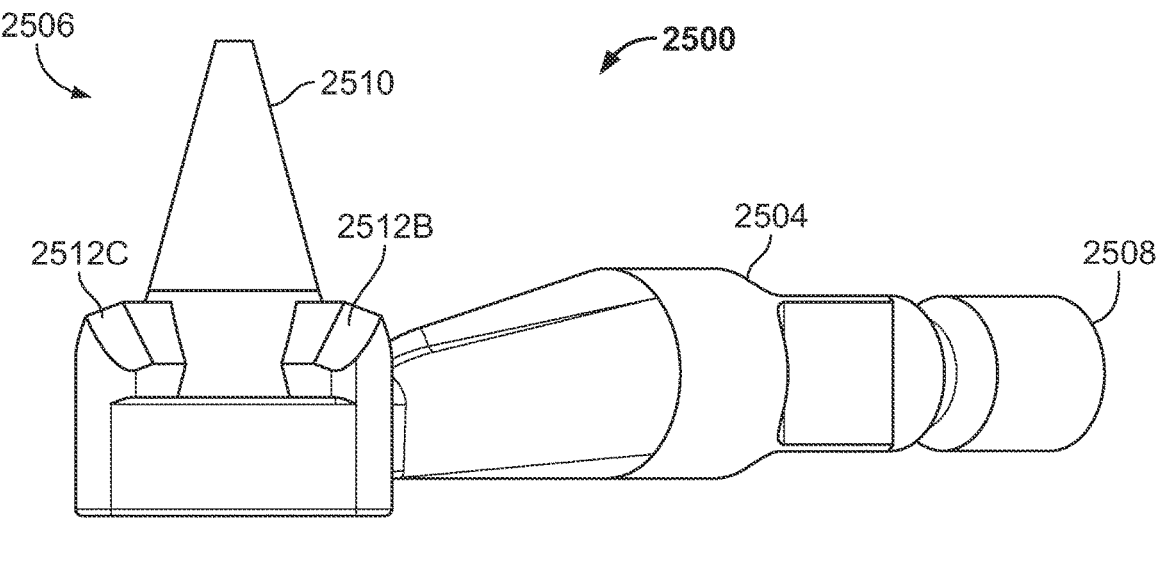
FIG. 63 is a side view of the spike broach of FIG. 60.
FIG. 64 is a cross-section view of the spike broach of FIG. 61.

Referring to FIG. 60A, one embodiment of a spike broach 2500A in accordance with the principles of this disclosure is shown. In some embodiments, the spike broach 2500A may include a central spike 2510A having a solid center and a partially cylindrical, partially conical contour. In this embodiment, the user may partially impact the conical portion of the central spike 2510A through the through-holes of the drill plate 2400, thus reducing the need for using the right-angle drill to drill holes in the prepared tibial surface. Then, once removing the drill plate 2400, the user may fully impact the central spike 2510A such both the cylindrical and conical portions are impacted through the tibial trial 2000 and into the prepared tibial surface to continue forming the intramedullary canal. In other embodiments, the user may partially impact an elongated cylindrical portion of the central spike 2510A through the through-holes of the drill plate 2400.

Wire Guide

Figure 65:
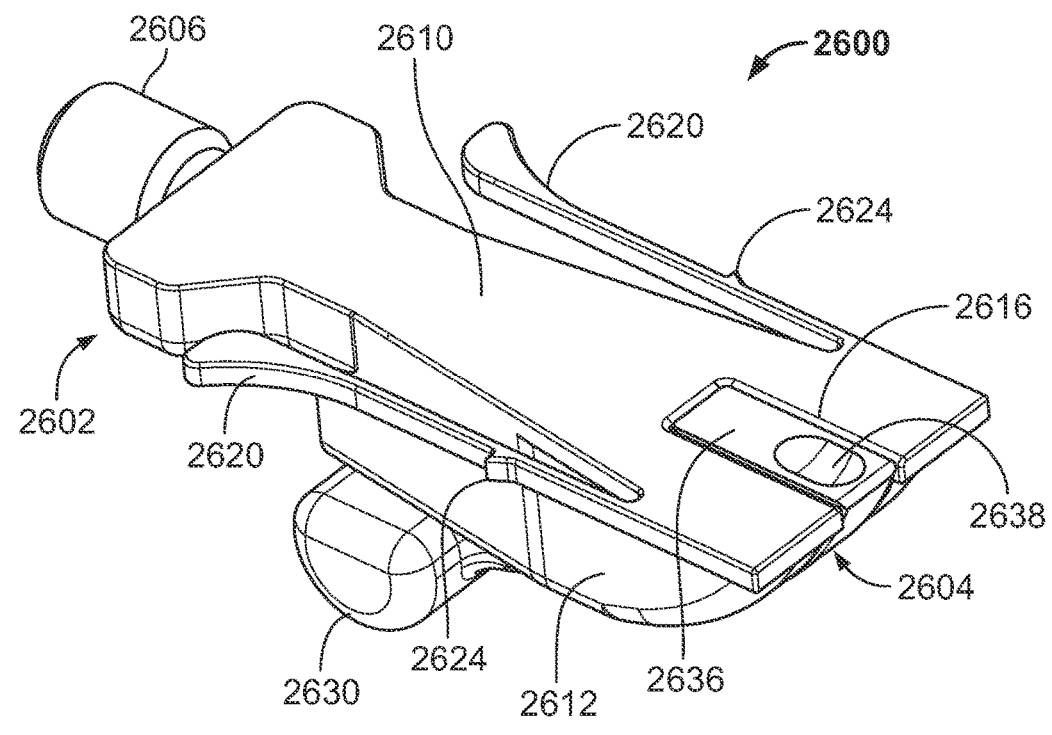
FIG. 65 is a perspective view of a wire guide, according to one embodiment.
Figure 66:
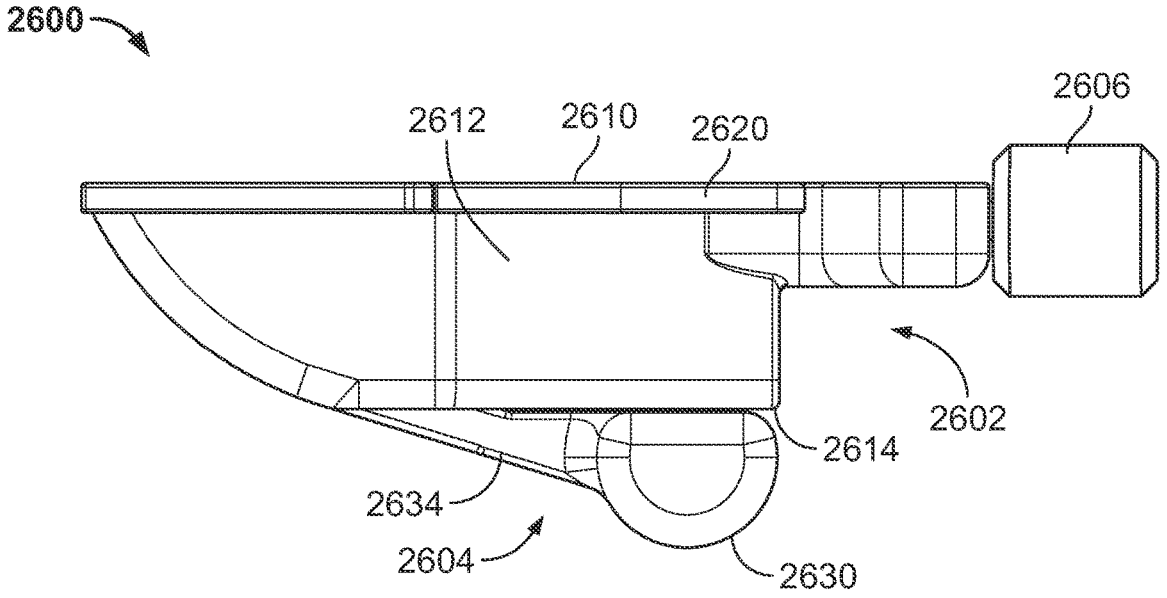
FIG. 66 is a side view of the wire guide of FIG. 65.

Turning now to FIGS. 65-71, an exemplary wire guide 2600, according to one embodiment, is shown. In some embodiments, the wire guide base 2602 may comprise a body 2612 having a superior surface 2610 and an inferior surface 2614 defining an underside of the body 2612. As shown in FIG. 65, the superior surface 2610 may be generally flat and uniform. In this regard, when the wire guide 2600 is installed on the tibial trial 2000 and/or the distractor 2100, portions of the superior surface 2610 may engage with the one or more channels 2024, 2026 such that the wire guide 2600 is secured to the tibial trial 2000.

In some embodiments, once the spike broach 2500 is used to continue forming the intramedullary canal, the user may then install the wire guide 2600 into the tibial trial 2000 (e.g., into the one or more channels 2024, 2026) and before inserting the guide wire. For instance, in some embodiments, the wire guide 2600 may be installed in the tibial trial 2000 while the spike broach 2500 (having a cannulated spike assembly 2506) remains within the workspace. In this case, the user may insert the guide wire through the wire guide 2600 and spike broach 2500 and into the medullary cavity, wherein one or more features of the wire guide 2600 are in fluid communication with one or more features of the spike broach 2500 (e.g., guide wire channel 2516). In other embodiments, the wire guide 2600 may be installed after the spike broach 2500 is removed from the workspace. In this case, the user can use the wire guide 2600 to insert a guide wire directly into the medullary cavity.

Figure 70:
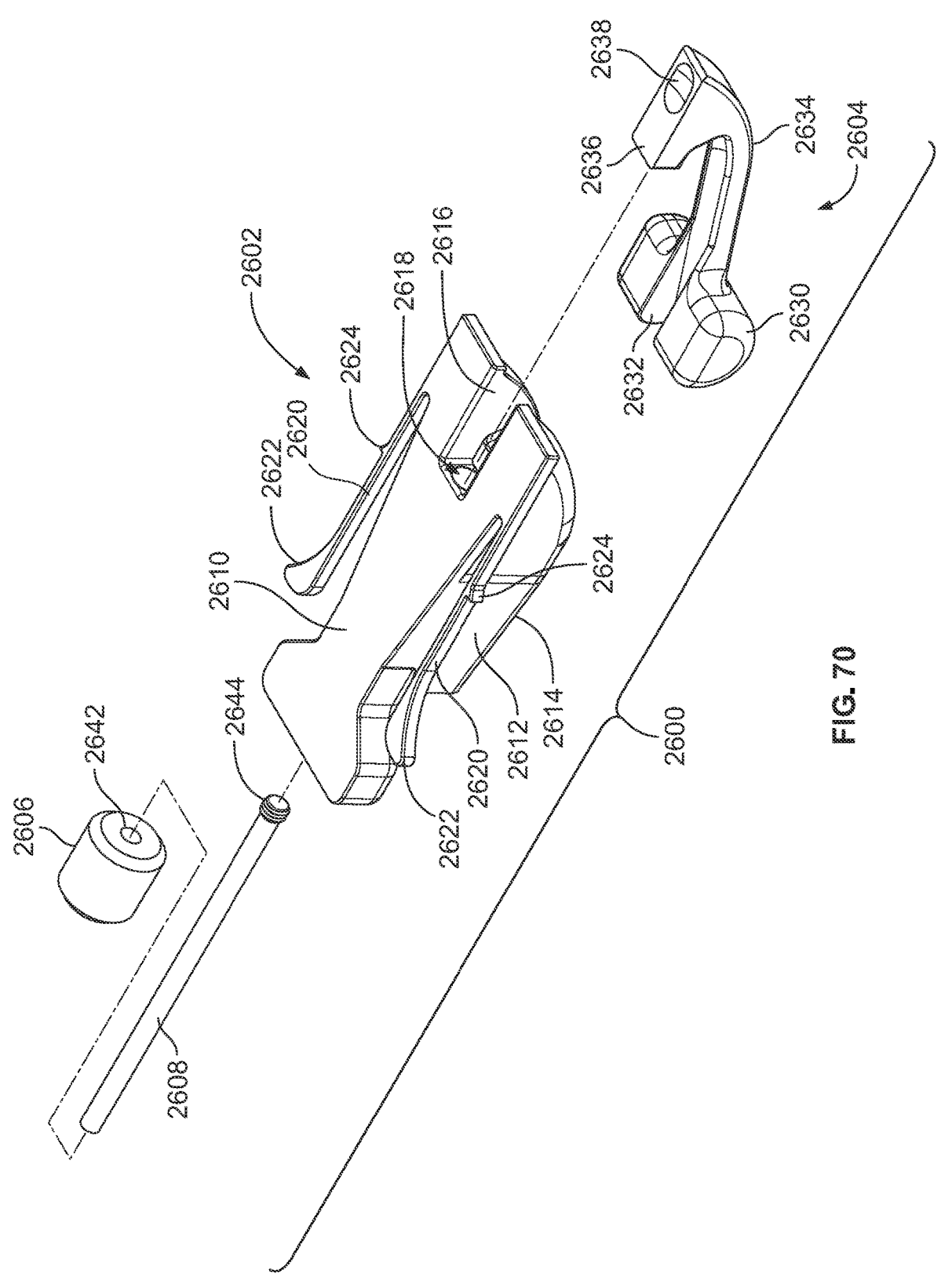
FIG. 70 is an exploded view of the wire guide of FIG. 65.

With reference to FIG. 70, in some embodiments, the wire guide 2600 may include a wire guide base 2602, a wire guide attachment 2604, a knob 2606, and a threaded rod 2608. In some embodiments, the wire guide base 2602 and the wire guide attachment 2604 can be removably coupled to each other. In this regard, as will be described in more detail herein, the knob 2606 and/or the threaded rod 2608 can be used to removably couple the wire guide base 2602 to the wire guide attachment 2604. In some embodiments, the knob 2606 and the threaded rod 2608 are integrally formed as a single component. In some embodiments, the knob 2606 and the threaded rod 2608 are removably coupled to each other. For example, as shown in FIG. 70, the knob 2606 may include a threaded rod receptacle 2642 for receiving and coupling to the threaded rod 2608. In some embodiments, the wire guide base 2602 and the wire guide attachment 2604 can be integrally formed as a single component. In this regard, the wire guide 2600 may not include a knob 2606 and/or a threaded rod 2608.

For embodiments in which the wire guide attachment 2604 can be removably coupled to the wire guide base 2602, the wire guide base 2602 may further comprise an attachment cutout 2616 and a threaded rod through hole 2618 designed to couple the wire guide attachment 2604 to the wire guide base 2602. In such embodiments, the attachment cutout 2616 may receive a portion of the wire guide attachment 2604 and the threaded rod 2608 may be inserted, via the threaded rod through hole 2618, into the portion of the wire guide attachment 2604 received by the attachment cutout 2626. In some embodiments, a first guide wire channel cutout 2628 may be formed in the body 2612 and/or the inferior surface 2614 of the wire guide base 2602 (see FIG. 69). As will be described in more detail herein, while the wire guide base 2602 is coupled to the wire guide attachment 2604, the first guide wire channel cutout 2628 may define, in part, a channel used for inserting a guide wire through the intramedullary canal and further into the medullary cavity.

In some embodiments, the wire guide base 2602 may further comprise at least one trial engagement tab 2620 such that the wire guide 2600 may be configured for insertion into the interior portions of the tibial trial 2000 (e.g., one or more channels 2024, 2026) and/or distractor 2100. As shown, the at least one trial engagement tab 2620 may be positioned on either side of the body 2402. Each of the trial engagement tabs 2620 may include an engagement protrusion 2624 and a release grip 2622 (see FIG. 70). In one non-limiting example, the trial engagement tabs 2620 may be configured to engage and slide within the one or more channels 2024, 2026 such that the user can install the wire guide 2600 into the tibial trial 2000. When inserted into the tibial trial 2000, the engagement protrusions 2624 may engage with corresponding notches 2028 of the one or more channels 2024, 2026, thus maintaining a fixed position of the wire guide 2600 relative to the tibial trial 2000. In another non-limiting example, the user can squeeze, compress, or otherwise apply force to the release grips 2622 such that the trial engagement tabs 2620 bend. This may allow the user to initially insert the wire guide 2600, or, if already inserted, disengage the engagement protrusions 2624 from the notches 2028 to remove the wire guide 2600. In certain embodiments, at least a portion of the trial engagement tabs 2620 may be resilient to allow elastic deflection of the engagement protrusions 2624 in relation to the notches 2028. In some embodiments, the engagement protrusions 2624 form a snap-fit connection with the interior portions (e.g., notches 2-28) formed in the first and/or second channels 2024, 2026.

In some embodiments, the wire guide 2600 may be installed or inserted into the tibial trial 2000 using one of the one or more channels 2024, 2026 (e.g., channel 2026) while the distractor 2100 uses another of the one or more channels 2024, 2026 (e.g., channel 2024). In other embodiments, the wire guide 2600 may be installed or inserted into the tibial trial 2000 using the one or more channels 2024, 2026 while the distractor 2100 is otherwise secured to the tibial trial 2000 (e.g., using threaded pin 2136 and apertures 2049). In some embodiments, the wire guide 2600 may be installed or inserted into the tibial trial 2000 while the spike assembly 2506 of the spike broach 2500 is inserted through the access opening 2020. In such embodiments, the superior surface 2610 of the wire guide base 2602 may be positioned underneath the first arm 2502 of the spike broach 2500 as the first and second guide rails 2124, 2126 engage with the first and/or second channels 2024, 2026.

Referring again to FIG. 70, in some embodiments, the wire guide attachment 2604 may comprise an attachment base 2630 in which a second guide wire channel cutout 2632 is formed. As shown, the wire guide attachment 2604 may further comprise a neck 2634 that extends outward in the posterior direction from the second guide wire channel cutout 2632 formed in the attachment base 2630. The neck 2634 may connect the attachment base 2630 to a mating portion 2636, wherein the mating portion 2636 may be used to couple the wire guide attachment 2604 to the wire guide base 2602. For example, the mating portion 2636 may be shaped and configured to be received within the attachment cutout 2616. In some embodiments, the mating portion 2636 may include a receptacle for receiving the threaded rod 2608. In one non-limiting example, the mating portion 2636 may include a receptacle (fitted with female threads) that is configured to receive and engage the male threads 2644 of the threaded rod 2608. In other embodiments, the mating portion 2636 may include a different type of receptacle and/or fastening element for coupling the wire guide attachment 2604 to the wire guide base 2602. As further shown, the wire guide attachment 2604 may comprise a guide wire hole 2638 positioned at a superior-facing end of the neck 2634 and adjacent to the mating portion 2636. In this regard, the guide wire hole 2638 is oriented to face in the superior direction. As will be described herein, a guide wire can be inserted through the forming intramedullary canal and into the medullary cavity via the guide wire hole 2638.

In some embodiments, to assemble the wire guide 2600, the user may couple the wire guide base 2602 to the wire guide attachment 2604 by first inserting the mating portion 2636 of the wire guide attachment 2604 into the attachment cutout 2616 formed in the wire guide base 2602. While the mating portion 2636 is inserted in the attachment cutout 2616, the receptacle formed in the mating portion 2636 may be aligned with the threaded rod via hole 2618. In this regard, the user can then insert the threaded rod 2608 through the hole 2618 such that the threads 2644 engage with the corresponding female threads of the receptacle formed in the mating portion 2636. Then the user can fasten the threaded rod 2608 to the female threads of the receptacle formed in the mating portion 2636 to secure the wire guide attachment 2604 to the wire guide base 2602. For example, the user can twist the knob 2606 (coupled to the threaded rod 2608) to fasten the threaded rod 2608 to the female threads of the receptacle formed in the mating portion 2636. In some embodiments, the user may twist the knob 2606 manually, while in other embodiments, the user may turn the knob 2606 using a wrench or similar tool to fasten the threaded rod 2608 to the female threads of the receptacle formed in the mating portion 2636. Additionally, in some embodiments, a hexagonal receptacle 2640 may be formed in the knob 2606 and the user may turn the knob 2606 using a hexagonal wrench (see FIG. 69). In other embodiments, the user may turn the knob 2606 using a different type of fastening tool, such as a Phillips head screwdriver, a Torx® wrench, a flathead screwdriver, or any other suitable fastening tool.

Figure 69:
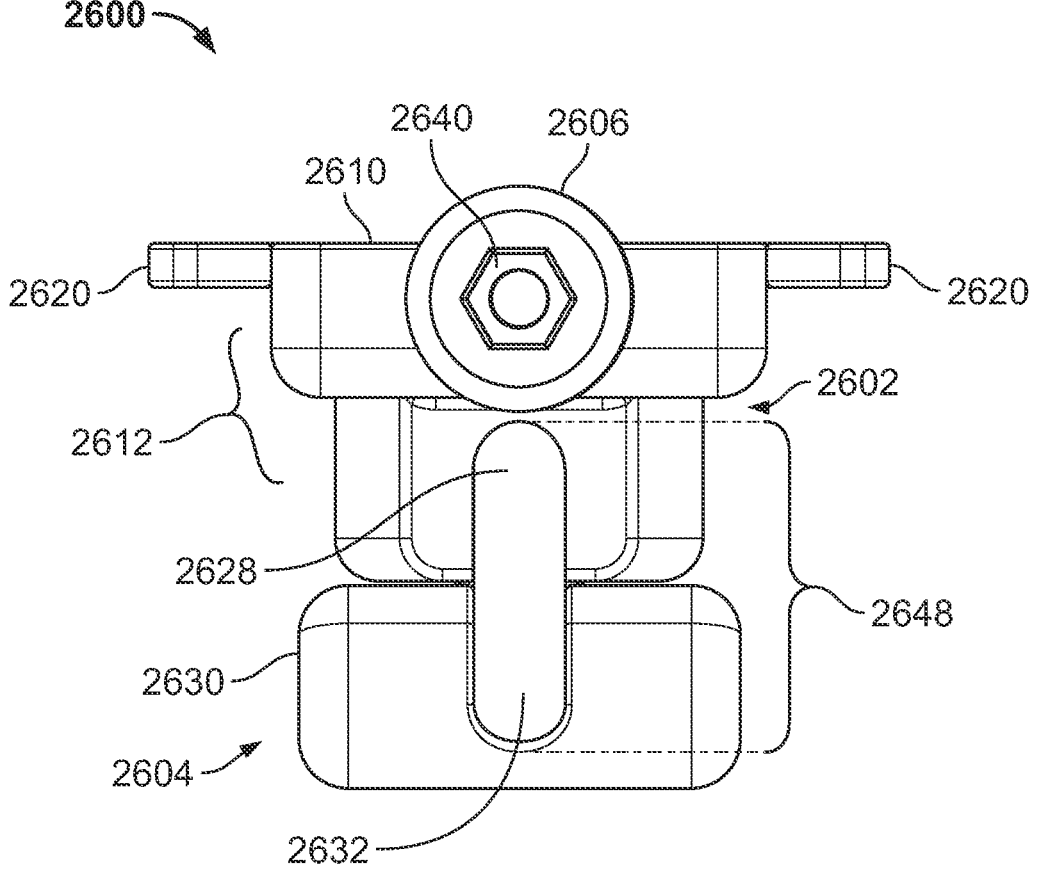
FIG. 69 is a back view of the wire guide of FIG. 65.
Figure 71:
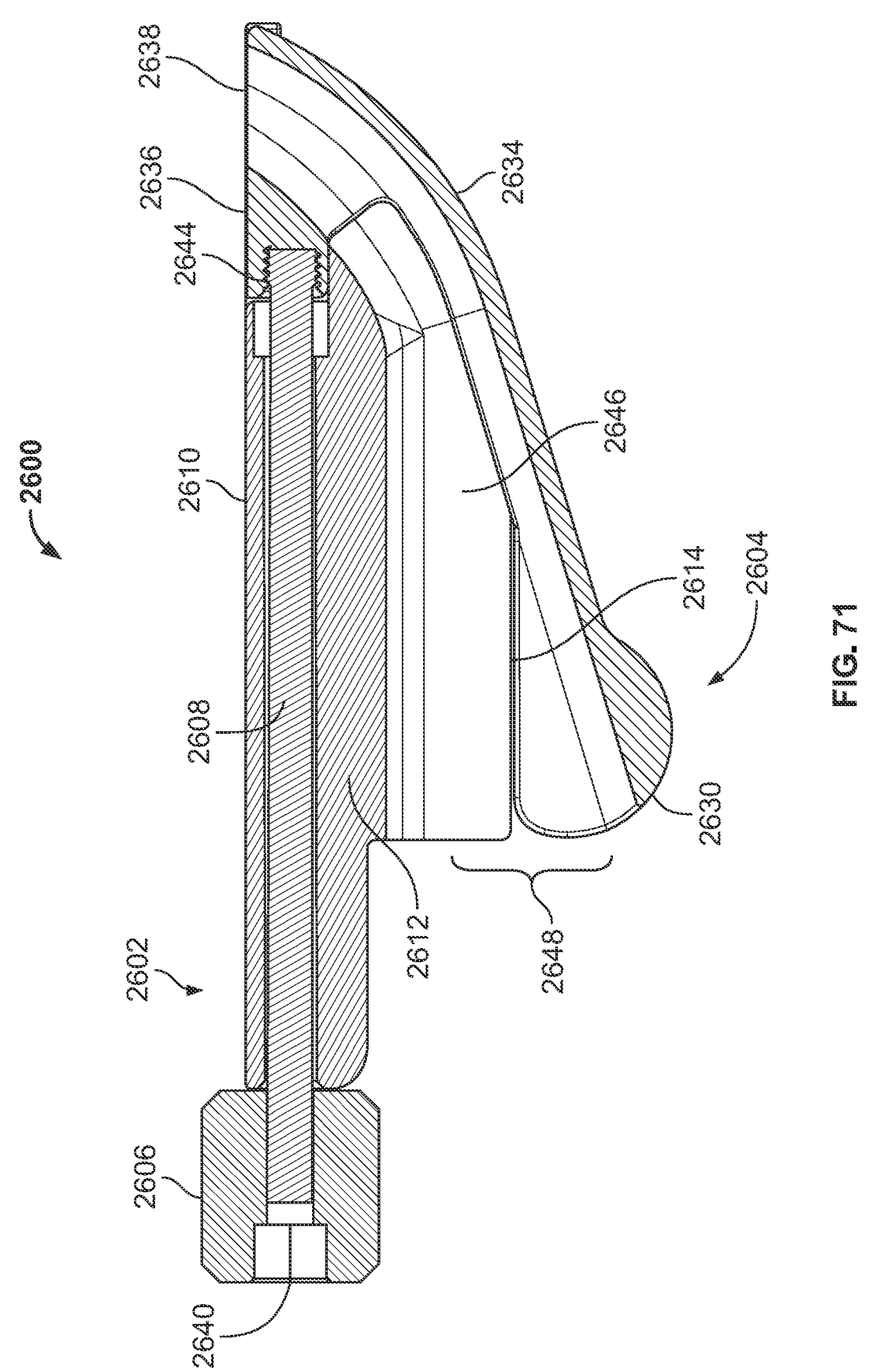
FIG. 71 is a cross-section of the wire guide of FIG. 68.

In some embodiments, while the wire guide attachment 2604 is coupled to the wire guide base 2602, the first guide wire channel cutout 2628 and the second guide wire channel cutout 2632 may combine to form a guide wire channel 2646 (see FIG. 71). In this regard, the guide wire channel 2646 may extend through the interior of the wire guide 2600 while the wire guide attachment 2604 is coupled to the wire guide base 2602. As shown in FIG. 69, the guide wire channel 2646 may be in fluid communication with a channel entrance 2648 disposed at an anterior end of the wire guide 2600 and defined by the first and second guide wire channel cutouts 2628, 2632. As shown in FIG. 71, the guide wire channel 2646 may also be in fluid communication with the guide wire hole 2638 formed in the wire guide attachment 2604. In this regard, the channel entrance 2648 may be in fluid communication with the guide wire hole 2638 formed in the wire guide attachment 2604 via the guide wire channel 24646 that extends through the interior of the wire guide 2600.

While the wire guide 2600 is installed on the tibial trial 2000 and/or the distractor 2100, the guide wire hole 2638 may be aligned with the access opening 2020 of the trial base 2002. In this regard, a user may insert a guide wire into the intramedullary canal and into the medullary cavity through the access opening 2020 via the guide wire channel 2646. For example, a user may insert a guide wire through the channel entrance 2648 to the guide wire channel 2646. Then, the user may push the guide wire through the guide wire channel 2646 such that the guide wire exits the guide wire hole 2638 and passes through the access opening 2020 and into the intramedullary canal. For embodiments in which the wire guide 2600 is used while the spike assembly 2506 of the spike broach 2500 is inserted in the workspace, the guide wire may exit the guide wire hole 2638 and enter, the guide wire channel 2516 via an opening on the inferior side of the spike broach 2500. Then, the user may push the guide wire through the guide wire channel 2516 such that the guide wire exits the central opening 2514 of the central spike 2510 and enters the medullary cavity.

In some embodiments, after the guide wire has been inserted in the intramedullary canal, a user may uninstall, or remove, the wire guide 2600 from the tibial trial 2000 and/or the distractor 2100. In some embodiments, the user may remove the wire guide 2600 while the wire guide attachment 2604 is still coupled to the wire guide base 2602. In this regard, to remove the wire guide 2600, the user may inwardly "press" the trial engagement tabs 2620 and slide the trial engagement tabs 2620 from the one or more channels 2024, 2026.

In other embodiments, to mitigate movement and/or dragging of the inserted guide wire during removal of the wire guide 2600, a user may decouple the wire guide attachment 2604 from the wire guide base 2602 before removing the wire guide 2600. In this regard, a user may turn the knob 2606 to unfasten the threaded rod 2608 from the receptacle formed in the mating portion 2636 of the wire guide attachment 2604, thereby decoupling the wire guide attachment 2604 from the wire guide base 2602. Then, the user may remove the wire guide attachment 2604 by sliding the wire guide attachment 2604 along the inserted guide wire, thus mitigating movement and/or dragging of the guide wire. After removing the wire guide attachment 2604, the user may then remove the wire guide base 2602 from the tibial trial 2000 and/or the distractor 2100 without contacting the guide wire. For example, the user may inwardly "press" the trial engagement tabs 2620 and slide the trial engagement tabs 2620 from the one or more channels 2024, 2026. to remove the wire guide base 2602.

With reference to FIG. 68, in some embodiments, when measured at a posterior end of the wire guide base 2602, the wire guide 2600 may include a width 2650 measuring about 10.0 to 15.0 mm, about 15.0 to 20.0 mm, about 20.0 to 25.0 mm, about 25.0 to 30.0 mm, about 30.0 to 35.0 mm, about 35.0 to 40.0 mm, about 40.0 to 50.0 mm, about 45.0 to 55.0 mm, about 50.0 to 60.0 mm, about 55.0 to 65.0 mm, about 60.0 to 70.0 mm, or any other suitable length in accordance with the principles of this disclosure. The width 2650 of the wire guide 2600 may correspond with, for example, the width of the trial base 2002. In this regard, the wire guide 2600 may engage with the first and/or second channels 2024, 2026 of the trial base 2002.

Reamer Assembly

Referring now to FIGS. 72A, 73-77, and 78A, one embodiment of a flexible reamer assembly is shown, comprising a flexible reamer 2700 and a reamer guide 2750, in accordance with the principles of this disclosure. In some embodiments, the flexible reamer 2700 includes a reamer head 2702, wherein the reamer head 2702 includes at least one cutting surface 2703 that may be used to continue forming the intramedullary canal. The reamer head 2702 may be attached to a shaft 2704, wherein the shaft includes a flexible portion 2706. In the embodiment shown, the shaft 2704 includes an outer diameter of approximately 4.0 to 6.0 mm or any other suitable diameters may be used without departing from the principles of this disclosure. Further, a proximal end of the flexible reamer 2700 may include a drive element 2714 which may be selectively inserted into a standard power drill chuck.

Figure 77:
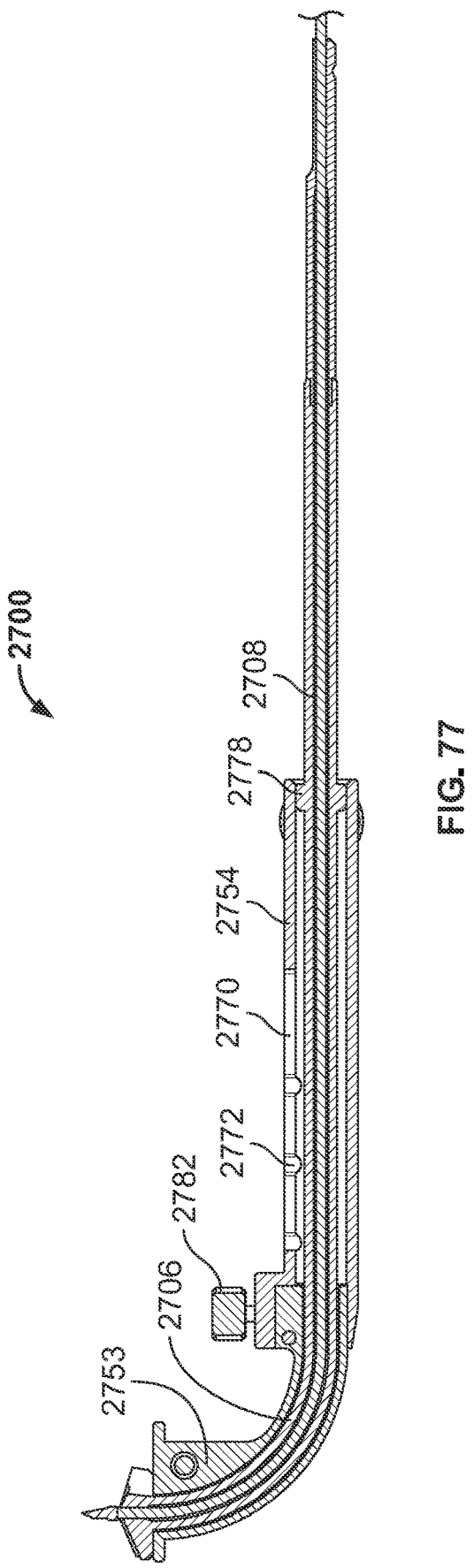
FIG. 77 is a cross-section view of the reamer assembly of FIG. 74.

With reference to FIG. 77, in some embodiments, the flexible reamer 2700 may be cannulated, meaning that the shaft 2704 may be hollow and include a passageway 2708 disposed along the length of the shaft 2704. In some embodiments, the cannulation may extend throughout the flexible portion 2706 such that the flexible reamer 2700 may follow a curved path of a guide wire via a passageway 2708. Thus, the passageway 2708 may be designed to support a guide wire within the flexible reamer 2700 (e.g., a user may push a guide wire through the flexible reamer 2700, via the passageway 2708, and into the medullary cavity) such that the reamer head 2702 of a cannulated flexible reamer 2700 can travel along the inserted guide wire to guide the reamer head 2702 when continuing formation of the intramedullary canal.

According to some embodiments, the flexible portion 2706 may include one or more cuts 2710 disposed along a length of the shaft 2704, each cut 2710 having a sufficient depth to allow flexing about the cut 2710. In some embodiments, the one or more cuts 2710 may extend circumferentially around an outer surface of shaft 2704 and may have a sinusoidal, wave, or other suitable shape to enhance flexibility. In some embodiments, the flexible portion 2706 may be 3D-printed with the one or more cuts 2710, while in other embodiments, the one or more cuts 2710 may be machined or otherwise included onto the flexible portion 2706. In certain embodiments, the one or more cuts 2710 may pass partially through the shaft 2704 to form discrete, interlocking portions 2712 of the shaft 2704, which may be interlocked by the shape of the cuts 2710. In some embodiments, the interlocking portions 2712 may be shaped like dovetail or jig-saw puzzle pieces. In certain embodiments, each interlocking portion 2712 may be slightly offset from adjacent interlocking portions 2712 to improve stability and functionality of the flexible portion 2706.

Figure 78:
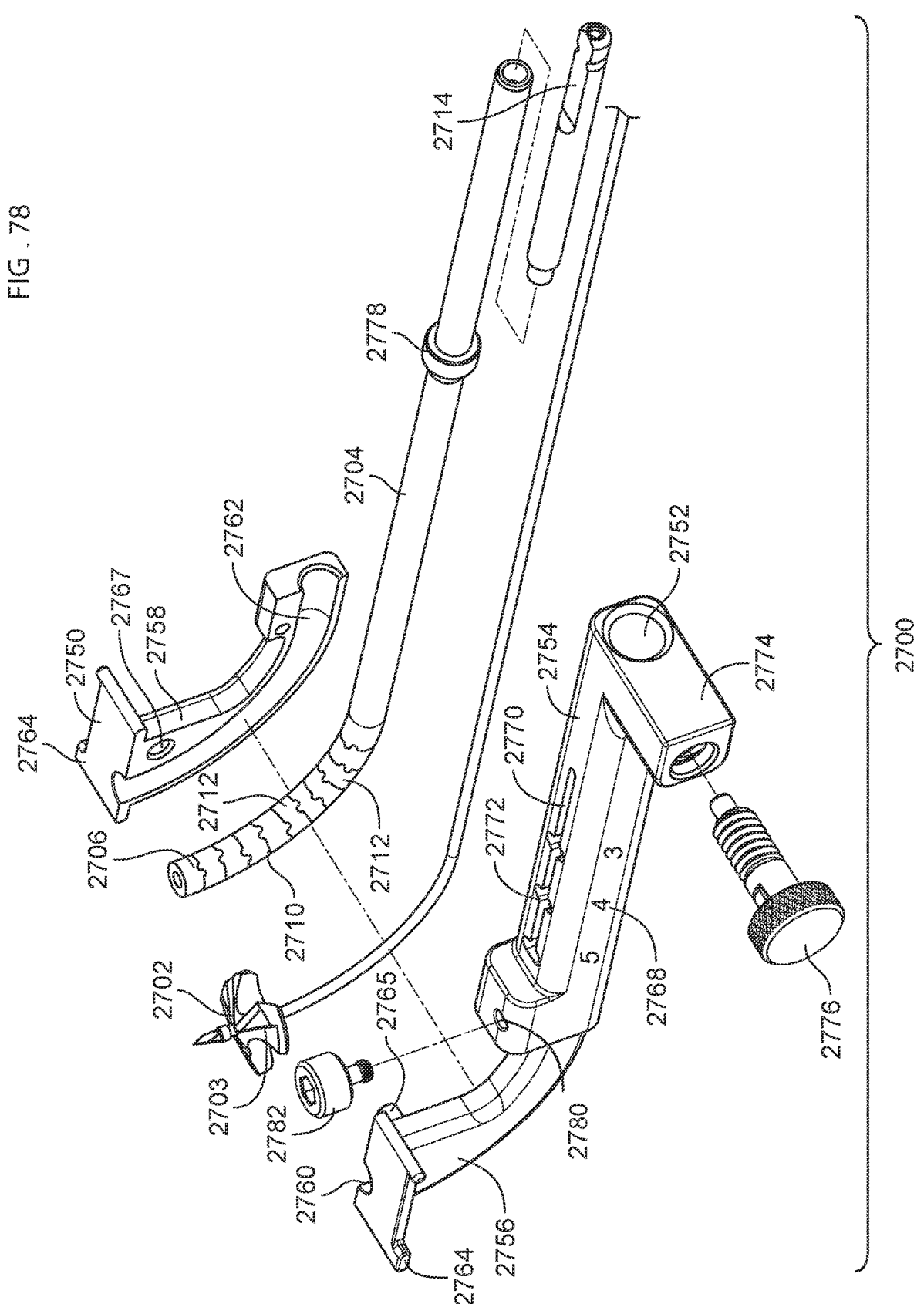
FIG. 78 is an exploded view of the reamer of FIG. 72.

According to some embodiments, the flexible reamer assembly may include a reamer guide 2750 that guides the path of the flexible reamer 2700 into the medullary cavity as the flexible reamer 2700 reams over the guide wire. In some embodiments, the reamer guide 2750 may include a first guide portion 2756 having a straight guide portion 2754 and a second guide portion 2758. In some embodiments, the first guide portion 2756 and the second guide portion 2758, when coupled, fastened, or otherwise assembled, form a curved guide portion 2753. As shown in FIG. 78, the first guide portion 2756 may include a first channel 2760 and the second guide portion 2758 may include a second channel 2762. Thus, the reamer guide 2750, when the first guide portion 2756 and the second guide portion 2758 are assembled, may form an overall guide passageway 2752 sized for the shaft 2704 to pass through. In this regard, the reamer guide 2750 may guide the flexible reamer 2700 into the prepared tibial surface via the guide passageway 2752 to continue forming the intramedullary canal.

In certain embodiments, the curved guide portion 2753 may be removably attached to the straight guide portion 2754. In the embodiment shown, the first guide portion 2756 may include a threaded hole 2780 into which a screw 2782 is selectively inserted. In certain embodiments, the screw 2782 selectively engages the threaded hole 2780 of first guide portion 2756. In other embodiments, alternative temporary fasteners may be used without departing from the principles of this disclosure.

According to some embodiments, the flexible reamer 2700 may be inserted at an angle relative to the intramedullary axis and then bend to align with the intramedullary axis. In some embodiments, the guide passageway 2752 may include certain features that allow for the flexible portion 2706 of the shaft 2704 to ream vertically into the medullary cavity through a single anterior access point to the patient's ankle joint. As shown, the guide passageway 2752 may include a curved guide portion 2753 that enables the flexible portion 2706 to bend approximately 45 to 90° as it passes through the straight guide portion 2754 of the guide passageway 2752, while in other embodiments, the curved guide portion 2753 may enable the flexible portion 2706 to bend more or less than 90°. In certain embodiments, it may be desirable to bend the flexible portion 2706 according to a patient-specific angle, such that the flexible reamer 2700 is positioned to ream a patient-specific path of the intramedullary canal. In such embodiments, the curved guide portion 2753 may include a patient-specific contour.

In certain embodiments, the curved guide portion 2753 may further include at least one locating feature 2764 that selectively engages interior portions of the tibial trial 2000 (e.g., first and second channels 2024, 2026). In other embodiments, the at least one locating feature 2764 and/or the curved guide portion 2753 may selectively engage a reamer lock plate 2800 (see FIG. 79) which, in turn, may selectively engage with interior portions of the tibial trial 2000. In certain embodiments, it may be desirable to separate the reamer guide 2750 from the reamer lock plate 2800 for ease of assembly of the reamer guide 2750 and/or ease of insertion and removal of the reamer guide 2750 from the tibial trial 2000. In some embodiments, the reamer guide 2750, when assembled within the overall flexible reamer assembly, may engage with the channels 2024, 2026 of the tibial trial 2000 such that the reamer guide 2750 positions the reamer head 2702 through the access opening 2020.

As shown in FIG. 78, the first guide portion 2756 may include at least one locating pin 2765 that selectively engages at least one locating hole 2767 disposed within the second guide portion 2754. The locating pin 2765 and the corresponding locating hole 2767 may engage to align the first channel 2760 and the second channel 2762, thereby forming a portion of the guide passageway 2752. In some embodiments, the curved guide portion 2753 may be assembled on a "back table" during or prior to the TAR procedure. In other embodiments, curved guide portion 2753 may be pre-assembled or may be assembled on a back table.

In some embodiments, the straight guide portion 2754 may be removably attached to the first guide portion 2756 (and thus the curved guide portion 2753). In certain embodiments, the straight guide portion 2754 may include a body 2766 having at least one slot 2770 that provides visibility with regards to the position of the shaft 2704 of the flexible reamer 2700 relative to the reamer guide 2750. In certain embodiments, at least one visual indicator 2768 may be included on the slot 2770 and/or on the body 2766. In some embodiments, the slot 2770 may include at least one stem portion indicator 2772 to indicate a depth of reaming to accommodate a corresponding number of modular members of modular stem system 1000.

In some embodiments, the visual indicator 2768 may indicate a distance in units of measurement including, but not limited to millimeters, centimeters, or inches. In other embodiments, the visual indicator 2768 may include etchings or markings on the straight guide portion 2754 to indicate a number of modular members of the modular stem system 1000 used for the TAR procedure. As shown in FIG. 78, for example, the straight guide portion 2754 may include indications of "3," "4," and "5" to visualize for the user the depth of reaming corresponding with either 3, 4, or 5 modular members. In certain embodiments, the shaft 2704 may further include at least one depth indicator as well, corresponding to the visual indicators 2708 on the straight guide portion 2754.

In certain embodiments, the straight guide portion 2754 may further include a set screw block 2774 extending from one side of the straight guide portion 2754, wherein a set screw 2776 may be inserted into the set screw block 2774 to selectively engage the shaft 2704, thus securing the flexible reamer 2700 in a desired position. In some embodiments, the shaft 2704 may optionally include a shoulder portion 2778 that engages the set screw 2776 to prevent over-insertion of the flexible reamer 2700 into the medullary cavity. In some embodiments, a guide lock (not shown) may be inserted into the at least one stem portion indicator 2772. The guide lock may provide a positive stop by engaging the shoulder portion 2778 as the flexible reamer 2700 advances into the medullary cavity, thereby preventing over-reaming of the intramedullary canal.

In certain embodiments, the flexible reamer 2700 may be assembled with the reamer guide 2750 on a back table (i.e., away from or outside of the patient). For instance, the user may capture the flexible portion 2706 between the first channel 2760 of the first guide portion 2756 and the second channel 2762 of the second guide portion 2758 to assemble the flexible reamer 2700 with the reamer guide 2750. In other embodiments, the user may assemble the flexible reamer assembly in any suitable manner without departing from the principles of this disclosure.

In certain embodiments, the flexible reamer assembly (including the flexible reamer 2700 and reamer guide 2750) may be assembled with a guide wire contained therein on a back table, without departing from the principles of this disclosure. Such embodiment may be used when a non-cannulated embodiment of the spike broach 2500 is used for the TAR procedure. In such embodiments, the guide wire and the flexible reamer assembly may be inserted into the medullary cavity either simultaneously or by alternating the advancement of the guide wire and the flexible reamer 2700 into the medullary cavity to continue forming the intramedullary canal.

Figure 72:
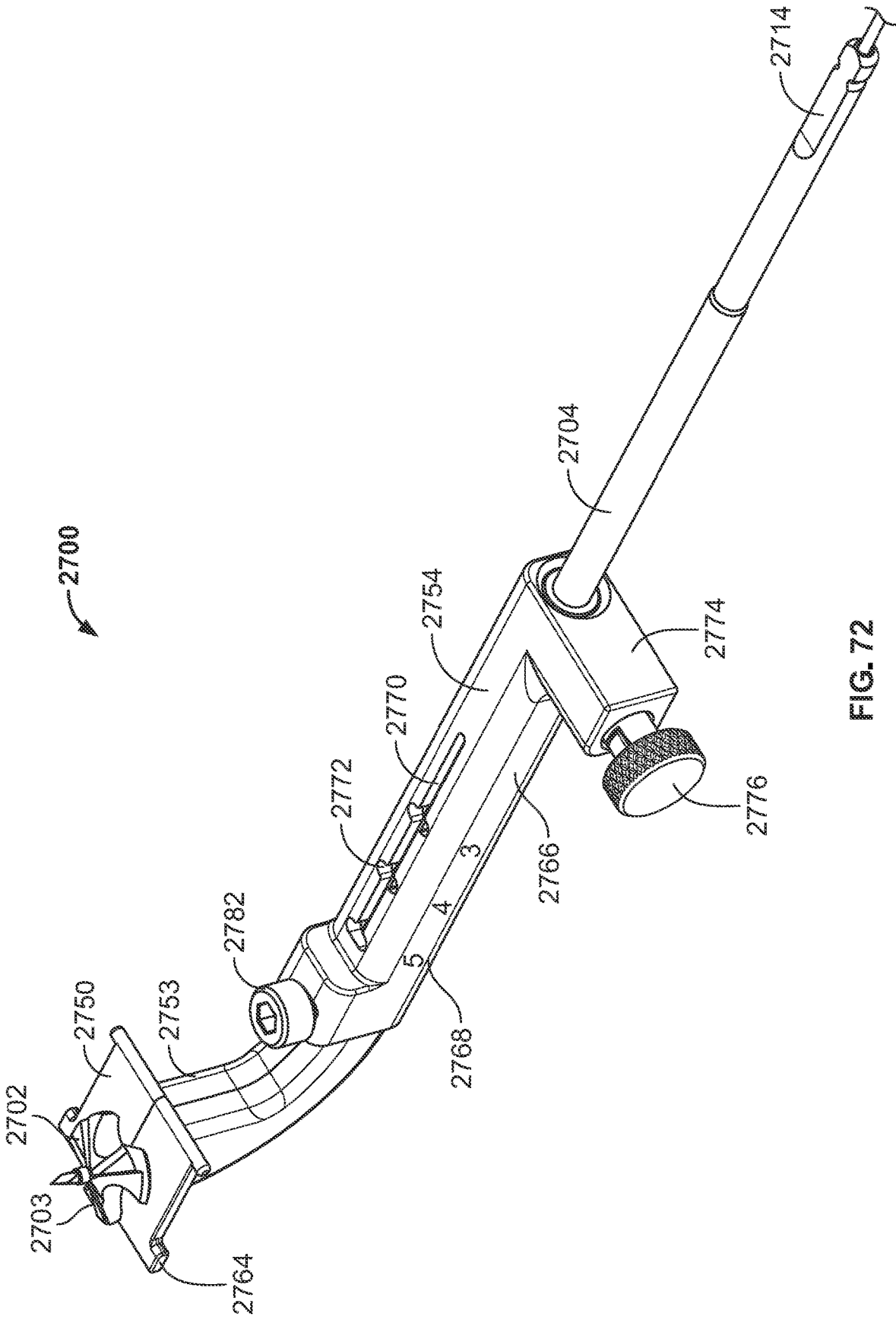
FIG. 72 is a perspective view of a reamer assembly, according to one embodiment.
Figure 72A:
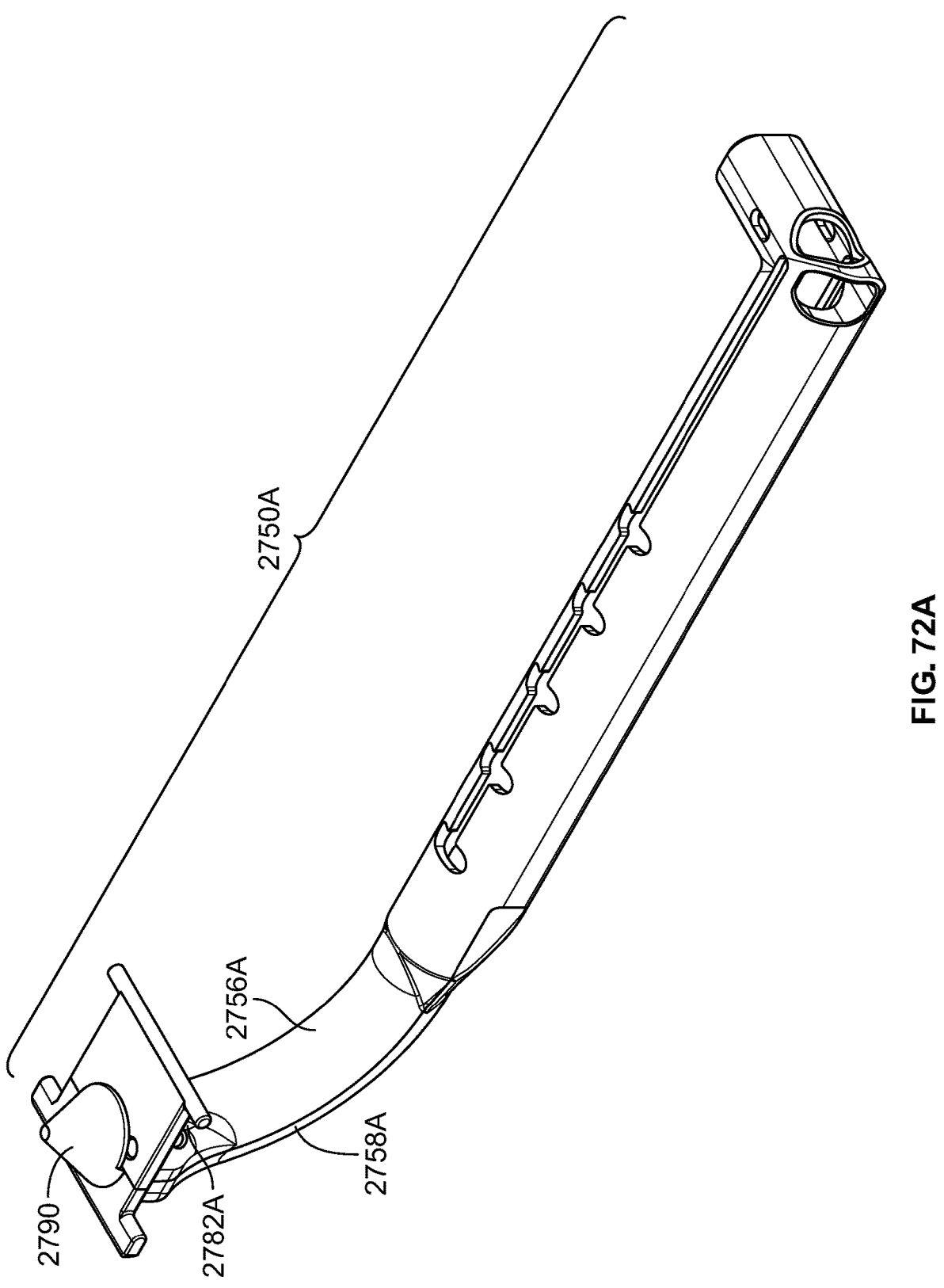
FIG. 72A is a perspective view of a reamer guide, according to one embodiment.
Figures 73, 74:
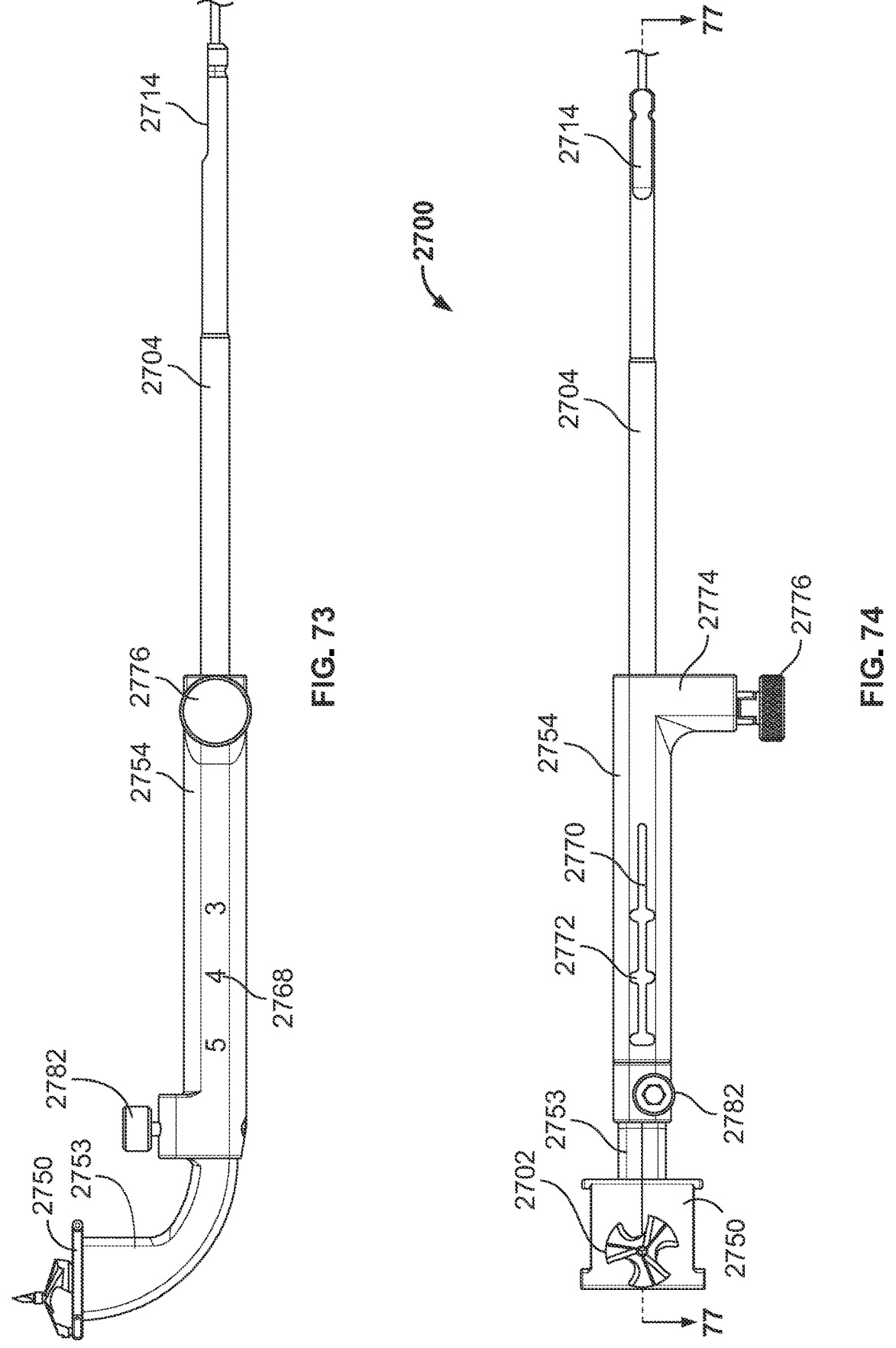
FIG. 73 is a side view of the reamer assembly of FIG. 72.
FIG. 74 is a top view of the reamer assembly of FIG. 72.
Figures 75, 76:
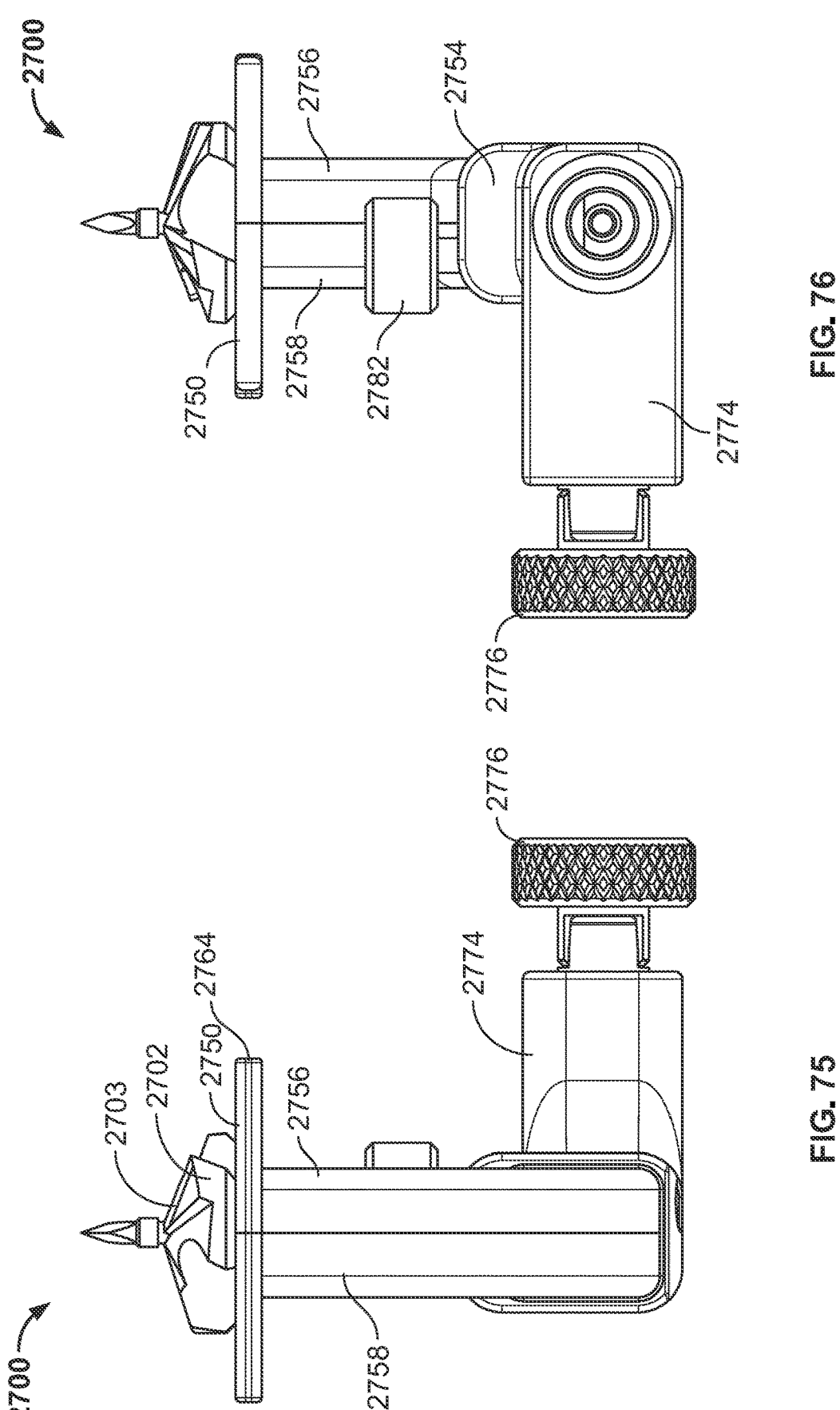
FIG. 75 is a front view of the reamer assembly of FIG. 72.
FIG. 76 is a back view of the reamer assembly of FIG. 72.
Figure 78A:
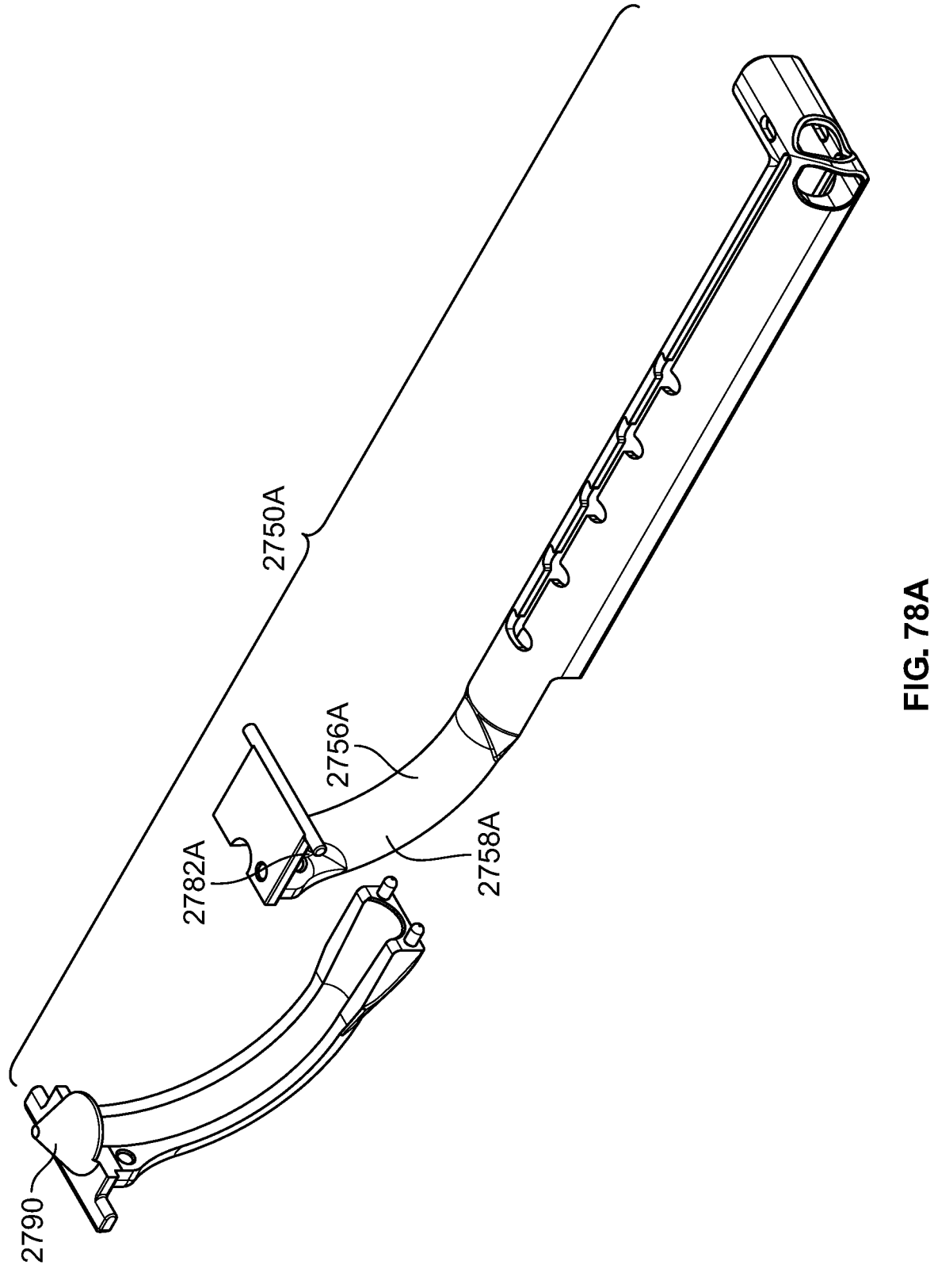
FIG. 78A is an exploded view of the reamer of FIG. 72A.

Referring now to FIGS. 72A and 78A, an additional embodiment of the reamer guide 2750A for use with the flexible reamer assembly is shown. In this embodiment, the reamer guide 2750A may include a first guide portion 2756A and a second guide portion 2758A that can be assembled in the posterior-anterior direction and fastened together using a screw 2782A. In some embodiments, the second guide portion 2758A may include a wire guide attachment 2790, wherein the wire guide attachment 2790 guides a guide wire contained within the assembled reamer guide 2750 (as part of the overall flexible reamer assembly). In some embodiments, the wire guide attachment 2790 may be removably coupled to the second guide portion 2758A while in other embodiments, the wire guide attachment 2790 may be integrally formed with the second guide portion 2758A. The user may thus advance the guide wire with the flexible reamer 2700 using the wire guide attachment 2790 during the TAR procedure.

Figure 79:
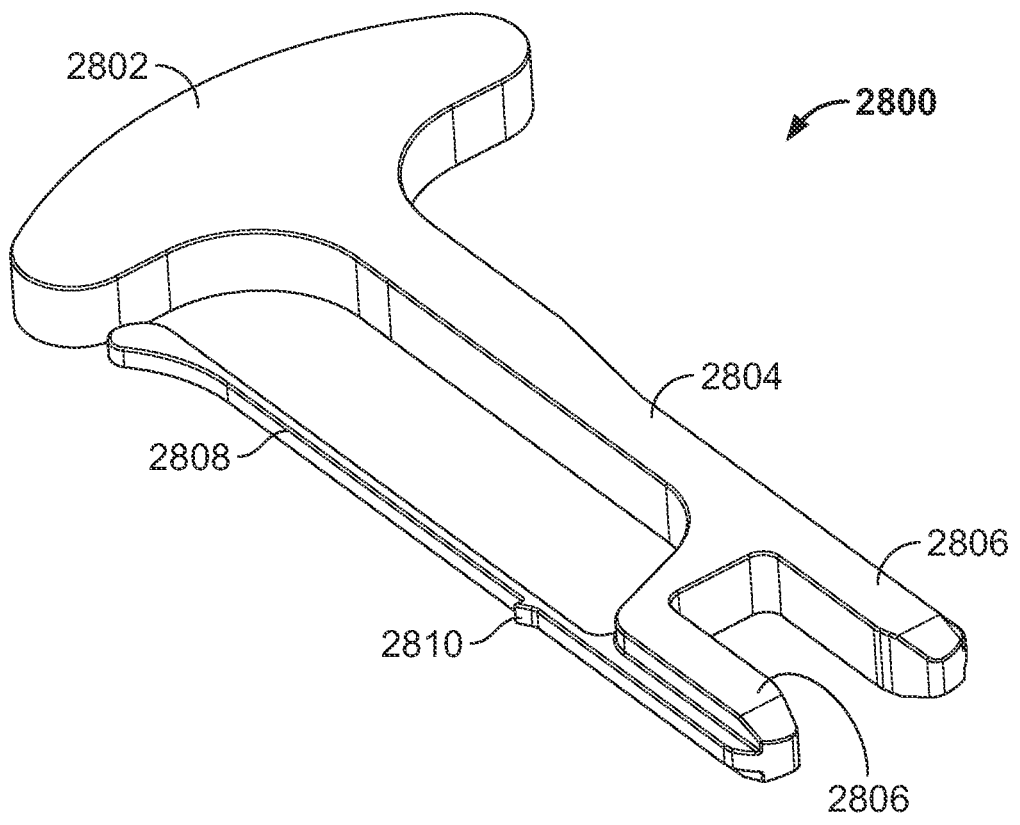
FIG. 79 is a perspective view of a reamer locking tool, according to one embodiment.

Turning now to FIG. 79, one embodiment of a reamer locking tool, or reamer lock plate 2800, in accordance with the principles of this disclosure, is shown. In some embodiments, the reamer lock plate 2800 may be used to secure a desirable position of the flexible reamer assembly in relation to the tibial trial 2000. In particular, the reamer lock plate 2800 may selectively engage with the reamer guide 2750 and to temporarily secure the reamer guide 2750 to the tibial trial 2000. As shown, the reamer lock plate 2800 may include a handle portion 2802 connected by a handle body 2804. In some embodiments, the handle portion 2802 may be disposed on a first end of the handle body 2804 while one or more prongs 2806 may be disposed on a second end of the handle body 2804. In certain embodiments, the one or more prongs 2806 may have any suitable alternative shape without departing from the principles of this disclosure. In the embodiment shown, a resilient locking arm 2808 may extend from the second end of the body 2804 towards the handle portion 2802. In other embodiments, the resilient locking arm 2808 may extend from a prong 2806 towards the handle portion 2802. In some embodiments, the resilient locking arm 2808 may be configured to bend about a point of connection with the body 2804 and thus may be relatively flexible. As shown, the resilient locking arm 2808 may include a locking tab 2810 extending therefrom.

In use, the reamer lock plate 2800 may be inserted into the tibial trial 2000 (e.g., first and second channels 2024, 2026) such that the locking tab 2810 selectively engages with interior portions of the tibial trial 2000 to secure the position of the reamer lock plate 2800. In some embodiments, the locking tab 2810 may also prevent the reamer lock plate 2800 from inadvertently disengaging from the tibial trial 2000. When the user wishes to remove the reamer lock plate 2800 (e.g., when reaming is complete), the user may apply force to the resilient locking arm 2808 such that the locking tab 2810 disengages from interior portions of the tibial trial

2000, thereby allowing the user to remove the reamer lock plate 2800 from the tibial trial 2000.

Sight Alignment Tool

Turning now to FIGS. 80-83, an exemplary sight alignment tool 2900, according to one embodiment, is shown. Generally, the sight alignment tool 2900 may be used as part of the TAR procedure to approximate and verify a precise alignment of other tools and instruments as the user prepares the tibial surface/medullary cavity for implant installation. In some cases, this precision may improve the success of the TAR procedure and the long-term health of the final TAR system. In some embodiments, the sight alignment tool 2900 may be placed on/near or inserted into the tibial trial 2000 (described with reference to FIGS. 22-29), and may include visual and/or auditory markers that allow the user to assess alignment in different planes. Based on feedback from the sight alignment tool 2900, the user can make any necessary adjustments to finalize the tibial trial 2000 position. In some embodiments, the sight alignment tool 2900 may be a manual tool (e.g., adjusted manually, yielding information manually), electronic tool (e.g., adjusted digitally, yielding information digitally), or any suitable combination thereof. In embodiments including an electronic sight alignment tool, a digital level (having an accelerometer and/or gyroscope) may be used to determine different angles of the sight alignment tool and any other tools (e.g., the tibial trial 2000, distractor 2100, guide wire, etc.) in relation to a reference point.

According to some embodiments, the sight alignment tool 2900 may include a projection arm 2902, a first portion 2904, and a second portion 2906. In some embodiments, the projection arm 2902 may be a generally thin, flat component including a first portion 2904 and a second portion 2906 connected via an elbow-bend 2908. In some embodiments, the first portion 2904 may include a pronged surface 2910 positioned at a first end 2909 configured or otherwise sized to engage with the alignment slot 2042 of the tibial trial 2000 (see FIGS. 22-29). When a user engages the pronged surface 2910 with the alignment slot 2042, the first portion 2904 may extend from the tibial trial 2000 in the anterior direction and the second portion 2906 may "wrap around" the tibial trial 2000 at an angle via the elbow-bend 2908. This may give the user a visual indication of lateral alignment from the anterior-posterior direction.

In some embodiments, the second portion 2906 may include a length 2914 having one or more notches 2912 positioned along the length 2914. Further, the second portion 2906 may include a depth indicator 2916 configured to engage with the one or more notches 2912. Moving, translating, and/or sliding the depth indicator 2916 along the length 2914 of the second portion 2906 may adjust a position of an anterior-posterior measuring location 2918. This may give the user a visual indication of anterior-posterior alignment from the lateral direction. In some embodiments, the one or more notches 2912 can be spaced about 0.5 to 1.5 mm apart, about 1.0-3.0 mm apart, about 2.0 to 4.0 mm apart, about 3.0 to 5.0 mm apart, about 4.0 to 6.0 mm apart, about 5.0 to 7.0 mm apart, about 6.0 to 8.0 mm apart, about 7.0 to 9.0 mm apart, about 8.0 to 1.0 mm apart, or any other suitable distance apart. In embodiments including an electronic sight alignment tool, information pertaining to the measuring location 2918 may be available to the user on a display incorporated on the depth indicator 2916 or any other suitable position on the sight alignment tool 2900.

In some embodiments, the length 2914 of the second portion 2906 can measure about 50.0 to 60.0 mm, about 55.0 to 65.0 mm, about 60.0 to 70.0 mm, about 65.0 to 75.0 mm, about 70.0 to 80.0 mm, about 75.0 to 85.0 mm, about 80.0 to 90.0 mm, about 85.0 to 95.0 mm, about 90.0 to 100.0 mm, or any suitable length in accordance with the principles of this disclosure. In some embodiments, a length 2914 of the first portion 2904 can measure about 70.0 to 80.0 mm, about 75.0 to 85.0 mm, about 80.0 to 90.0 mm, about 85.0 to 95.0 mm, about 90.0 to 100.0 mm, about 95.0 to 105.0 mm, about 100.0 to 110.0 mm, or any suitable length in accordance with the principles of this disclosure. In some embodiments, the overall projection arm 2902 can include a width 2926 measuring about 5.0 to 7.0 mm, about 6.0 to 8.0 mm, about 7.0 to 9.0 mm, about 8.0 to 10.0 mm, about 9.0 to 11.0 mm, about 10.0 to 12.0 mm, about 11.0 to 13.0 mm, or any suitable width in accordance with the principles of this disclosure. In some embodiments, the overall projection arm 2902 can include a thickness 2928 measuring about 0.5 to 1.25 mm, about 0.75 to 1.5 mm, about 1.0 to 1.75 mm, about 1.25 to 2.0, about 1.5 to 2.25 mm, about 1.75 to 2.5 mm, 2.0 to 2.75 mm, about 2.25 to 3.0 mm, or any suitable thickness in accordance with the principles of this disclosure.

In some embodiments, the sight alignment tool 2900 may include an extension tool 2920 coupled to the depth indicator 2916. In some embodiments, the depth indicator 2916 may include an opening to receive the extension tool 2920 such that the extension tool 2920 is removably coupled with the depth indicator 2916. In some embodiments, the extension tool 2920 may be a rod, a tube, or any other suitable measuring reference tool. In some embodiments, the extension tool 2920 may include markings along its length 2922 to indicate different measurements to the user. In such embodiments, when using X-ray imaging, the user may assess vertical and/or anterior-posterior alignment of the tibial trial or other tools (e.g., guide wire, reamer). In embodiments including an electronic sight alignment tool, feedback pertaining to the position of the extension tool 2920 may be accessible to the user on a display positioned on any suitable location on the sight alignment tool 2900. Further, feedback based on the anterior-posterior and/or lateral positioning of the sight alignment tool 2900 In some embodiments, the extension tool 2920 includes a length 2922 measuring about 10.0 to 30.0 cm, about 15.0 to 25.0 cm, about 20.0 to 30.0 cm, about 25.0 to 35.0 cm, about 30.0 to 40.0 cm, about 35.0 to 45.0 cm, about 40.0 to 50.0 cm, or any suitable length in accordance with the principles of this disclosure.

According to some embodiments, the projection arm 2902 may provide a leveling mechanism that allows the user to ensure that the tibial trial 2000, guide wire, and/or final implant (e.g., modular stem system 1000) is aligned properly with respect to the patient tibia, while the extension tool 2920 may provide a vertical reference for alignment. In one non-limiting example, the sight alignment tool 2900 can be used to verify initial alignment of the tibial trial 2000 in order to finalize its position. In another non-limiting example, the sight alignment tool 2900 can be used to approximate alignment of a guide wire inserted into the medullary cavity over the course of the TAR procedure. In another non-limiting example, the sight alignment tool 2900 can be used to approximate the path and alignment of the reamer head 2702 as the flexible reamer 2700 (described with reference to FIGS. 72-79) is used to widen the medullary canal. In another non-limiting example, the sight alignment tool 2900 can be used to assess tension in soft tissues (e.g., ligaments, tendons) surrounding the ankle joint and to verify proper soft tissue balancing in addition to alignment. In another non-limiting example, the sight alignment tool 2900 can be used to evaluate range of motion of the ankle joint (e.g., ensure smooth movement) with the tibial trial in place. In some embodiments, the sight alignment tool 2900 may be equipped with variously positioned sensors and a controller configured to receive feedback signals based on the anterior-posterior and/or lateral positioning of the projection arm 2902 and extension tool 2920. The feedback signals may then alert the user to adjust the position of the tibial trial 2000, guide wire, or any other suitable tool.

Compressor Assembly

Turning now to FIGS. 84-93, one embodiment of a compressor assembly 3000 is shown. In some embodiments, the compressor assembly 3000 may include a compressor 3002, a stem inserter tool 3001, and a stem inserter guide 3003. The compressor assembly 3000 may be designed to engage with the tibial trial 2000 once preparation of the intramedullary canal is complete, such that a user may insert portions of the modular stem system 1000 (e.g., one or more modular members 1080, 1062, 1042). In some embodiments, the compressor assembly 3000 may include features that enable a user to insert modular members, fasten adjacent modular members together, and/or impact the inserted modular members and/or overall modular stem system 1000 into the intramedullary canal.

As shown in FIGS. 86 and 87, according to some embodiments, the compressor 3002 may include a body 3004, a shaft 3006, and a support 3007. The shaft 3006 may be at least partially inserted into the body 3004 at a first end of the shaft 3006, and may be coupled to the support 3007 at a second end of the shaft 3006. In some embodiments, the body 3004 may include one or more support bars 3008, wherein the one or more support bars 3008 each include holes 3010 disposed therein. When the compressor assembly 3000 is inserted into or otherwise engaged with the tibial trial 2000, the holes 3010 may align with through holes on the anterior face 2014 of the tibial trial 2000 (e.g., apertures 2048, 2049) such that the user may insert fasteners into the holes 3010 to secure the body 3004 to the tibial trial 2000.

Figure 91:
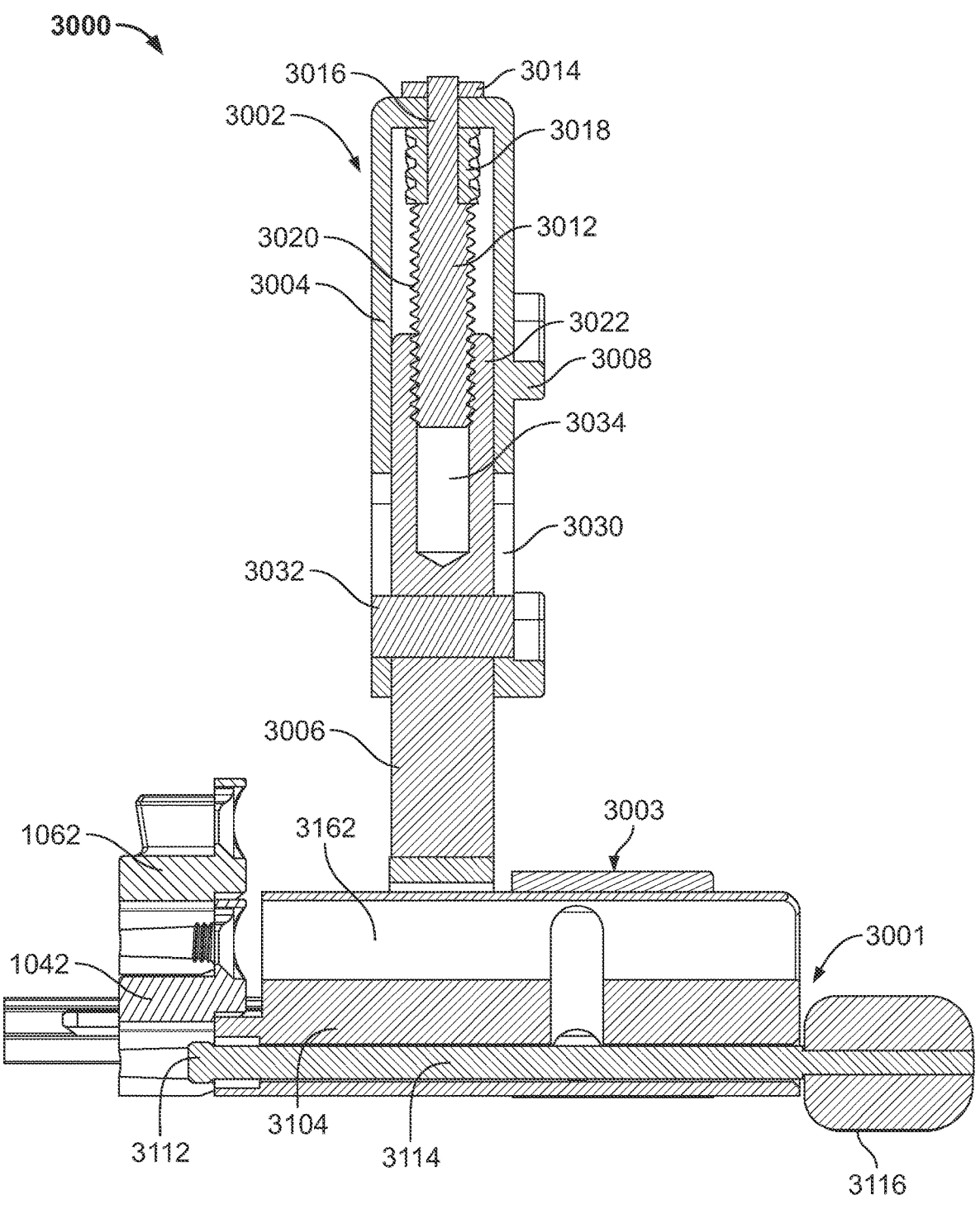
FIG. 91 is a cross-section view of the compressor assembly of FIG. 89.
Figure 92:
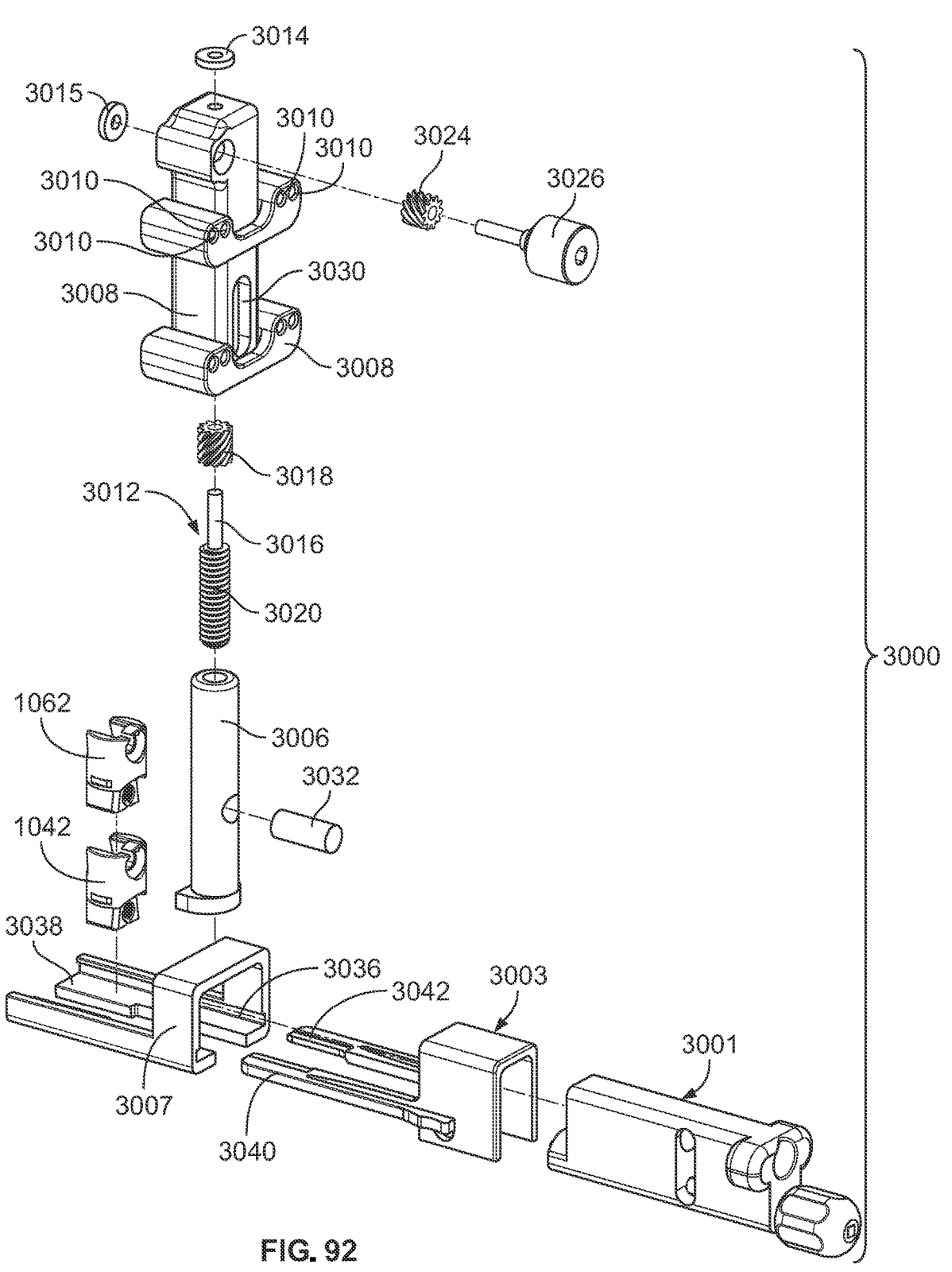
FIG. 92 is an exploded view of the compressor assembly of FIG. 84.
Figure 93:
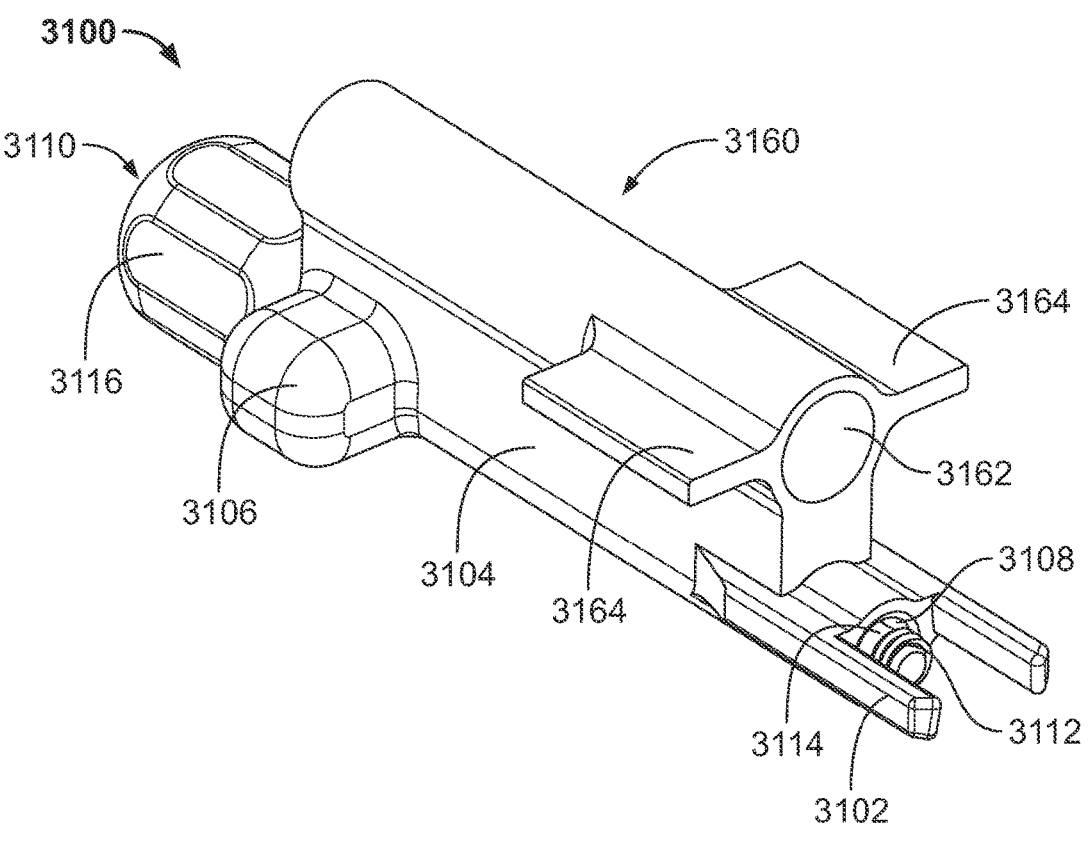
FIG. 93 is a perspective view of an exemplary stem inserter and fastener guide, according to one embodiment.
Figure 94:
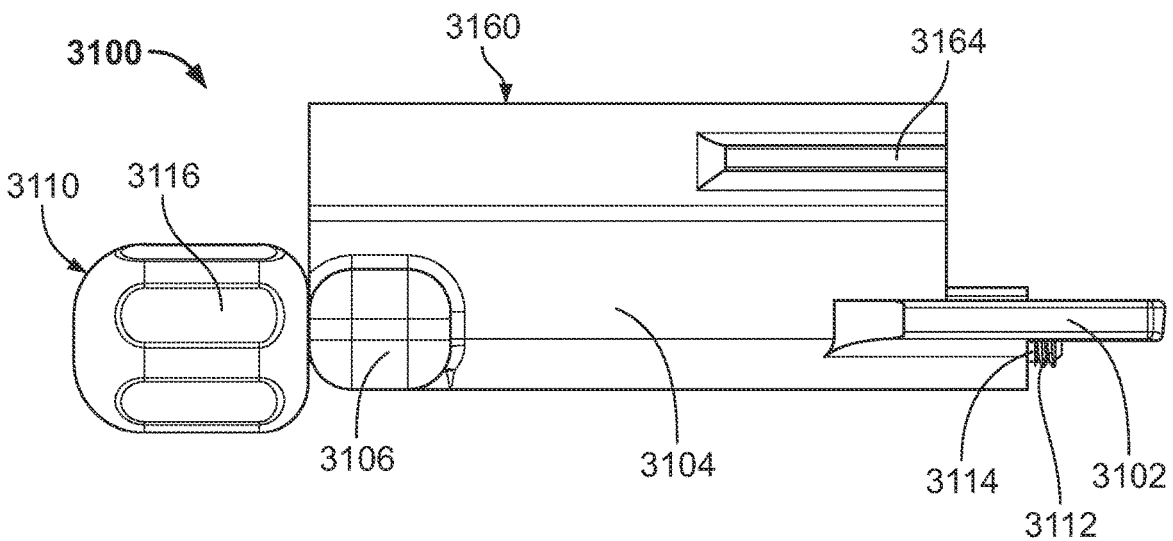
FIG. 94 is a side view of the stem inserter and fastener guide of FIG. 93.
Figure 95:
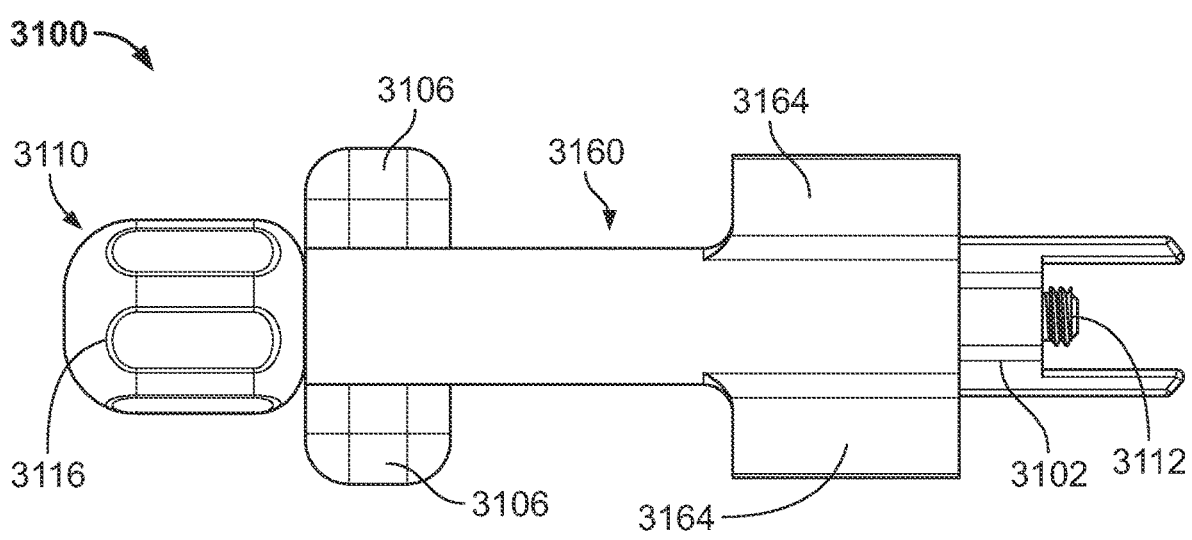
FIG. 95 is a bottom view of the stem inserter and fastener guide of FIG. 93.
Figure 96:
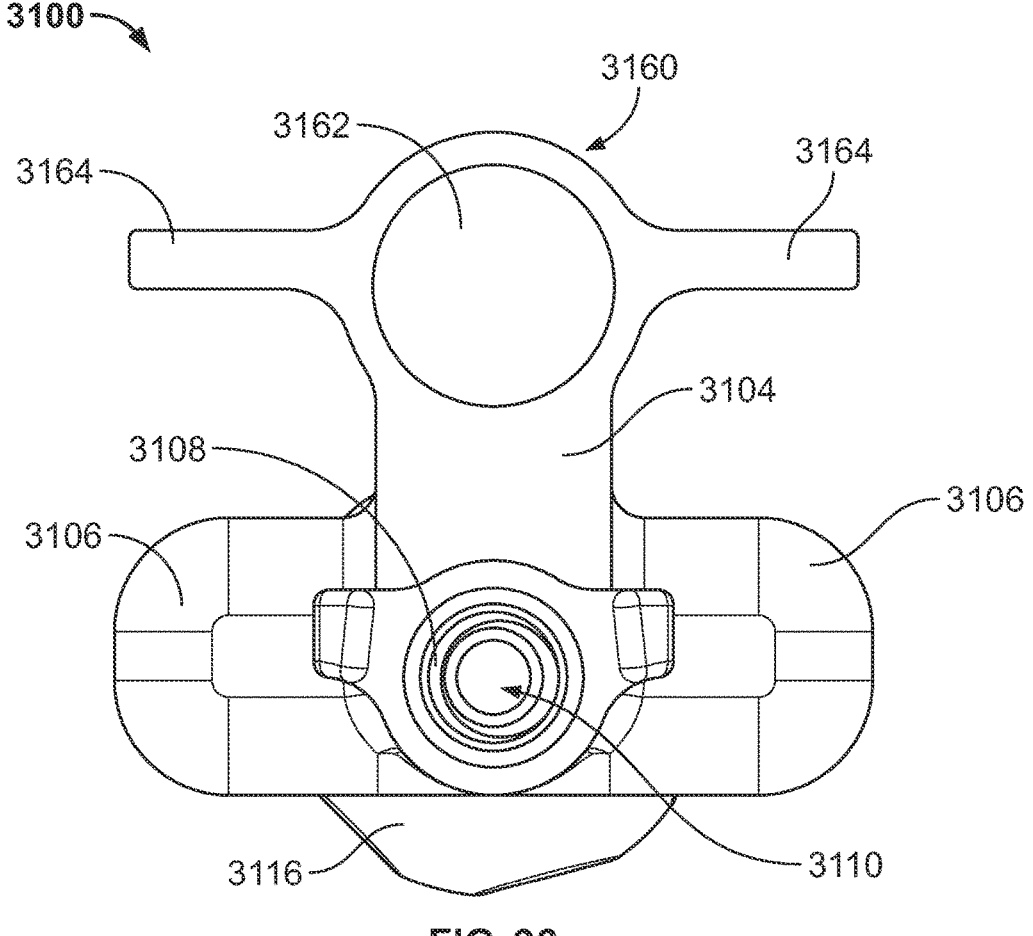
FIG. 96 is a front view of the stem inserter and fastener guide of FIG. 93.

With reference to FIG. 91, in some embodiments, the body 3004 may include a gear shaft 3012 secured to the body 3004 by a cap 3014, wherein the cap 3014 may be designed to allow rotation for the gear shaft 3012. The gear shaft 3012 may include a cylinder 3016, fixed with a first gear 3018, positioned at a first end of the gear shaft 3012. Additionally, the gear shaft 3012 may include teeth 3020 at a second end of the gear shaft 3012, wherein the teeth 3020 couple with an internally threaded section 3022 of the shaft 3006. In some embodiments, teeth of the first gear 3018 may engage with teeth of a second gear 3024. In some embodiments, the second gear 3024 may be coupled to the handle 3026 such that rotation of the handle 3026 corresponds with rotation of the first gear 3018 and the gear shaft 3012. In some embodiments, the handle 3026 may rotate while longitudinally coupled with the body 3004 via the cap 3015.

According to some embodiments, the shaft 3006 may extend through a portion of the body 3004 (e.g., a hole 3034), thereby allowing the shaft 3006 to move vertically along the gear shaft 3012 as the handle 3026 is turned. In some embodiments, the shaft 3006 may be coupled to the support 3007 and thus move the support 3007 vertically. Thus, the support 3007, which includes an alignment slot 3036 and a support surface 3038, may be controllably inserted into the prepared tibial surface.

In some embodiments, the stem inserter guide 3003 may be inserted into the alignment slot 3036 such that one or more prongs 3040 positioned at one end of the stem inserter guide 3003 engage with the support surface 3038. Similarly, vertical movement of the compressor 3002 may move the stem inserter guide 3003 such that one or more modular members (e.g., modular members 1080, 1062, 1042) loaded in the compressor assembly 3000 are inserted into the intramedullary canal. Further, the stem inserter guide 3003 may include a counter-torque surface 3042 that engages with one or more indentations (e.g., indentations 1088, 1071, 1051) disposed on the outer surfaces of the modular members. In some embodiments, the counter-torque surface 3042 may prevent each modular member from rotating during installation.

In some embodiments the compressor 3002 may include a measurement device 3028 comprising a window 3030 and an indicator 3032. The indicator may be coupled to the shaft 3006 such that movement of the indicator 3032 may be viewable through the window 3030, thereby providing information to the user regarding the position of inserted modular members in the intramedullary canal. The body 3004 may also include markings (not shown) alongside the window 3030 that may provide additional information to the user regarding the position of inserted modular members. In some embodiments, the indicator 3032 may contact the window 3030 and thus prevent the shaft 3006 from rotating in relation to the body 3008.

According to some embodiments, with reference to FIG. 91, a stem inserter 3001 may be used in conjunction with the compressor assembly 3000 to facilitate insertion of a desired number of modular members into the intramedullary canal. The stem inserter 3001 may be configured to slide into the stem inserter guide 3003 and the support 3007. Additionally, the stem inserter 3001 may include some or all of the features and functionalities as an additional stem inserter embodiment (i.e., stem inserter 3100) discussed with reference to FIGS. 93-96 below. For the sake of brevity, similar features will use the same part numbers.

In some embodiments, the stem inserter 3001 may grasp a modular member such that one modular can be aligned and coupled to an inserted, adjacent modular member. Then, a user may align and couple a threaded portion 3112 with an opening of a modular member (e.g., openings 1057, 1077, 1086) by turning a knob 3116 in a first direction. Next, the user may insert each modular member, in a step-wise fashion, into the intramedullary canal and in alignment with a previously inserted modular member. In some embodiments, a fastener 1090 may be inserted through a passage 3162 disposed on an anterior portion of the stem inserter 3001 such that the user may couple adjacent modular members together. In some embodiments, the knob 3116 may be turned in a second direction to remove the threaded part 3112 from the opening of an inserted modular member so that the stem inserter 3001 can be removed from the compressor assembly 3000. In some embodiments, the stem inserter 3001 can also be used to guide the right-angle drill 2200 in maintaining a particular position on a predefined axis.

Stem Insertion Tools

FIGS. 93-96 illustrates an exemplary embodiment of a stem inserter 3100 designed to insert modular members (such as modular members 1080, 1062, 1042) into the intramedullary canal formed over the course of the TAR procedure. In some embodiments, the stem inserter 3100 may include a body portion 3104 with a stem support 3102 and one or more protrusions 3106 extending therefrom at any suitable positions on the body portion 3104. In some embodiments, a hole 3108 may extend through the body portion 3104 such that a coupling piece 3110 may be removably inserted through the hole 3108, the coupling piece 3110 comprising a threaded part 3112, shaft 3114, and knob 3116. In some embodiments, the body 3104 may include a fastener guide 3160, the fastener guide 3160 including a passage 3162 and wings 3164 located on each side of the fastener guide 3160. In some embodiments, the fastener guide 3160 may be integrated with the body portion 3104, while in other embodiments, the fastener guide 3160 may be removably coupled to with the body portion 3104.

According to some embodiments, when the user wishes to insert the stem portion 1020 of the modular stem system 1000, the stem support 3102 may support an individual modular member (e.g., modular members 1080, 1062, 1042) via indentations on the modular member (e.g., indentations 1088, 1071, 1051). In particular, the user may load a modular member onto the stem support 3102 and turn the knob 3116 in order for the threaded part 3112 to engage an opening disposed on the modular member (e.g., openings 1057, 1077, 1086), thereby orienting and aligning the modular member. Next, the stem inserter 3100 can be inserted into the tibial trial 2000 wherein, in some embodiments, the wings 3164 may engage with the first and/or second channels 2024, 2026, thereby further aligning the modular member with the intramedullary canal (and/or any inserted modular members) accessible through the access opening 2020. In some embodiments, the protrusions 3106 may provide a gripping surface for the user.

Furthermore, once a modular member is in place, the user may fasten adjacent modular members together. In some embodiments, a screwdriver (not shown) or torque limiting driver (not shown) may be used to insert a fastener (e.g., fasteners 1090) through the passage 3162 to engage with openings of adjacent modular members (e.g., openings 1032, 1052, 1072; fixation openings 1057, 1077, 1086), and thus fasten adjacent modular members together. Once the fastener 1090 is inserted, the threaded part 3112 of the coupling piece 3110 may be removed from the modular member, and the stem inserter 3100 may be removed from the tibial trial 2000. In some embodiments, a stem impactor 3500 or compressor 3002 may be used to impact or compress each inserted modular member into the intramedullary canal. In alternate embodiments, the stem inserter 3100 may include variations (e.g., no wings 3164, compatibility with the compressor assembly 3000, etc.).

Figure 97:
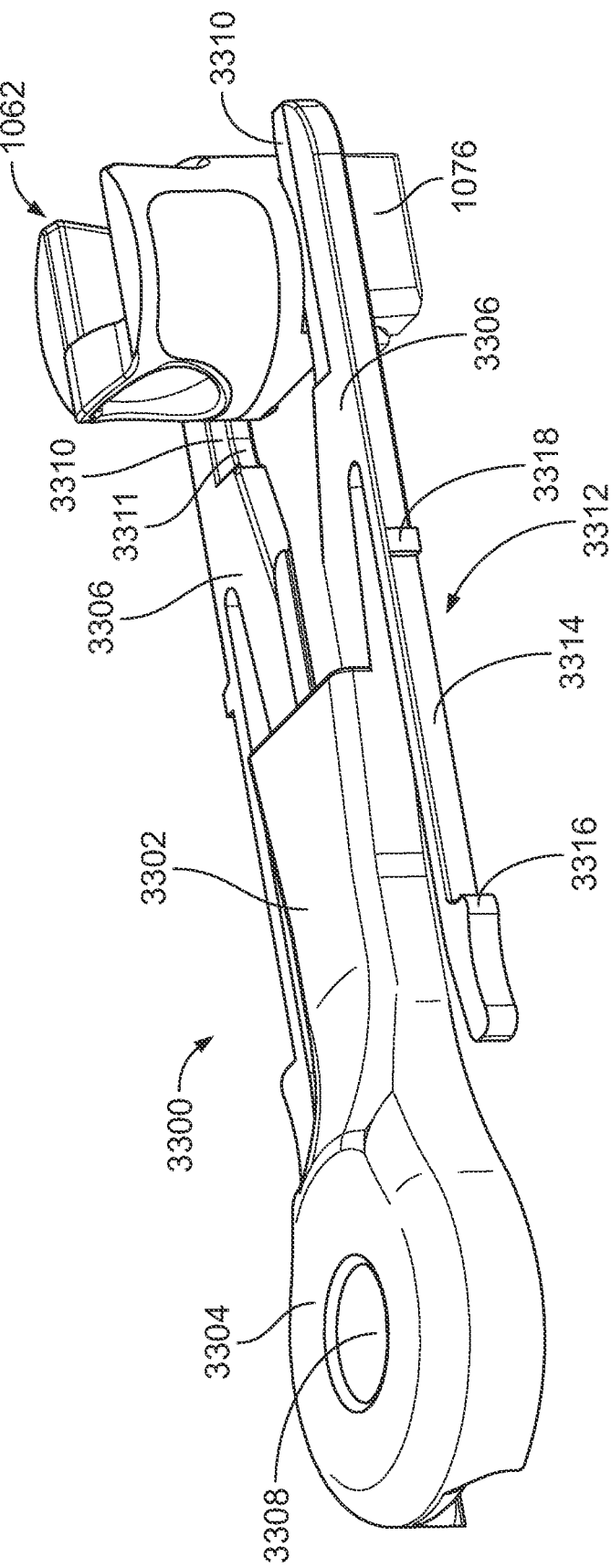
FIG. 97 is a perspective view of a counter-torque lock, according to one embodiment.

FIG. 97 illustrates one embodiment of a stem counter-torque lock 3300. The stem counter-torque lock 3300 may be used to verify desirable positioning and alignment of each modular member of the modular stem system 1000, as each modular member is inserted into the intramedullary canal. In some embodiments, the stem counter-torque lock 3300 may include a body 3302 having a pull tab 3304 and prongs 3306. In some embodiments, the pull tab 3304 may include a hole 3308 disposed thereon. Each prong 3306 may include a top counter-torque surface 3310 and a side counter-torque surface 3311. In some embodiments, locking mechanisms 3312 may be coupled to the body 3302 and may each include an arm 3314, grip 3316, and locking protrusions 3318.

When installing the modular stem system 1000 into the intramedullary canal, the stem counter-torque lock 3300 may be used to verify a desirable orientation of the inserted modular members. In some embodiments, the top counter-torque surface 3310 and side counter-torque surface 3311 may engage with indentations on the modular members (e.g., indentations 1088, 1071, 1051) such that the prongs contact the indentations, thereby verifying rotational alignment with the tibial trial 2000. In some embodiments, use of the stem counter-torque lock 3300 may occur at any point of in the modular stem insertion portion of the TAR procedure.

In some embodiments, the locking mechanism 3312 may allow the stem counter-torque lock 3300 to lock in place in an alignment slot (e.g., alignment slot 2042, 2046) of the tibial trial 2000. When removing the stem counter-torque lock 3300 from the tibial trial 2000, the user may apply force to the grip 3316 to release the locking protrusions 3318 from the alignment slot.

Figures 98, 99:
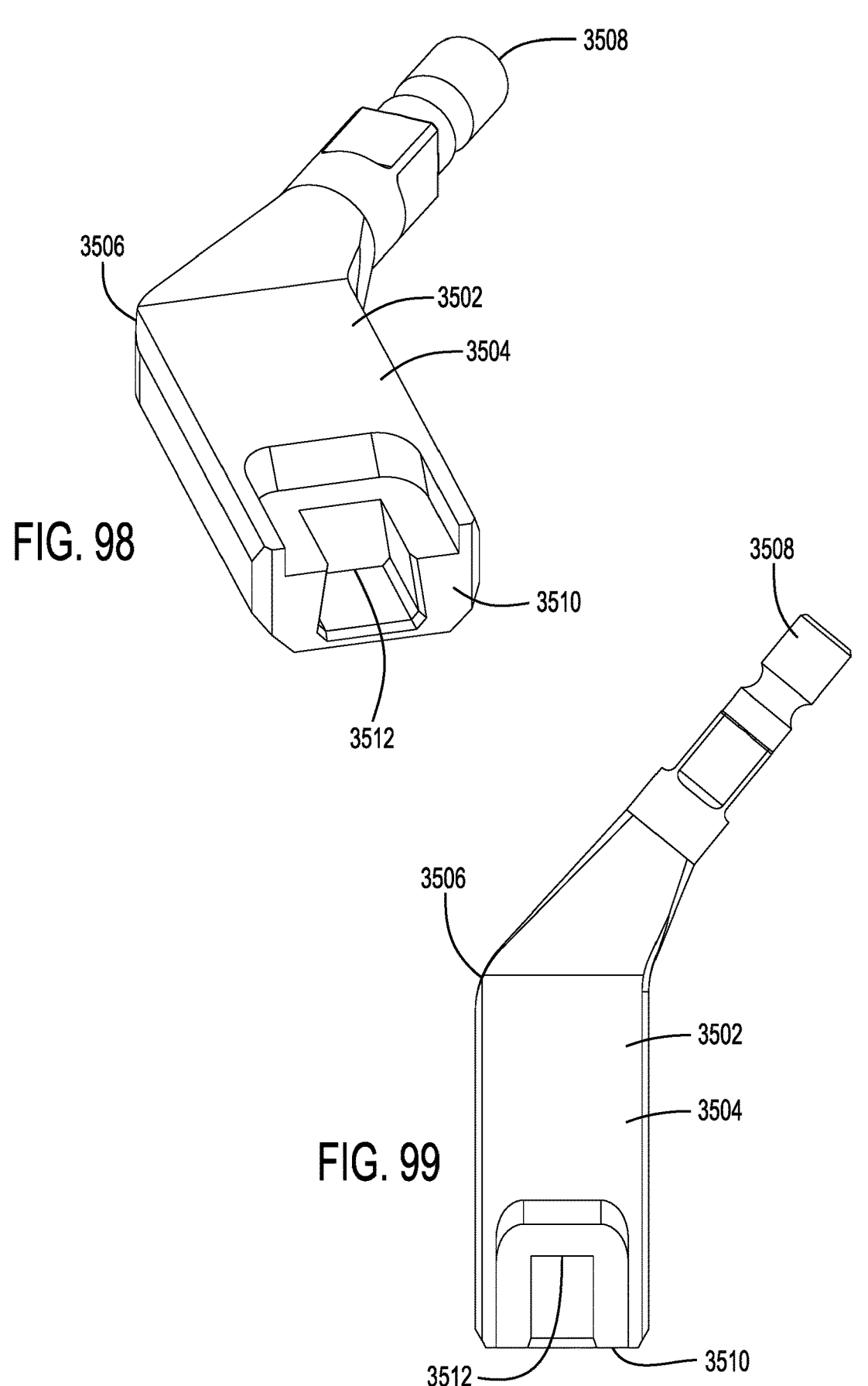
FIG. 98 is a perspective view of an exemplary impactor, according to one embodiment.
FIG. 99 is a top view of the exemplary impactor of FIG. 98.

Turning now to FIGS. 98 and 99, an exemplary stem impactor 3500, according to one embodiment, is shown. Generally, the stem impactor 3500 may be used as part of the TAR procedure to facilitate the insertion of individual modular members into the intramedullary canal. In some cases, the stem impactor 3500 can be used in the final stages of the TAR procedure to finalize the fit of the installed modular members within the intramedullary canal, before the user fastens the pieces together to form the overall modular stem. In some embodiments, the stem impactor 3500 may include a body 3502 having a proximal end 3508 and a distal end 3510 with an elbow-bend 3506 positioned therebetween. In some embodiments, the stem impactor 3500 may be configured to mate with an individual modular member such that the top surface of that modular member mates with the bottom surface of an adjacent modular member already inserted within the medullary cavity. In some embodiments, the elbow-bend 3506 may be configured to allow the user to avoid contact with the patient foot while using the stem impactor 3500.

According to some embodiments, a portion of the distal end 3510 and/or a portion of a top surface 3504 proximal the distal end 3510 may include an engagement feature 3512. The engagement feature 3512 may be adapted to enhance mating between adjacent modular members (see FIGS. 2-15) as a user inserts modular members into the medullary cavity. For instance, in certain embodiments, a male fixation feature of one modular member may selectively engage with the female fixation feature of an adjacent modular member. When the user applies upwards force to the impactor 3500, the engagement feature 3512 may facilitate desirable compaction between adjacent modular members. Then, in some embodiments, the engagement feature 3512 may be suitably sized to engage with portions of the modular members such that removal of the stem impactor 3500 from a modular member occurs in the anterior-posterior direction. In other embodiments, the stem impactor 3500 may include an additional engagement feature 3512 opposite the top surface 3504 (e.g., on a bottom surface), such that the stem impactor 3500 is reversible (e.g., usable for either foot of a patient). In some embodiments, the engagement feature 3512 may form joints with suitable fixation features of modular members such as, but not limited to, dovetail joints, box joints, dowel joints, Knapp joints, or any other suitable joint configured to facilitate mating between adjacent modular members. In some embodiments, a portion of the body 3502 near the proximal end 3508 may include various features that improve grip to the user or other suitable tools as the user applies upwards force to the stem impactor 3500.

Methods

FIG. 100 describes a method 4000 of preparing the tibial surface for modular stem insertion. As shown in FIG. 100, at step 4005, a user (e.g., surgeon), receives a TAR tool kit, including tools and instruments suited for the preparation of the tibial surface, including, but not limited to, a tibial trial 2000, a distractor 2100, a right-angle drill 2200 and drill plate 2400, a spike broach 2500, a wire guide 2600, and a flexible reamer assembly.

At step 4010, the user makes an anterior incision to the ankle joint space to gain access to the tibia and talus from the anterior direction.

At step 4015, the user resects portions of the tibia and talus to create prepared surfaces on the respective bones. In some embodiments, the prepared surfaces may be generally flat to open a desirable workspace for further tibial surface processing. In other embodiments, any other suitable surface contour may be created.

Figure 104:
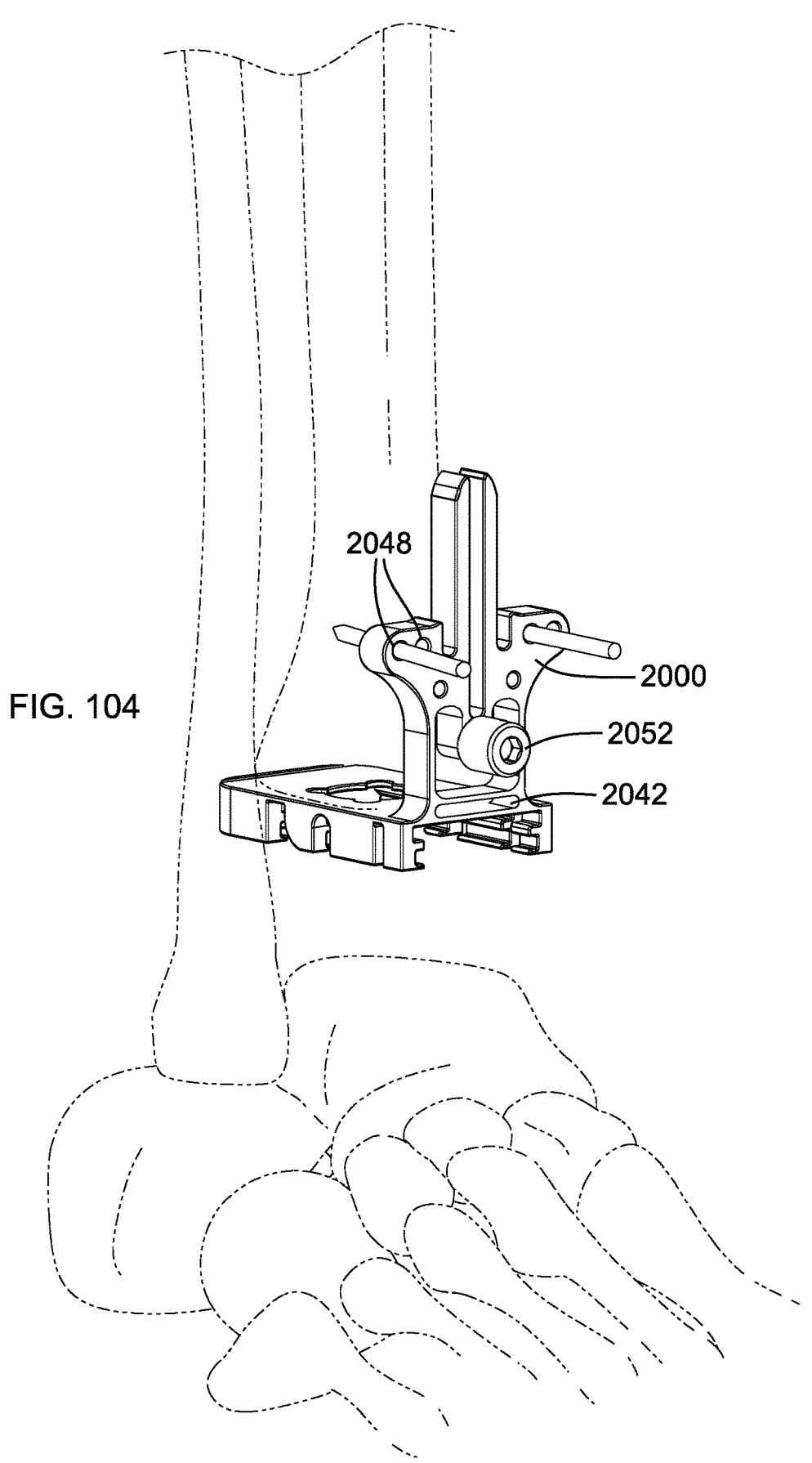
FIG. 104 shows an exemplary view of an exemplary TAR assembly for the preparation of a patient tibial surface, according to one embodiment.
Figure 105:
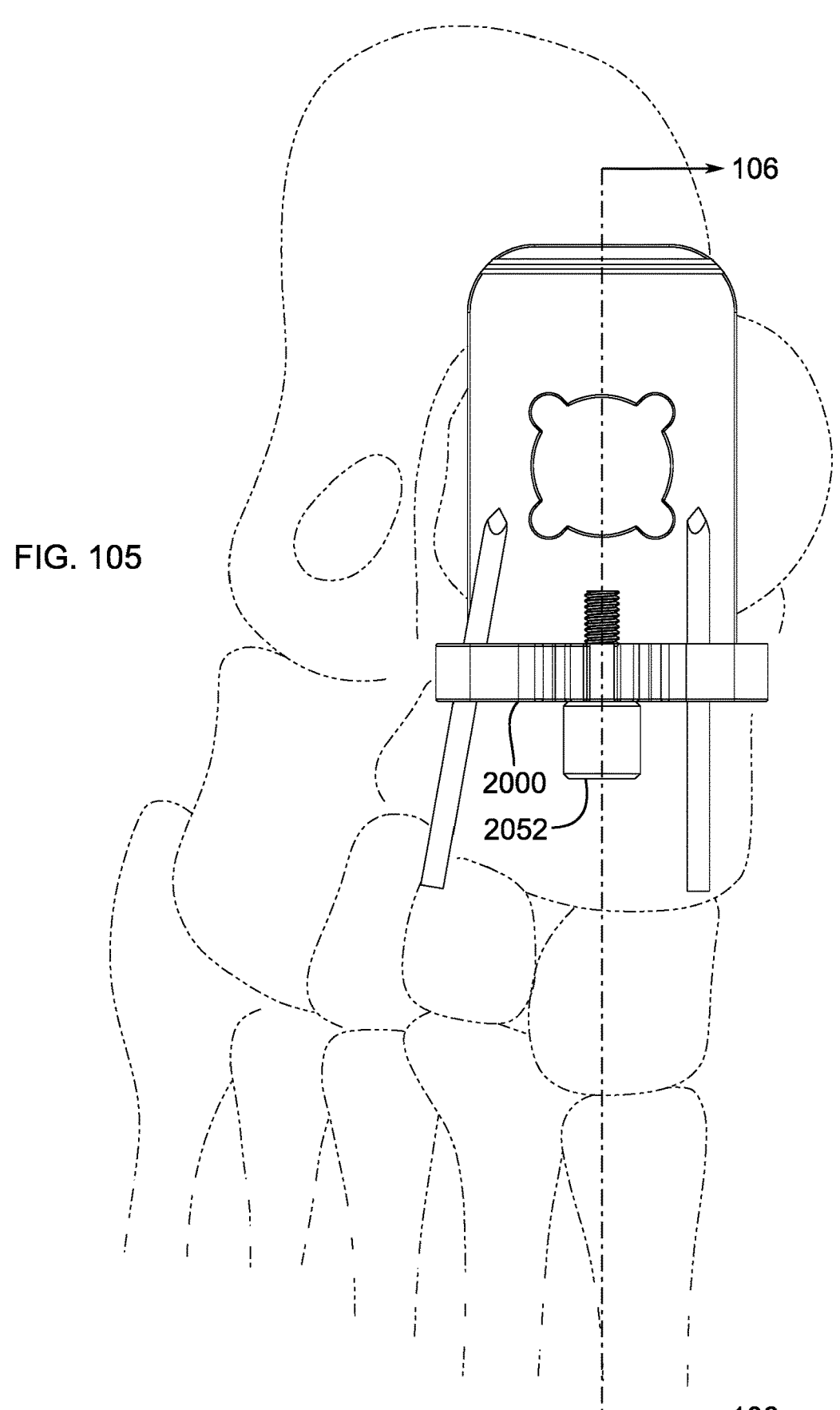
FIG. 105 shows an exemplary view of an exemplary TAR assembly for the preparation of a patient tibial surface, according to one embodiment.

At step 4020, and with reference to FIGS. 104-106, the user installs the tibial trial 2000 onto the prepared tibial surface in a desired position. In some embodiments, certain features of the tibial trial 2000 may be used to position the trial 2000 in a desirable position, which, in turn, may function as an overall reference point for other tools of the TAR procedure. For instance, alignment can be set 1) in the anterior-posterior direction using a central fastener opening (not shown) which is accessible from the anterior direction on a trial face of the tibial trial 2000 and a screw, bolt, or any other suitable fastener 2052; and 2) in the medial-lateral direction using apertures 2048 which are accessible from the anterior direction on arm portions of the tibial trial 2000 and guide wires, nails, pins, or any other suitable fasteners.

At step 4025, the user inserts the sight alignment tool (such as the sight alignment tool 2900 of FIGS. 80-82) into an alignment slot 2042 which is accessible from the anterior direction on the trial face to verify precise vertical and horizontal alignment of the trial 2000 with the underlying patient anatomy. Once precise alignment is verified, the user may then finalize the tibial trial 2000 position with the aforementioned fasteners 2052. In some embodiments, the sight alignment tool 2900 may then be removed while in other embodiments, the sight alignment tool 2900 may remain in place on the tibial trial 2000 for the duration of the tibial surface preparation procedure.

Figure 107:
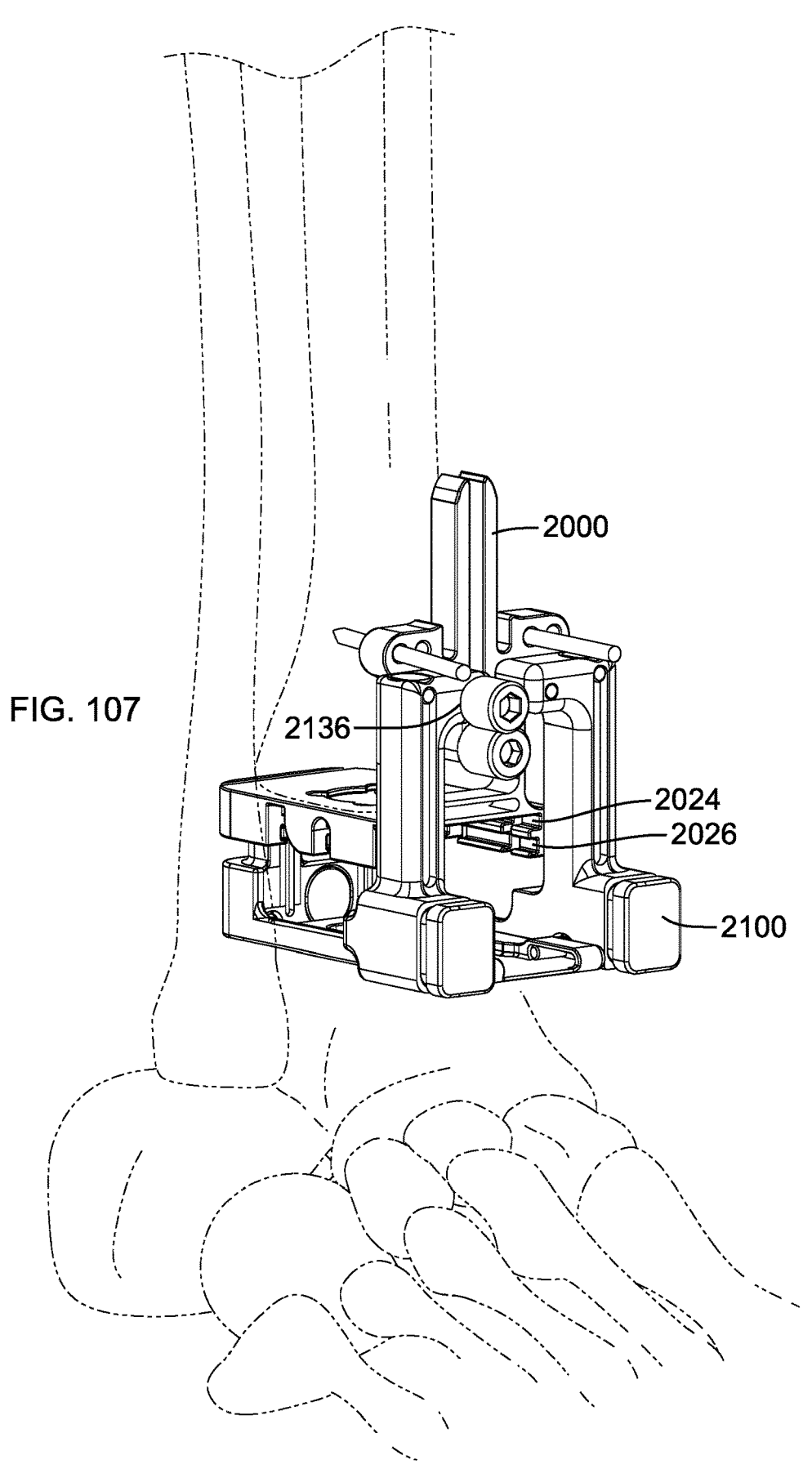
FIG. 107 shows an exemplary view of an exemplary TAR assembly for the preparation of a patient tibial surface, according to one embodiment.
Figure 108:
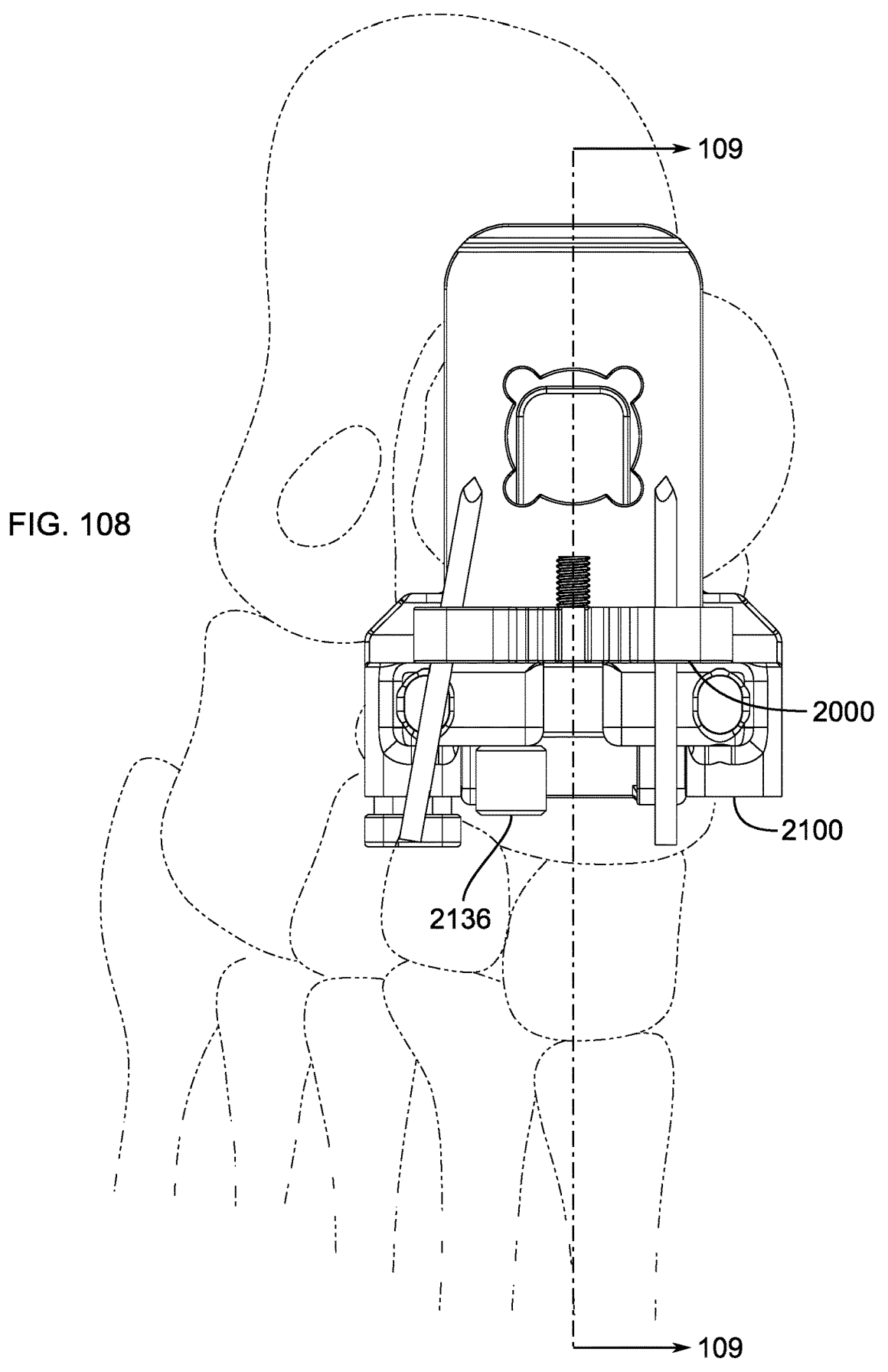
Figure 109:
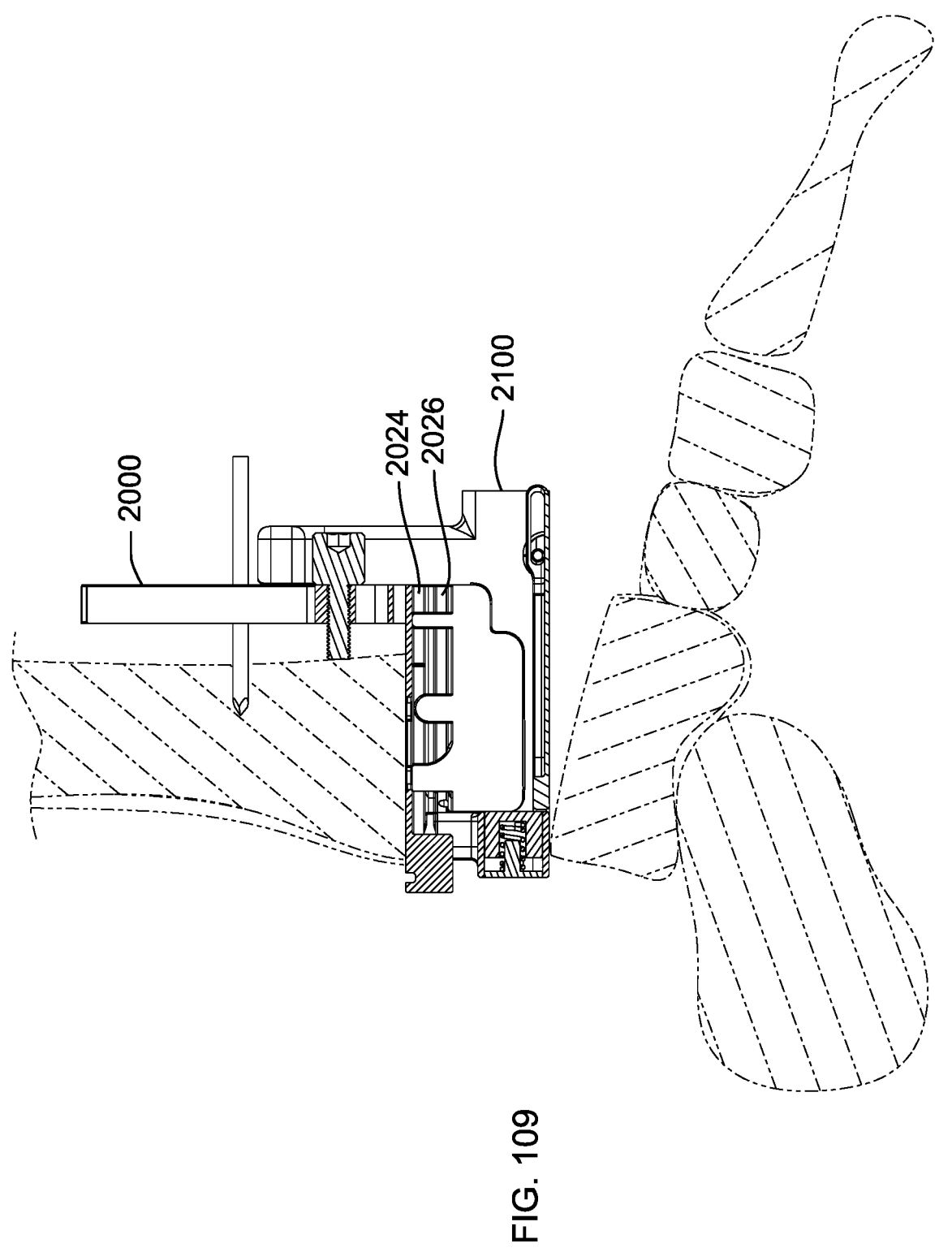
FIG. 109 shows an exemplary view of an exemplary TAR assembly for the preparation of a patient tibial surface, according to one embodiment.

At step 4030, and with reference to FIGS. 107-109, the user inserts the distractor 2100, in a first configuration, into the tibial trial 2000 by engaging a portion of the distractor with one or more channels 2024, 2026 (accessible from the anterior direction) on the tibial trial. In some embodiments, the distractor 2100 engages with the one or more channels 2024, 2026 via a dovetail joint, T-slot joint, or any other suitable mechanism. In some embodiments, certain features of the tibial trial 2000, such as apertures 2049 on the arm portions, may be used to position the distractor 2100 in a desirable position with regards to the tibial trial 2000. For instance, a screw, bolt, or any other suitable fastener may be configured to engage with the apertures 2049 and secure positioning of the distractor 2100. Optionally, in some embodiments, steps 4020 and 4030 may be combined such that the distractor 2100 is inserted with the tibial trial 2000, thus defining the trial 2000 position while simultaneously beginning distraction of the joint space.

Figure 110:
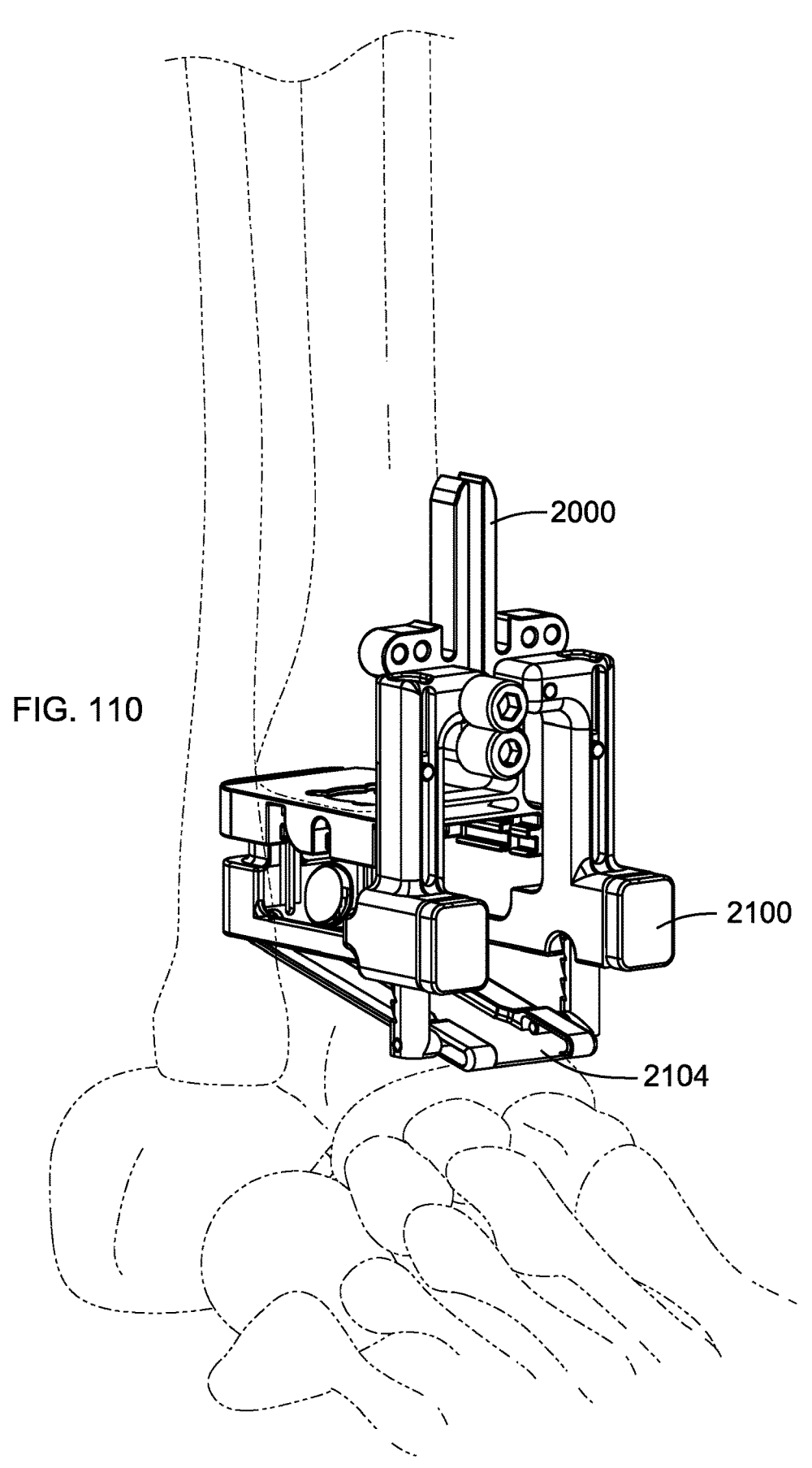
FIG. 110 shows an exemplary view of an exemplary TAR assembly for the preparation of a patient tibial surface, according to one embodiment.
Figure 111:
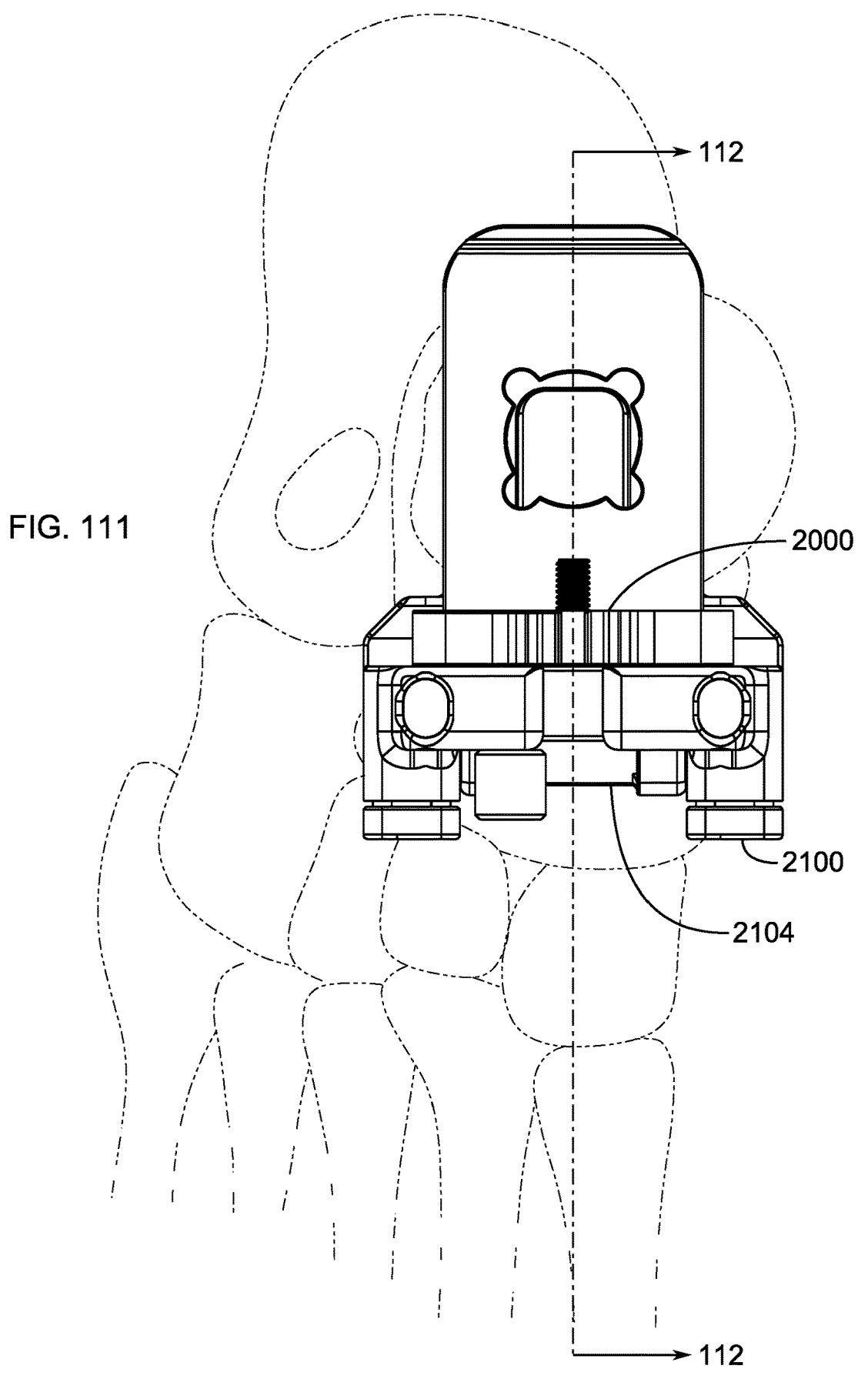
Figure 112:
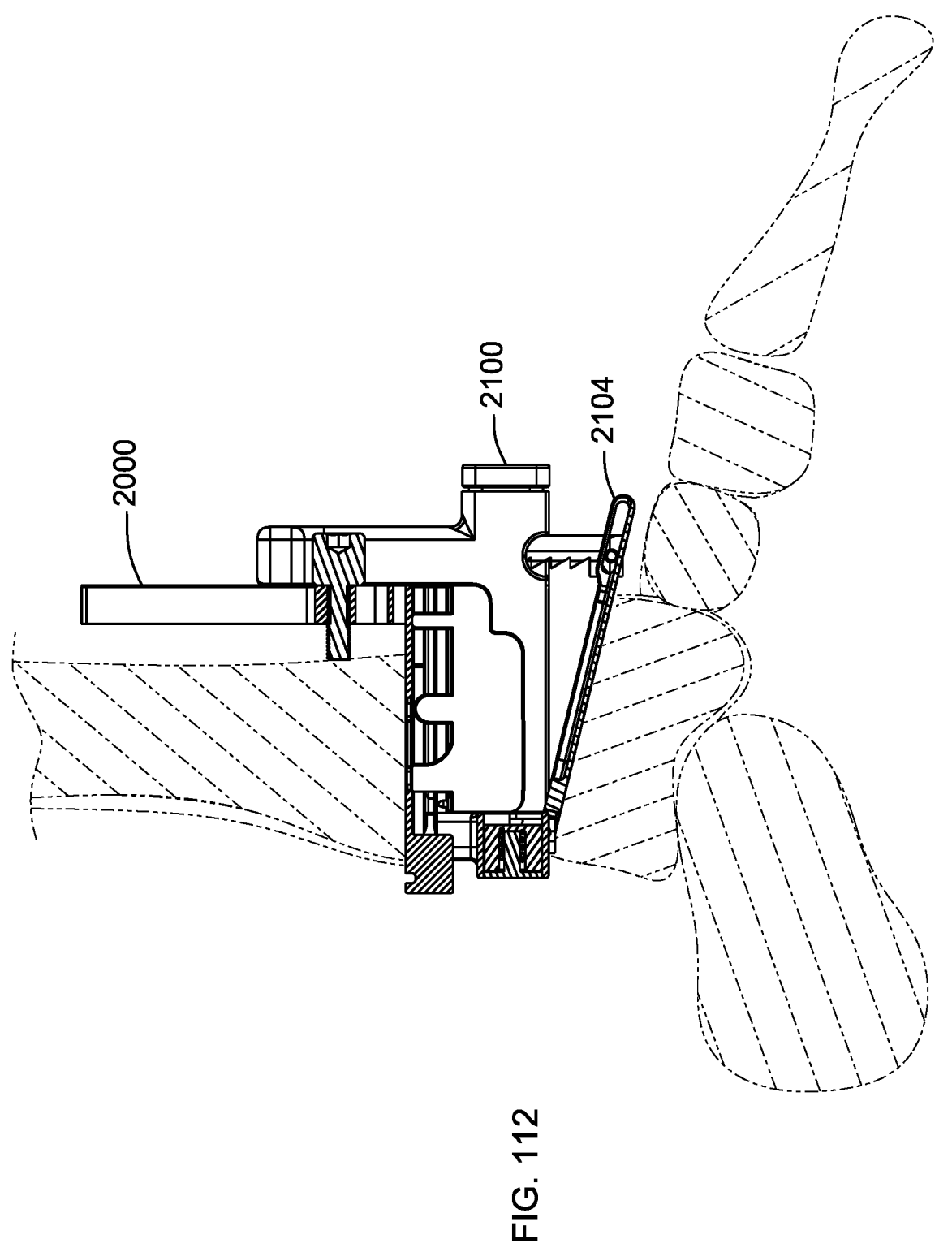
FIG. 112 shows an exemplary view of an exemplary TAR assembly for the preparation of a patient tibial surface, according to one embodiment.

At step 4035, and with reference to FIGS. 110-112, the user distracts the ankle joint space by setting the distractor 2100 in a second configuration. In some embodiments, this may involve rotating a bottom portion, or distractor plate 2104, of the distractor 2100 at least partially about a back hinge such that the distractor plate 2104 angles downwards and moves in a parallel plane to the trial face. In some embodiments, movement of the distractor plate 2104 may form a height differential between distraction in the posterior part of the joint space and distraction in the anterior part of the joint space. Thus, the distractor 2100 may hold open the joint space and maintain an appropriate level of distraction (e.g., minimum working channel, or "workspace") between the tibia bone and the talus bone. Depending on user preference, in some embodiments, either a dynamic distractor (particularly for a tighter joint) or a static distractor can be used. In other embodiments, use of the distractor (e.g., steps 4030 and 4035) may be omitted depending on user preference. In this case, manual action by another user or by any other suitable tool can be used to distract the ankle joint space.

In an alternative embodiment, depending on user preference, use of the distractor 2100 (e.g., steps 4030 and 4035) may occur at a later stage in the process 4000 (e.g., after the steps pertaining to drilling and before the steps pertaining to reaming). In this case, steps pertaining to drilling (which will be discussed in relation with steps 4040 and 4045) may not require the additional anterior clearance delivered by the distractor 2100 while steps pertaining to reaming (which will be discussed in relation with steps 4075 and 4080) and/or a subsequent procedure 5000 may require additional anterior clearance.

At step 4040, the user inserts the right-angle drill plate (such as the drill plate 2400 of FIGS. 58-59), wherein a first side of the drill plate 2400 faces upwards, from the anterior direction into the tibial trial 2000. In some embodiments, a locking mechanism on the drill plate 2400 may engage with interior portions of the tibial trial 2000 (e.g., first 2024 and second 2026 channels). In some embodiments, step 4040 may be omitted.

Figure 113:
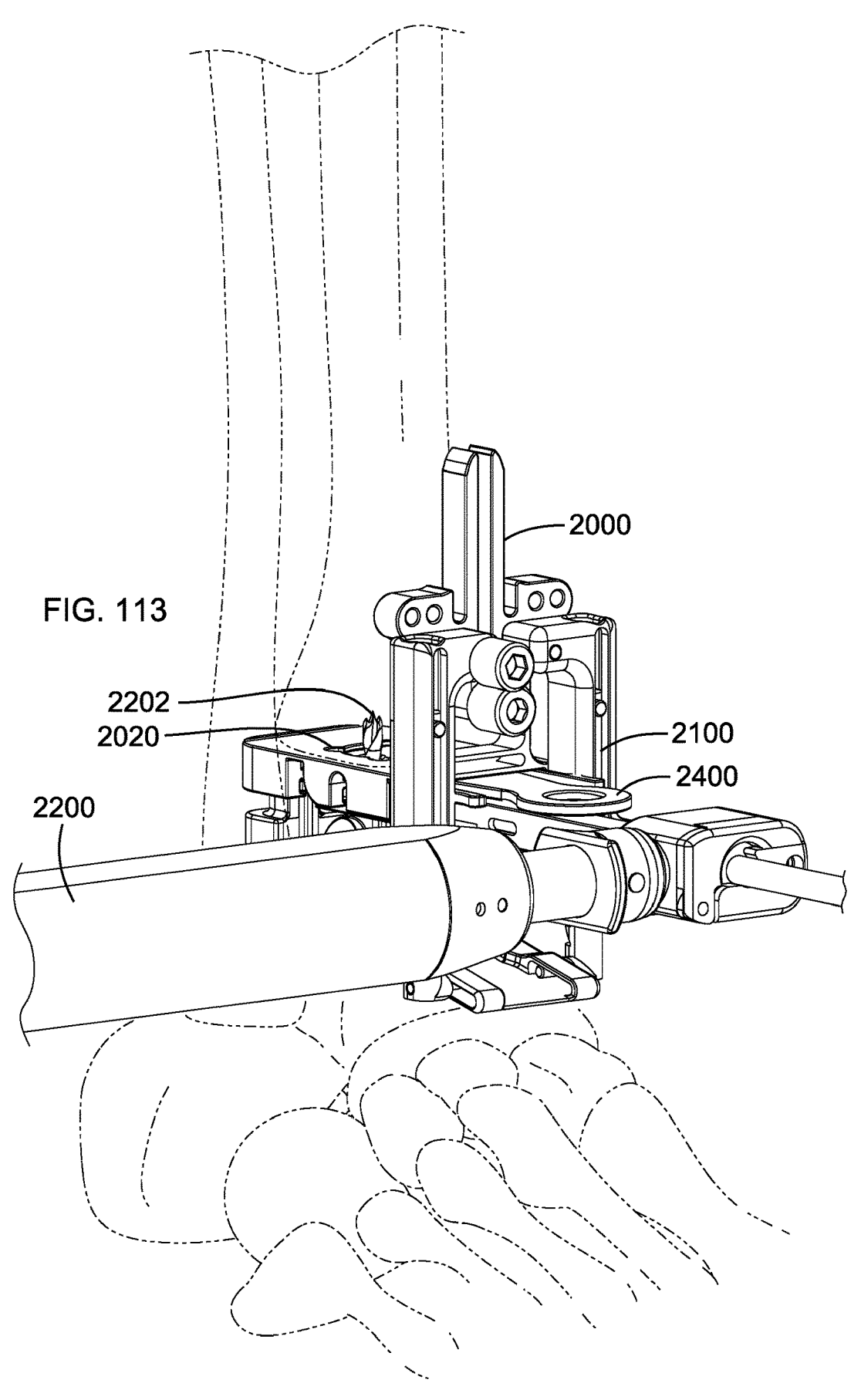
Figure 114:
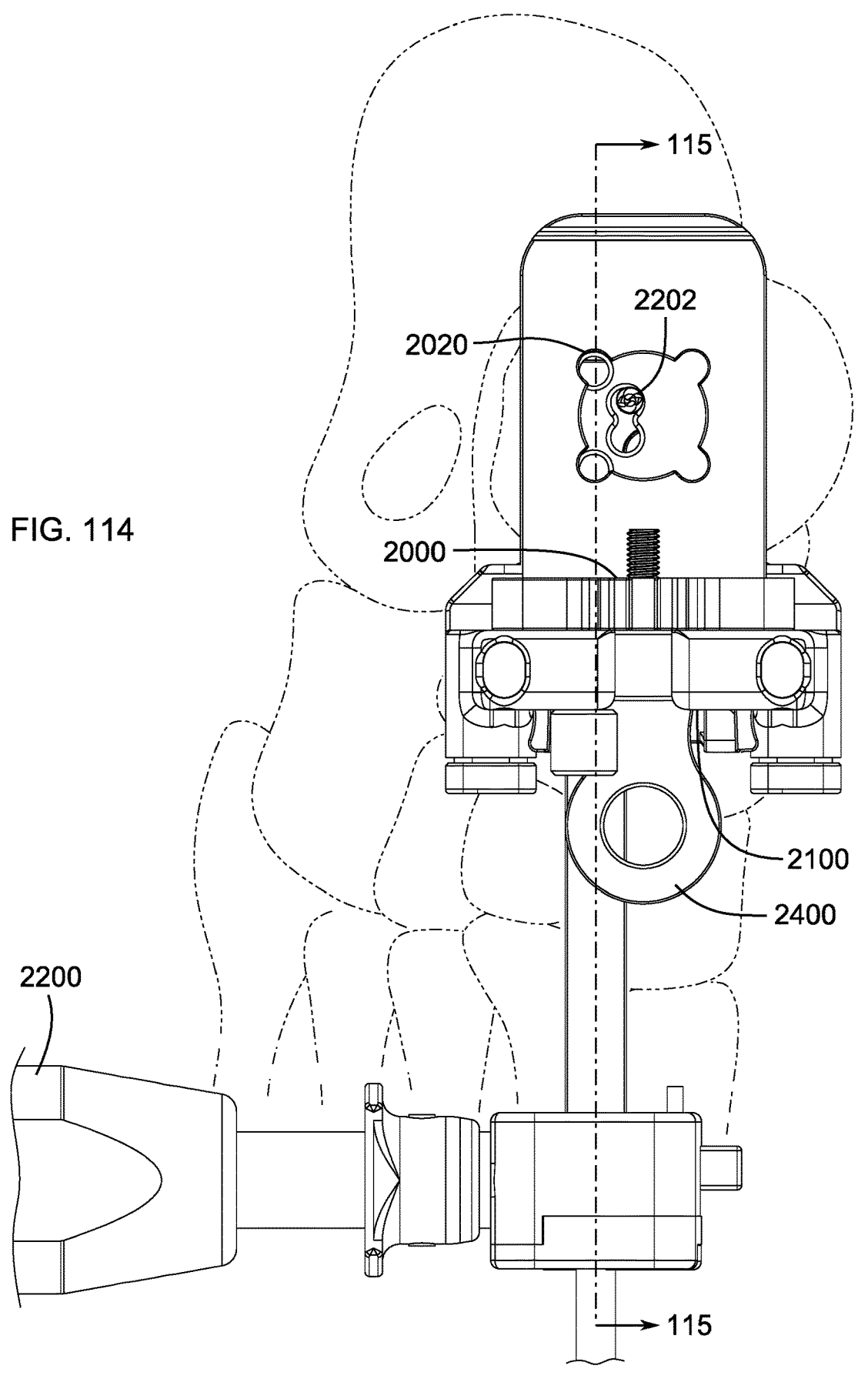
Figure 115:
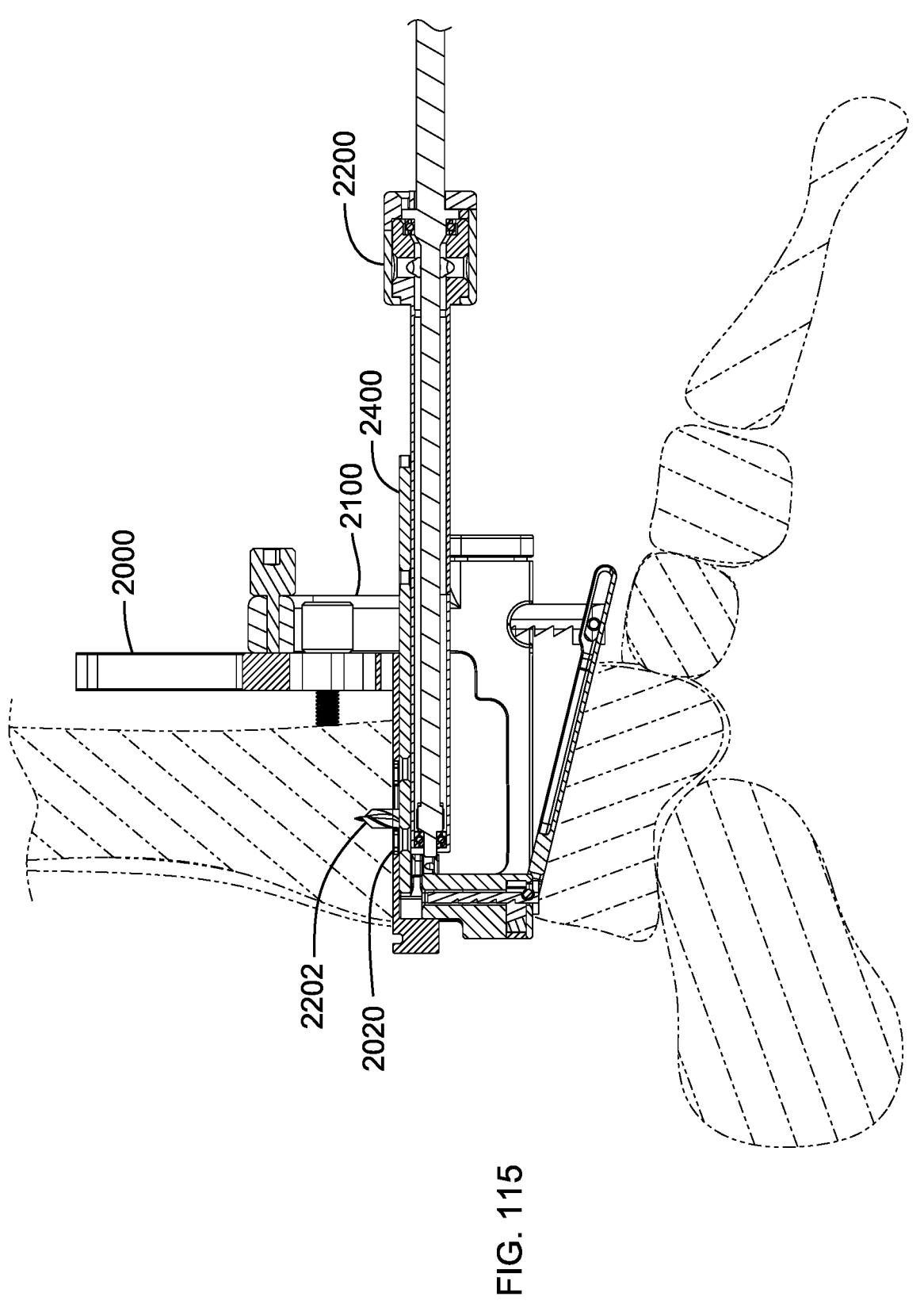

At step 4045, and with reference to FIGS. 113-115, the user inserts the right-angle drill 2200 from the anterior direction into the tibial trial 2000. In some embodiments, the right-angle drill 2200 may engage with interior portions of the tibial trial 2000 (e.g., first 2024 and second 2026 channels). The user may then drill upwards into a portion of the tibial surface and begin forming an intramedullary canal in the medullary cavity for use with procedure 5000. In embodiments including the right-angle drill plate 2400, the user may drill a pattern of holes through the openings of the drill plate 2400 to begin forming the intramedullary canal. In this case, the drill plate 2400 may include an asymmetric pattern of openings or through-holes (e.g., in a partial X-shape) for the user to drill through at step 4045. Thus, the user may have improved flexibility in targeting a specific pattern of bone to drill while reducing user judgment. In embodiments without the drill plate 2400, the user may drill directly through the inferior surface of the tibial trial 2000 (e.g., through a access opening) to begin forming the intramedullary canal. In this case, the user may proceed to step 4060.

In some embodiments, when using the right-angle drill plate 2400, the user may remove the drill plate 2400 and right-angle drill 2202, and re-insert the drill plate 2400 (wherein a second side of the drill plate 2400 faces upwards) in a manner similar to step 4040. Then, when using the right-angle drill plate 2400, the user may re-insert the right-angle drill 2200 and drill into portions of the tibial surface in a manner similar to step 4045. Thus, in some embodiments, by "flipping over" the drill plate 2400, the user may continue forming the particular pattern of holes (e.g., in an X-shape) to continue forming the intramedullary canal. The drill 2200 and drill plate 2400 can then be removed.

At step 4050, the user inserts a spike broach (such as the spike broach 2500 of FIGS. 60-64), having a guide wire channel 2516, into the distracted joint space beneath the inferior face of the tibial trial 2000 such that the spike assembly 2506 of the spike broach 2500 extends through the access opening 2020. In some embodiments, the spike broach 2500 may engage with internal portions of the tibial trial 2000, such as the first 2024 and second channels 2026, while in other embodiments, the spike broach 2500 may articulate with the inferior face of the tibial trial 2000 but not the first 2024 and second 2026 channels.

At step 4055, the user impacts the spike broach 2500 upwards into the tibial surface (over the drilled holes of steps 4045) to increase the size of the intramedullary canal. Here, the spike broach 2500 may remove and/or compact additional bone to increase space in the intramedullary canal for insertion of the modular stem system 1000. In some embodiments, the user may use an offset impactor having a C-shaped bracket enabling impaction from a distal end (e.g., to avoid contact with the patient foot). In other embodiments, the user may use any impactor, hammer, other suitable tool, or other manual techniques to impact the spike broach 2500.

Figure 116:
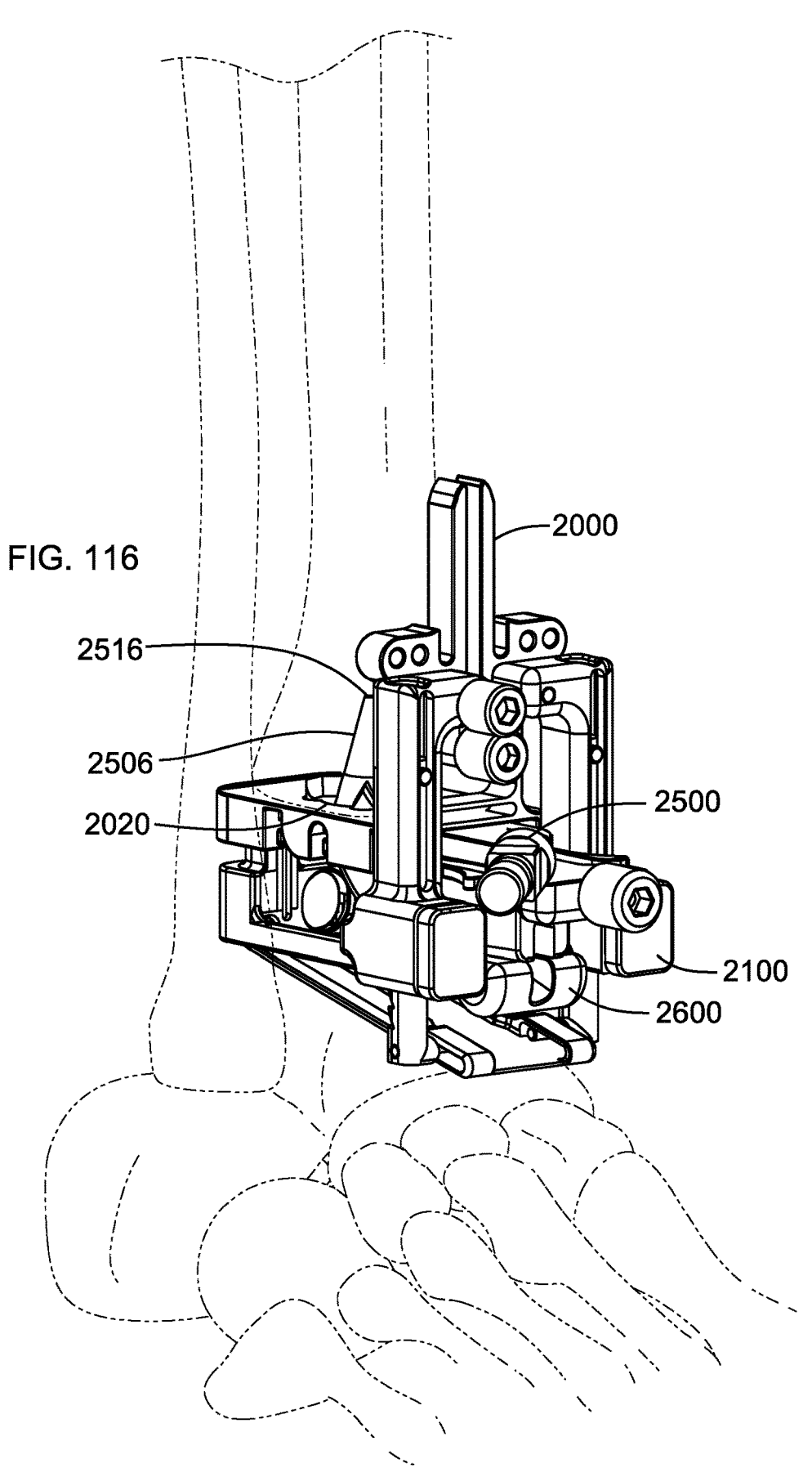
Figure 117:
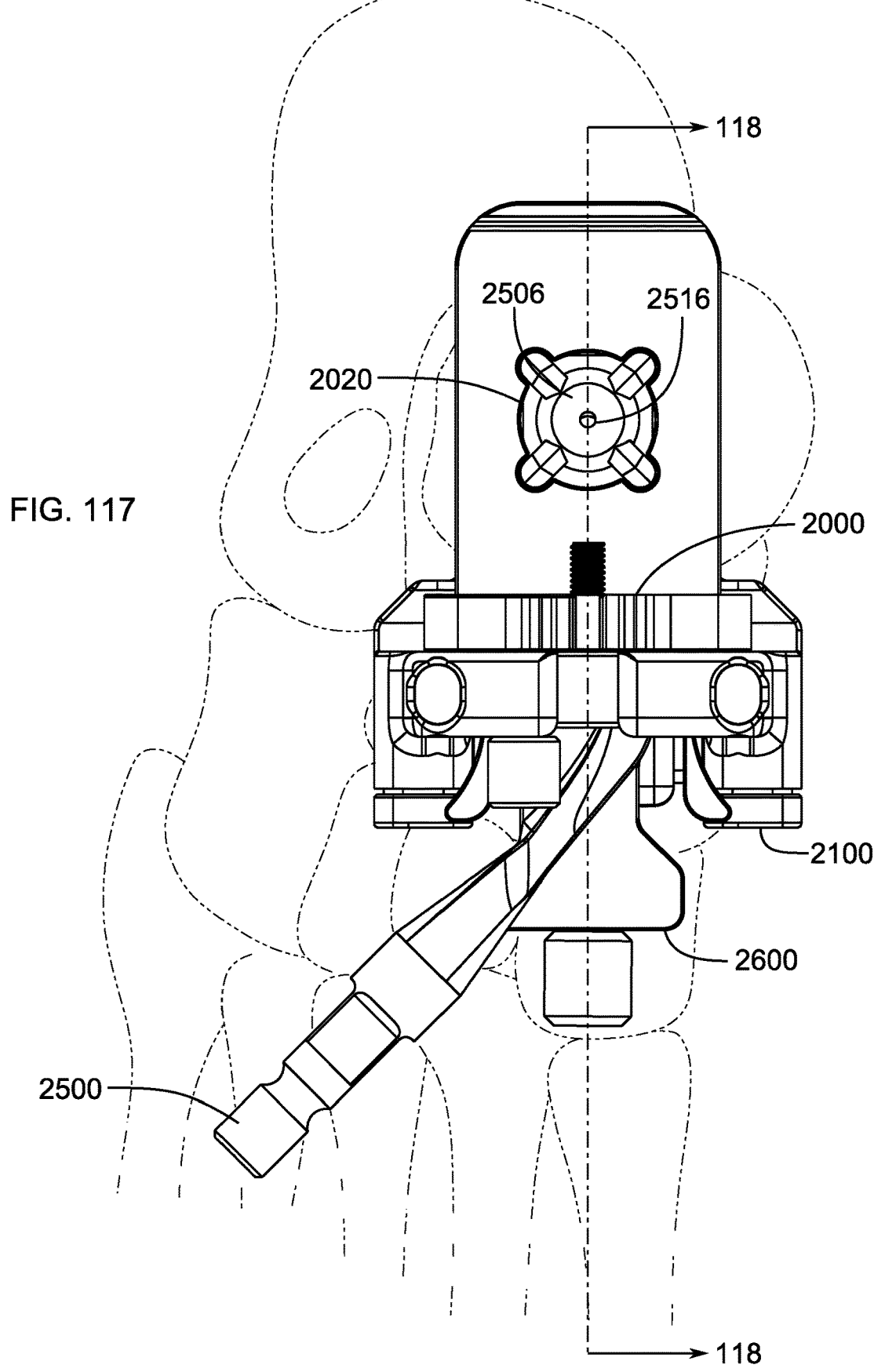
Figure 118:
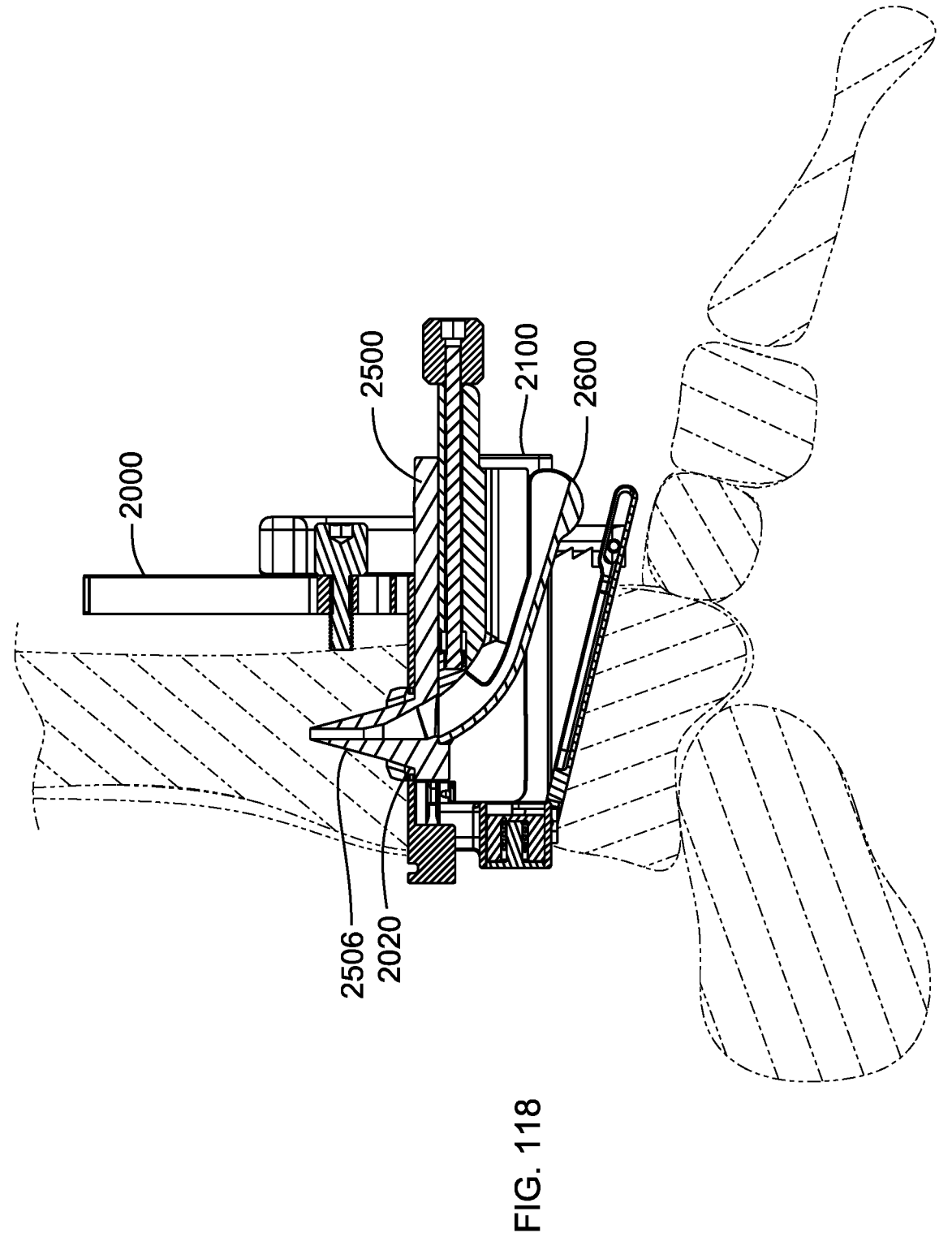

At step 4060, and with reference to FIGS. 116-118, the user inserts the wire guide 2600 (in a first configuration) into the tibial trial 2000 from the anterior direction such that the wire guide 2600 locks the spike broach 2500 into a desired position. In some embodiments, the wire guide 2600 may engage with interior portions of the tibial trial 2000 (e.g., first 2024 and second channels 2026).

Figure 119:
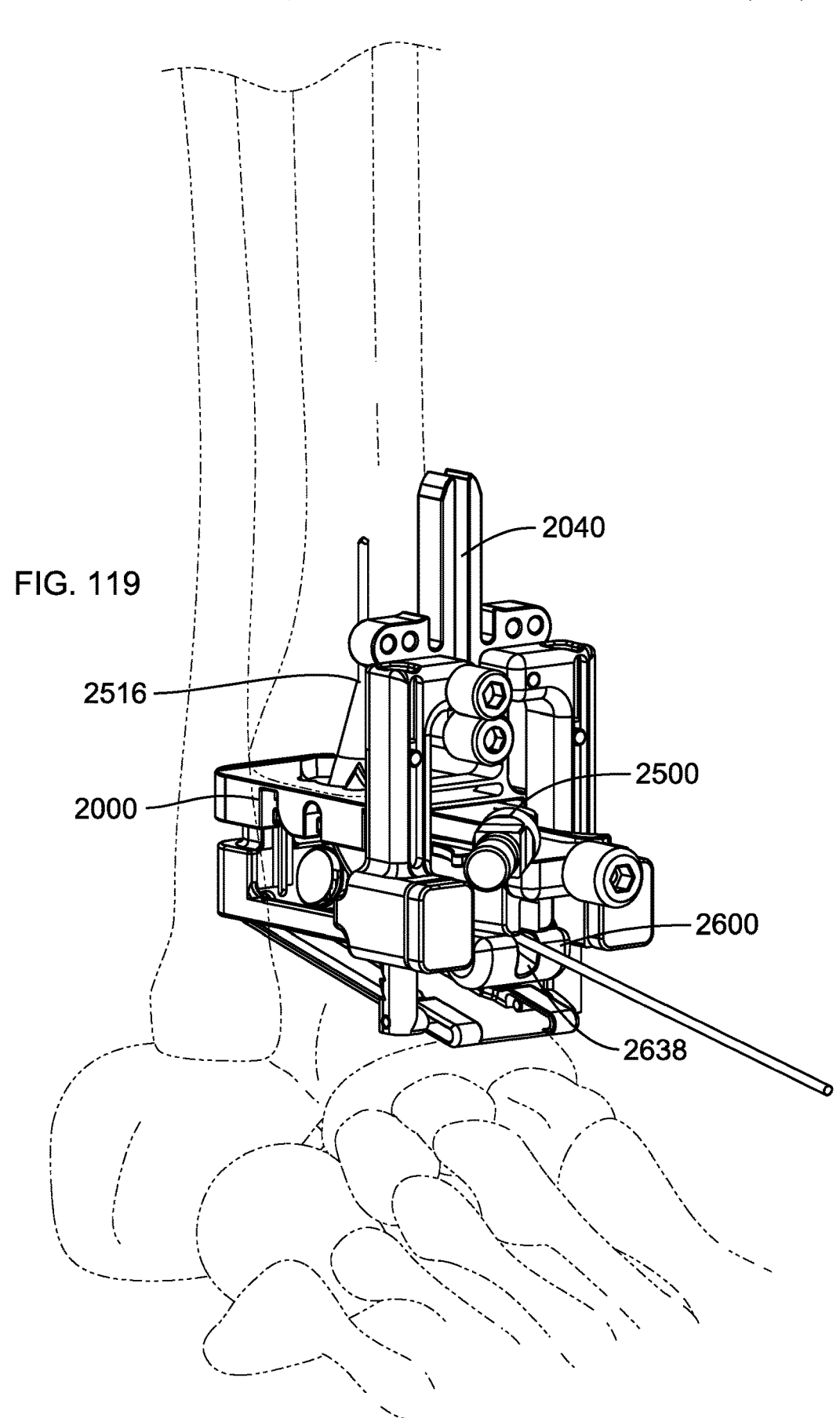
Figure 120:
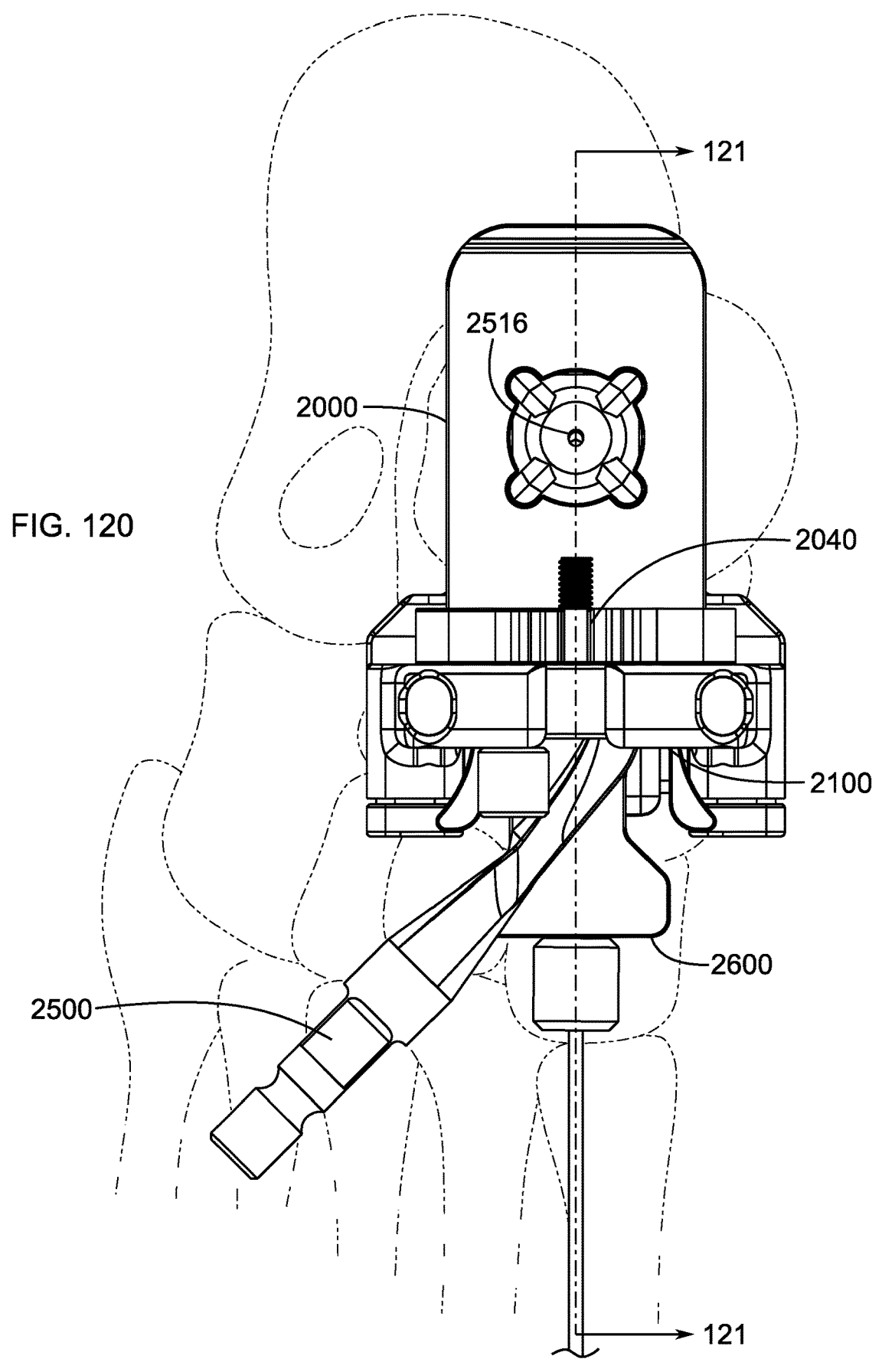
Figure 121:
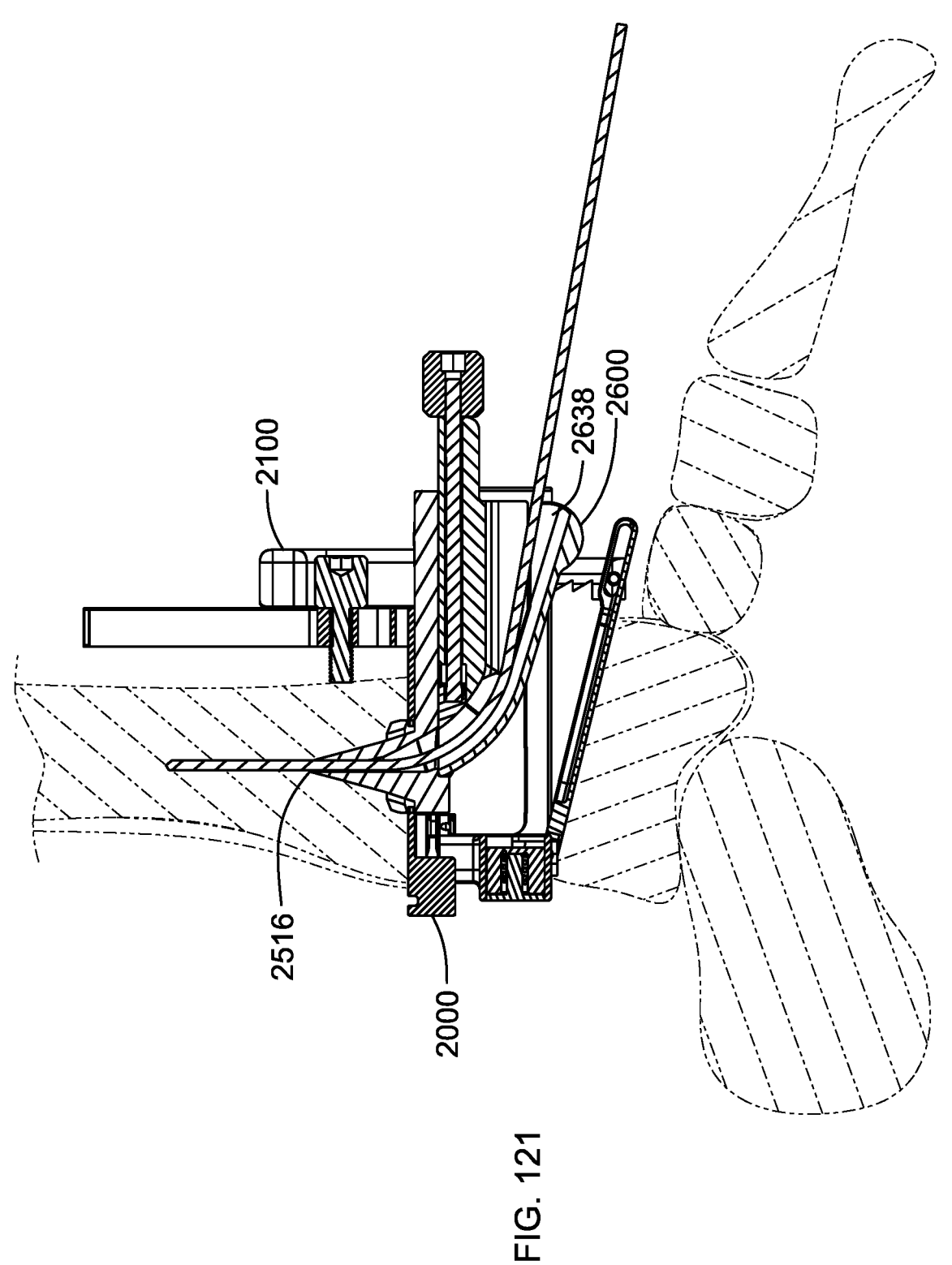
Figure 122:
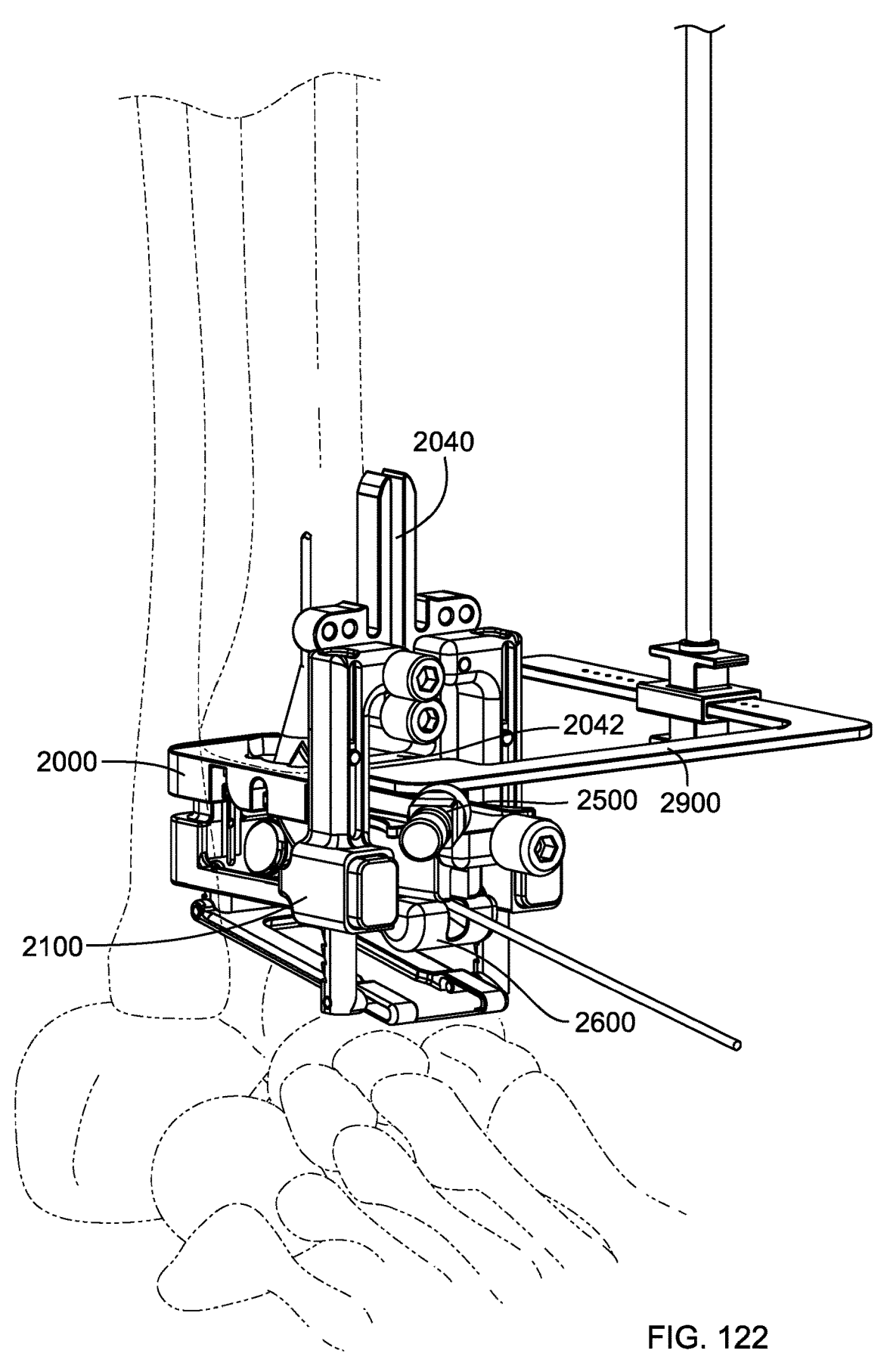
Figure 123:
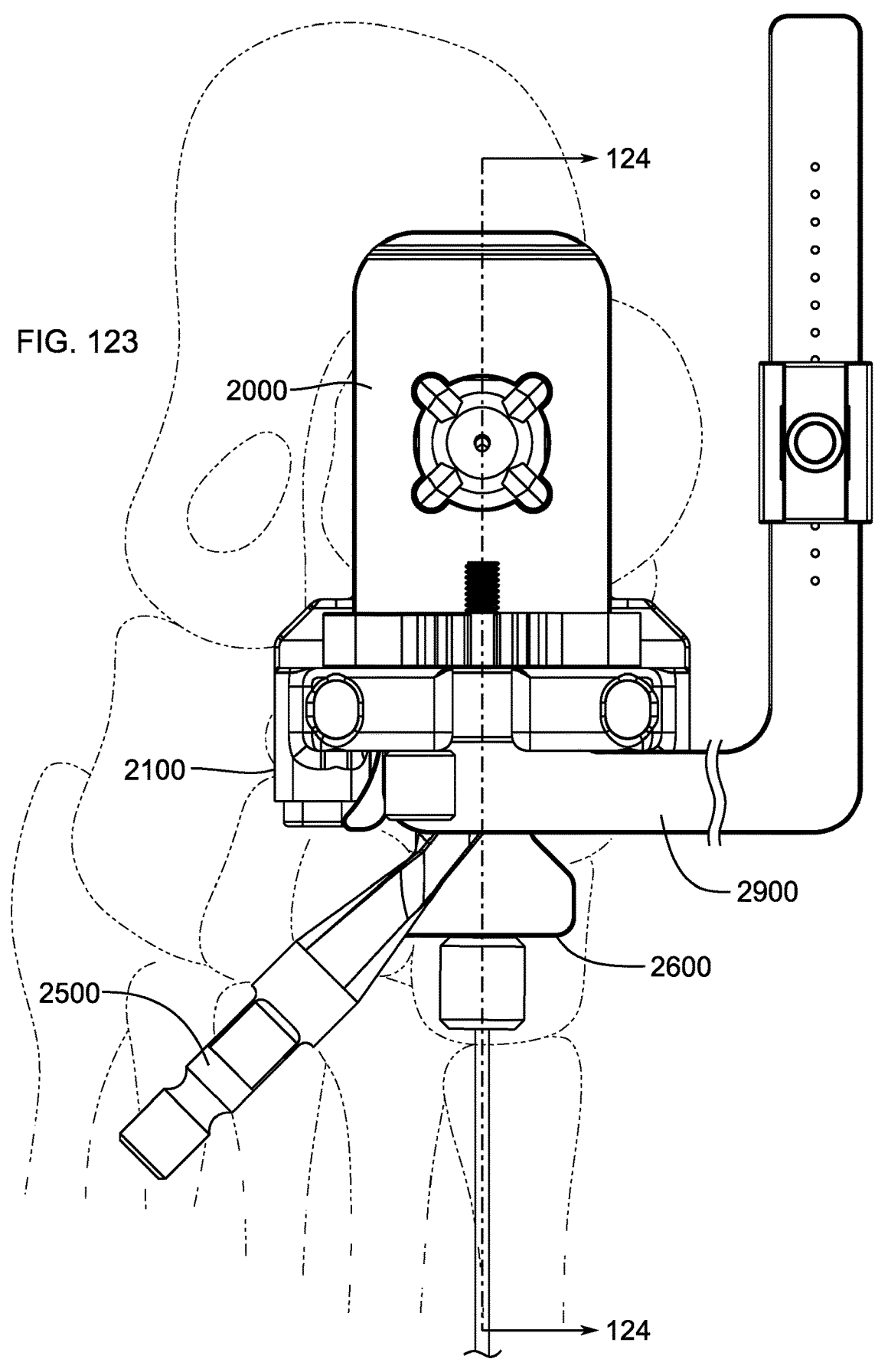
Figure 124:
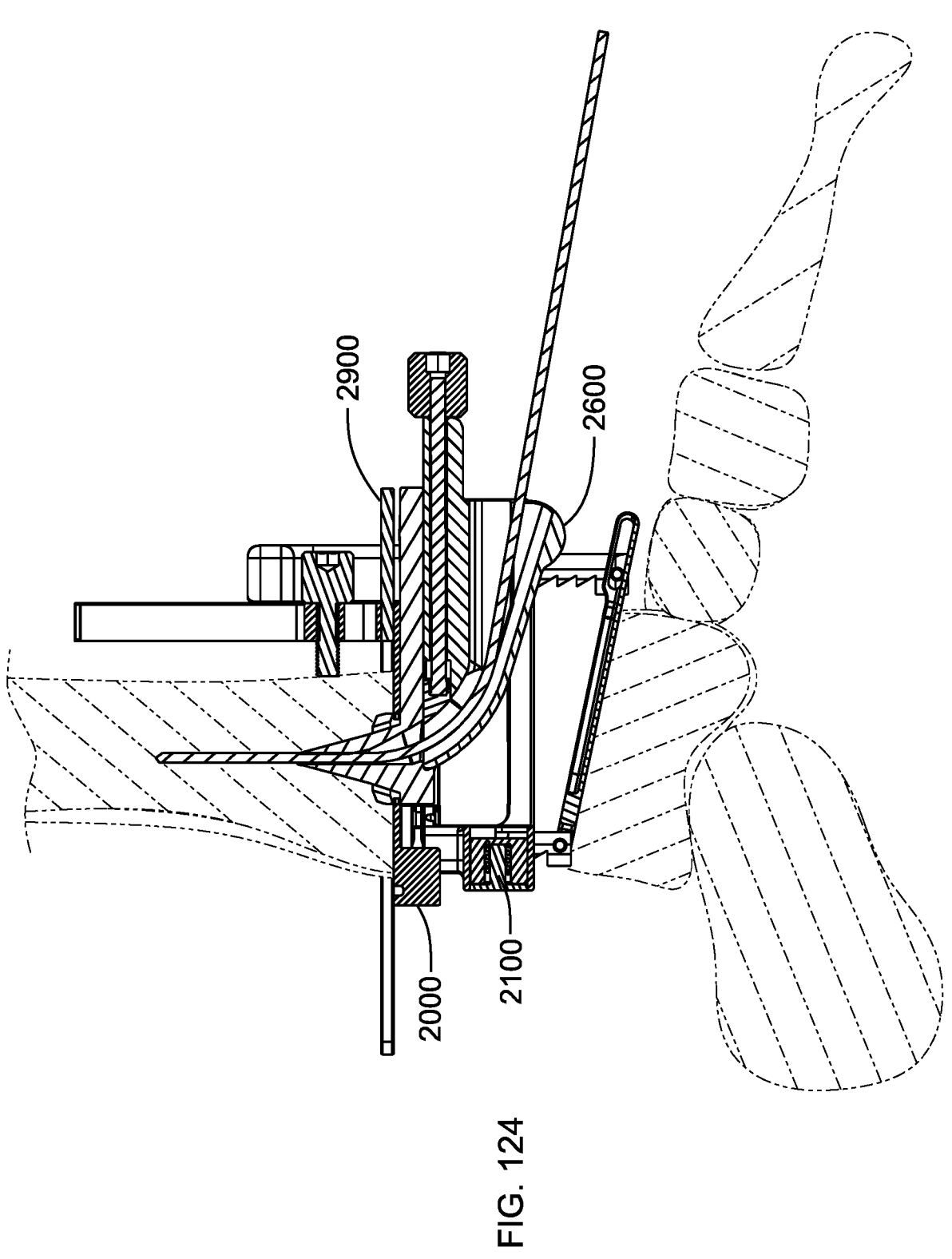

At step 4065, and with reference to FIGS. 119-121, the user inserts a guide wire into an anterior opening 2638 on the wire guide 2600 such that the guide wire travels through an elbow-bend channel in the wire guide 2600, through the guide wire channel 2516 of the spike broach 2500, and upwards into the medullary cavity. In some embodiments, the combination of the wire guide 2600 and spike broach 2500 may be configured to enable bend into the distracted joint space as well as vertical alignment with a central axis of the intramedullary canal. In some embodiments, a user may monitor progression of the guide wire into the medullary cavity under X-ray imaging and via a viewing slot 2040 on the trial face. In some embodiments, and with reference to FIGS. 122-124, the sight alignment tool 2900 may be inserted into the alignment slot 2042 on the tibial trial 2000 to further verify positioning and alignment of the guide wire or other tools.

At step 4070, the user removes the wire guide 2600 (to a second configuration) while leaving the guide wire within the medullary cavity. In some embodiments, the wire guide 2600 may be disassembled by loosening a fastener (e.g., screw, bolt, etc.), while in other embodiments, the wire guide 2600 may carefully slide out of the tibial trial 2000 and over the guide wire. Then, the user removes the spike broach 2500 while leaving the guide wire within the medullary cavity. In some embodiments, the spike broach 2500 may carefully slide out of the distracted jointed space and over the guide wire, while in other embodiments, the spike broach 2500 may be disassembled prior to removal.

At step 4075, and with reference to FIGS. 125-127, the user inserts the flexible reamer assembly (including, at least, a reamer blade 2702, flexible reamer 2700, reamer guide 2750, reamer lock plate 2800, etc.) into the tibial trial 2000 from the anterior direction. To do so, the user may first slide the reamer blade 2702, having a hollow central channel in fluid communication with the flexible reamer 2700, over the guide wire and then insert the overall reamer assembly into the channels 2024, 2026 of the tibial trial 2000. In some embodiments, portions of the flexible reamer assembly may engage with interior portions of the tibial trial 200 (e.g., first and second channels 2024, 2026). In some embodiments, the flexible reamer assembly may be assembled outside of the patient, such as on a back table. In this case, the reamer guide 2750 may comprise two halves that, when assembled, form a clamshell-like housing for the flexible reamer 2700. In some embodiments, a fastener, such as the reamer lock plate 2800, may lock the flexible reamer assembly into a desirable position within the tibial trial 2000 such that the reamer blade 2702 is positioned at the access opening 2020.

At step 4080, the user reams over the guide wire to widen the intramedullary canal to a predetermined and/or patient-specific distance. In some embodiments, the guide wire and the reamer blade 2702 may be driven independently (e.g., one after another), while in other embodiments, the guide wire and the reamer blade 2702 may be driven in parallel (e.g., in a step-wise manner). In some embodiments, the flexible reamer 2700 may include markings that may assist the user with reaming to the desired distance within the medullary cavity. In some embodiments, progression of the guide wire and/or reamer blade 2702 may be verified under X-ray imaging using the viewing slot 2040 of the tibial trial 2000. In some embodiments, the sight alignment tool 2900 may be inserted into the alignment slot 2042 on the tibial trial 2000 to further verify positioning and alignment of the guide wire and/or reamer blade 2702.

At step 4085, the user removes one or more tools and instruments from the patient while leaving the tibial trial 2000 and distractor 2100 (if used) in place. In some embodiments, the user may also remove the distractor 2100.

FIG. 101 describes a similar method 4200 of preparing the tibial surface for modular stem insertion. As shown in FIG. 101, at step 4205, a user (e.g., surgeon), receives a TAR tool kit, including tools and instruments suited for the preparation of the tibial surface, including, but not limited to, a tibial trial 2000, a distractor 2100, a right-angle drill 2200 and drill plate 2400, a spike broach 2500, a wire guide 2600, and a flexible reamer assembly (including a reamer lock plate 2800). The user may choose either method 4000 or method 4200 to prepare the tibial surface. In particular, method 4200 may reduce one or more total steps as compared to method 4000, thus reducing margin for error.

At step 4210, the user makes an anterior incision to the ankle joint space in a manner substantially similar to step 4010 of method 4000.

At step 4215, the user resects portions of the tibia and talus in a manner substantially similar to step 4015 of method 4000.

At step 4220, the user inserts the tibial trial in a desirable position (see FIGS. 100-102) in a manner substantially similar to step 4020 of method 4000.

At step 4225, the user inserts the sight alignment tool 2900 into an alignment slot 2042 on the tibial trial 2000 in a manner substantially similar to step 4025 of method 4000.

At step 4230, the user inserts the distractor 2100, in a first configuration, into the tibial trial 2000 in a manner substantially similar to step 4030 of method 4000 (see FIGS. 103-105).

At step 4235, the user distracts the ankle joint space by setting the distractor 2100 in a second configuration in a manner substantially similar to step 4035 of method 4000. In other embodiments, use of the distractor 2100 (e.g., steps 4230 and 4235) may be omitted depending on user preference. In this case, another user or any other suitable tool be used to distract the ankle joint space. In an alternative embodiment, depending on user preference, use of the distractor 2100 (e.g., steps 4230 and 4235) may occur at a later stage in the process 4200 (e.g., after the steps pertaining to drilling and before the steps pertaining to reaming). In this case, steps pertaining to drilling may not require the additional anterior clearance delivered by the distractor 2100 while steps pertaining to reaming and/or procedure 5000 may require additional anterior clearance.

At step 4240, the user inserts the right-angle drill plate 2400 in a manner substantially similar to step 4040 of method 4000. In some embodiments, the drill plate 2400 may include an asymmetric pattern of openings or through-holes for the user to drill through at step 4245, thus giving the user flexibility in targeting a specific pattern of bone to drill (e.g., in an X-shape) while reducing user judgment. In some embodiments, step 4240 may be omitted.

At step 4245, the user inserts the right-angle drill from the anterior direction into the tibial trial 2000 in a manner substantially similar to step 4045 of method 4000. In embodiments including the right-angle drill plate 2400, the user may drill a pattern of holes through the openings of the drill plate 2400 to begin forming the intramedullary canal. In embodiments without the drill plate, the user may drill directly through the inferior surface of the tibial trial (e.g., through a access opening) to begin forming the intramedullary canal. In this case, the user may remove the right-angle drill 2200 and proceed to step 4260.

In some embodiments, when using the right-angle drill plate 2400, the user may remove the drill plate 2400 and right-angle drill 2202, and re-insert the drill plate 2400 (wherein a second side of the drill plate faces upwards) in a manner similar to step 4040. Then, when using the right-angle drill plate 2400, the user may re-insert the right-angle drill 2200 and drill into portions of the tibial surface in a manner similar to step 4245. Thus, in some embodiments, by "flipping over" the drill plate 2400, the user may continue forming the particular pattern of holes (e.g., in an X-shape) to continue forming the intramedullary canal. The drill 2200 and drill plate 2400 can then be removed.

At step 4250, the user inserts a spike broach (having a solid interior) into the distracted joint space beneath the inferior face of the tibial trial 2000 such that the top face of the spike broach extends through the access opening. In some embodiments, the spike broach may engage with internal portions of the tibial trial 2000, such as the first 2024 and second 2026 channels, while in other embodiments, the spike broach may articulate with the inferior face but not the first and second channels.

At step 4255, the user impacts the spike broach upwards into the tibial surface (over the drilled holes of steps 4245) to increase the size of the intramedullary canal. Here, the spike broach may remove or compact additional bone to increase space in the medullary cavity for insertion of the modular stem. In some embodiments, the user may use an offset impactor having a C-shaped bracket enabling impaction from a distal end (e.g., to get around the foot). In other embodiments, the user may use any impactor, hammer, or other suitable tool known in the art for this step. The user may then remove the spike broach.

At step 4260, the user inserts the flexible reamer assembly (including, at least, a reamer blade 2702, flexible reamer 2700, reamer guide 2750, reamer lock plate 2800, etc.) into the tibial trial 2000 from the anterior direction. In some embodiments, portions of the flexible reamer assembly may engage with interior portions of the tibial trial 2000 (e.g., first and second channels). In some embodiments, the reamer blade 2702 may include a hollow central channel in fluid communication with the flexible reamer 2700. In some embodiments, the flexible reamer assembly may be assembled outside of the patient. In this case, the reamer guide 2750 may comprise two halves that, when assembled, form a clamshell housing for the flexible reamer 2700. In some embodiments, a fastener, such as the reamer lock plate

2800, may lock the flexible reamer assembly into a desirable position within the tibial trial 2000 such that the reamer blade 2702 is positioned at the access opening 2020.

At step 4265, the user inserts a guide wire through an anterior opening on the flexible reamer assembly such that the guide wire travels through the flexible reamer 2700, out the central channel of the reamer blade 2702, and upwards into the medullary cavity. In some embodiments, the reamer guide 2750 may be configured to enable bend into the distracted joint space as well as vertical alignment with a central axis of the intramedullary canal. In some embodiments, a user may monitor progression of the guide wire into the medullary cavity under X-ray imaging and via a viewing slot 2040 on the trial face. In some embodiments, the sight alignment tool 2900 may be inserted into the alignment slot 2042 on the tibial trial to further verify positioning and alignment of the guide wire.

At step 4270, the user reams over the guide wire to widen the intramedullary canal to a predetermined and/or patient-specific distance in a manner substantially similar to step 4080 of method 4000. In some embodiments, the guide wire and the reamer blade 2702 may be driven independently (e.g., one after another), while in other embodiments, the guide wire and the reamer blade 2702 may be driven in parallel (e.g., in a step-wise manner). In some embodiments, the flexible reamer 2700 may include markings that may assist the user with reaming to the desired distance within the medullary cavity. In some embodiments, progression of the guide wire and/or reamer blade 2702 may be verified under X-ray imaging using the viewing slot 2040 of the tibial trial 2000. In some embodiments, the sight alignment tool 2900 may be inserted into the alignment slot 2042 on the tibial trial 2000 to further verify positioning and alignment of the guide wire and/or reamer blade.

At step 4275, the user removes one or more tools and instruments from the patient while leaving the tibial trial 2000 and distractor 2100 (if used) in place. In some embodiments, the user may also remove the distractor 2100.

FIG. 102 describes a procedure 5000 of installing the modular stem system 1000 into the prepared tibial surface. As shown in FIG. 102, at step 5005, a user (e.g., surgeon), receives a TAR installation kit, including tools and instruments suited for the insertion of a tibial implant (such as the modular stem system 1000 as disclosed with reference to FIGS. 2-15) into the prepared tibial surface, including, but not limited to, a stem inserter tool 3100, a fastener guide 3160, a counter torque lock 3300, and an impactor tool 3500.

At step 5010, the user loads the stem inserter tool 3100 with a first modular member. In some embodiments, the user may manually load the stem inserter tool 3100 with the first modular member, while in other embodiments, a separate tool or instrument may be used to "grasp" the modular member and position it within the stem inserter tool 3100. In some embodiments, first modular member may be the terminal modular member 1080.

At step 5015, the user inserts the loaded stem inserter tool 3100 into the prepared tibial space. In some embodiments, one or more features of the stem inserter tool 3100 may engage with the tibial trial 2000. In some embodiments, the stem inserter 3100, when in a loaded configuration, may be inserted into the tibial trial 2000 such that the wings 3164 of the stem inserter 3100 may engage with the one or more channels (e.g., channels 2024, 2026) of the tibial trial 2000.

At step 5020, the user inserts the first modular member into the intramedullary canal. In some embodiments, the user may turn or otherwise engage a knob disposed on the stem inserter 3100 to at least partially insert the modular member. In some embodiments, the turning of the knob is directly related to the degree of insertion of the modular member such that the more the user turns the knob, the further the modular member is inserted into the intramedullary canal.

At step 5025, the user loads the stem inserter tool 3100 with a second modular member in a manner substantially similar to step 5010. In some embodiments, this may be modular member 1062. In some embodiments, the stem inserter tool 3100 may first be removed from the tibial trial 2000 and then loaded with the second modular member, while in other embodiments, the stem inserter tool 3100 may remain in place while it is loaded with the second modular member.

At step 5030, the user inserts the second modular member into the intramedullary canal in a manner substantially similar to step 5020. In some embodiments, the second modular member, when inserted, is adjacent to the first modular member. In some embodiments, the insertion of the second modular member at least partially impacts the first modular member further into the medullary canal.

At step 5035, the user loads the fastener guide 3160 with a fastener 1090. In some embodiments, the fastener guide 3160 may be coupled to or integrally formed with the stem inserter tool 3100 such that the fastener guide 3160 is already aligned with certain features (e.g., fastener hole) of the modular members once inserted. In other embodiments, the fastener guide 3160 may be a separate device from the stem inserter tool 3100, and is brought into alignment with the modular members via manual action by the user.

At step 5040, the user fastens the second modular member to the first modular member using the loaded fastener 1090. In some embodiments, the user may use a torque limiting driver to fasten the fastener to the modular member, while in other embodiments, the user may perform the action manually.

At step 5045, the user uses counter torque lock 3300 to verify a desirable position of the modular members within the medullary canal. In some embodiments, the user may engage certain features of the counter torque lock 3300 with indentations on the second modular member to verify medial-lateral and anterior-posterior alignment of the second modular member with regards to the first modular member (and thus intramedullary canal).

At step 5050, the user impacts the inserted modular members further into the medullary canal using an impactor tool. In some embodiments, the user may engage certain features (e.g., engagement feature 3512) with complementary features of the second modular member (e.g., male fixation feature). Then, the user may apply force to impact the second modular member against the first modular member, and thus impact the overall stem portion 1020 into the intramedullary canal.

In some embodiments, the user may repeat steps 5025 to 5050 as many times as is desired to achieve a desirable length of an overall stem portion 1020 of the modular stem system 1000, In some embodiments, the total length of the stem portion 1020 may be determined pre-operatively and may be patient-specific.

At step 5055, the user inserts the base tibial component 1001 adjacent to the most recently inserted modular member. In some embodiments, step 5055 may be performed manually or via tools to grip and align the base tibial component 1001.

At step 5060, the user fastens the base tibial component 1001 to a modular member using a fastener 1090. In some embodiments, the user may load the fastener guide 3160 with a fastener 1090 and use a torque limiting driver, while in other embodiments, the user may take manual action to insert and secure the fastener 1090.

At step 5070, the user finalizes the overall modular stem system 1000. In some embodiments, this may involve additional impaction once the base tibial component 1001 is installed to the adjacent modular member. In some embodiments, the user may perform various tests to ensure proper alignment, orientation, and strength of the installed modular stem system 1000.

FIG. 103 describes a method 5200 of installing the modular stem system into the prepared tibial surface. As shown in FIG. 103, at step 5205, a user (e.g., surgeon), receives a TAR installation kit, including tools and instruments suited for the insertion of a tibial implant (such as the modular stem as disclosed with reference to FIGS. 2-15) into the prepared tibial space, including, but not limited to, a compressor assembly 3000.

At step 5210, the user inserts the compressor assembly 3000 into the prepared tibial space.

In some embodiments, one or more features of the compressor assembly 3000 may engage with the tibial trial 2000. In some embodiments, the compressor assembly 3000, may be inserted into the tibial trial 2000 such that certain features of the compressor assembly 3000 may engage with the one or more channels (e.g., channels 2024, 2026) and thus secure the compressor assembly 3000 to the tibial trial 2000.

At step 5215, the user loads the compressor assembly with a first modular member. In some embodiments, this may be the terminal modular member 1080. In some embodiments, the user loads a stem inserter tool 3001 configured to engage with the compressor assembly 3000. The compressor assembly 3000 includes a stem inserter 3001, which, once in a loaded configuration, may be inserted into the compressor assembly 3000 such that one or more wings 3164 of the stem inserter 3001 may engage with interior sections of the compressor assembly 3000. In other embodiments, the stem inserter tool 3001 be integrally formed with the compressor assembly 3000, or otherwise coupled to the compressor assembly 3000.

At step 5220, the user inserts the first modular member into the medullary canal. In some embodiments, the user may turn or otherwise engage a knob 3116 disposed on the stem inserter 3001 to at least partially insert the modular member. In some embodiments, the turning of the knob 3116 is directly related to the degree of insertion of the modular member such that the more the user turns the knob 3116, the further the modular member is inserted into the intramedullary canal.

At step 5225, the user loads the stem inserter tool 3001 with a second modular member in a manner substantially similar to step 5010. In some embodiments, this may be modular member 1062. In some embodiments, the stem inserter tool 3001 may first be removed from the tibial trial 2000 and then loaded with the second modular member, while in other embodiments, the stem inserter tool 3001 may remain in place while it is loaded with the second modular member.

At step 5230, the user inserts the second modular member into the intramedullary canal in a manner substantially similar to step 5220. In some embodiments, the second modular member, when inserted, is adjacent to the first modular member. In some embodiments, the insertion of the second modular member at least partially impacts the first modular member further into the intramedullary canal.

At step 5235, the user loads compressor assembly 3000 with fastener 1090. In some embodiments, the compressor assembly 3000 includes a passage 3162 integrally formed with the stem inserter tool 3001 such that the passage 3162 is already aligned with certain features (e.g., fastener hole) of the modular members once inserted.

At step 5240, the user fastens the second modular member to the first modular member using the loaded fastener 1090. In some embodiments, the user may use a torque limiting driver to do the fastening, while in other embodiments, the user may manually do the fastening. In other embodiments, certain features of the compressor assembly 3000 facilitate tightening and loosing of the fastener 1090.

At step 5245, the user impacts the modular members further into the intramedullary canal in manner substantially similar to step 5220. For instance, the user may turn or otherwise engage the knob 3116 to impact the modular members, wherein the turning of the knob 3116 is directly related to the degree of insertion of the modular members.

In some embodiments, the user may repeat steps 52305 to 5245 as many times as is desired to achieve a desirable length of an overall stem portion 1020 of the modular stem system 1000, In some embodiments, the total length of the stem portion 1020 may be determined pre-operatively and may be patient-specific.

At step 5250, the user inserts the base component adjacent to the most recently inserted modular member in a manner substantially similar to step 5055.

At step 5255, the user fastens the base tibial component 1001 to a modular member using a fastener 1090 in a manner substantially similar to step 5060.

At step 5260, the user finalizes the overall modular stem system 1000 in a manner substantially similar to step 5070.

In at least one embodiment, the one or more of the implant structures (e.g., modular stem, talus implant, etc.) are produced by additive manufacturing methods, such as, for example, laser powder bed fusion, including, but not limited to, selective laser melting (SLM) processes. As described herein, a laser powder bed fusion process refers to a technique of iteratively lasing and melting a (typically metal) powder material into stacked patterns to create a layered, three-dimensional structure. The process generally includes: 1) receiving and processing a design; 2) configuring powder bed; 3) performing contour scan; 4) performing infill scan; and 5) determining whether the final layer of the design is formed. If the final layer of the design is formed, the process ends. According to one embodiment, if the final layer of the design is not formed (e.g., there are more layers to form), then the process returns to the second step. Exemplary processes for producing one of more implants described herein can be found in the following patent and patent application incorporated herein by reference as if set forth in their entireties:

U.S. Pat. No. 11,026,798, issued on Jun. 8, 2021, and entitled SHEET BASED TRIPLY PERIODIC MINIMAL SURFACE IMPLANTS FOR PROMOTING OSSEOINTEGRATION AND METHODS FOR PRODUCING SAME; and U.S. patent application Ser. No. 17/314,378, filed on May 7, 2021, and entitled SPATIALLY VARIED IMPLANTS AND PROCESSES FOR MAKING AND USING SAME.

ALTERNATE EMBODIMENTS

It is understood that the present disclosure is highly customizable, and any type of implant can be configured with any number and placement of docking recesses of any shape and size to receive any number and type of tissue attachment. Various alternate embodiments are contemplated herein, configured for use in various applications including, but not limited to, other joint replacement procedures involving the hip, knee, elbow, shoulder, wrist, fingers, and toes.

As will be understood, the tools and implants discussed herein may include additional visual and/or fluoroscopic features indicating depth, length, and/or angular measurement markings, or any other markings positioned at predetermined intervals. The markings may correlate with specific patient anatomy and may assist a user in performing surgical procedures and/or orientating the tools and implants to the patient's anatomy.

Furthermore, the tools (e.g., tibial trial, sight alignment tool, distractor, right-angle drill, drill plate, broach, reamer assembly, compressor assembly, stem inserter, fastener guide, counter-torque lock, impactor, etc.) discussed herein may be used in applications involving augmented reality (AR), where digital superimposition of virtual objects (e.g., CT scan of patient anatomy) onto physical objects (e.g., patient anatomy) or within space may aid the preoperative planning, surgical execution, and post operations of orthopedic procedures. In some embodiments, an optical tracking system may be applied to the tools such that features of predetermined size (e.g., a section of a sphere) may be identified. Attachment points (e.g., threaded attachment holes) on the tools may accept the placement of an optical tracking sensor detectable by the optical tracking system. The tools may also be equipped with additional sensors connected to an AR and/or IoT system that assist with data preparation and recording, visualization, and registration/tracking, thereby improving information transfer and consideration during surgery, and offering opportunities for continuous learning.

Figure 22:
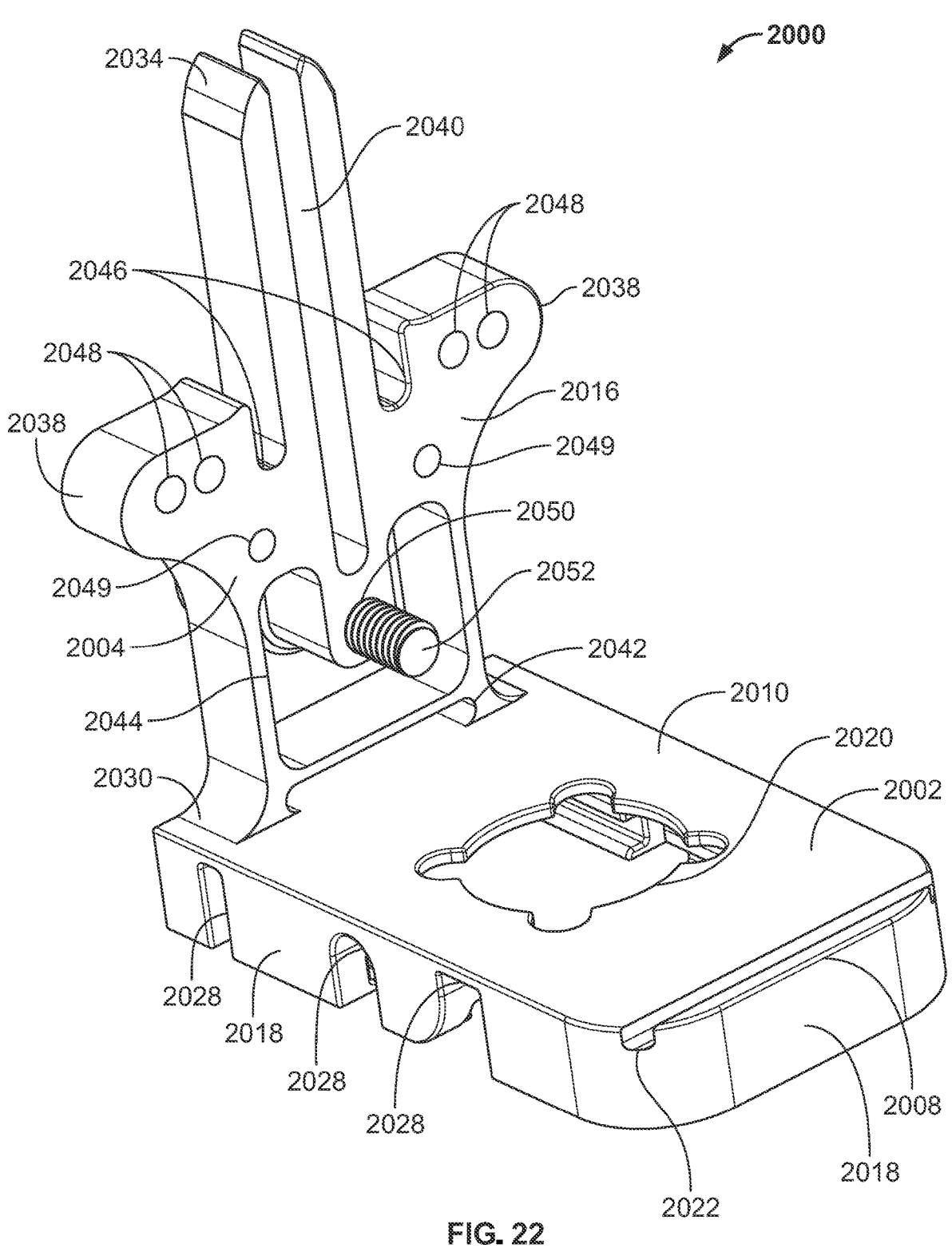
FIG. 22 is a rear perspective view of an exemplary tibial trial, according to one embodiment.
Figure 23:
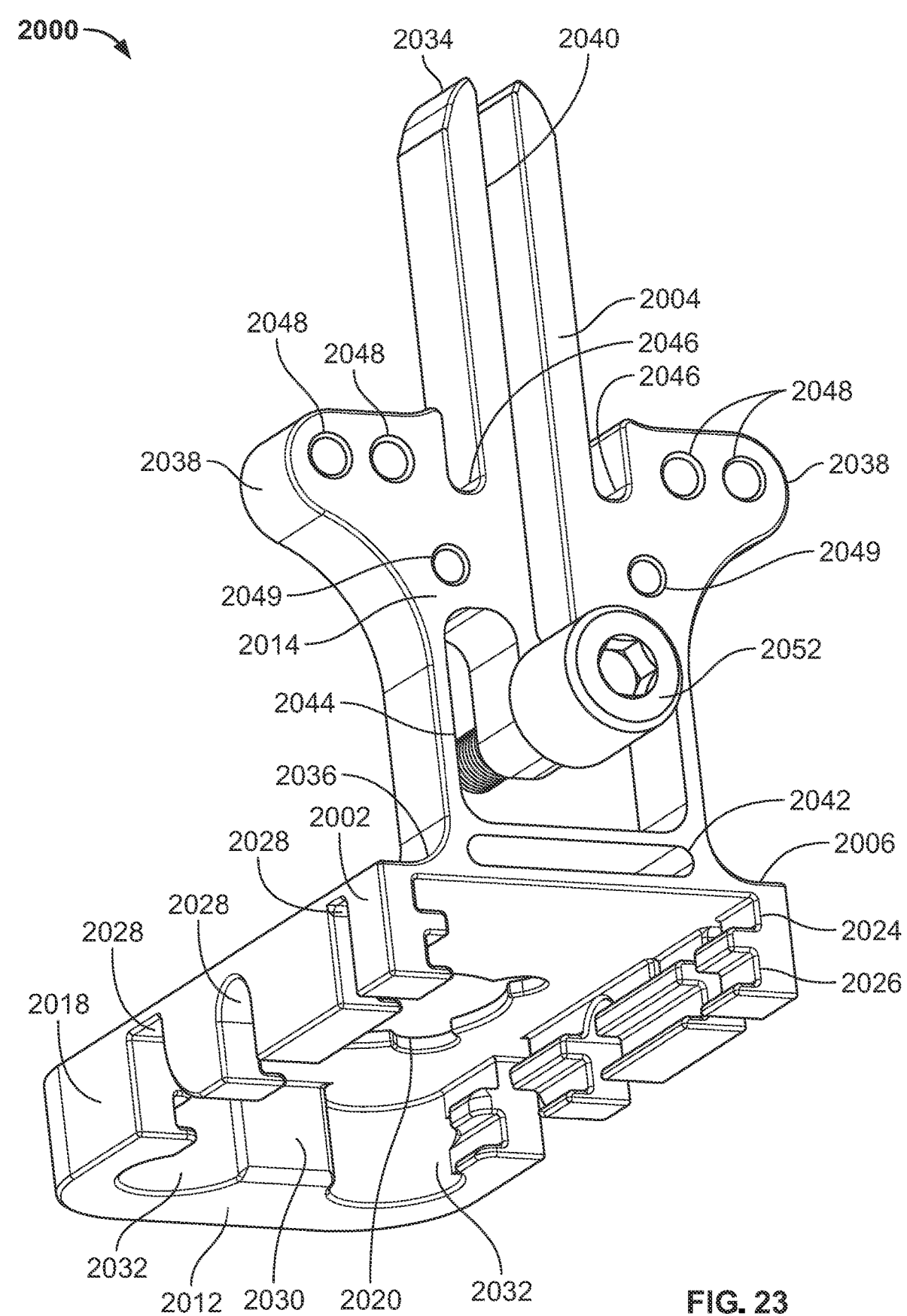
FIG. 23 is a perspective view of the exemplary tibial trial of FIG. 22.

For example, with reference to the embodiment of FIG. 22, the one or more apertures (e.g., 2048, 2049), alignment slots (e.g., 2040, 2042), or any other suitable openings (e.g., 2020, 2028, 2044), may be equipped with sensors that aid in optical tracking and data recordation. In connection with an AR and/or IoT system, the captured information may be interfaced with other tools of the TAR procedure such that AR and IoT capabilities may also streamline the TAR procedure by controlling or partially controlling the operation of other tools (e.g., distractor, RAD, etc.), thereby yielding higher accuracy in surgical execution, reduction of radiation exposure, and decreased surgery time and mistakes.

What is claimed is:

1. A total ankle replacement (TAR) system comprising:
a tibial implant, the tibial implant comprising:
a base component comprising:
an anterior surface;
a posterior surface;
a base plate, the base plate comprising
a first surface and a second surface;
the first surface including an attachment feature;
the second surface including an anchoring member,
the anchoring member comprising a front surface,
the front surface defining a first opening; and
a stem component comprising a longitudinal axis, the stem component coupled to the anchoring member, the stem component comprising:
a first modular member comprising a back surface, the back surface defining a second opening,
wherein a first fastener is inserted through the first opening and into at least a portion of the second opening in a direction perpendicular to the longitudinal axis and extending between the anterior surface and the posterior surface to couple the first modular member to the anchoring member, the first fastener further oriented in a horizontal direction relative to the second surface.

2. The TAR system of claim 1 wherein the first modular member is positioned at an offset angle relative to an axis orthogonal to the second surface.

3. The TAR system of claim 2, wherein a first fixation feature of the first modular member engages with the anchoring member.

4. The TAR system of claim 3, wherein a second fixation feature of the first modular member engages with a first fixation feature of a second modular member.

5. The TAR system of claim 4, wherein a second fastener is used to fasten the second modular member to the first modular member.

6. The TAR system of claim 5, wherein the second fixation feature of the first modular member defines a female portion of a dovetail joint and the first fixation feature of the second modular member defines a male portion of a dovetail joint.

7. The TAR system of claim 1, wherein the first opening includes at least one anti-backout feature.

8. The TAR system of claim 7, wherein the at least one anti-backout feature includes a flexible pawl, the flexible pawl selectively engaging with one tooth of the first fastener.

9. The TAR system of claim 1, wherein the tibial implant includes one or more regions for osteointegration.

10. The TAR system of claim 9, wherein the one or more regions comprises a gyroid structure.

11. A system for replacing a tibial side of a patient's ankle joint, wherein the tibial side of the ankle joint includes a tibia having a medullary cavity, the system comprising:

a tibial implant comprising:
    a stem component, the stem component comprising a longitudinal axis and a modular member, the modular member comprising a back surface, the back surface defining a first opening; and
    a base component, the base component comprising a front surface, the front surface defining a second opening,
    wherein the stem component is coupled to the base component by inserting a fastener through the second opening and into the first opening in a direction perpendicular to the longitudinal axis and extending from an anterior surface of the base component toward a posterior surface of the base component;
one or more tools for preparing the tibia for installation of the tibial implant, the one or more tools comprising a tibial trial, a distractor, a right-angle drill, a broach, a reamer assembly, and a guide wire; and
one or more instruments for installing the tibial implant into a prepared tibial surface, the one or more instruments comprising a stem inserter and an impactor.

12. The system of claim 11, wherein the tibial trial comprises:
    a trial face having a viewing slot, an alignment slot, and a fastener opening; and
    a trial base having one or more channels and an access opening.

13. The system of claim 12, wherein a sight alignment tool is inserted into the alignment slot to verify a desirable position of the tibial trial.

14. The system of claim 13, wherein the tibial trial is secured to the patient's tibia using a fastener and the fastener opening.

* * * * *